United States Patent
Beauchamp et al.

(10) Patent No.: US 12,122,750 B2
(45) Date of Patent: Oct. 22, 2024

(54) AT₂R ANTAGONISTS AND USES THEREOF

(71) Applicant: Eli Lilly and Company, Indianapolis, IN (US)

(72) Inventors: Thomas James Beauchamp, Fishers, IN (US); Zhaogen Chen, Carmel, IN (US); Scott Eugene Conner, Carmel, IN (US); Jon Andre Erickson, Carmel, IN (US); Maria Cristina Garcia Paredes, Carmel, IN (US); Jayana Pankajkumar Lineswala, Brownsburg, IN (US); Emanuele Sher, Hampton (GB); Bishnu Thapa, Greenwood, IN (US); Leonard Larry Winneroski, Whitestown, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 18/315,533

(22) Filed: May 11, 2023

(65) Prior Publication Data

US 2023/0373919 A1    Nov. 23, 2023

Related U.S. Application Data

(60) Provisional application No. 63/342,828, filed on May 17, 2022, provisional application No. 63/413,691, filed on Oct. 6, 2022.

(51) Int. Cl.
| | |
|---|---|
| *C07D 211/62* | (2006.01) |
| *C07D 401/04* | (2006.01) |
| *C07D 401/06* | (2006.01) |
| *C07D 405/12* | (2006.01) |
| *C07D 405/14* | (2006.01) |
| *C07D 471/04* | (2006.01) |

(52) U.S. Cl.
CPC .......... *C07D 211/62* (2013.01); *C07D 401/04* (2013.01); *C07D 401/06* (2013.01); *C07D 405/12* (2013.01); *C07D 405/14* (2013.01); *C07D 471/04* (2013.01)

(58) Field of Classification Search
CPC .. C07D 211/62; C07D 401/04; C07D 401/06; C07D 405/12
See application file for complete search history.

(56) References Cited

U.S. PATENT DOCUMENTS

2003/0055244 A1    3/2003    Scarborough et al.

FOREIGN PATENT DOCUMENTS

| EP | 0204254 | 12/1986 | |
| WO | WO-0130780 A2 * | 5/2001 | ............... A61P 7/02 |
| WO | 2007/106938 | 9/2007 | |
| WO | 2023006893 | 2/2023 | |

OTHER PUBLICATIONS

Balogh, et al., "Angiotensin receptors and neuropathic pain" Pain Reports, 2021, vol. 6, p. e869.
Hesselink, et al., "EMA401: an old antagonist of the AT2R for a new indication in neuropathic pain" Journal of Pain Research, 2017, vol. 10, p. 439.
Written Opinion for International Application No. PCT/US2023/021802.
International Search Report for International Application No. PCT/US2023/021802.
Wu, et al., "Synthesis and Structure-Activity Relationships of a Novel Series of Non-Peptide AT₂-Selective Angiotensin II Receptor Antagonists," Bioorganic & Medicinal Chemistry Letters, vol. 3, No. 10, pp. 2023-2028 (1993).
Sim, et al., "Research of the structure-activity relationship in the series of piperidine analgesic agents using electron topological method," Institute of Chemistry of the Academy of Sciences of Moldova, Kishinev, pp. 30-33 (1993).

* cited by examiner

*Primary Examiner* — John S Kenyon
*Assistant Examiner* — Rehana Ismail
(74) *Attorney, Agent, or Firm* — Gabriel Magallanes

(57) ABSTRACT

This invention provides certain piperidine compounds as AT₂R antagonists, e.g., compounds of formula (I):

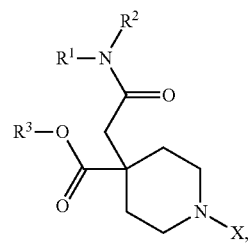

or pharmaceutically acceptable salts thereof, wherein $R^1$, $R^2$, $R^3$, and X are as defined herein, pharmaceutical compositions thereof, and methods of using the same to treat pain associated with AT₂R activity.

28 Claims, No Drawings

AT$_2$R ANTAGONISTS AND USES THEREOF

The present disclosure relates to compounds, pharmaceutical compositions, and methods, which include antagonists of the angiotensin II receptor 2 (AT$_2$R), and their use in the treatment of chronic pain, including nociceptive, neuropathic, and mixed pain, and in particular, the treatment of osteoarthritis (OA) pain, or diabetic peripheral neuropathy pain (DPNP), or chronic low back pain (CLBP). Chronic pain can be divided into different categories based on the mechanism: nociceptive, neuropathic, and mixed. Nociceptive pain is caused by stimuli, including inflammation, that potentially or actually cause an injury to non-neuronal tissues. This activates nociceptive receptors in the peripheral sensory system. Pain due to osteoarthritis is a classic example of somatic nociceptive pain. Neuropathic pain is caused by injuries to or disease of the central or peripheral nervous system, leading to maladaptive hypersensitivity of the sensory nervous system. Pain due to diabetic peripheral neuropathy is a classic example of peripheral neuropathic pain. Conditions that exhibit features of both nociceptive and neuropathic pain are categorized as mixed pain (e.g., chronic low back pain may be a non-limiting example).

Chronic pain is a highly prevalent condition with huge societal impact. In 2016, an estimated 20.4% of the adult population in the United States experienced chronic pain, defined as pain on most days, or every day in the past 6 months, based on data from the National Health Interview Survey. An estimated 8% of the population had chronic pain that limited their lives or work activities on most days or every day in the past 6 months. As a result, chronic pain is a leading cause for health care expenditure with the annual cost for managing chronic pain in the United States in 2010 estimated at approximately $635 billion. Despite the high disease burden and societal impact, management of chronic pain is currently unsatisfactory. Nonpharmacologic therapy alone is seldom adequate for pain relief or functional improvement, and available pharmacologic therapies vary and offer modest benefit and some have significant safety risks. Presently, the most frequently used drugs to alleviate the most common types of chronic pain are acetaminophen, nonsteroidal anti-inflammatory drugs, and opioids. Gabapentinoids, other anticonvulsants (such as sodium divalproate, carbamazepine, or lamotrigine) and some antidepressants (such as tricyclics or duloxetine) can be used for some specific pain disorders. The current pharmacologic armamentarium typically provides low levels of efficacy, tolerability issues, and/or deleterious side effects. Opioids are effective against acute pain, but they are a limited treatment option for chronic pain because of high abuse risk and potentially serious adverse reactions. The physical, emotional, and financial impact of chronic pain on the patient and society, combined with a lack of efficacious and tolerable treatment options, make it a significant unmet medical need.

Existing treatments for neuropathic pain show modest efficacy and unfavorable side-effects. The renin-angiotensin system (RAS) is implicated in neuropathic pain (see, e.g., Pain Rep. 2021, 6, e869). AT$_2$R is related to the pain mechanism in the nervous system, expressed in damaged nerves and invading immune cells (Proc. Natl. Acad. Sci. USA, 2018, 115, E8057-E8066). Damaged nerves and painful neuromas have higher AT$_2$R expression than normal nerves. AT$_2$R antagonists have been proven to be useful for relieving pains in animal experiments (Pain. Medicine. 2013, 14, 1557; Pain. Medicine. 2013, 14, 692) and clinical trials (Lancet. 2014, 383, 1637-1647). A related review report can be found in, for example, Expert. Opin. Ther. Targets. 2015, 19, 25-35. Angiotensin II (Ang II) is an octapeptide substance produced by the hydrolysis of angiotensin I under the action of angiotensin converting enzyme and has various functions including regulating blood pressure, body fluid balance and pain perception. Angiotensin receptors are G-protein coupled receptors, and Ang II activates angiotensin II receptor 1 (AT$_1$R) and angiotensin II receptor 2 (AT$_2$R).

Angiotensin type 2 receptor (AT$_2$R) is associated with chronic neuropathic pain and inflammatory pain (see, e.g., Behav Pharmacol, 2014, 25, 137, Pain Med, 2013, 14, 1557, Pain Med, 2013, 14, 692, WO 2007/106938, and WO 2006/066361), which have eluded efficient treatment options. EMA401 (Olodanrigan), which is a highly selective AT$_2$R antagonist, has been reported to possess analgesic properties. EMA401 was studied in Phase 1 and Phase 2 trials (Lancet, 2014, 383, 1637) for its high selectivity for AT$_2$R and good oral bioavailability but was terminated because of pre-clinical toxicity findings. There are no other known AT$_2$R antagonists approved in clinical trials for the treatment of pain. There remains an unmet need for AT$_2$R antagonists having desirable clinical properties to provide alternative therapies for treating pain disorders, such as osteoarthritis (OA) pain, or diabetic peripheral neuropathy pain (DPNP), chronic low back pain (CLBP), or other forms of chronic pain.

SUMMARY

The present disclosure provides compounds, pharmaceutically acceptable salts thereof, and compositions thereof, useful in the treatment of pain associated with AT$_2$R activity, including methods of preparing the compounds and compositions thereof, and methods of using the compounds and compositions in the treatment of pain.

The present disclosure provides a compound of formula (I):

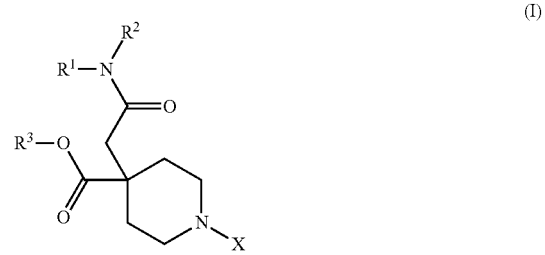

or a pharmaceutically acceptable salt thereof, wherein $R^1$, $R^2$, $R^3$, and X are as described herein.

In some embodiments, a compound of the present disclosure is selected from the examples described in Table I, or stereoisomers thereof, or pharmaceutically acceptable salts thereof.

In some embodiments, a compound of the present disclosure is selected from the examples described in Table I, or pharmaceutically acceptable salts thereof.

In some embodiments, a compound of the present disclosure is selected from the examples described in Table I.

The present disclosure provides a pharmaceutical composition comprising a compound, and/or salt of a compound of the present disclosure, and a pharmaceutically acceptable carrier, diluent, or excipient.

In some embodiments, the present disclosure provides a pharmaceutical composition comprising a compound of the present disclosure, and a pharmaceutically acceptable carrier, diluent, or excipient.

In some embodiments, the present disclosure provides a pharmaceutical composition comprising a salt of a compound of the present disclosure, and a pharmaceutically acceptable carrier, diluent, or excipient.

In some embodiments, the present disclosure provides a method of treating pain comprising administering to a subject in need thereof a therapeutically effective amount of a compound of the present disclosure, or a pharmaceutically acceptable salt thereof.

In some embodiments, the present disclosure provides a compound of the present disclosure, or a pharmaceutically acceptable salt thereof, for use in treating pain.

In some embodiments, the present disclosure provides a use of the compound of the present disclosure, or a pharmaceutically acceptable salt thereof, in the manufacture of a medicament, for the treatment of pain

DETAILED DESCRIPTION

The present disclosure relates to compounds, pharmaceutically acceptable salts, and stereoisomers thereof, useful in the treatment of a pain associated with $AT_2R$ activity, including methods of preparing the compounds, compositions comprising the compounds, and methods of using the compounds (e.g., in the treatment of pain).

The present disclosure provides a compound of formula (I):

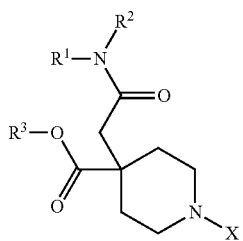

wherein:
- $R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;
- each $R^{1a}$ independently is halogen, $C_1$-$C_6$ alkyl, $C_1$-$C_6$ alkoxyl, or $C_3$-$C_6$ cycloalkyl;
- $R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;
- each $R^{2a}$ independently is halogen, $C_1$-$C_6$ alkyl, $C_1$-$C_6$ alkoxyl, or $C_3$-$C_6$ cycloalkyl;
- $R^3$ is H or $C_1$-$C_6$ alkyl;
- X is $C_5$-$C_{10}$ heteroaryl, $C_6$-$C_{10}$ aryl,

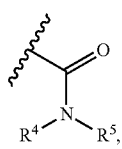 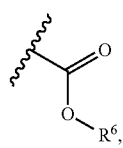

-continued

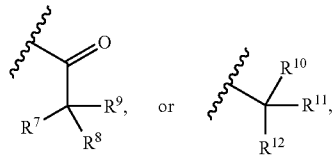

wherein the $C_5$-$C_{10}$ heteroaryl or $C_6$-$C_{10}$ aryl is optionally substituted with one or more $X^a$;
- each $X^a$ independently is halogen, $C_1$-$C_6$ alkyl, $C_1$-$C_6$ alkoxyl, or $C_3$-$C_6$ cycloalkyl;
- $R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;
- each $R^{4a}$ independently is halogen, cyano, $C_1$-$C_6$ alkyl, $C_1$-$C_6$ alkoxyl, or $C_3$-$C_6$ cycloalkyl;
- $R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;
- each $R^{5a}$ independently is halogen, cyano, $C_1$-$C_6$ alkyl, $C_1$-$C_6$ alkoxyl, or $C_3$-$C_6$ cycloalkyl;
- $R^6$ is H or $C_1$-$C_6$ alkyl;
- $R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;
- each $R^{7a}$ independently is halogen, cyano, or $C_3$-$C_6$ cycloalkyl;
- $R^8$ is H, halogen, or $C_1$-$C_6$ alkyl;
- $R^9$ is H, halogen, or $C_1$-$C_6$ alkyl; or
- $R^8$ and $R^9$ together form a $C_3$-$C_6$ cycloalkyl;
- $R^{10}$ and $R^{11}$ are each H or $R^{10}$ and $R^{11}$ together form an oxo;
- $R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and
- each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

In another embodiment, present disclosure provides a compound of formula (I):

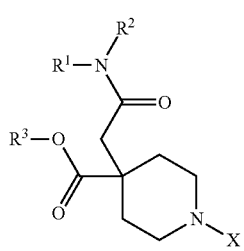

wherein:
- $R^1$ is methyl, ethyl, propyl, butan-2-yl, pentyl, 3-methylbutan-2-yl, cyclopropyl, cyclopentyl, cyclohexyl, tetrahydropyranyl, or phenyl, wherein the methyl, ethyl, propyl, butan-2-yl, pentyl, 3-methylbutan-2-yl, cyclopropyl, cyclopentyl, cyclohexyl, tetrahydropyranyl, or phenyl is optionally substituted with one or more $R^{1a}$;
- each $R^{1a}$ independently is fluorine, chlorine, methyl, isopropyl, methoxyl, or cyclopropyl;

R² is methyl, ethyl, propyl, butan-2-yl, pentyl, 3-methylbutan-2-yl, cyclopropyl, cyclopentyl, cyclohexyl, tetrahydropyranyl, or phenyl, wherein the methyl, ethyl, propyl, butan-2-yl, pentyl, 3-methylbutan-2-yl, cyclopropyl, cyclopentyl, cyclohexyl, tetrahydropyranyl, or phenyl is optionally substituted with one or more $R^{2a}$;

each $R^{2a}$ independently is fluorine, chlorine, methyl, isopropyl, methoxyl, or cyclopropyl;

R³ is H;

X is triazolyl, pyrimidinyl, pyridinyl, phenyl,

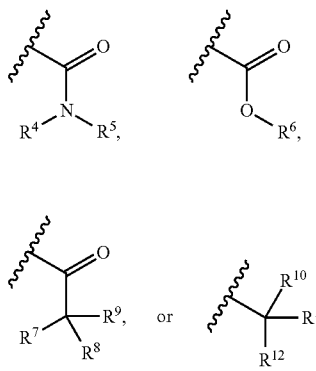

wherein the triazolyl, pyrimidinyl, pyridinyl, phenyl is optionally substituted with one or more $X^a$;

each $X^a$ independently is bromine, pentyl, or cyclopropyl;

R⁴ is methyl, ethyl, isopropyl, pentyl, cyclopentyl, or phenyl, wherein the methyl, ethyl, isopropyl, pentyl, cyclopentyl, or phenyl is optionally substituted with one or more $R^{4a}$;

each $R^{4a}$ independently is fluorine, methyl, methoxyl, or cyclopropyl;

R⁵ is methyl, ethyl, isopropyl, pentyl, cyclopentyl, or phenyl, wherein the methyl, ethyl, isopropyl, pentyl, cyclopentyl, or phenyl is optionally substituted with one or more $R^{5a}$;

each $R^{5a}$ independently is fluorine, methyl, methoxyl, or cyclopropyl

R⁶ is tert-butyl;

R⁷ is phenyl optionally substituted with one or more $R^{7a}$;

each $R^{7a}$ independently is fluorine;

R⁸ is H, F, or methyl;

R⁹ is H, F, or methyl; or

R⁸ and R⁹ together form cyclopropyl;

R¹⁰ and R¹¹ are each H or R¹⁰ and R¹¹ together form an oxo;

R¹² is indolinyl, tetrahydroquinolinyl, phenyl, or isopropyl-phenyl, wherein the indolinyl, tetrahydroquinolinyl, phenyl, or isopropyl-phenyl is optionally substituted with one or more $R^{12a}$; and each $R^{12a}$ independently is fluorine, cyano, isopropyl, methoxyl, or cyclopropyl; or a pharmaceutically acceptable salt thereof.

In another embodiment, the present disclosure provides a compound of formula (Ia),

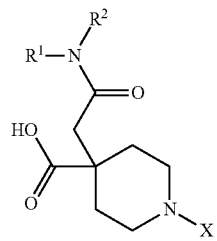

(Ia)

wherein:
R¹ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;

each $R^{1a}$ independently is halogen, $C_1$-$C_6$ alkyl, $C_1$-$C_6$ alkoxyl, or $C_3$-$C_6$ cycloalkyl;

R² is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;

each $R^{2a}$ independently is halogen, $C_1$-$C_6$ alkyl, $C_1$-$C_6$ alkoxyl, or $C_3$-$C_6$ cycloalkyl;

X is $C_5$-$C_{10}$ heteroaryl, $C_6$-$C_{10}$ aryl,

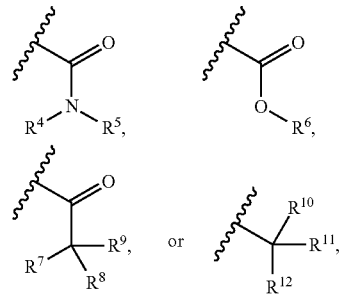

wherein the $C_5$-$C_{10}$ heteroaryl or $C_6$-$C_{10}$ aryl is optionally substituted with one or more $X^a$;

each $X^a$ independently is halogen, $C_1$-$C_6$ alkyl, $C_1$-$C_6$ alkoxyl, or $C_3$-$C_6$ cycloalkyl;

R⁴ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;

each $R^{4a}$ independently is halogen, cyano, $C_1$-$C_6$ alkyl, $C_1$-$C_6$ alkoxyl, or $C_3$-$C_6$ cycloalkyl;

R⁵ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;

each $R^{5a}$ independently is halogen, cyano, $C_1$-$C_6$ alkyl, $C_1$-$C_6$ alkoxyl, or $C_3$-$C_6$ cycloalkyl;

R⁶ is H or $C_1$-$C_6$ alkyl;

R⁷ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;

each $R^{7a}$ independently is halogen, cyano, or $C_3$-$C_6$ cycloalkyl;

R⁸ is H, halogen, or $C_1$-$C_6$ alkyl;

R⁹ is H, halogen, or $C_1$-$C_6$ alkyl; or

R⁸ and R⁹ together form a $C_3$-$C_6$ cycloalkyl;

R¹⁰ and R¹¹ are each H or R¹⁰ and R¹¹ together form an oxo;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and Each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

In another embodiment, the present disclosure provides a compound of formula (Ib),

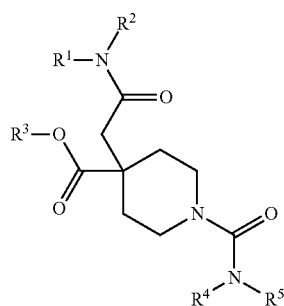

(Ib)

wherein:
- $R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;
- each $R^{1a}$ independently is halogen, $C_1$-$C_6$ alkyl, $C_1$-$C_6$ alkoxyl, or $C_3$-$C_6$ cycloalkyl;
- $R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;
- each $R^{2a}$ independently is halogen, $C_1$-$C_6$ alkyl, $C_1$-$C_6$ alkoxyl, or $C_3$-$C_6$ cycloalkyl;
- $R^3$ is H or $C_1$-$C_6$ alkyl;
- $R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;
- each $R^{4a}$ independently is halogen, cyano, $C_1$-$C_6$ alkyl, $C_1$-$C_6$ alkoxyl, or $C_3$-$C_6$ cycloalkyl;
- $R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$; and
- each $R^{5a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

In another embodiment, the present disclosure provides a compound of formula (Ic),

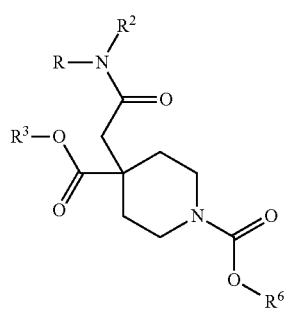

(Ic)

wherein:
- $R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;
- each $R^{1a}$ independently is halogen, $C_1$-$C_6$ alkyl, $C_1$-$C_6$ alkoxyl, or $C_3$-$C_6$ cycloalkyl;
- $R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;
- each $R^{2a}$ independently is halogen, $C_1$-$C_6$ alkyl, $C_1$-$C_6$ alkoxyl, or $C_3$-$C_6$ cycloalkyl;
- $R^3$ is H or $C_1$-$C_6$ alkyl; and
- $R^6$ is H or $C_1$-$C_6$ alkyl; or a pharmaceutically acceptable salt thereof.

In another embodiment, the present disclosure provides a compound of formula (Id),

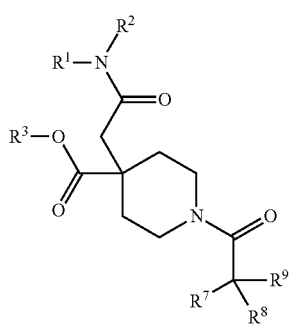

(Id)

wherein:
- $R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;
- each $R^{1a}$ independently is halogen, $C_1$-$C_6$ alkyl, $C_1$-$C_6$ alkoxyl, or $C_3$-$C_6$ cycloalkyl;
- $R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;
- each $R^{2a}$ independently is halogen, $C_1$-$C_6$ alkyl, $C_1$-$C_6$ alkoxyl, or $C_3$-$C_6$ cycloalkyl;
- $R^3$ is H or $C_1$-$C_6$ alkyl;
- $R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;
- each $R^{7a}$ independently is halogen, cyano, or $C_3$-$C_6$ cycloalkyl;
- $R^8$ is H, halogen, or $C_1$-$C_6$ alkyl; and
- $R^9$ is H, halogen or $C_1$-$C_6$ alkyl; or
- $R^8$ and $R^9$ together form a $C_3$-$C_6$ cycloalkyl; or a pharmaceutically acceptable salt thereof.

In another embodiment, the present disclosure provides a compound of formula (Ie),

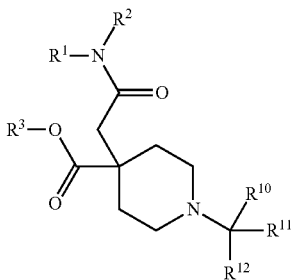

(Ie)

wherein:
R$^1$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{1a}$;
each R$^{1a}$ independently is halogen, C$_1$-C$_6$ alkyl, C$_1$-C$_6$ alkoxyl, or C$_3$-C$_6$ cycloalkyl;
R$^2$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{2a}$;
each R$^{2a}$ independently is halogen, C$_1$-C$_6$ alkyl, C$_1$-C$_6$ alkoxyl, or C$_3$-C$_6$ cycloalkyl;
R$^3$ is H or C$_1$-C$_6$ alkyl;
R$^{10}$ and R$^{11}$ are each H or R$^{10}$ and R$^{11}$ together form an oxo;
R$^{12}$ is C$_1$-C$_6$ alkyl, C$_3$-C$_6$ cycloalkyl, C$_6$-C$_{10}$ aryl, C$_1$-C$_3$-(phenyl), or C$_3$-C$_{10}$ heterocycloalkyl wherein the C$_1$-C$_6$ alkyl, C$_3$-C$_6$ cycloalkyl, C$_6$-C$_{10}$ aryl, C$_1$-C$_3$-(phenyl), or C$_3$-C$_{10}$ heterocycloalkyl is optionally substituted with one or more R$^{12a}$; and
each R$^{12a}$ independently is halogen, cyano, C$_1$-C$_6$ alkyl, C$_1$-C$_6$ alkoxyl, or C$_3$-C$_6$ cycloalkyl; or a pharmaceutically acceptable salt thereof.

In another embodiment, the present disclosure provides a compound of formula (If),

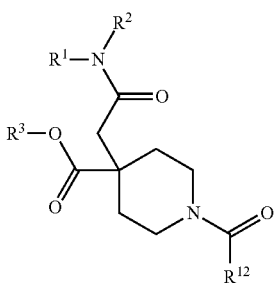

(If)

wherein:
R$^1$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{1a}$;
each R$^{1a}$ independently is halogen, C$_1$-C$_6$ alkyl, C$_1$-C$_6$ alkoxyl, or C$_3$-C$_6$ cycloalkyl;
R$^2$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{2a}$;
each R$^{2a}$ independently is halogen, C$_1$-C$_6$ alkyl, C$_1$-C$_6$ alkoxyl, or C$_3$-C$_6$ cycloalkyl;
R$^3$ is H or C$_1$-C$_6$ alkyl;
R$^{12}$ is C$_1$-C$_6$ alkyl, C$_3$-C$_6$ cycloalkyl, C$_6$-C$_{10}$ aryl, C$_1$-C$_3$-(phenyl), or C$_3$-C$_{10}$ heterocycloalkyl wherein the C$_1$-C$_6$ alkyl, C$_3$-C$_6$ cycloalkyl, C$_6$-C$_{10}$ aryl, C$_1$-C$_3$-(phenyl), or C$_3$-C$_{10}$ heterocycloalkyl is optionally substituted with one or more R$^{12a}$; and
each R$^{2a}$ independently is halogen, cyano, C$_1$-C$_6$ alkyl, C$_1$-C$_6$ alkoxyl, or C$_3$-C$_6$ cycloalkyl; or a pharmaceutically acceptable salt thereof.

In another embodiment, the present disclosure provides a compound of formula (Ig),

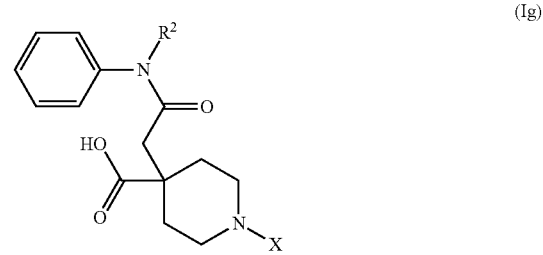

(Ig)

wherein:
R$^2$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{2a}$;
each R$^{2a}$ independently is halogen, C$_1$-C$_6$ alkyl, C$_1$-C$_6$ alkoxyl, or C$_3$-C$_6$ cycloalkyl;
X is C$_5$-C$_{10}$ heteroaryl, C$_6$-C$_{10}$ aryl,

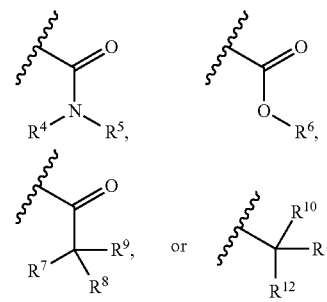

wherein the C$_5$-C$_{10}$ heteroaryl or C$_6$-C$_{10}$ aryl is optionally substituted with one or more X$^a$;
each X$^a$ independently is halogen, C$_1$-C$_6$ alkyl, C$_1$-C$_6$ alkoxyl, or C$_3$-C$_6$ cycloalkyl;
R$^4$ is H, C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{4a}$;
each R$^{4a}$ independently is halogen, cyano, C$_1$-C$_6$ alkyl, C$_1$-C$_6$ alkoxyl, or C$_3$-C$_6$ cycloalkyl;
R$^5$ is H, C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{5a}$;
each R$^{5a}$ independently is halogen, cyano, C$_1$-C$_6$ alkyl, C$_1$-C$_6$ alkoxyl, or C$_3$-C$_6$ cycloalkyl;
R$^6$ is H or C$_1$-C$_6$ alkyl;
R$^7$ is C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{7a}$;

each $R^{7a}$ independently is halogen, cyano, or $C_3$-$C_6$ cycloalkyl;

$R^8$ is H, halogen, or $C_1$-$C_6$ alkyl;

$R^9$ is H, halogen, or $C_1$-$C_6$ alkyl; or $R^8$ and $R^9$ together form a $C_3$-$C_6$ cycloalkyl;

$R^{10}$ and $R^{11}$ are each H or $R^{10}$ and $R^{11}$ together form an oxo;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

In another embodiment, the present disclosure provides a compound of formula (Ih),

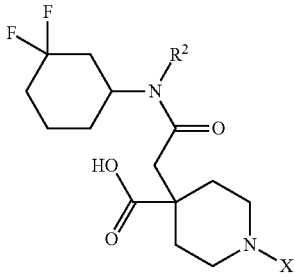

(Ih)

wherein:

$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;

each $R^{2a}$ independently is halogen, $C_1$-$C_6$ alkyl, $C_1$-$C_6$ alkoxyl, or $C_3$-$C_6$ cycloalkyl;

X is $C_5$-$C_{10}$ heteroaryl, $C_6$-$C_{10}$ aryl,

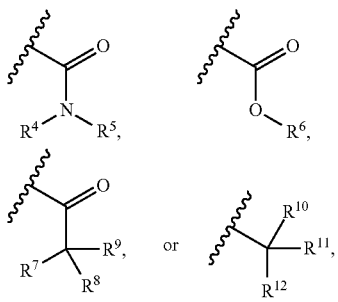

wherein the $C_5$-$C_{10}$ heteroaryl or $C_6$-$C_{10}$ aryl is optionally substituted with one or more $X^a$;

each $X^a$ independently is halogen, $C_1$-$C_6$ alkyl, $C_1$-$C_6$ alkoxyl, or $C_3$-$C_6$ cycloalkyl;

$R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;

each $R^{4a}$ independently is halogen, cyano, $C_1$-$C_6$ alkyl, $C_1$-$C_6$ alkoxyl, or $C_3$-$C_6$ cycloalkyl;

$R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;

each $R^{5a}$ independently is halogen, cyano, $C_1$-$C_6$ alkyl, $C_1$-$C_6$ alkoxyl, or $C_3$-$C_6$ cycloalkyl;

$R^6$ is H or $C_1$-$C_6$ alkyl;

$R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;

each $R^{7a}$ independently is halogen, cyano, or $C_3$-$C_6$ cycloalkyl;

$R^8$ is H, halogen, or $C_1$-$C_6$ alkyl;

$R^9$ is H, halogen, or $C_1$-$C_6$ alkyl; or $R^8$ and $R^9$ together form a $C_3$-$C_6$ cycloalkyl;

$R^{10}$ and $R^{11}$ are each H or $R^{10}$ and $R^{11}$ together form an oxo;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

In another embodiment, the present disclosure provides a compound of formula (Ih-a),

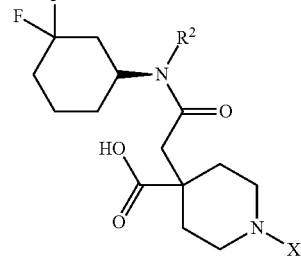

(Ih-a)

wherein:

$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;

each $R^{2a}$ independently is halogen, $C_1$-$C_6$ alkyl, $C_1$-$C_6$ alkoxyl, or $C_3$-$C_6$ cycloalkyl;

X is $C_5$-$C_{10}$ heteroaryl, $C_6$-$C_{10}$ aryl,

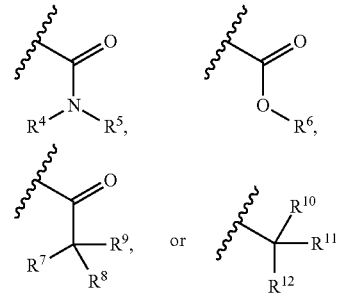

wherein the $C_5$-$C_{10}$ heteroaryl or $C_6$-$C_{10}$ aryl is optionally substituted with one or more $X^a$;

each $X^a$ independently is halogen, $C_1$-$C_6$ alkyl, $C_1$-$C_6$ alkoxyl, or $C_3$-$C_6$ cycloalkyl;

$R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;

each $R^{4a}$ independently is halogen, cyano, $C_1$-$C_6$ alkyl, $C_1$-$C_6$ alkoxyl, or $C_3$-$C_6$ cycloalkyl;

$R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;

each $R^{5a}$ independently is halogen, cyano, $C_1$-$C_6$ alkyl, $C_1$-$C_6$ alkoxyl, or $C_3$-$C_6$ cycloalkyl;

$R^6$ is H or $C_1$-$C_6$ alkyl;

$R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;

each $R^{7a}$ independently is halogen, cyano, or $C_3$-$C_6$ cycloalkyl;

$R^8$ is H, halogen, or $C_1$-$C_6$ alkyl;

$R^9$ is H, halogen, or $C_1$-$C_6$ alkyl; or $R^8$ and $R^9$ together form a $C_3$-$C_6$ cycloalkyl;

$R^{10}$ and $R^{11}$ are each H or $R^{10}$ and $R^{11}$ together form an oxo;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

In another embodiment, the present disclosure provides a compound of formula (Ih-b),

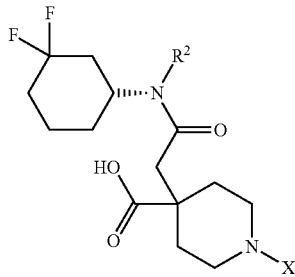

(Ih-b)

wherein:

$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;

each $R^{2a}$ independently is halogen, $C_1$-$C_6$ alkyl, $C_1$-$C_6$ alkoxyl, or $C_3$-$C_6$ cycloalkyl;

X is $C_5$-$C_{10}$ heteroaryl, $C_6$-$C_{10}$ aryl,

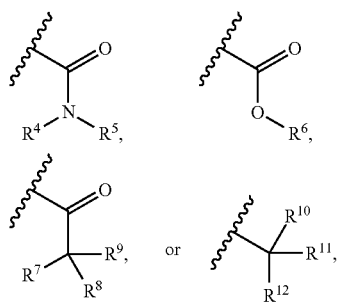

wherein the $C_5$-$C_{10}$ heteroaryl or $C_6$-$C_{10}$ aryl is optionally substituted with one or more $X^a$;

each $X^a$ independently is halogen, $C_1$-$C_6$ alkyl, $C_1$-$C_6$ alkoxyl, or $C_3$-$C_6$ cycloalkyl;

$R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;

each $R^{4a}$ independently is halogen, cyano, $C_1$-$C_6$ alkyl, $C_1$-$C_6$ alkoxyl, or $C_3$-$C_6$ cycloalkyl;

$R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;

each $R^{5a}$ independently is halogen, cyano, $C_1$-$C_6$ alkyl, $C_1$-$C_6$ alkoxyl, or $C_3$-$C_6$ cycloalkyl;

$R^6$ is H or $C_1$-$C_6$ alkyl;

$R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;

each $R^{7a}$ independently is halogen, cyano, or $C_3$-$C_6$ cycloalkyl;

$R^8$ is H, halogen, or $C_1$-$C_6$ alkyl;

$R^9$ is H, halogen, or $C_1$-$C_6$ alkyl; or $R^8$ and $R^9$ together form a $C_3$-$C_6$ cycloalkyl;

$R^{10}$ and $R^{11}$ are each H or $R^{10}$ and $R^{11}$ together form an oxo;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

In another embodiment, the present disclosure provides a compound of formula

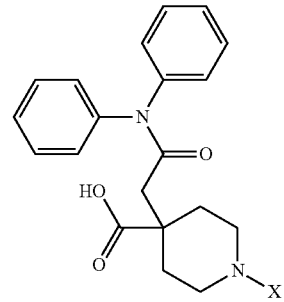

(Ii)

wherein:

X is $C_5$-$C_{10}$ heteroaryl, $C_6$-$C_{10}$ aryl,

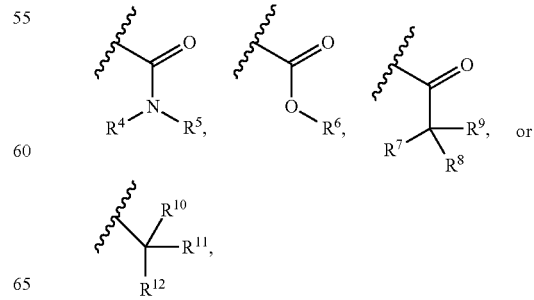

wherein the $C_5$-$C_{10}$ heteroaryl or $C_6$-$C_{10}$ aryl is optionally substituted with one or more $X^a$;
each $X^a$ independently is halogen, $C_1$-$C_6$ alkyl, $C_1$-$C_6$ alkoxyl, or $C_3$-$C_6$ cycloalkyl;
$R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;
each $R^{4a}$ independently is halogen, cyano, $C_1$-$C_6$ alkyl, $C_1$-$C_6$ alkoxyl, or $C_3$-$C_6$ cycloalkyl;
$R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;
each $R^{5a}$ independently is halogen, cyano, $C_1$-$C_6$ alkyl, $C_1$-$C_6$ alkoxyl, or $C_3$-$C_6$ cycloalkyl;
$R^6$ is H or $C_1$-$C_6$ alkyl;
$R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;
each $R^{7a}$ independently is halogen, cyano, or $C_3$-$C_6$ cycloalkyl;
$R^8$ is H, halogen, or $C_1$-$C_6$ alkyl;
$R^9$ is H, halogen, or $C_1$-$C_6$ alkyl; or
$R^8$ and $R^9$ together form a $C_3$-$C_6$ cycloalkyl;
$R^{10}$ and $R^{11}$ are each H or $R^{10}$ and $R^{11}$ together form an oxo;
$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and
each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

In another embodiment, the present disclosure provides a compound of formula (Ij),

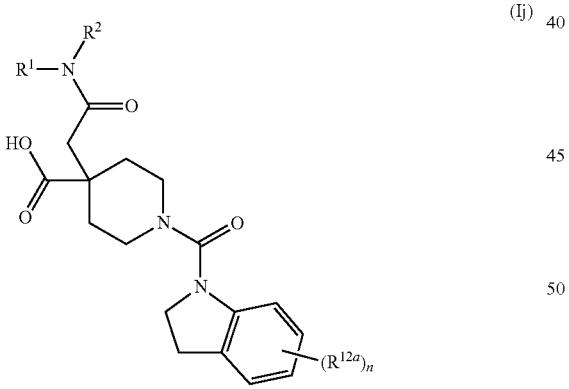

(Ij)

wherein:
n is 0, 1, or 2;
$R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;
each $R^{1a}$ independently is halogen, $C_1$-$C_6$ alkyl, $C_1$-$C_6$ alkoxyl, or $C_3$-$C_6$ cycloalkyl;
$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;
each $R^{2a}$ independently is halogen, $C_1$-$C_6$ alkyl, $C_1$-$C_6$ alkoxyl, or $C_3$-$C_6$ cycloalkyl; and
each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

In another embodiment, the present disclosure provides a compound of formula (Ik),

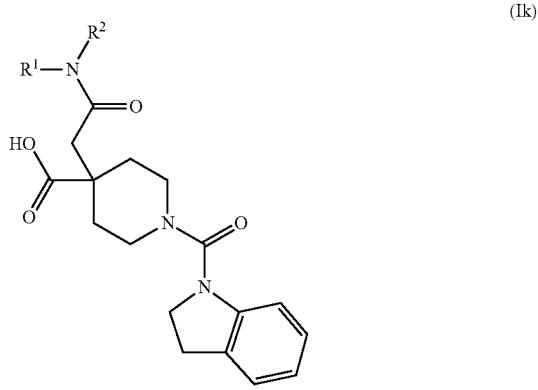

(Ik)

wherein:
$R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;
each $R^{1a}$ independently is halogen, $C_1$-$C_6$ alkyl, $C_1$-$C_6$ alkoxyl, or $C_3$-$C_6$ cycloalkyl;
$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$; and
each $R^{2a}$ independently is halogen, $C_1$-$C_6$ alkyl, $C_1$-$C_6$ alkoxyl, or $C_3$-$C_6$ cycloalkyl; or a pharmaceutically acceptable salt thereof.

In another embodiment, the present disclosure provides a compound of formula (Il),

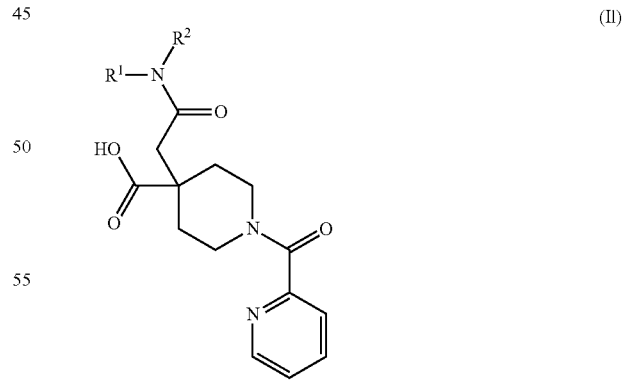

(Il)

wherein:
$R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;
each $R^{1a}$ independently is halogen, $C_1$-$C_6$ alkyl, $C_1$-$C_6$ alkoxyl, or $C_3$-$C_6$ cycloalkyl;

$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$; and each $R^{2a}$ independently is halogen, $C_1$-$C_6$ alkyl, $C_1$-$C_6$ alkoxyl, or $C_3$-$C_6$ cycloalkyl; or a pharmaceutically acceptable salt thereof.

In some embodiments, $R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$.

In some embodiments, $R^1$ is $C_1$-$C_6$ alkyl optionally substituted with one or more $R^{1a}$. In some embodiments, $R^1$ is $C_1$ alkyl optionally substituted with one or more $R^{1a}$. In some embodiments, $R^1$ is $C_2$ alkyl optionally substituted with one or more $R^{1a}$. In some embodiments, $R^1$ is $C_3$ alkyl optionally substituted with one or more $R^{1a}$. In some embodiments, $R^1$ is $C_4$ alkyl optionally substituted with one or more $R^{1a}$. In some embodiments, $R^1$ is $C_5$ alkyl optionally substituted with one or more $R^{1a}$. In some embodiments, $R^1$ is $C_6$ alkyl optionally substituted with one or more $R^{1a}$. In some embodiments, $R^1$ is methyl optionally substituted with one or more $R^{1a}$. In some embodiments, $R^1$ is ethyl optionally substituted with one or more $R^{1a}$. In some embodiments, $R^1$ is propyl optionally substituted with one or more $R^{1a}$. In some embodiments, $R^1$ is butyl optionally substituted with one or more $R^{1a}$. In some embodiments, $R^1$ is pentyl optionally substituted with one or more $R^{1a}$. In some embodiments, $R^1$ is hexyl optionally substituted with one or more $R^{1a}$.

In some embodiments, $R^1$ is $C_3$-$C_6$ cycloalkyl optionally substituted with one or more $R^{1a}$. In some embodiments, $R^1$ is $C_3$ cycloalkyl optionally substituted with one or more $R^{1a}$. In some embodiments, $R^1$ is $C_4$ cycloalkyl optionally substituted with one or more $R^{1a}$. In some embodiments, $R^1$ is $C_5$ cycloalkyl optionally substituted with one or more $R^{1a}$. In some embodiments, $R^1$ is $C_6$ cycloalkyl optionally substituted with one or more $R^{1a}$. In some embodiments, $R^1$ is cyclopropyl optionally substituted with one or more $R^{1a}$. In some embodiments, $R^1$ is cyclopentyl optionally substituted with one or more $R^{1a}$. In some embodiments, $R^1$ is cyclohexyl optionally substituted with one or more $R^{1a}$.

In some embodiments, $R^1$ is $C_3$-$C_9$ heterocycloalkyl optionally substituted with one or more $R^{1a}$. In some embodiments, $R^1$ is $C_3$ heterocycloalkyl optionally substituted with one or more $R^{1a}$. In some embodiments, $R^1$ is $C_4$ heterocycloalkyl optionally substituted with one or more $R^{1a}$. In some embodiments, $R^1$ is $C_5$ heterocycloalkyl optionally substituted with one or more $R^{1a}$. In some embodiments, $R^1$ is $C_6$ heterocycloalkyl optionally substituted with one or more $R^{1a}$. In some embodiments, $R^1$ is $C_7$ heterocycloalkyl optionally substituted with one or more $R^{1a}$. In some embodiments, $R^1$ is $C_8$ heterocycloalkyl optionally substituted with one or more $R^{1a}$. In some embodiments, $R^1$ is $C_9$ heterocycloalkyl optionally substituted with one or more $R^{1a}$. In some embodiments, $R^1$ is tetrahydropyranyl optionally substituted with one or more $R^{1a}$.

In some embodiments, $R^1$ is $C_6$-$C_{10}$ aryl optionally substituted with one or more $R^{1a}$. In some embodiments, $R^1$ is $C_6$ aryl optionally substituted with one or more $R^{1a}$. In some embodiments, $R^1$ is $C_7$ aryl optionally substituted with one or more $R^{1a}$. In some embodiments, $R^1$ is $C_8$ aryl optionally substituted with one or more $R^{1a}$. In some embodiments, $R^1$ is $C_9$ aryl optionally substituted with one or more $R^{1a}$. In some embodiments, $R^1$ is $C_{10}$ aryl optionally substituted with one or more $R^{1a}$. In some embodiments, $R^1$ is phenyl optionally substituted with one or more $R^{1a}$.

In some embodiments, $R^{1a}$ is halogen, $C_1$-$C_6$ alkyl, $C_1$-$C_6$ alkoxyl, or $C_3$-$C_6$ cycloalkyl.

In some embodiments, $R^{1a}$ is halogen. In some embodiments, $R^{1a}$ is fluorine. In some embodiments, $R^{1a}$ is chlorine. In some embodiments, $R^{1a}$ is bromine. In some embodiments, $R^{1a}$ is iodine.

In some embodiments, $R^{1a}$ is $C_1$-$C_6$ alkyl. In some embodiments, $R^{1a}$ is $C_1$ alkyl. In some embodiments, $R^{1a}$ is $C_2$ alkyl. In some embodiments, $R^{1a}$ is $C_3$ alkyl. In some embodiments, $R^{1a}$ is $C_4$ alkyl. In some embodiments, $R^{1a}$ is $C_5$ alkyl. In some embodiments, $R^{1a}$ is $C_6$ alkyl. In some embodiments, $R^{1a}$ is methyl. In some embodiments, $R^{1a}$ is ethyl. In some embodiments, $R^{1a}$ is propyl. In some embodiments, $R^{1a}$ is butyl. In some embodiments, $R^{1a}$ is pentyl. In some embodiments, $R^{1a}$ is hexyl.

In some embodiments, $R^{1a}$ is $C_1$-$C_6$ alkoxyl. In some embodiments, $R^{1a}$ is $C_1$ alkoxyl. In some embodiments, $R^{1a}$ is $C_2$ alkoxyl. In some embodiments, $R^{1a}$ is $C_3$ alkoxyl. In some embodiments, $R^{1a}$ is $C_4$ alkoxyl. In some embodiments, $R^{1a}$ is $C_5$ alkoxyl. In some embodiments, $R^{1a}$ is $C_6$ alkoxyl. In some embodiments, $R^{1a}$ is methoxyl.

In some embodiments, $R^{1a}$ is $C_3$-$C_6$ cycloalkyl. In some embodiments, $R^{1a}$ is $C_3$ cycloalkyl. In some embodiments, $R^{1a}$ is $C_4$ cycloalkyl. In some embodiments, $R^{1a}$ is $C_5$ cycloalkyl. In some embodiments, $R^{1a}$ is $C_6$ cycloalkyl. In some embodiments, Ra is cyclopropyl. It is understood that in some embodiments when $R^{1a}$ is a cycloalkyl, said cycloalkyl may be bonded to $R^1$ via a covalent bond or a ring-atom of said cycloalkyl may share an atom of $R^1$. In some embodiments, $R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$.

In some embodiments, $R^2$ is $C_1$-$C_6$ alkyl optionally substituted with one or more $R^{2a}$. In some embodiments, $R^2$ is $C_1$ alkyl optionally substituted with one or more $R^{2a}$. In some embodiments, $R^2$ is $C_2$ alkyl optionally substituted with one or more $R^{2a}$. In some embodiments, $R^2$ is $C_3$ alkyl optionally substituted with one or more $R^{2a}$. In some embodiments, $R^2$ is $C_4$ alkyl optionally substituted with one or more $R^{2a}$. In some embodiments, $R^2$ is $C_5$ alkyl optionally substituted with one or more $R^{2a}$. In some embodiments, $R^2$ is $C_6$ alkyl optionally substituted with one or more $R^{2a}$. In some embodiments, $R^2$ is methyl optionally substituted with one or more $R^{2a}$. In some embodiments, $R^2$ is ethyl optionally substituted with one or more $R^{2a}$. In some embodiments, $R^2$ is propyl optionally substituted with one or more $R^{2a}$. In some embodiments, $R^2$ is butyl optionally substituted with one or more $R^{2a}$. In some embodiments, $R^2$ is pentyl optionally substituted with one or more $R^{2a}$. In some embodiments, $R^2$ is hexyl optionally substituted with one or more $R^{2a}$.

In some embodiments, $R^2$ is $C_3$-$C_6$ cycloalkyl optionally substituted with one or more $R^{2a}$. In some embodiments, $R^2$ is $C_3$ cycloalkyl optionally substituted with one or more $R^{2a}$. In some embodiments, $R^2$ is $C_4$ cycloalkyl optionally substituted with one or more $R^{2a}$. In some embodiments, $R^2$ is $C_5$ cycloalkyl optionally substituted with one or more $R^{2a}$. In some embodiments, $R^2$ is $C_6$ cycloalkyl optionally substituted with one or more $R^{2a}$. In some embodiments, $R^2$ is cyclopropyl optionally substituted with one or more $R^{2a}$. In some embodiments, $R^2$ is cyclopentyl optionally substituted with one or more $R^{2a}$. In some embodiments, $R^2$ is cyclohexyl optionally substituted with one or more $R^{2a}$.

In some embodiments, $R^2$ is $C_3$-$C_9$ heterocycloalkyl optionally substituted with one or more $R^{2a}$. In some embodiments, $R^2$ is $C_3$ heterocycloalkyl optionally substituted with one or more $R^{2a}$. In some embodiments, $R^2$ is $C_4$ heterocycloalkyl optionally substituted with one or more $R^{2a}$. In some embodiments, $R^2$ is $C_5$ heterocycloalkyl optionally substituted with one or more $R^{2a}$. In some embodiments, $R^2$ is $C_6$ heterocycloalkyl optionally substituted with one or more $R^{2a}$. In some embodiments, $R^2$ is $C_7$ heterocycloalkyl optionally substituted with one or more $R^{2a}$. In some embodiments, $R^2$ is $C_8$ heterocycloalkyl optionally substituted with one or more $R^{2a}$. In some embodiments, $R^2$ is $C_9$ heterocycloalkyl optionally substituted with one or more $R^{2a}$. In some embodiments, $R^2$ is tetrahydropyranyl optionally substituted with one or more $R^{2a}$.

In some embodiments, $R^2$ is $C_6$-$C_{10}$ aryl optionally substituted with one or more $R^{2a}$. In some embodiments, $R^2$ is $C_6$ aryl optionally substituted with one or more $R^{2a}$. In some embodiments, $R^2$ is $C_7$ aryl optionally substituted with one or more $R^{2a}$. In some embodiments, $R^2$ is $C_8$ aryl optionally substituted with one or more $R^{2a}$. In some embodiments, $R^2$ is $C_9$ aryl optionally substituted with one or more $R^{2a}$. In some embodiments, $R^2$ is $C_{10}$ aryl optionally substituted with one or more $R^{2a}$. In some embodiments, $R^2$ is phenyl optionally substituted with one or more $R^{2a}$.

In some embodiments, $R^{2a}$ is halogen, $C_1$-$C_6$ alkyl, $C_1$-$C_6$ alkoxyl, or $C_3$-$C_6$ cycloalkyl.

In some embodiments, $R^{2a}$ is halogen. In some embodiments, $R^{2a}$ is fluorine. In some embodiments, $R^{2a}$ is chlorine. In some embodiments, $R^{2a}$ is bromine. In some embodiments, $R^{2a}$ is iodine.

In some embodiments, $R^{2a}$ is $C_1$-$C_6$ alkyl. In some embodiments, $R^{2a}$ is $C_1$ alkyl. In some embodiments, $R^{2a}$ is $C_2$ alkyl. In some embodiments, $R^{2a}$ is $C_3$ alkyl. In some embodiments, $R^{2a}$ is $C_4$ alkyl. In some embodiments, $R^{2a}$ is $C_5$ alkyl. In some embodiments, $R^{2a}$ is $C_6$ alkyl. In some embodiments, $R^{2a}$ is methyl. In some embodiments, $R^{2a}$ is ethyl. In some embodiments, $R^{2a}$ is propyl. In some embodiments, $R^{2a}$ is butyl. In some embodiments, $R^{2a}$ is pentyl. In some embodiments, $R^{2a}$ is hexyl.

In some embodiments, $R^{2a}$ is $C_1$-$C_6$ alkoxyl. In some embodiments, $R^{2a}$ is $C_1$ alkoxyl. In some embodiments, $R^{2a}$ is $C_2$ alkoxyl. In some embodiments, $R^{2a}$ is $C_3$ alkoxyl. In some embodiments, $R^{2a}$ is $C_4$ alkoxyl. In some embodiments, $R^{2a}$ is $C_5$ alkoxyl. In some embodiments, $R^{2a}$ is $C_6$ alkoxyl. In some embodiments, $R^{2a}$ is methoxyl.

In some embodiments, $R^{2a}$ is $C_3$-$C_6$ cycloalkyl. In some embodiments, $R^{2a}$ is $C_3$ cycloalkyl. In some embodiments, $R^{2a}$ is $C_4$ cycloalkyl. In some embodiments, $R^{2a}$ is $C_5$ cycloalkyl. In some embodiments, $R^{2a}$ is $C_6$ cycloalkyl. In some embodiments, $R^{2a}$ is cyclopropyl.

It is understood that in some embodiments when $R^{2a}$ is a cycloalkyl, said cycloalkyl may be bonded to $R^2$ via a covalent bond or a ring-atom of said cycloalkyl may share an atom of $R^2$.

In some embodiments, $R^3$ is H or $C_1$-$C_6$ alkyl. In some embodiments, $R^3$ is H. In some embodiments, $R^3$ is $C_1$-$C_6$ alkyl.

In some embodiments, X is $C_5$-$C_{10}$ heteroaryl, $C_6$-$C_{10}$ aryl,

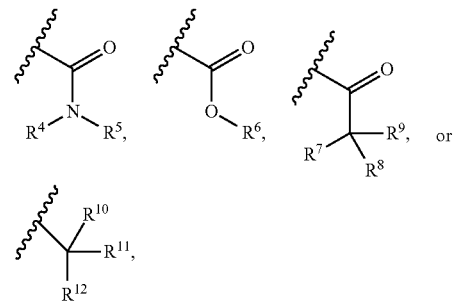

wherein the $C_5$-$C_{10}$ heteroaryl or $C_6$-$C_{10}$ aryl is optionally substituted with one or more $X^a$.

In some embodiments, X is $C_5$-$C_{10}$ heteroaryl or $C_6$-$C_{10}$ aryl, wherein the $C_5$-$C_{10}$ heteroaryl or $C_6$-$C_{10}$ aryl is optionally substituted with one or more $X^a$.

In some embodiments, X is $C_5$-$C_{10}$ heteroaryl optionally substituted with one or more $X^a$. In some embodiments, X is $C_5$ heteroaryl optionally substituted with one or more $X^a$. In some embodiments, X is $C_6$ heteroaryl optionally substituted with one or more $X^a$. In some embodiments, X is $C_7$ heteroaryl optionally substituted with one or more $X^a$. In some embodiments, X is $C_8$ heteroaryl optionally substituted with one or more $X^a$. In some embodiments, X is $C_9$ heteroaryl optionally substituted with one or more $X^a$. In some embodiments, X is $C_{10}$ heteroaryl optionally substituted with one or more $X^a$. In some embodiments, X is pyridyl, pyrimidyl, or 1,2,4-triazolyl, wherein the pyridyl, pyrimidyl, or 1,2,4-triazolyl is optionally substituted with one or more $X^a$. In some embodiments, X is pyridyl optionally substituted with one or more $X^a$. In some embodiments, X is pyrimidyl optionally substituted with one or more $X^a$. In some embodiments, X is triazolyl optionally substituted with one or more $X^a$. In some embodiments, X is 1,2,4-triazolyl optionally substituted with one or more $X^a$. In some embodiments, X is pyridyl.

In some embodiments, X is $C_6$-$C_{10}$ aryl optionally substituted with one or more $X^a$. In some embodiments, X is $C_6$ aryl optionally substituted with one or more $X^a$. In some embodiments, X is $C_7$ aryl optionally substituted with one or more $X^a$. In some embodiments, X is $C_8$ aryl optionally substituted with one or more $X^a$. In some embodiments, X is $C_9$ aryl optionally substituted with one or more $X^a$. In some embodiments, X is $C_{10}$ aryl optionally substituted with one or more $X^a$. In some embodiments, X is phenyl.

In some embodiments, $X^a$ is halogen, $C_1$-$C_6$ alkyl, $C_1$-$C_6$ alkoxyl, or $C_3$-$C_6$ cycloalkyl.

In some embodiments, $X^a$ is halogen. In some embodiments, $X^a$ is fluorine. In some embodiments, $X^a$ is chlorine. In some embodiments, $X^a$ is bromine. In some embodiments, $X^a$ is iodine.

In some embodiments, $X^a$ is $C_1$-$C_6$ alkyl. In some embodiments, $X^a$ is $C_1$ alkyl. In some embodiments, $X^a$ is $C_2$ alkyl. In some embodiments, $X^a$ is $C_3$ alkyl. In some embodiments, $X^a$ is $C_4$ alkyl. In some embodiments, $X^a$ is $C_5$ alkyl. In some embodiments, $X^a$ is $C_6$ alkyl. In some embodiments, $X^a$ is methyl. In some embodiments, $X^a$ is ethyl. In some embodiments, $X^a$ is propyl. In some embodiments, $X^a$ is butyl. In some embodiments, $X^a$ is pentyl. In some embodiments, $X^a$ is hexyl.

In some embodiments, $X^a$ is $C_1$-$C_6$ alkoxyl. In some embodiments, $X^a$ is $C_1$ alkoxyl. In some embodiments, $X^a$ is $C_2$ alkoxyl. In some embodiments, $X^a$ is $C_3$ alkoxyl. In some embodiments, $X^a$ is $C_4$ alkoxyl. In some embodiments, $X^a$ is $C_5$ alkoxyl. In some embodiments, $X^a$ is $C_6$ alkoxyl.

In some embodiments, $X^a$ is $C_3$-$C_6$ cycloalkyl. In some embodiments, $X^a$ is $C_3$ cycloalkyl. In some embodiments, $X^a$ is $C_4$ cycloalkyl. In some embodiments, $X^a$ is $C_5$ cycloalkyl. In some embodiments, $X^a$ is $C_6$ cycloalkyl. In some embodiments, $X^a$ is cyclopropyl.

In some embodiments, X is

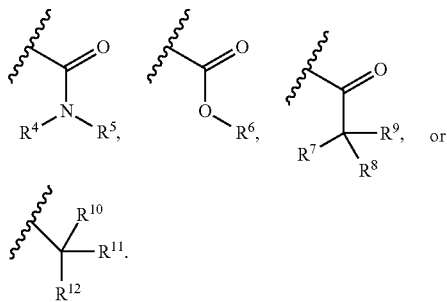

In some embodiments, X is

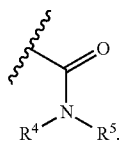

In some embodiments, X is

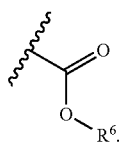

In some embodiments, X is

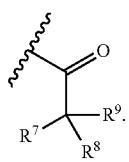

In some embodiments, X is

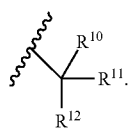

In some embodiments, $R^4$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$.

In some embodiments, $R^4$ is H.

In some embodiments, $R^4$ is $C_1$-$C_6$ alkyl optionally substituted with one or more $R^{4a}$. In some embodiments, $R^4$ is $C_1$ alkyl optionally substituted with one or more $R^{4a}$. In some embodiments, $R^4$ is $C_2$ alkyl optionally substituted with one or more $R^{4a}$. In some embodiments, $R^4$ is $C_3$ alkyl optionally substituted with one or more $R^{4a}$. In some embodiments, $R^4$ is $C_4$ alkyl optionally substituted with one or more $R^{4a}$. In some embodiments, $R^4$ is $C_5$ alkyl optionally substituted with one or more $R^{4a}$. In some embodiments, $R^4$ is $C_6$ alkyl optionally substituted with one or more $R^{4a}$. In some embodiments, $R^4$ is methyl. In some embodiments, $R^4$ is ethyl. In some embodiments, $R^4$ is propyl. In some embodiments, $R^4$ is butyl. In some embodiments, $R^4$ is pentyl. In some embodiments, $R^4$ is hexyl.

In some embodiments, $R^4$ is $C_3$-$C_6$ cycloalkyl optionally substituted with one or more $R^{4a}$. In some embodiments, $R^4$ is $C_3$ cycloalkyl optionally substituted with one or more $R^{4a}$. In some embodiments, $R^4$ is $C_4$ cycloalkyl optionally substituted with one or more $R^{4a}$. In some embodiments, $R^4$ is $C_5$ cycloalkyl optionally substituted with one or more $R^{4a}$. In some embodiments, $R^4$ is $C_6$ cycloalkyl optionally substituted with one or more $R^{4a}$. In some embodiments, $R^4$ is cyclopropyl optionally substituted with one or more $R^{4a}$. In some embodiments, $R^4$ is cyclobutyl optionally substituted with one or more $R^{4a}$. In some embodiments, $R^4$ is cyclopentyl optionally substituted with one or more $R^{4a}$. In some embodiments, $R^4$ is cyclohexyl optionally substituted with one or more $R^{4a}$.

In some embodiments, $R^4$ is $C_6$-$C_{10}$ aryl optionally substituted with one or more $R^{4a}$. In some embodiments, $R^4$ is $C_6$ aryl optionally substituted with one or more $R^{4a}$. In some embodiments, $R^4$ is $C_7$ aryl optionally substituted with one or more $R^{4a}$. In some embodiments, $R^4$ is $C_8$ aryl optionally substituted with one or more $R^{4a}$. In some embodiments, $R^4$ is $C_9$ aryl optionally substituted with one or more $R^{4a}$. In some embodiments, $R^4$ is $C_{10}$ aryl optionally substituted with one or more $R^{4a}$. In some embodiments, $R^4$ is phenyl optionally substituted with one or more $R^{4a}$.

In some embodiments, $R^{4a}$ is halogen, cyano, $C_1$-$C_6$ alkyl, $C_1$-$C_6$ alkoxyl, or $C_3$-$C_6$ cycloalkyl.

In some embodiments, $R^{4a}$ is halogen. In some embodiments, $R^{4a}$ is fluorine. In some embodiments, $R^{4a}$ is chlorine. In some embodiments, $R^{4a}$ is bromine. In some embodiments, $R^{4a}$ is iodine.

In some embodiments, $R^{4a}$ is cyano.

In some embodiments, $R^{4a}$ is $C_1$-$C_6$ alkyl. In some embodiments, $R^{4a}$ is $C_1$ alkyl. In some embodiments, $R^{4a}$ is $C_2$ alkyl. In some embodiments, $R^{4a}$ is $C_3$ alkyl. In some embodiments, $R^{4a}$ is $C_4$ alkyl. In some embodiments, $R^{4a}$ is $C_5$ alkyl. In some embodiments, $R^{4a}$ is $C_6$ alkyl. In some embodiments, $R^{4a}$ is methyl. In some embodiments, $R^{4a}$ is ethyl. In some embodiments, $R^{4a}$ is propyl. In some embodiments, $R^{4a}$ is butyl. In some embodiments, $R^{4a}$ is pentyl. In some embodiments, $R^{4a}$ is hexyl.

In some embodiments, $R^{4a}$ is $C_1$-$C_6$ alkoxyl. In some embodiments, $R^{4a}$ is $C_1$ alkoxyl. In some embodiments, $R^{4a}$ is $C_2$ alkoxyl. In some embodiments, $R^{4a}$ is $C_3$ alkoxyl. In some embodiments, $R^{4a}$ is $C_4$ alkoxyl. In some embodiments, $R^{4a}$ is $C_5$ alkoxyl. In some embodiments, $R^{4a}$ is $C_6$ alkoxyl. In some embodiments, $R^{4a}$ is methoxyl.

In some embodiments, $R^{4a}$ is ethoxyl. In some embodiments, $R^{4a}$ is propoxyl. In some embodiments, $R^{4a}$ is butoxyl. In some embodiments, $R^{4a}$ is pentoxyl. In some embodiments, $R^{4a}$ is hexoxyl.

In some embodiments, $R^{4a}$ is $C_3$-$C_6$ cycloalkyl. In some embodiments, $R^{4a}$ is $C_3$ cycloalkyl. In some embodiments, $R^{4a}$ is $C_4$ cycloalkyl. In some embodiments, $R^{4a}$ is $C_5$ cycloalkyl. In some embodiments, $R^{4a}$ is $C_6$ cycloalkyl. In some embodiments, $R^{4a}$ is cyclopropyl. In some embodiments, $R^{4a}$ is cyclobutyl. In some embodiments, $R^{4a}$ is cyclopentyl. In some embodiments, $R^{4a}$ is cyclohexyl.

In some embodiments, $R^5$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$.

In some embodiments, $R^5$ is H.

In some embodiments, $R^5$ is $C_1$-$C_6$ alkyl optionally substituted with one or more $R^{5a}$. In some embodiments, $R^5$ is $C_1$ alkyl optionally substituted with one or more $R^{5a}$. In some embodiments, $R^5$ is $C_2$ alkyl optionally substituted with one or more $R^{5a}$. In some embodiments, $R^5$ is $C_3$ alkyl optionally substituted with one or more $R^{5a}$. In some embodiments, $R^5$ is $C_4$ alkyl optionally substituted with one or more $R^{5a}$. In some embodiments, $R^5$ is $C_5$ alkyl optionally substituted with one or more $R^{5a}$. In some embodiments, $R^5$ is $C_6$ alkyl optionally substituted with one or more $R^{5a}$. In some embodiments, $R^5$ is methyl. In some embodiments, $R^5$ is ethyl. In some embodiments, $R^5$ is propyl. In some embodiments, $R^5$ is butyl. In some embodiments, $R^5$ is pentyl. In some embodiments, $R^5$ is hexyl.

In some embodiments, $R^5$ is $C_3$-$C_6$ cycloalkyl optionally substituted with one or more $R^{5a}$. In some embodiments, $R^5$ is $C_3$ cycloalkyl optionally substituted with one or more $R^{5a}$. In some embodiments, $R^5$ is $C_4$ cycloalkyl optionally substituted with one or more $R^{5a}$. In some embodiments, $R^5$ is $C_5$ cycloalkyl optionally substituted with one or more $R^{5a}$. In some embodiments, $R^5$ is $C_6$ cycloalkyl optionally substituted with one or more $R^{5a}$. In some embodiments, $R^5$ is cyclopropyl optionally substituted with one or more $R^{5a}$. In some embodiments, $R^5$ is cyclobutyl optionally substituted with one or more $R^{5a}$. In some embodiments, $R^5$ is cyclopentyl optionally substituted with one or more $R^{5a}$. In some embodiments, $R^5$ is cyclohexyl optionally substituted with one or more $R^{5a}$.

In some embodiments, $R^5$ is $C_6$-$C_{10}$ aryl optionally substituted with one or more $R^{5a}$. In some embodiments, $R^5$ is $C_6$ aryl optionally substituted with one or more $R^{5a}$. In some embodiments, $R^5$ is $C_7$ aryl optionally substituted with one or more $R^{5a}$. In some embodiments, $R^5$ is $C_8$ aryl optionally substituted with one or more $R^{5a}$. In some embodiments, $R^5$ is $C_9$ aryl optionally substituted with one or more $R^{5a}$. In some embodiments, $R^5$ is $C_{10}$ aryl optionally substituted with one or more $R^{5a}$. In some embodiments, $R^5$ is phenyl optionally substituted with one or more $R^{5a}$.

In some embodiments, $R^5$, is halogen, cyano, $C_1$-$C_6$ alkyl, $C_1$-$C_6$ alkoxyl, or $C_3$-$C_6$ cycloalkyl.

In some embodiments, $R^5$, is halogen. In some embodiments, $R^5$, is fluorine. In some embodiments, $R^5$, is chlorine. In some embodiments, $R^5$, is bromine. In some embodiments, $R^5$, is iodine.

In some embodiments, $R^5$, is cyano.

In some embodiments, $R^5$, is $C_1$-$C_6$ alkyl. In some embodiments, $R^5$, is $C_1$ alkyl. In some embodiments, $R^5$, is $C_2$ alkyl. In some embodiments, $R^5$, is $C_3$ alkyl. In some embodiments, $R^5$, is $C_4$ alkyl. In some embodiments, $R^5$, is $C_5$ alkyl. In some embodiments, $R^5$, is $C_6$ alkyl. In some embodiments, $R^5$, is methyl. In some embodiments, $R^5$, is ethyl. In some embodiments, $R^5$, is propyl. In some embodiments, $R^{5a}$ is butyl. In some embodiments, $R^{5a}$ is pentyl. In some embodiments, $R^{5a}$ is hexyl.

In some embodiments, $R^5$, is $C_1$-$C_6$ alkoxyl. In some embodiments, $R^5$, is $C_1$ alkoxyl. In some embodiments, $R^5$, is $C_2$ alkoxyl. In some embodiments, $R^5$, is $C_3$ alkoxyl. In some embodiments, $R^5$, is $C_4$ alkoxyl. In some embodiments, $R^5$, is $C_5$ alkoxyl. In some embodiments, $R^5$, is $C_6$ alkoxyl. In some embodiments, $R^5$, is methoxyl. In some embodiments, $R^5$, is ethoxyl. In some embodiments, $R^5$, is propoxyl. In some embodiments, $R^5$, is butoxyl. In some embodiments, $R^5$, is pentoxyl. In some embodiments, $R^5$, is hexoxyl.

In some embodiments, $R^5$, is $C_3$-$C_6$ cycloalkyl. In some embodiments, $R^5$, is $C_3$ cycloalkyl. In some embodiments, $R^5$, is $C_4$ cycloalkyl. In some embodiments, $R^5$, is $C_5$ cycloalkyl. In some embodiments, $R^5$, is $C_6$ cycloalkyl. In some embodiments, $R^{5a}$ is cyclopropyl. In some embodiments, $R^5$, is cyclobutyl. In some embodiments, $R^5$, is cyclopentyl. In some embodiments, $R^5$, is cyclohexyl.

In some embodiments, $R^6$ is H or $C_1$-$C_6$ alkyl. In some embodiments, $R^6$ is H. In some embodiments, $R^6$ is $C_1$-$C_6$ alkyl. In some embodiments, $R^6$ is $C_1$ alkyl. In some embodiments, $R^6$ is $C_2$ alkyl. In some embodiments, $R^6$ is $C_3$ alkyl. In some embodiments, $R^6$ is $C_4$ alkyl. In some embodiments, $R^6$ is $C_5$ alkyl. In some embodiments, $R^6$ is $C_6$ alkyl. In some embodiments, $R^6$ is tert-butyl.

In some embodiments, $R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$.

In some embodiments, $R^7$ is $C_1$-$C_6$ alkyl optionally substituted with one or more $R^{7a}$. In some embodiments, $R^7$ is $C_1$ alkyl optionally substituted with one or more $R^{7a}$. In some embodiments, $R^7$ is $C_2$ alkyl optionally substituted with one or more $R^{7a}$. In some embodiments, $R^7$ is $C_3$ alkyl optionally substituted with one or more $R^{7a}$. In some embodiments, $R^7$ is $C_4$ alkyl optionally substituted with one or more $R^{7a}$. In some embodiments, $R^7$ is $C_5$ alkyl optionally substituted with one or more $R^{7a}$. In some embodiments, $R^7$ is $C_6$ alkyl optionally substituted with one or more $R^{7a}$. In some embodiments, $R^7$ is methyl. In some embodiments, $R^7$ is ethyl. In some embodiments, $R^7$ is propyl. In some embodiments, $R^7$ is butyl. In some embodiments, $R^7$ is pentyl. In some embodiments, $R^7$ is hexyl.

In some embodiments, $R^7$ is $C_3$-$C_6$ cycloalkyl optionally substituted with one or more $R^{7a}$. In some embodiments, $R^7$ is $C_3$ cycloalkyl optionally substituted with one or more $R^{7a}$. In some embodiments, $R^7$ is $C_4$ cycloalkyl optionally substituted with one or more $R^{7a}$. In some embodiments, $R^7$ is $C_5$ cycloalkyl optionally substituted with one or more $R^{7a}$. In some embodiments, $R^7$ is $C_6$ cycloalkyl optionally substituted with one or more $R^{7a}$. In some embodiments, $R^7$ is cyclopropyl optionally substituted with one or more $R^{7a}$. In some embodiments, $R^7$ is cyclobutyl optionally substituted with one or more $R^{7a}$. In some embodiments, $R^7$ is cyclopentyl optionally substituted with one or more $R^{7a}$. In some embodiments, $R^7$ is cyclohexyl optionally substituted with one or more $R^{7a}$.

In some embodiments, $R^7$ is $C_6$-$C_{10}$ aryl optionally substituted with one or more $R^{7a}$. In some embodiments, $R^7$ is $C_6$ aryl optionally substituted with one or more $R^{7a}$. In some embodiments, $R^7$ is $C_7$ aryl optionally substituted with one or more $R^{7a}$. In some embodiments, $R^7$ is $C_8$ aryl optionally substituted with one or more $R^{7a}$. In some embodiments, $R^7$ is $C_9$ aryl optionally substituted with one or more $R^{7a}$. In some embodiments, $R^7$ is $C_{10}$ aryl optionally substituted with one or more $R^{7a}$. In some embodiments, $R^7$ is phenyl optionally substituted with one or more $R^{7a}$.

In some embodiments, $R^7$, is halogen, cyano, $C_1$-$C_6$ alkyl, $C_1$-$C_6$ alkoxyl, or $C_3$-$C_6$ cycloalkyl.

In some embodiments, $R^7$, is halogen. In some embodiments, $R^{7a}$ is fluorine. In some embodiments, $R^7$, is chlorine. In some embodiments, $R^{7a}$ is bromine. In some embodiments, $R^{7a}$ is iodine.

In some embodiments, $R^{7a}$ is cyano.

In some embodiments, $R^{7a}$ is $C_1$-$C_6$ alkyl. In some embodiments, $R^{7a}$ is $C_1$ alkyl. In some embodiments, $R^{7a}$ is $C_2$ alkyl. In some embodiments, $R^{7a}$ is $C_3$ alkyl. In some embodiments, $R^{7a}$ is $C_4$ alkyl. In some embodiments, $R^{7a}$ is $C_5$ alkyl. In some embodiments, $R^{7a}$ is $C_6$ alkyl. In some embodiments, $R^{7a}$ is methyl. In some embodiments, $R^7$, is ethyl. In some embodiments, $R^{7a}$ is propyl. In some embodiments, $R^{7a}$ is butyl. In some embodiments, $R^{7a}$ is pentyl. In some embodiments, $R^7$, is hexyl.

In some embodiments, $R^{7a}$ is $C_1$-$C_6$ alkoxyl. In some embodiments, $R^{7a}$ is $C_1$ alkoxyl. In some embodiments, $R^{7a}$ is $C_2$ alkoxyl. In some embodiments, $R^{7a}$ is $C_3$ alkoxyl. In some embodiments, $R^{7a}$ is $C_4$ alkoxyl. In some embodiments, $R^{7a}$ is $C_5$ alkoxyl. In some embodiments, $R^{7a}$ is $C_6$ alkoxyl. In some embodiments, $R^{7a}$ is methoxyl. In some embodiments, $R^{7a}$ is ethoxyl. In some embodiments, $R^{7a}$ is propoxyl. In some embodiments, $R^{7a}$ is butoxyl. In some embodiments, $R^{7a}$ is pentoxyl. In some embodiments, $R^{7a}$ is hexoxyl.

In some embodiments, $R^{7a}$ is $C_3$-$C_6$ cycloalkyl. In some embodiments, $R^{7a}$ is $C_3$ cycloalkyl. In some embodiments, $R^{7a}$ is $C_4$ cycloalkyl. In some embodiments, $R^{7a}$ is $C_5$ cycloalkyl. In some embodiments, $R^{7a}$ is $C_6$ cycloalkyl. In some embodiments, $R^{7a}$ is cyclopropyl. In some embodiments, $R^{7a}$ is cyclobutyl. In some embodiments, $R^{7a}$ is cyclopentyl. In some embodiments, $R^{7a}$ is cyclohexyl.

In some embodiments, $R^8$ is H or $C_1$-$C_6$ alkyl. In some embodiments, $R^8$ is H. In some embodiments, $R^8$ is halogen. In some embodiments, $R^8$ is F. In some embodiments, $R^8$ is $C_1$-$C_6$ alkyl. In some embodiments, $R^8$ is $C_1$ alkyl. In some embodiments, $R^8$ is $C_2$ alkyl. In some embodiments, $R^8$ is $C_3$ alkyl. In some embodiments, $R^8$ is $C_4$ alkyl. In some embodiments, $R^8$ is $C_5$ alkyl. In some embodiments, $R^8$ is $C_6$ alkyl. In some embodiments, $R^8$ is methyl. In some embodiments, $R^8$ is ethyl. In some embodiments, $R^8$ is propyl. In some embodiments, $R^8$ is butyl. In some embodiments, $R^8$ is pentyl. In some embodiments, $R^8$ is hexyl.

In some embodiments, $R^9$ is H or $C_1$-$C_6$ alkyl. In some embodiments, $R^9$ is H. In some embodiments, $R^9$ is halogen. In some embodiments, $R^9$ is F. In some embodiments, $R^9$ is $C_1$-$C_6$ alkyl. In some embodiments, $R^9$ is $C_1$ alkyl. In some embodiments, $R^9$ is $C_2$ alkyl. In some embodiments, $R^9$ is $C_3$ alkyl. In some embodiments, $R^9$ is $C_4$ alkyl. In some embodiments, $R^9$ is $C_5$ alkyl. In some embodiments, $R^9$ is $C_6$ alkyl. In some embodiments, $R^9$ is methyl. In some embodiments, $R^9$ is ethyl. In some embodiments, $R^9$ is propyl. In some embodiments, $R^9$ is butyl. In some embodiments, $R^9$ is pentyl. In some embodiments, $R^9$ is hexyl.

In some embodiments, $R^8$ and $R^9$ come together to form a $C_3$-$C_6$ cycloalkyl. In some embodiments, $R^8$ and $R^9$ come together to form a $C_3$. In some embodiments, $R^8$ and $R^9$ come together to form a $C_4$. In some embodiments, $R^8$ and $R^9$ come together to form a $C_5$. In some embodiments, $R^8$ and $R^9$ come together to form a $C_6$. In some embodiments, $R^8$ and $R^9$ come together to form a cyclopropyl.

In some embodiments, $R^{10}$ and $R^{11}$ are each H or $R^{10}$ and $R^{11}$ together form an oxo. In some embodiments, $R^{10}$ and $R^{11}$ are each H. In some embodiments, $R^{10}$ and $R^{11}$ together form an oxo.

In some embodiments, $R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$.

In some embodiments, $R^{12}$ is $C_1$-$C_6$ alkyl optionally substituted with one or more $R^{12a}$. In some embodiments, $R^{12}$ is $C_1$ alkyl optionally substituted with one or more $R^{12a}$. In some embodiments, $R^{12}$ is $C_2$ alkyl optionally substituted with one or more $R^{12a}$. In some embodiments, $R^{12}$ is $C_3$ alkyl optionally substituted with one or more $R^{12a}$. In some embodiments, $R^{12}$ is $C_4$ alkyl optionally substituted with one or more $R^{12a}$. In some embodiments, $R^{12}$ is $C_5$ alkyl optionally substituted with one or more $R^{12a}$. In some embodiments, $R^{12}$ is $C_6$ alkyl optionally substituted with one or more $R^{12a}$. In some embodiments, $R^{12}$ is methyl. In some embodiments, $R^{12}$ is ethyl. In some embodiments, $R^{12}$ is propyl. In some embodiments, $R^{12}$ is butyl. In some embodiments, $R^{12}$ is pentyl. In some embodiments, $R^{12}$ is hexyl.

In some embodiments, $R^{12}$ is $C_3$-$C_6$ cycloalkyl optionally substituted with one or more $R^{12a}$. In some embodiments, $R^{12}$ is $C_3$ cycloalkyl optionally substituted with one or more $R^{12a}$. In some embodiments, $R^{12}$ is $C_4$ cycloalkyl optionally substituted with one or more $R^{12a}$. In some embodiments, $R^{12}$ is $C_5$ cycloalkyl optionally substituted with one or more $R^{12a}$. In some embodiments, $R^{12}$ is $C_6$ cycloalkyl optionally substituted with one or more $R^{12a}$. In some embodiments, $R^{12}$ is cyclopropyl optionally substituted with one or more $R^{12a}$. In some embodiments, $R^{12}$ is cyclobutyl optionally substituted with one or more $R^{12a}$. In some embodiments, $R^{12}$ is cyclopentyl optionally substituted with one or more $R^{12a}$. In some embodiments, $R^{12}$ is cyclohexyl optionally substituted with one or more $R^{12a}$.

In some embodiments, $R^{12}$ is $C_6$-$C_{10}$ aryl optionally substituted with one or more $R^{12a}$. In some embodiments, $R^{12}$ is $C_6$ aryl optionally substituted with one or more $R^{12a}$. In some embodiments, $R^{12}$ is $C_7$ aryl optionally substituted with one or more $R^{12a}$. In some embodiments, $R^{12}$ is $C_8$ aryl optionally substituted with one or more $R^{12a}$. In some embodiments, $R^{12}$ is $C_9$ aryl optionally substituted with one or more $R^{12a}$. In some embodiments, $R^{12}$ is $C_{10}$ aryl optionally substituted with one or more $R^{12a}$. In some embodiments, $R^{12}$ is phenyl optionally substituted with one or more $R^{12a}$.

In some embodiments, $R^{12}$ is $C_1$-$C_3$-(phenyl). In some embodiments, $R^{12}$ is $C_1$-(phenyl). In some embodiments, $R^{12}$ is $C_2$-(phenyl). In some embodiments, $R^{12}$ is $C_3$-(phenyl). In some embodiments, $R^{12}$ is isopropyl-phenyl.

In some embodiments, $R^{12}$ is $C_3$-$C_{10}$ heterocycloalkyl optionally substituted with one or more $R^{12a}$. In some embodiments, $R^{12}$ is $C_3$ heterocycloalkyl optionally substituted with one or more $R^{12a}$. In some embodiments, $R^{12}$ is $C_4$ heterocycloalkyl optionally substituted with one or more $R^{12a}$. In some embodiments, $R^{12}$ is $C_5$ heterocycloalkyl optionally substituted with one or more $R^{12a}$. In some embodiments, $R^{12}$ is $C_6$ heterocycloalkyl optionally substituted with one or more $R^{12a}$. In some embodiments, $R^{12}$ is $C_7$ heterocycloalkyl optionally substituted with one or more $R^{12a}$. In some embodiments, $R^{12}$ is $C_8$ heterocycloalkyl optionally substituted with one or more $R^{12a}$. In some embodiments, $R^{12}$ is $C_9$ heterocycloalkyl optionally substituted with one or more $R^{12a}$. In some embodiments, $R^{12}$ is $C_{10}$ heterocycloalkyl optionally substituted with one or more $R^{12a}$. In some embodiments, $R^{12}$ is cyclopropyl optionally substituted with one or more $R^{12a}$. In some embodiments, $R^{12}$ is indolinyl optionally substituted with one or more $R^{12a}$. In some embodiments, $R^{12}$ is tetrahydroquinolinyl optionally substituted with one or more $R^{12a}$.

In some embodiments, $R^{12a}$ is halogen, cyano, $C_1$-$C_6$ alkyl, $C_1$-$C_6$ alkoxyl, or $C_3$-$C_6$ cycloalkyl.

In some embodiments, $R^{12a}$ is halogen. In some embodiments, $R^{12a}$ is fluorine. In some embodiments, $R^{12a}$ is chlorine. In some embodiments, $R^{12a}$ is bromine. In some embodiments, $R^{12a}$ is iodine.

In some embodiments, $R^{12a}$ is cyano.

In some embodiments, $R^{12a}$ is $C_1$-$C_6$ alkyl. In some embodiments, $R^{12a}$ is $C_1$ alkyl. In some embodiments, $R^{12a}$ is $C_2$ alkyl. In some embodiments, $R^{12a}$ is $C_3$ alkyl. In some embodiments, $R^{12a}$ is $C_4$ alkyl. In some embodiments, $R^{12a}$ is $C_5$ alkyl. In some embodiments, $R^{12a}$ is $C_6$ alkyl. In some embodiments, $R^{12a}$ is methyl. In some embodiments, $R^{12a}$ is ethyl. In some embodiments, $R^{12a}$ is propyl. In some embodiments, $R^{12a}$ is butyl. In some embodiments, $R^{12a}$ is pentyl. In some embodiments, $R^{12a}$ is hexyl.

In some embodiments, $R^{12a}$ is $C_1$-$C_6$ alkoxyl. In some embodiments, $R^{12a}$ is $C_1$ alkoxyl. In some embodiments, $R^{12a}$ is $C_2$ alkoxyl. In some embodiments, $R^{12a}$ is $C_3$ alkoxyl. In some embodiments, $R^{12a}$ is $C_4$ alkoxyl. In some embodiments, $R^{12a}$ is $C_5$ alkoxyl. In some embodiments, $R^{12a}$ is $C_6$ alkoxyl. In some embodiments, $R^{12'}$ is methoxyl. In some embodiments, $R^{12a}$ is ethoxyl. In some embodiments, $R^{12'}$ is propoxyl. In some embodiments, $R^{12a}$ is butoxyl. In some embodiments, $R^{12'}$ is pentoxyl. In some embodiments, $R^{12a}$ is hexoxyl.

In some embodiments, $R^{12a}$ is $C_3$-$C_6$ cycloalkyl. In some embodiments, $R^{12a}$ is $C_3$ cycloalkyl. In some embodiments, $R^{12a}$ is $C_4$ cycloalkyl. In some embodiments, $R^{12a}$ is $C_5$ cycloalkyl. In some embodiments, $R^{12a}$ is $C_6$ cycloalkyl. In some embodiments, $R^{12a}$ is cyclopropyl. In some embodiments, $R^{12a}$ is cyclobutyl. In some embodiments, $R^{12a}$ is cyclopentyl. In some embodiments, $R^{12a}$ is cyclohexyl.

In some embodiments, n is 0, 1, or 2. In some embodiments, n is 0. In some embodiments, n is 1. In some embodiments, n is 2.

In some embodiments, $R^1$ is phenyl and $R^2$ is phenyl.

In some embodiments, X is

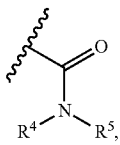

$R^4$ is phenyl, and $R^5$ is methyl.

In some embodiments, X is

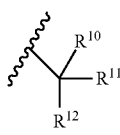

and $R^{10}$ and $R^{11}$ together form an oxo.

In some embodiments, wherein X is

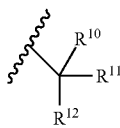

and $R^{12}$ is

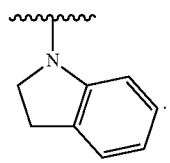

In some embodiments, X is

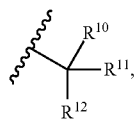

$R^{10}$ and $R^{11}$ together form an oxo, and $R^{12}$ is

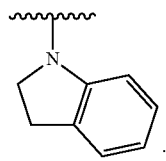 [SMILES: *N1CCc2ccccc21]

In some embodiments, at least one of $R^1$ and $R^2$ are

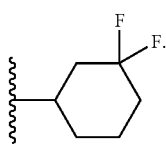

The present disclosure provides a compound which is

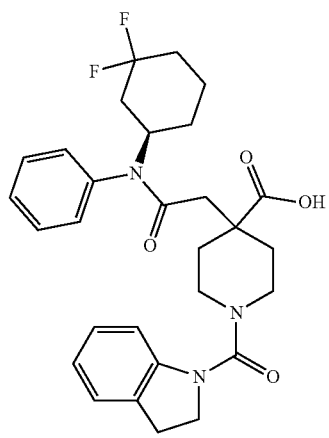 [SMILES: O=C(N1CCC(CC(=O)N(c2ccccc2)[C@@H]2CCCC(F)(F)C2)(C(=O)O)CC1)N1CCc2ccccc21]

or a pharmaceutically acceptable salt thereof.

The present disclosure provides a compound which is

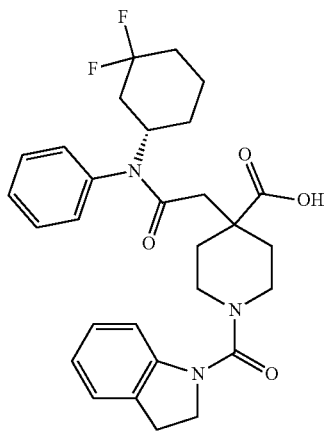 [SMILES: O=C(N1CCC(CC(=O)N(c2ccccc2)[C@H]2CCCC(F)(F)C2)(C(=O)O)CC1)N1CCc2ccccc21]

or a pharmaceutically acceptable salt thereof.

The present disclosure provides a compound which is

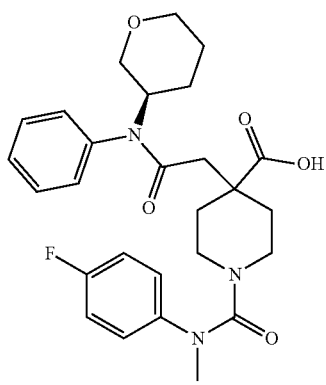 [SMILES: CN(C(=O)N1CCC(CC(=O)N(c2ccccc2)[C@@H]2CCCOC2)(C(=O)O)CC1)c1ccc(F)cc1]

or a pharmaceutically acceptable salt thereof.

The present disclosure provides a compound which is

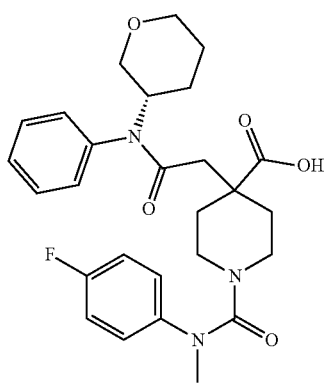 [SMILES: CN(C(=O)N1CCC(CC(=O)N(c2ccccc2)[C@H]2CCCOC2)(C(=O)O)CC1)c1ccc(F)cc1]

or a pharmaceutically acceptable salt thereof.

The present disclosure provides a compound which is

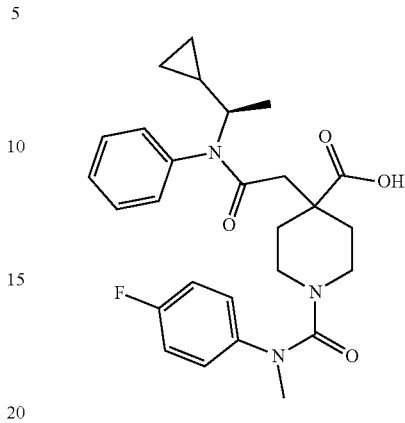

or a pharmaceutically acceptable salt thereof.

The present disclosure provides a compound which is

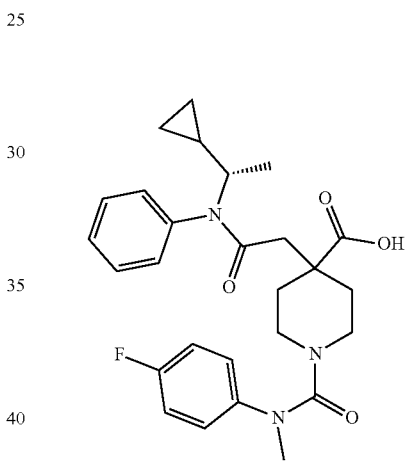

or a pharmaceutically acceptable salt thereof.

The present disclosure provides a compound which is

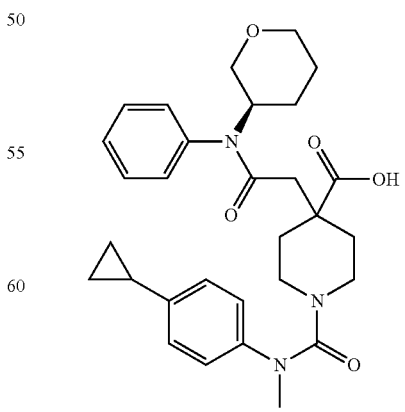

or a pharmaceutically acceptable salt thereof.

The present disclosure provides a compound which is

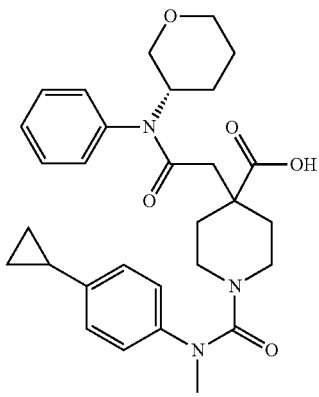 [SMILES: CN(C(=O)N1CCC(CC(=O)N(c2ccccc2)[C@H]2CCCOC2)(C(=O)O)CC1)c1ccc(C2CC2)cc1]

or a pharmaceutically acceptable salt thereof.

The present disclosure provides a compound which is

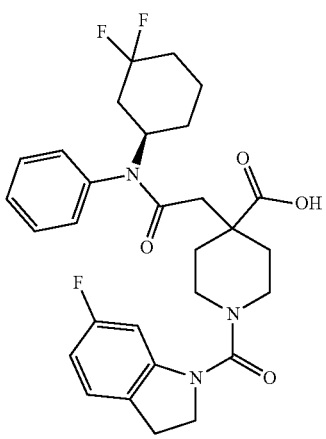 [SMILES: O=C(N1CCC(CC(=O)N(c2ccccc2)[C@@H]2CCCC(F)(F)C2)(C(=O)O)CC1)N1CCc2ccc(F)cc21]

or a pharmaceutically acceptable salt thereof.

The present disclosure provides a compound which is

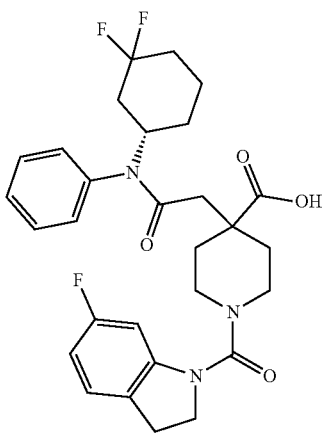 [SMILES: O=C(N1CCC(CC(=O)N(c2ccccc2)[C@H]2CCCC(F)(F)C2)(C(=O)O)CC1)N1CCc2ccc(F)cc21]

or a pharmaceutically acceptable salt thereof.

The present disclosure provides a compound which is

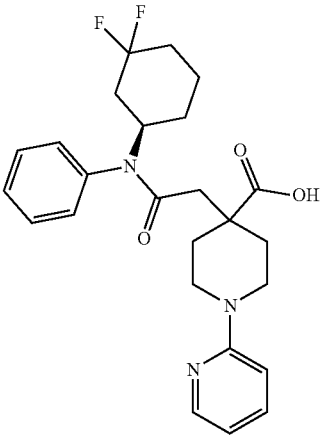 [SMILES: O=C(CC1(C(=O)O)CCN(c2ccccn2)CC1)N(c1ccccc1)[C@@H]1CCCC(F)(F)C1]

or a pharmaceutically acceptable salt thereof.

The present disclosure provides a compound which is

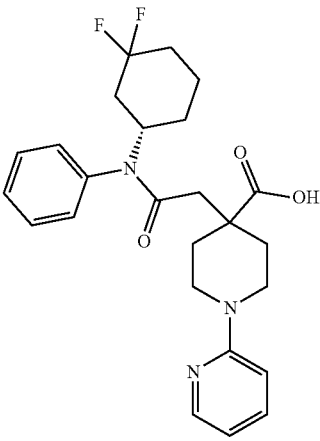 [SMILES: O=C(CC1(C(=O)O)CCN(c2ccccn2)CC1)N(c1ccccc1)[C@H]1CCCC(F)(F)C1]

or a pharmaceutically acceptable salt thereof.

In some embodiments, the compound is selected from the compounds described in Table I and pharmaceutically acceptable salts and stereoisomers thereof.

In some embodiments, the compound is selected from the compounds described in Table I and pharmaceutically acceptable salts thereof.

In some embodiments, the compound is selected from the compounds described in Table I.

TABLE I

| Example No. | Structure | Name | ES/MS (m/z) (M + H) |
|---|---|---|---|
| 1 | 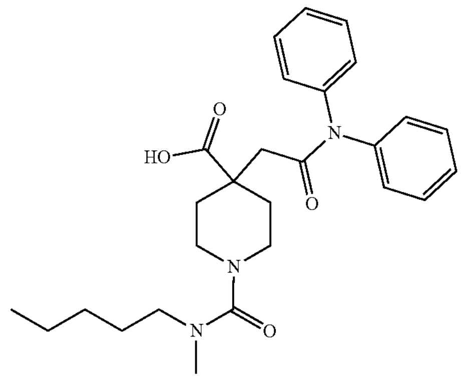 [SMILES: CCCCCN(C)C(=O)N1CCC(CC(=O)N(c2ccccc2)c2ccccc2)(C(=O)O)CC1] | 1-[methyl(pentyl)carbamoyl]-4-[2-oxo-2-(N-phenylanilino)ethyl]piperidine-4-carboxylic acid | 466.5 |
| 2 | 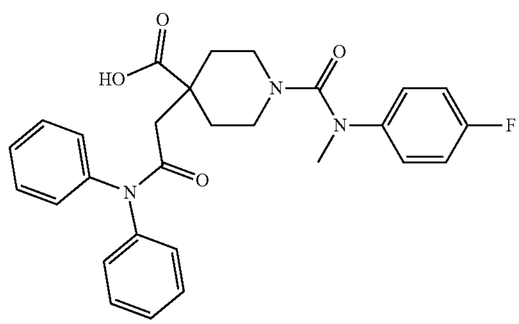 [SMILES: CN(C(=O)N1CCC(CC(=O)N(c2ccccc2)c2ccccc2)(C(=O)O)CC1)c1ccc(F)cc1] | 4-(2-(diphenylamino)-2-oxoethyl)-1-((4-fluorophenyl)(methyl)carbamoyl)piperidine-4-carboxylic acid | 490.4 |
| 3 | 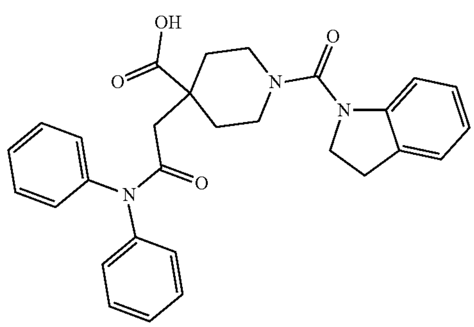 [SMILES: O=C(N1CCC(CC(=O)N(c2ccccc2)c2ccccc2)(C(=O)O)CC1)N1CCc2ccccc21] | 1-(indoline-1-carbonyl)-4-[2-oxo-2-(N-phenylanilino)ethyl]piperidine-4-carboxylic acid | 484.4 |
| 4 | 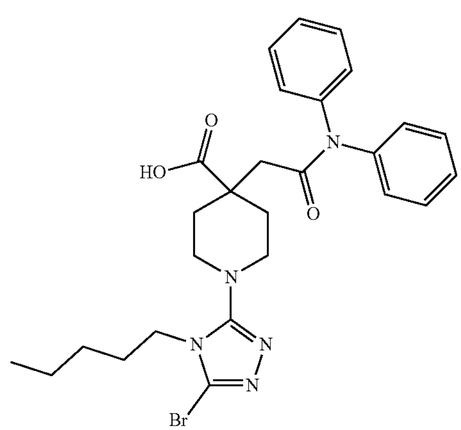 [SMILES: CCCCCn1c(Br)nnc1N1CCC(CC(=O)N(c2ccccc2)c2ccccc2)(C(=O)O)CC1] | 1-(5-bromo-4-pentyl-1,2,4-triazol-3-yl)-4-[2-oxo-2-(N-phenylanilino)ethyl]piperidine-4-carboxylic acid | 556.4 (Br[81]) |

TABLE I-continued

| Example No. | Structure | Name | ES/MS (m/z) (M + H) |
|---|---|---|---|
| 5 | 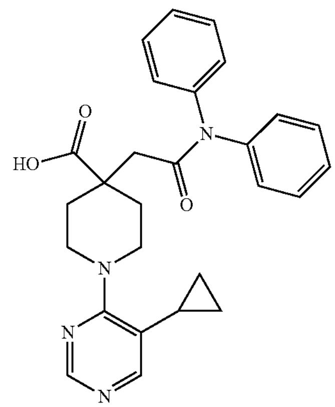 [SMILES: O=C(CC1(C(=O)O)CCN(c2ncncc2C2CC2)CC1)N(c1ccccc1)c1ccccc1] | 1-(5-cyclopropylpyrimidin-4-yl)-4-[2-oxo-2-(N-phenylanilino)ethyl]piperidine-4-carboxylic acid | 457.4 |
| 6 | 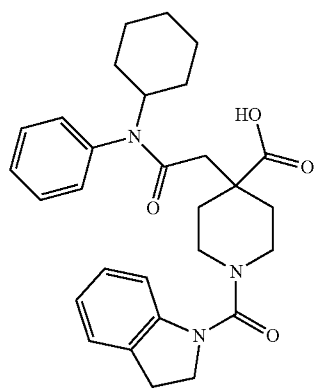 [SMILES: O=C(N1CCC(CC(=O)N(c2ccccc2)C2CCCCC2)(C(=O)O)CC1)N1CCc2ccccc21] | 4-[2-(N-cyclohexylanilino)-2-oxo-ethyl]-1-(indoline-1-carbonyl)piperidine-4-carboxylic acid | 490.4 |
| 7 | 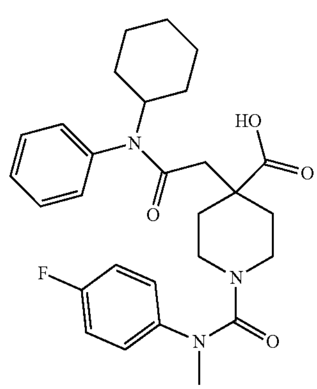 [SMILES: CN(C(=O)N1CCC(CC(=O)N(c2ccccc2)C2CCCCC2)(C(=O)O)CC1)c1ccc(F)cc1] | 4-[2-(N-cyclohexylanilino)-2-oxo-ethyl]-1-[(4-fluorophenyl)-methyl-carbamoyl]piperidine-4-carboxylic acid | 496.4 |

TABLE I-continued

| Example No. | Structure | Name | ES/MS (m/z) (M + H) |
|---|---|---|---|
| 8 | 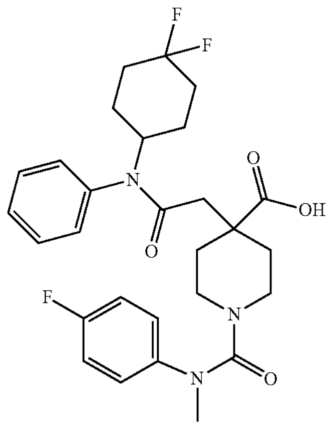 [SMILES: CN(C(=O)N1CCC(CC(=O)N(c2ccccc2)C2CCC(F)(F)CC2)(C(=O)O)CC1)c1ccc(F)cc1] | 4-[2-(N-(4,4-difluorocyclohexyl)anilino)-2-oxo-ethyl]-1-[(4-fluorophenyl)-methyl-carbamoyl]piperidine-4-carboxylic acid | 532.4 |
| 9 | 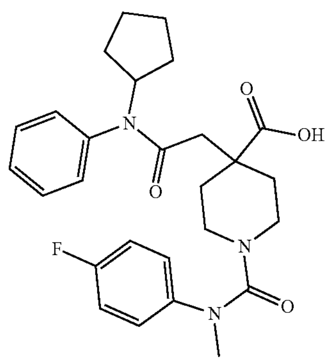 [SMILES: CN(C(=O)N1CCC(CC(=O)N(c2ccccc2)C2CCCC2)(C(=O)O)CC1)c1ccc(F)cc1] | 4-[2-(N-cyclopentylanilino)-2-oxo-ethyl]-1-[(4-fluorophenyl)-methyl-carbamoyl]piperidine-4-carboxylic acid | 482.4 |
| 10 | 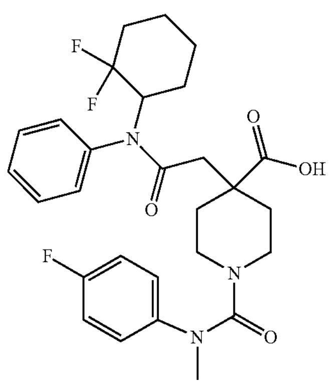 [SMILES: CN(C(=O)N1CCC(CC(=O)N(c2ccccc2)C2CCCCC2(F)F)(C(=O)O)CC1)c1ccc(F)cc1] | 4-[2-(N-(2,2-difluorocyclohexyl)anilino)-2-oxo-ethyl]-1-[(4-fluorophenyl)-methyl-carbamoyl]piperidine-4-carboxylic acid | 532.4 |
| 11 | 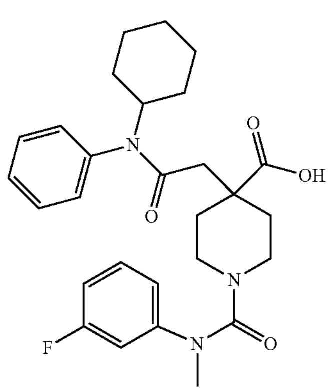 [SMILES: CN(C(=O)N1CCC(CC(=O)N(c2ccccc2)C2CCCCC2)(C(=O)O)CC1)c1cccc(F)c1] | 4-[2-(N-cyclohexylanilino)-2-oxo-ethyl]-1-[(3-fluorophenyl)-methyl-carbamoyl]piperidine-4-carboxylic acid | 496.5 |

TABLE I-continued

| Example No. | Structure | Name | ES/MS (m/z) (M + H) |
|---|---|---|---|
| 12 | 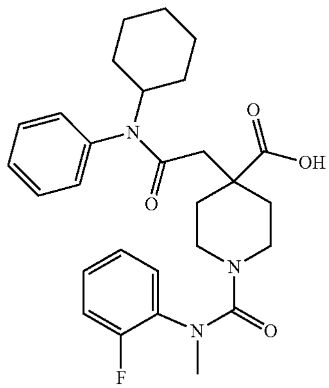 [SMILES: CN(C(=O)N1CCC(CC(=O)N(c2ccccc2)C2CCCCC2)(C(=O)O)CC1)c1ccccc1F] | 4-[2-(N-cyclohexylanilino)-2-oxo-ethyl]-1-[(2-fluorophenyl)-methyl-carbamoyl]piperidine-4-carboxylic acid | 496.5 |
| 13 | 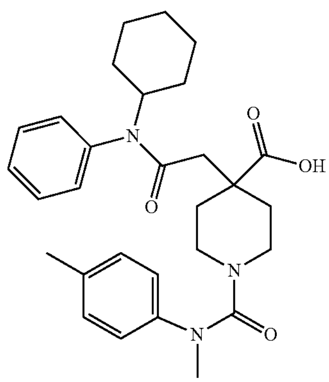 [SMILES: Cc1ccc(N(C)C(=O)N2CCC(CC(=O)N(c3ccccc3)C3CCCCC3)(C(=O)O)CC2)cc1] | 4-[2-(N-cyclohexylanilino)-2-oxo-ethyl]-1-[methyl(p-tolyl)carbamoyl]piperidine-4-carboxylic acid | 492.5 |
| 14 | 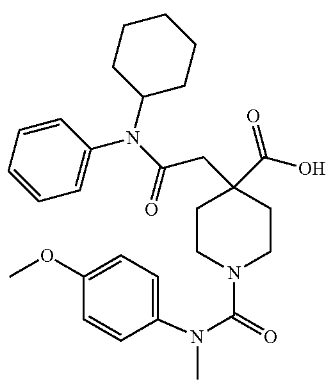 [SMILES: COc1ccc(N(C)C(=O)N2CCC(CC(=O)N(c3ccccc3)C3CCCCC3)(C(=O)O)CC2)cc1] | 4-[2-(N-cyclohexylanilino)-2-oxo-ethyl]-1-[(4-methoxyphenyl)-methyl-carbamoyl]piperidine-4-carboxylic acid | 508.5 |
| 15 | 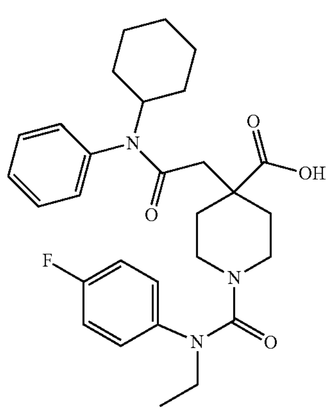 [SMILES: CCN(C(=O)N1CCC(CC(=O)N(c2ccccc2)C2CCCCC2)(C(=O)O)CC1)c1ccc(F)cc1] | 4-[2-(N-cyclohexylanilino)-2-oxo-ethyl]-1-[ethyl-(4-fluorophenyl)carbamoyl]piperidine-4-carboxylic acid | 510.5 |

TABLE I-continued

| Example No. | Structure | Name | ES/MS (m/z) (M + H) |
|---|---|---|---|
| 16 | 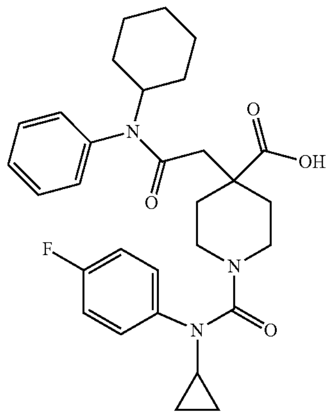 [SMILES: O=C(CC1(C(=O)O)CCN(C(=O)N(c2ccc(F)cc2)C2CC2)CC1)N(c1ccccc1)C1CCCCC1] | 4-[2-(N-cyclohexylanilino)-2-oxo-ethyl]-1-[cyclopropyl-(4-fluorophenyl)carbamoyl]piperidine-4-carboxylic acid | 522.4 |
| 17 | 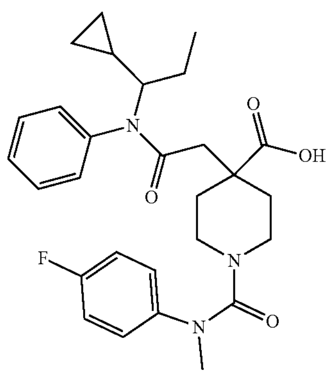 [SMILES: CCC(C1CC1)N(C(=O)CC1(C(=O)O)CCN(C(=O)N(C)c2ccc(F)cc2)CC1)c1ccccc1] | 4-[2-[N-(1-cyclopropylpropyl)anilino]-2-oxo-ethyl]-1-[(4-fluorophenyl)-methyl-carbamoyl]piperidine-4-carboxylic acid | 496.2 |
| 18 | 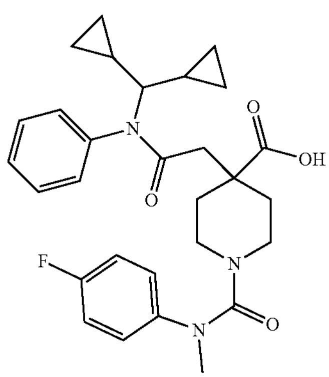 [SMILES: CN(C(=O)N1CCC(CC(=O)N(c2ccccc2)C(C2CC2)C2CC2)(C(=O)O)CC1)c1ccc(F)cc1] | 4-[2-[N-(dicyclopropylmethyl)anilino]-2-oxo-ethyl]-1-[(4-fluorophenyl)-methyl-carbamoyl]piperidine-4-carboxylic acid | 508.5 |
| 19 | 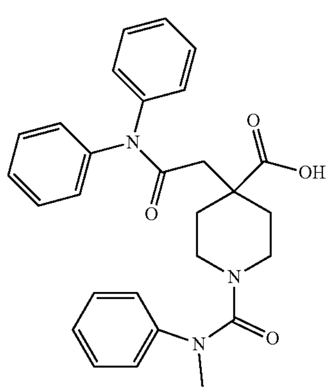 [SMILES: CN(C(=O)N1CCC(CC(=O)N(c2ccccc2)c2ccccc2)(C(=O)O)CC1)c1ccccc1] | 1-[methyl(phenyl)carbamoyl]-4-[2-oxo-2-(N-phenylanilino)ethyl]piperidine-4-carboxylic acid | 472.4 |

| Example No. | Structure | Name | ES/MS (m/z) (M + H) |
|---|---|---|---|
| 20 | 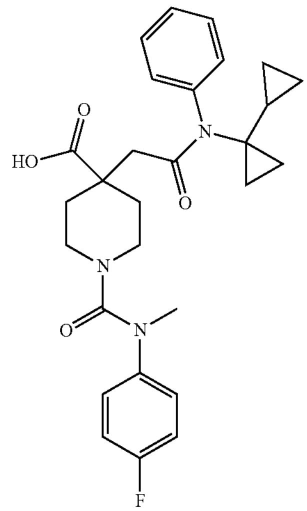 [SMILES: CN(C(=O)N1CCC(CC(=O)N(c2ccccc2)C2(C3CC3)CC2)(C(=O)O)CC1)c1ccc(F)cc1] | 4-[2-(N-(1-cyclopropylcyclopropyl)anilino)-2-oxo-ethyl]-1-[(4-fluorophenyl)-methyl-carbamoyl]piperidine-4-carboxylic acid | 494.2 |
| 21 | 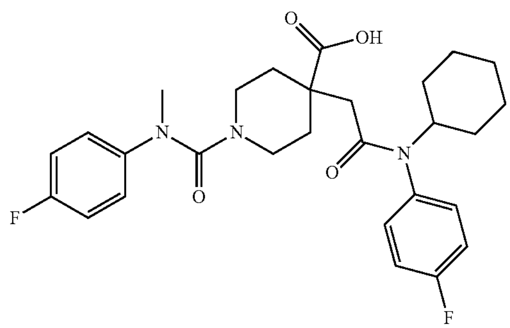 [SMILES: CN(C(=O)N1CCC(CC(=O)N(c2ccc(F)cc2)C2CCCCC2)(C(=O)O)CC1)c1ccc(F)cc1] | 4-[2-(N-cyclohexyl-4-fluoro-anilino)-2-oxo-ethyl]-1-[(4-fluorophenyl)-methyl-carbamoyl]piperidine-4-carboxylic acid | 514.2 |
| 22 | 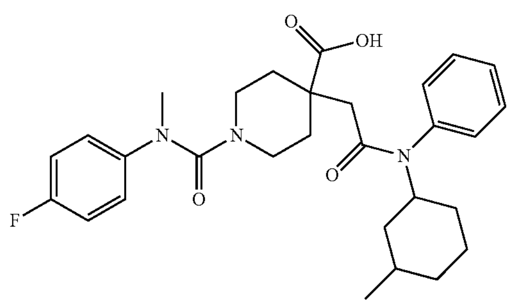 [SMILES: CC1CCCC(N(C(=O)CC2(C(=O)O)CCN(C(=O)N(C)c3ccc(F)cc3)CC2)c2ccccc2)C1] | 1-[(4-fluorophenyl)-methyl-carbamoyl]-4-[2-(N-(3-methylcyclohexyl)anilino)-2-oxo-ethyl]piperidine-4-carboxylic acid | 510.2 |
| 23 | 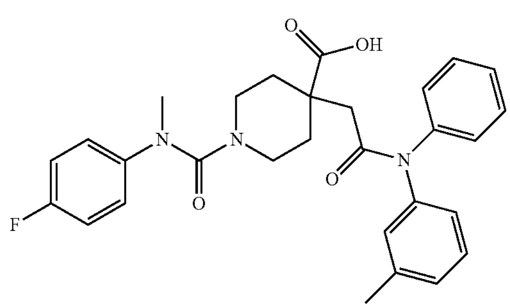 [SMILES: Cc1cccc(N(C(=O)CC2(C(=O)O)CCN(C(=O)N(C)c3ccc(F)cc3)CC2)c2ccccc2)c1] | 1-[(4-fluorophenyl)-methyl-carbamoyl]-4-[2-[N-(m-tolyl)anilino]-2-oxo-ethyl]piperidine-4-carboxylic acid | 504.2 |

TABLE I-continued

| Example No. | Structure | Name | ES/MS (m/z) (M + H) |
|---|---|---|---|
| 24 | 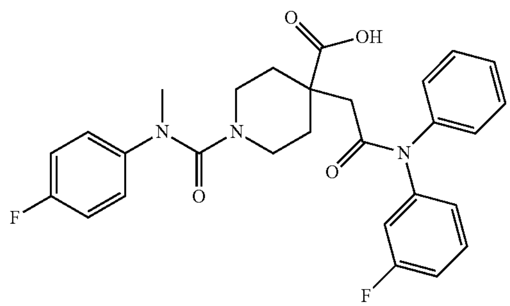 [SMILES: CN(C(=O)N1CCC(CC(=O)N(c2ccccc2)c2cccc(F)c2)(C(=O)O)CC1)c1ccc(F)cc1] | 4-[2-(N-(3-fluorophenyl)anilino)-2-oxo-ethyl]-1-[(4-fluorophenyl)-methyl-carbamoyl]piperidine-4-carboxylic acid | 508.2 |
| 25 | 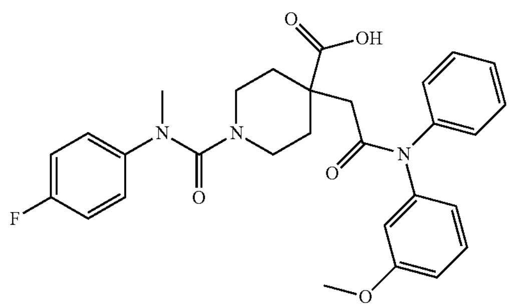 [SMILES: COc1cccc(N(C(=O)CC2(C(=O)O)CCN(C(=O)N(C)c3ccc(F)cc3)CC2)c2ccccc2)c1] | 1-[(4-fluorophenyl)-methyl-carbamoyl]-4-[2-(N-(3-methoxyphenyl)anilino)-2-oxo-ethyl]piperidine-4-carboxylic acid | 520.2 |
| 26 | 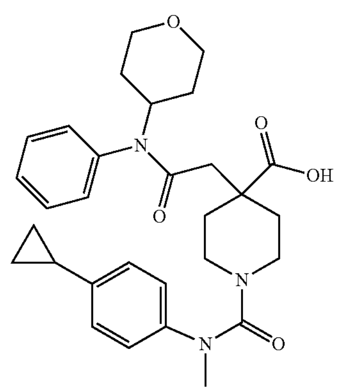 [SMILES: CN(C(=O)N1CCC(CC(=O)N(c2ccccc2)C2CCOCC2)(C(=O)O)CC1)c1ccc(C2CC2)cc1] | 1-[(4-cyclopropylphenyl)-methyl-carbamoyl]-4-[2-oxo-2-(N-tetrahydropyran-4-ylanilino)ethyl]piperidine-4-carboxylic acid | 520.5 |
| 27 | 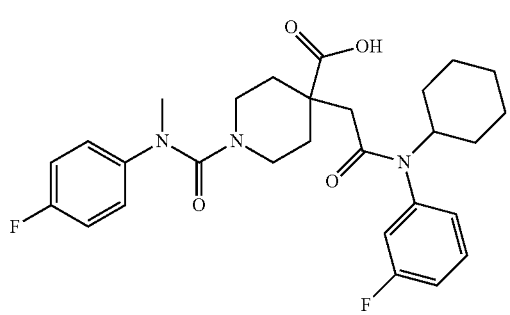 [SMILES: CN(C(=O)N1CCC(CC(=O)N(c2cccc(F)c2)C2CCCCC2)(C(=O)O)CC1)c1ccc(F)cc1] | 4-[2-(N-cyclohexyl-3-fluoro-anilino)-2-oxo-ethyl]-1-[(4-fluorophenyl)-methyl-carbamoyl]piperidine-4-carboxylic acid | 514.2 |

TABLE I-continued

| Example No. | Name | ES/MS (m/z) (M + H) |
|---|---|---|
| 28 | 1-[(4-fluorophenyl)-methyl-carbamoyl]-4-[2-(N-(4-isopropylphenyl)anilino)-2-oxo-ethyl]piperidine-4-carboxylic acid | 532.2 |
| 29 | 1-[(4-fluorophenyl)-methyl-carbamoyl]-4-[2-oxo-2-[N-(p-tolyl)anilino]ethyl]piperidine-4-carboxylic acid | 504.2 |
| 30 | 4-[2-(N-(4-fluorophenyl)anilino)-2-oxo-ethyl]-1-[(4-fluorophenyl)-methyl-carbamoyl]piperidine-4-carboxylic acid | 508.2 |
| 31 | 4-[2-(N-(4-chlorophenyl)anilino)-2-oxo-ethyl]-1-[(4-fluorophenyl)-methyl-carbamoyl]piperidine-4-carboxylic acid | 524.2 |

TABLE I-continued

| Example No. | Structure | Name | ES/MS (m/z) (M + H) |
|---|---|---|---|
| 32 | 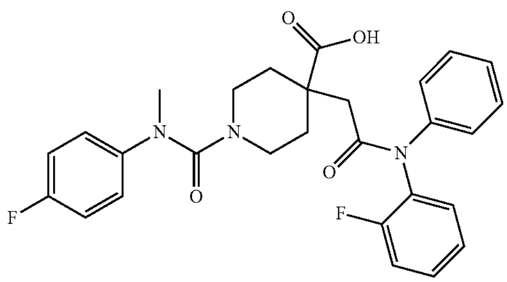 [SMILES: CN(C(=O)N1CCC(CC(=O)N(c2ccccc2)c2ccccc2F)(C(=O)O)CC1)c1ccc(F)cc1] | 4-[2-(N-(2-fluorophenyl)anilino)-2-oxo-ethyl]-1-[(4-fluorophenyl)-methyl-carbamoyl]piperidine-4-carboxylic acid | 508.2 |
| 33 | 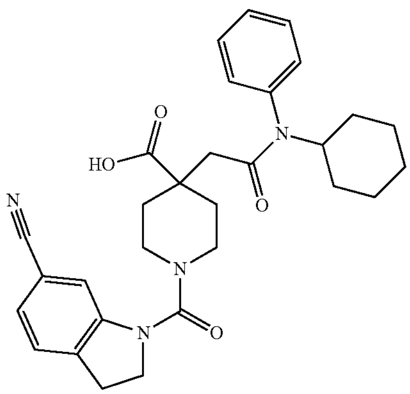 [SMILES: N#Cc1ccc2c(c1)N(C(=O)N1CCC(CC(=O)N(c3ccccc3)C3CCCCC3)(C(=O)O)CC1)CC2] | 1-(6-cyanoindoline-1-carbonyl)-4-[2-(N-cyclohexylanilino)-2-oxo-ethyl]piperidine-4-carboxylic acid | 515.5 |
| 34 | 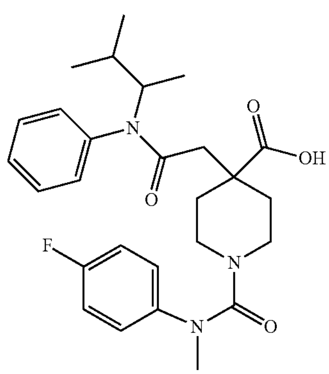 [SMILES: CC(C)C(C)N(C(=O)CC1(C(=O)O)CCN(C(=O)N(C)c2ccc(F)cc2)CC1)c1ccccc1] | 4-[2-(N-[(1)-1,2-dimethylpropyl]anilino)-2-oxo-ethyl]-1-[(4-fluorophenyl)-methyl-carbamoyl]piperidine-4-carboxylic acid | 484.4 |
| 35 | 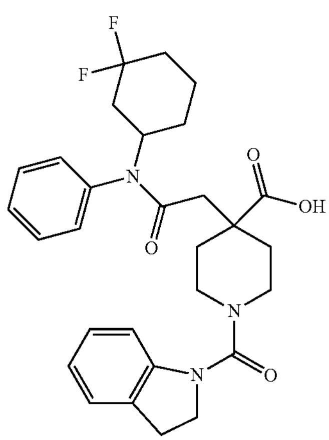 [SMILES: O=C(N1CCC(CC(=O)N(c2ccccc2)C2CCCC(F)(F)C2)(C(=O)O)CC1)N1CCc2ccccc21] | 4-[2-(N-(3,3-difluorocyclohexyl)anilino)-2-oxo-ethyl]-1-(indoline-1-carbonyl)piperidine-4-carboxylic acid | 526.2 |

TABLE I-continued

| Example No. | Structure | Name | ES/MS (m/z) (M + H) |
|---|---|---|---|
| 35A (isomer 1) | 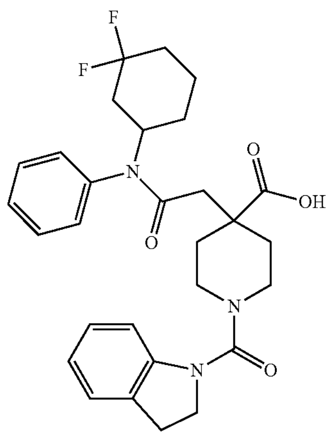 [SMILES: O=C(N1CCC(CC(=O)N(c2ccccc2)C2CCCC(F)(F)C2)(C(=O)O)CC1)N1CCc2ccccc21] | 4-[2-(N-(3,3-difluorocyclohexyl)anilino)-2-oxo-ethyl]-1-(indoline-1-carbonyl)piperidine-4-carboxylic acid | 526.2 |
| 35B (isomer 2) | 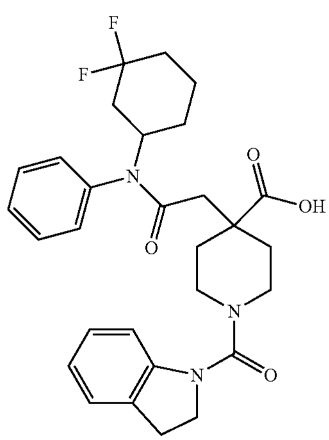 [SMILES: O=C(N1CCC(CC(=O)N(c2ccccc2)C2CCCC(F)(F)C2)(C(=O)O)CC1)N1CCc2ccccc21] | 4-[2-(N-(3,3-difluorocyclohexyl)anilino)-2-oxo-ethyl]-1-(indoline-1-carbonyl)piperidine-4-carboxylic acid | 526.2 |
| 36 | 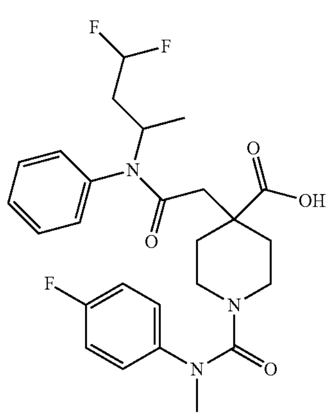 [SMILES: CC(CC(F)F)N(C(=O)CC1(C(=O)O)CCN(C(=O)N(C)c2ccc(F)cc2)CC1)c1ccccc1] | 4-[2-(N-(3,3-difluoro-1-methyl-propyl)anilino)-2-oxo-ethyl]-1-[(4-fluorophenyl)-methyl-carbamoyl]piperidine-4-carboxylic acid | 506.4 |

TABLE I-continued

| Example No. | Structure | Name | ES/MS (m/z) (M + H) |
|---|---|---|---|
| 37 | 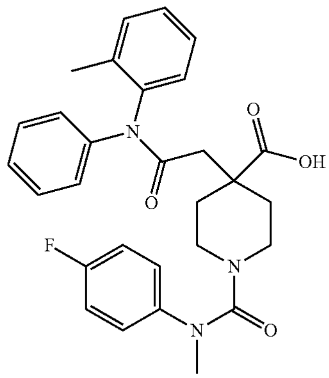 [SMILES: Cc1ccccc1N(C(=O)CC1(C(=O)O)CCN(C(=O)N(C)c2ccc(F)cc2)CC1)c1ccccc1] | 1-[(4-fluorophenyl)-methyl-carbamoyl]-4-[2-[N-(o-tolyl)anilino]-2-oxo-ethyl]piperidine-4-carboxylic acid | 504.4 |
| 38 | 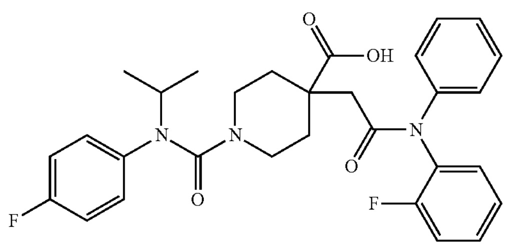 [SMILES: CC(C)N(C(=O)N1CCC(CC(=O)N(c2ccccc2)c2ccccc2F)(C(=O)O)CC1)c1ccc(F)cc1] | 4-[2-(N-(2-fluorophenyl)anilino)-2-oxo-ethyl]-1-[(4-fluorophenyl)-isopropyl-carbamoyl]piperidine-4-carboxylic acid | 536.5 |
| 39 | 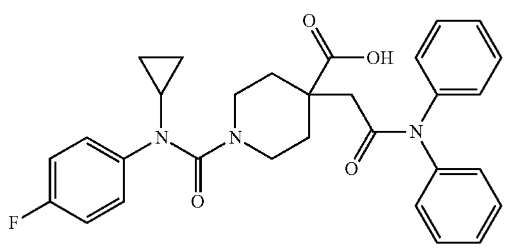 [SMILES: O=C(CC1(C(=O)O)CCN(C(=O)N(c2ccc(F)cc2)C2CC2)CC1)N(c1ccccc1)c1ccccc1] | 1-[cyclopropyl-(4-fluorophenyl)carbamoyl]-4-[2-oxo-2-(N-phenylanilino)ethyl]piperidine-4-carboxylic acid | 516.3 |
| 40 | 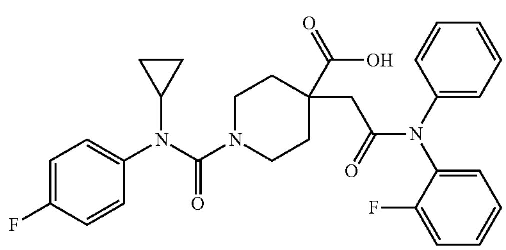 [SMILES: O=C(CC1(C(=O)O)CCN(C(=O)N(c2ccc(F)cc2)C2CC2)CC1)N(c1ccccc1)c1ccccc1F] | 1-[cyclopropyl-(4-fluorophenyl)carbamoyl]-4-[2-(N-(2-fluorophenyl)anilino)-2-oxo-ethyl]piperidine-4-carboxylic acid | 534.4 |
| 41 | 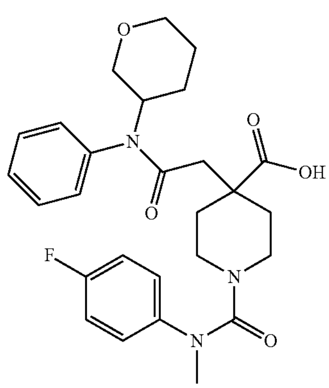 | 1-[(4-fluorophenyl)-methyl-carbamoyl]-4-[2-oxo-2-(N-tetrahydropyran-3-ylanilino)ethyl]piperidine-4-carboxylic acid | 498.4 |

TABLE I-continued

| Example No. | Structure | Name | ES/MS (m/z) (M + H) |
|---|---|---|---|
| 41A (isomer 1) | 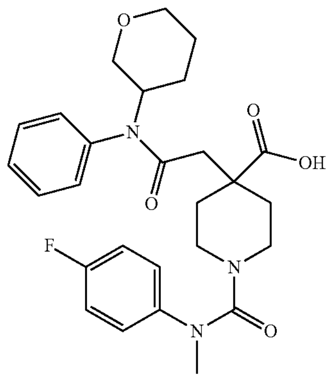 | 1-[(4-fluorophenyl)-methyl-carbamoyl]-4-[2-oxo-2-(N-tetrahydropyran-3-ylanilino)ethyl]piperidine-4-carboxylic acid | 498.4 |
| 41B (isomer 2) | 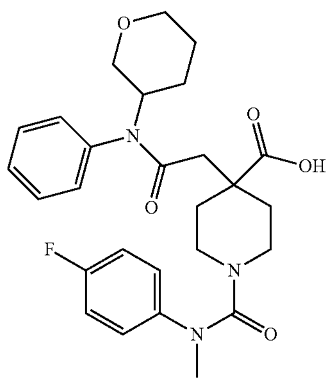 | 1-[(4-fluorophenyl)-methyl-carbamoyl]-4-[2-oxo-2-(N-tetrahydropyran-3-ylanilino)ethyl]piperidine-4-carboxylic acid | 498.4 |
| 42 | 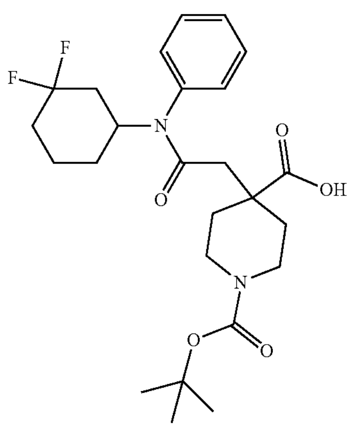 [SMILES: CC(C)(C)OC(=O)N1CCC(CC(=O)N(c2ccccc2)C2CCCC(F)(F)C2)(C(=O)O)CC1] | 1-tert-butoxycarbonyl-4-[2-(N-(3,3-difluorocyclohexyl)anilino)-2-oxo-ethyl]piperidine-4-carboxylic acid | 425.0 (M + H − Bu$^t$) |
| 43 | 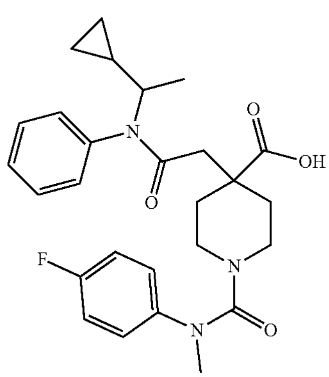 [SMILES: CC(C1CC1)N(C(=O)CC1(C(=O)O)CCN(C(=O)N(C)c2ccc(F)cc2)CC1)c1ccccc1] | 4-[2-[N-(1-cyclopropylethyl)anilino]-2-oxo-ethyl]-1-[(4-fluorophenyl)-methyl-carbamoyl]piperidine-4-carboxylic acid | 482.5 |

TABLE I-continued

| Example No. | Structure | Name | ES/MS (m/z) (M + H) |
|---|---|---|---|
| 43A (isomer 1) | 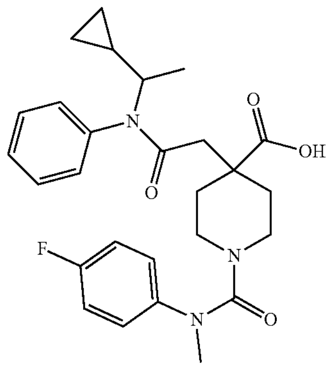 [SMILES: CC(C1CC1)N(C(=O)CC1(C(=O)O)CCN(C(=O)N(C)c2ccc(F)cc2)CC1)c1ccccc1] | 4-[2-[N-(1-cyclopropylethyl)anilino]-2-oxo-ethyl]-1-[(4-fluorophenyl)-methyl-carbamoyl]piperidine-4-carboxylic acid | 482.5 |
| 43B (isomer 2) | 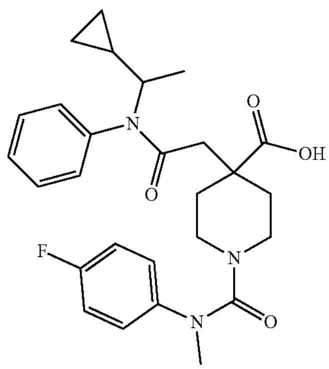 [SMILES: CC(C1CC1)N(C(=O)CC1(C(=O)O)CCN(C(=O)N(C)c2ccc(F)cc2)CC1)c1ccccc1] | 4-[2-[N-(1-cyclopropylethyl)anilino]-2-oxo-ethyl]-1-[(4-fluorophenyl)-methyl-carbamoyl]piperidine-4-carboxylic acid | 482.5 |
| 44 | 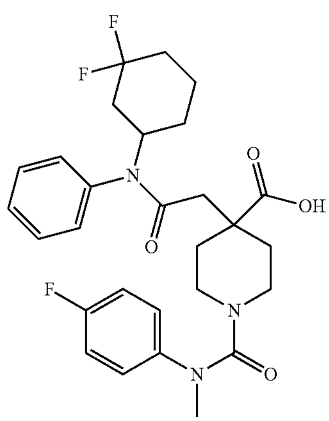 [SMILES: CN(C(=O)N1CCC(CC(=O)N(c2ccccc2)C2CCCC(F)(F)C2)(C(=O)O)CC1)c1ccc(F)cc1] | 4-[2-(N-(3,3-difluorocyclohexyl)anilino)-2-oxo-ethyl]-1-[(4-fluorophenyl)-methyl-carbamoyl]piperidine-4-carboxylic acid | 532.4 |
| 44A (isomer 1) | 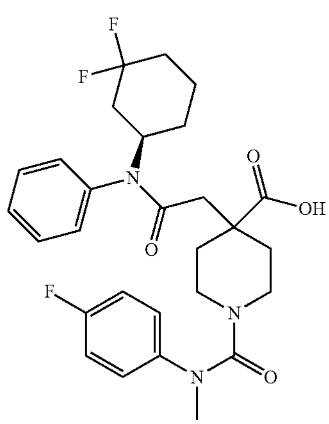 [SMILES: CN(C(=O)N1CCC(CC(=O)N(c2ccccc2)[C@@H]2CCCC(F)(F)C2)(C(=O)O)CC1)c1ccc(F)cc1] | 4-[2-(N-[(1R)-3,3-difluorocyclohexyl]anilino)-2-oxo-ethyl]-1-[(4-fluorophenyl)-methyl-carbamoyl]piperidine-4-carboxylic acid | 532.4 |

TABLE I-continued

| Example No. | Structure | Name | ES/MS (m/z) (M + H) |
|---|---|---|---|
| 44B (isomer 2) | 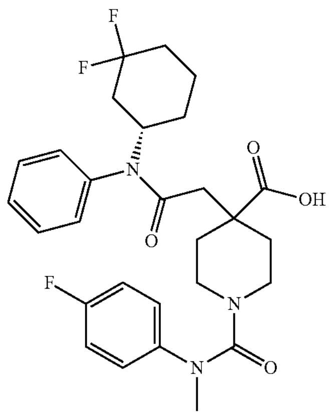 [SMILES: CN(C(=O)N1CCC(CC(=O)N(c2ccccc2)[C@H]2CCCC(F)(F)C2)(C(=O)O)CC1)c1ccc(F)cc1] | 4-[2-(N-[(1S)-3,3-difluorocyclohexyl]anilino)-2-oxo-ethyl]-1-[(4-fluorophenyl)-methyl-carbamoyl]piperidine-4-carboxylic acid | 532.5 |
| 45 | 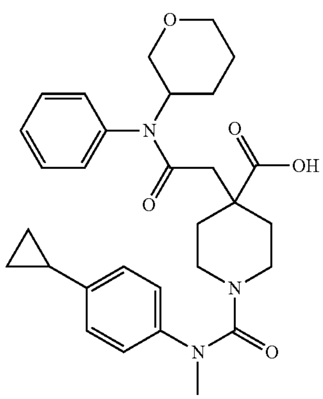 [SMILES: CN(C(=O)N1CCC(CC(=O)N(c2ccccc2)C2CCCOC2)(C(=O)O)CC1)c1ccc(C2CC2)cc1] | 1-[(4-cyclopropylphenyl)-methyl-carbamoyl]-4-[2-oxo-2-(N-tetrahydropyran-3-ylanilino)ethyl]piperidine-4-carboxylic acid | 520.5 |
| 45A (isomer 1) | 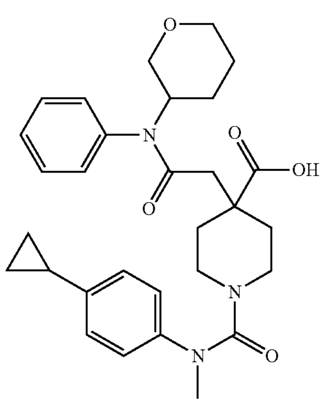 [SMILES: CN(C(=O)N1CCC(CC(=O)N(c2ccccc2)C2CCCOC2)(C(=O)O)CC1)c1ccc(C2CC2)cc1] | 1-[(4-cyclopropylphenyl)-methyl-carbamoyl]-4-[2-oxo-2-(N-tetrahydropyran-3-ylanilino)ethyl]piperidine-4-carboxylic acid | 520.3 |

TABLE I-continued

| Example No. | Structure | Name | ES/MS (m/z) (M + H) |
|---|---|---|---|
| 45B (isomer 2) | 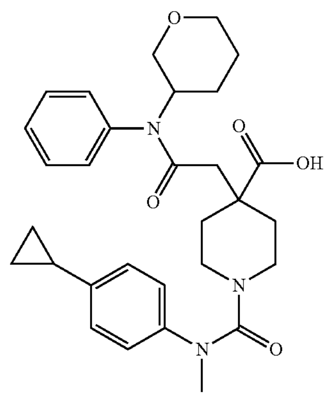 [SMILES: CN(C(=O)N1CCC(CC(=O)N(c2ccccc2)C2CCCOC2)(C(=O)O)CC1)c1ccc(C2CC2)cc1] | 1-[(4-cyclopropylphenyl)-methyl-carbamoyl]-4-[2-oxo-2-(N-tetrahydropyran-3-ylanilino)ethyl]piperidine-4-carboxylic acid | 520.3 |
| 46 | 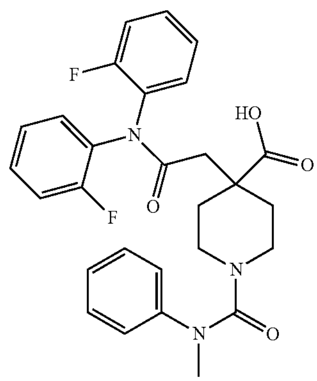 [SMILES: CN(C(=O)N1CCC(CC(=O)N(c2ccccc2F)c2ccccc2F)(C(=O)O)CC1)c1ccccc1] | 4-[2-(2-fluoro-N-(2-fluorophenyl)anilino)-2-oxo-ethyl]-1-[methyl(phenyl)carbamoyl]piperidine-4-carboxylic acid | 508.5 |
| 47 | 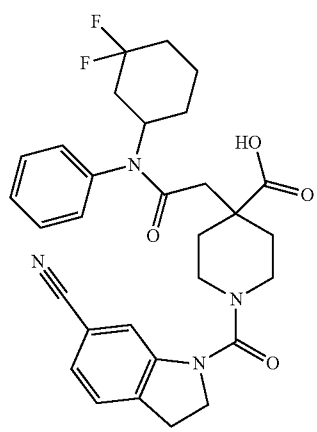 [SMILES: N#Cc1ccc2c(c1)N(C(=O)N1CCC(CC(=O)N(c3ccccc3)C3CCCC(F)(F)C3)(C(=O)O)CC1)CC2] | 1-(6-cyanoindoline-1-carbonyl)-4-[2-(N-(3,3-difluorocyclohexyl)anilino)-2-oxo-ethyl]piperidine-4-carboxylic acid | 551.5 |
| 48 | 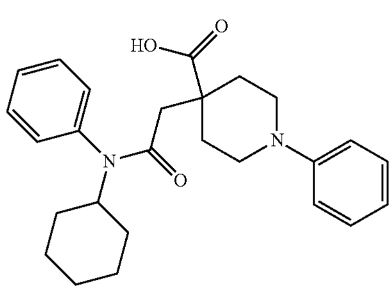 [SMILES: O=C(CC1(C(=O)O)CCN(c2ccccc2)CC1)N(c1ccccc1)C1CCCCC1] | 4-[2-(N-cyclohexylanilino)-2-oxo-ethyl]-1-phenyl-piperidine-4-carboxylic acid | 421.2 |

TABLE I-continued

| Example No. | Structure | Name | ES/MS (m/z) (M + H) |
|---|---|---|---|
| 49 | 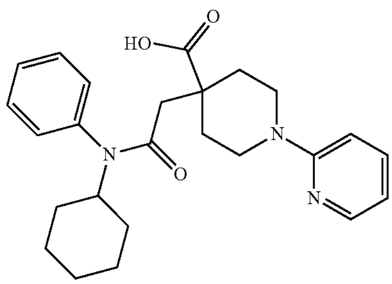 [SMILES: O=C(CC1(C(=O)O)CCN(c2ccccn2)CC1)N(c1ccccc1)C1CCCCC1] | 4-[2-(N-cyclohexylanilino)-2-oxo-ethyl]-1-(2-pyridyl)piperidine-4-carboxylic acid | 422.2 |
| 50 | 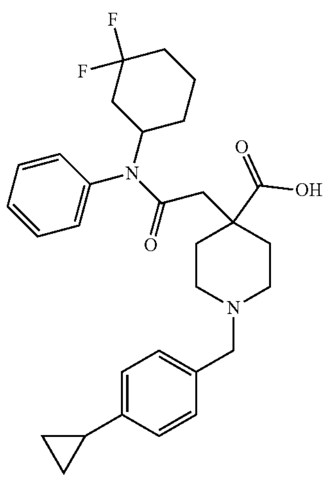 [SMILES: O=C(CC1(C(=O)O)CCN(Cc2ccc(C3CC3)cc2)CC1)N(c1ccccc1)C1CCCC(F)(F)C1] | 1-[(4-cyclopropylphenyl)methyl]-4-[2-(N-(3,3-difluorocyclohexyl)anilino)-2-oxo-ethyl]piperidine-4-carboxylic acid | 511.5 |
| 51 | 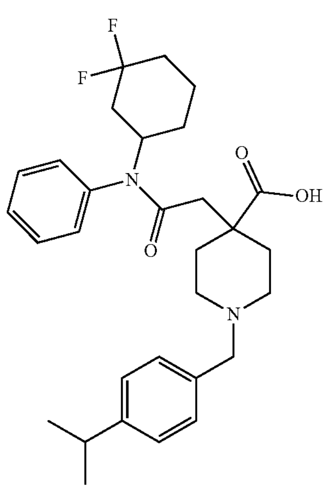 [SMILES: CC(C)c1ccc(CN2CCC(CC(=O)N(c3ccccc3)C3CCCC(F)(F)C3)(C(=O)O)CC2)cc1] | 4-[2-(N-(3,3-difluorocyclohexyl)anilino)-2-oxo-ethyl]-1-[(4-isopropylphenyl)methyl]piperidine-4-carboxylic acid | 513.5 |

TABLE I-continued

| Example No. | Structure | Name | ES/MS (m/z) (M + H) |
|---|---|---|---|
| 52 | 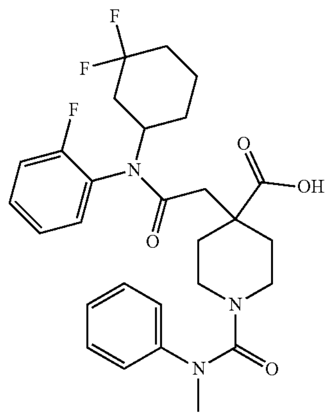 [SMILES: CN(C(=O)N1CCC(CC(=O)N(c2ccccc2F)C2CCCC(F)(F)C2)(C(=O)O)CC1)c1ccccc1] | 4-[2-(N-(3,3-difluorocyclohexyl)-2-fluoro-anilino)-2-oxo-ethyl]-1-[methyl(phenyl)carbamoyl]piperidine-4-carboxylic acid | 532.5 |
| 53 | 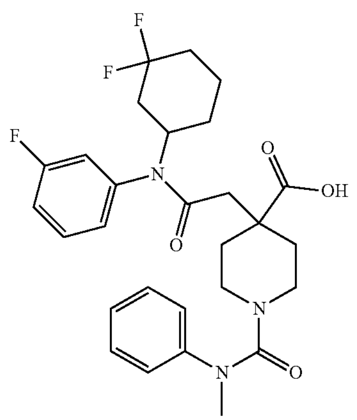 [SMILES: CN(C(=O)N1CCC(CC(=O)N(c2cccc(F)c2)C2CCCC(F)(F)C2)(C(=O)O)CC1)c1ccccc1] | 4-[2-(N-(3,3-difluorocyclohexyl)-3-fluoro-anilino)-2-oxo-ethyl]-1-[methyl(phenyl)carbamoyl]piperidine-4-carboxylic acid | 532.5 |
| 54 | 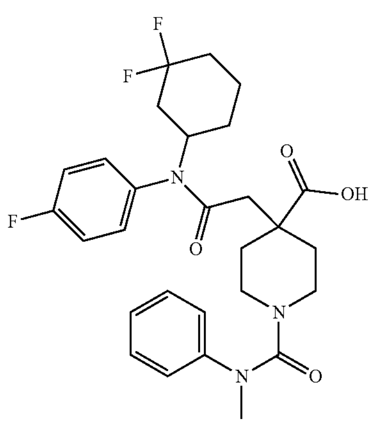 [SMILES: CN(C(=O)N1CCC(CC(=O)N(c2ccc(F)cc2)C2CCCC(F)(F)C2)(C(=O)O)CC1)c1ccccc1] | 4-[2-(N-(3,3-difluorocyclohexyl)-4-fluoro-anilino)-2-oxo-ethyl]-1-[methyl(phenyl)carbamoyl]piperidine-4-carboxylic acid | 532.5 |

TABLE I-continued

| Example No. | Structure | Name | ES/MS (m/z) (M + H) |
|---|---|---|---|
| 55 | 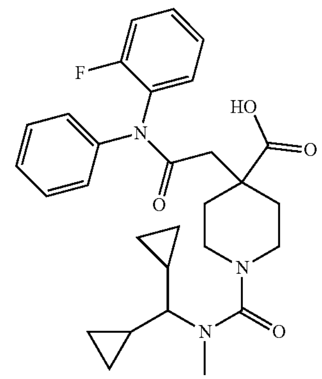 [SMILES: CN(C(=O)N1CCC(CC(=O)N(c2ccccc2)c2ccccc2F)(C(=O)O)CC1)C(C1CC1)C1CC1] | 1-[dicyclopropylmethyl(methyl)carbamoyl]-4-[2-(N-(2-fluorophenyl)anilino)-2-oxo-ethyl]piperidine-4-carboxylic acid | 508.2 |
| 56 | 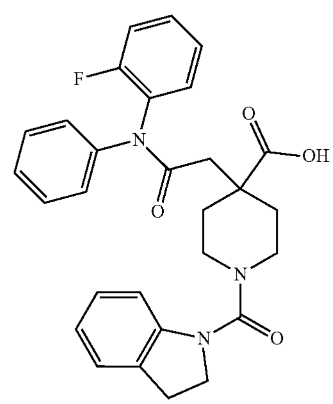 [SMILES: O=C(N1CCC(CC(=O)N(c2ccccc2)c2ccccc2F)(C(=O)O)CC1)N1CCc2ccccc21] | 4-[2-(N-(2-fluorophenyl)anilino)-2-oxo-ethyl]-1-(indoline-1-carbonyl)piperidine-4-carboxylic acid | 502.4 |
| 57 | 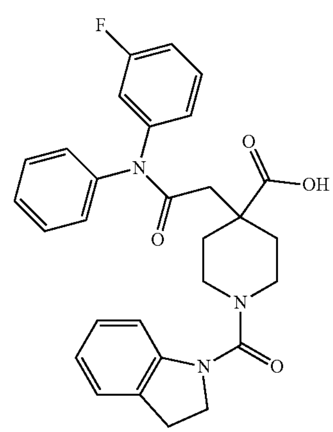 [SMILES: O=C(N1CCC(CC(=O)N(c2ccccc2)c2cccc(F)c2)(C(=O)O)CC1)N1CCc2ccccc21] | 4-[2-(N-(3-fluorophenyl)anilino)-2-oxo-ethyl]-1-(indoline-1-carbonyl)piperidine-4-carboxylic acid | 502.4 |

TABLE I-continued

| Example No. | Structure | Name | ES/MS (m/z) (M + H) |
|---|---|---|---|
| 58 | 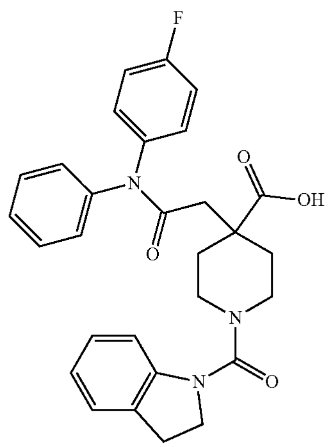 [SMILES: O=C(N1CCC(CC(=O)N(c2ccccc2)c2ccc(F)cc2)(C(=O)O)CC1)N1CCc2ccccc21] | 4-[2-(N-(4-fluorophenyl)anilino)-2-oxo-ethyl]-1-(indoline-1-carbonyl)piperidine-4-carboxylic acid | 502.4 |
| 59 | 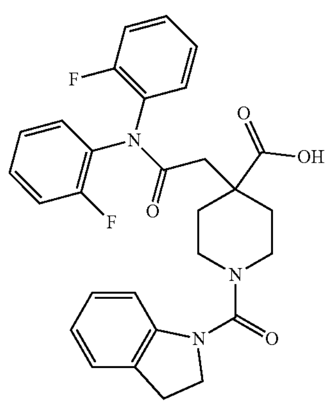 [SMILES: O=C(N1CCC(CC(=O)N(c2ccccc2F)c2ccccc2F)(C(=O)O)CC1)N1CCc2ccccc21] | 4-[2-(2-fluoro-N-(2-fluorophenyl)anilino)-2-oxo-ethyl]-1-(indoline-1-carbonyl)piperidine-4-carboxylic acid | 520.3 |
| 60 | 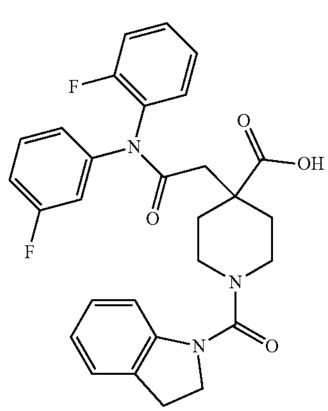 [SMILES: O=C(N1CCC(CC(=O)N(c2cccc(F)c2)c2ccccc2F)(C(=O)O)CC1)N1CCc2ccccc21] | 4-[2-(3-fluoro-N-(2-fluorophenyl)anilino)-2-oxo-ethyl]-1-(indoline-1-carbonyl)piperidine-4-carboxylic acid | 520.4 |

TABLE I-continued

| Example No. | Structure | Name | ES/MS (m/z) (M + H) |
|---|---|---|---|
| 61 | 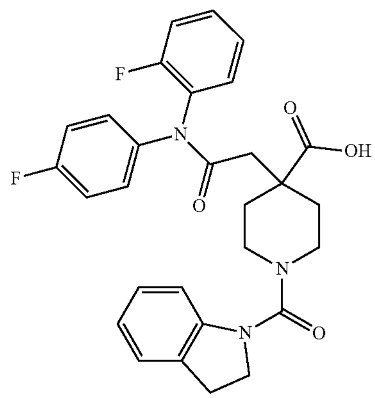 [SMILES: O=C(N1CCC(CC(=O)N(c2ccc(F)cc2)c2ccccc2F)(C(=O)O)CC1)N1CCc2ccccc21] | 4-[2-(4-fluoro-N-(2-fluorophenyl)anilino)-2-oxo-ethyl]-1-(indoline-1-carbonyl)piperidine-4-carboxylic acid | 520.4 |
| 62 | 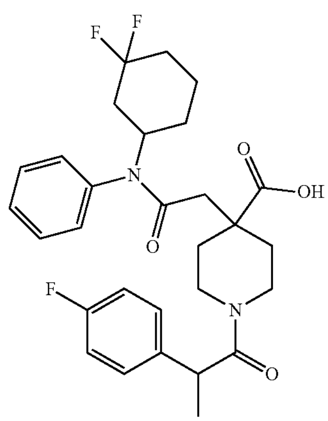 [SMILES: CC(C(=O)N1CCC(CC(=O)N(c2ccccc2)C2CCCC(F)(F)C2)(C(=O)O)CC1)c1ccc(F)cc1] | 4-[2-(N-(3,3-difluorocyclohexyl)anilino)-2-oxo-ethyl]-1-[2-(4-fluorophenyl)propanoyl]piperidine-4-carboxylic acid | 531.5 |
| 63 | 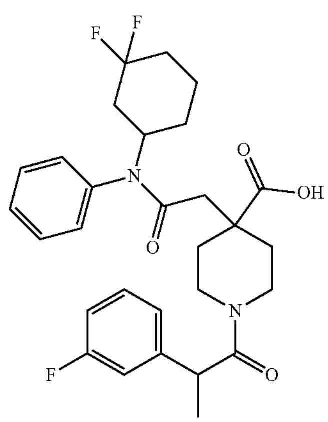 [SMILES: CC(C(=O)N1CCC(CC(=O)N(c2ccccc2)C2CCCC(F)(F)C2)(C(=O)O)CC1)c1cccc(F)c1] | 4-[2-(N-(3,3-difluorocyclohexyl)anilino)-2-oxo-ethyl]-1-[2-(3-fluorophenyl)propanoyl]piperidine-4-carboxylic acid | 531.4 |

TABLE I-continued

| Example No. | Structure | Name | ES/MS (m/z) (M + H) |
|---|---|---|---|
| 64 | 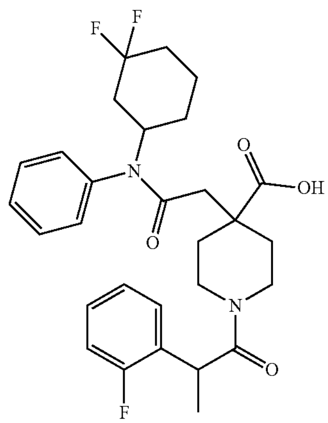 [SMILES: CC(C(=O)N1CCC(CC(=O)N(c2ccccc2)C2CCCC(F)(F)C2)(C(=O)O)CC1)c1ccccc1F] | 4-[2-(N-(3,3-difluorocyclohexyl)anilino)-2-oxo-ethyl]-1-[2-(2-fluorophenyl)propanoyl]piperidine-4-carboxylic acid | 531.5 |
| 65 | 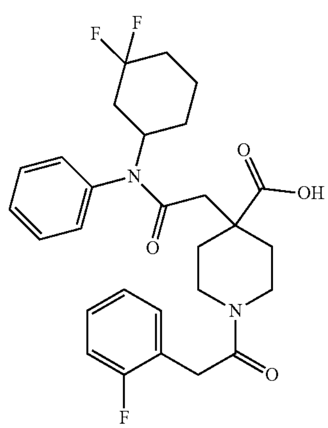 [SMILES: O=C(Cc1ccccc1F)N1CCC(CC(=O)N(c2ccccc2)C2CCCC(F)(F)C2)(C(=O)O)CC1] | 4-[2-(N-(3,3-difluorocyclohexyl)anilino)-2-oxo-ethyl]-1-[2-(2-fluorophenyl)acetyl]piperidine-4-carboxylic acid | 517.4 |
| 66 | 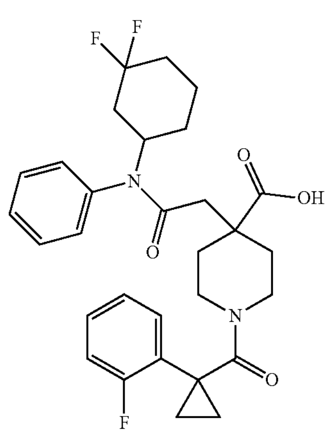 [SMILES: O=C(CC1(C(=O)O)CCN(C(=O)C2(c3ccccc3F)CC2)CC1)N(c1ccccc1)C1CCCC(F)(F)C1] | 4-[2-(N-(3,3-difluorocyclohexyl)anilino)-2-oxo-ethyl]-1-[1-(2-fluorophenyl)cyclopropanecarbonyl]piperidine-4-carboxylic acid | 543.4 |

TABLE I-continued

| Example No. | Structure | Name | ES/MS (m/z) (M + H) |
|---|---|---|---|
| 67 | 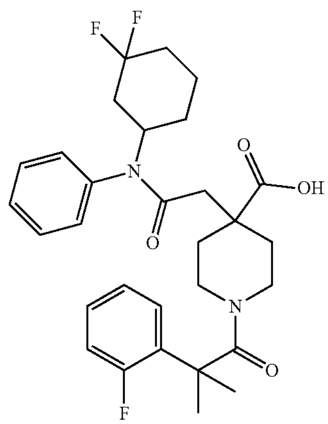 [SMILES: CC(C)(C(=O)N1CCC(CC(=O)N(c2ccccc2)C2CCCC(F)(F)C2)(C(=O)O)CC1)c1ccccc1F] | 4-[2-(N-(3,3-difluorocyclohexyl)anilino)-2-oxo-ethyl]-1-[2-(2-fluorophenyl)-2-methyl-propanoyl]piperidine-4-carboxylic acid | 545.6 |
| 68 | 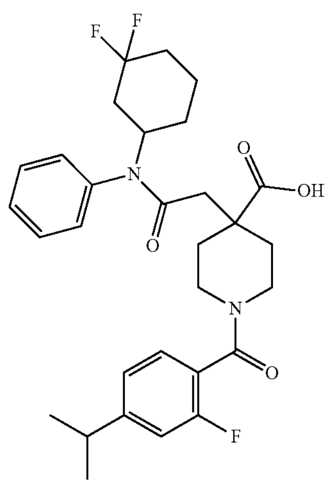 [SMILES: CC(C)c1ccc(C(=O)N2CCC(CC(=O)N(c3ccccc3)C3CCCC(F)(F)C3)(C(=O)O)CC2)c(F)c1] | 4-[2-(N-(3,3-difluorocyclohexyl)anilino)-2-oxo-ethyl]-1-(2-fluoro-4-isopropyl-benzoyl)piperidine-4-carboxylic acid | 545.5 |
| 69 | 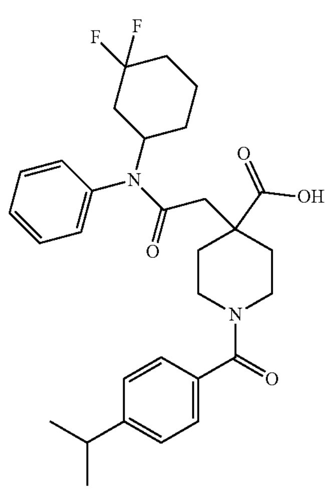 [SMILES: CC(C)c1ccc(C(=O)N2CCC(CC(=O)N(c3ccccc3)C3CCCC(F)(F)C3)(C(=O)O)CC2)cc1] | 4-[2-(N-(3,3-difluorocyclohexyl)anilino)-2-oxo-ethyl]-1-(4-isopropylbenzoyl)piperidine-4-carboxylic acid | 527.3 |

TABLE I-continued

| Example No. | Structure | Name | ES/MS (m/z) (M + H) |
|---|---|---|---|
| 70 | 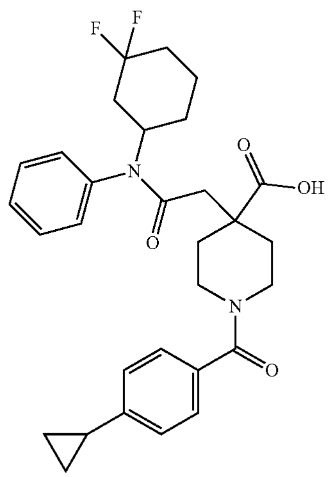 [SMILES: O=C(c1ccc(C2CC2)cc1)N1CCC(CC(=O)N(c2ccccc2)C2CCCC(F)(F)C2)(C(=O)O)CC1] | 1-(4-cyclopropylbenzoyl)-4-[2-(N-(3,3-difluorocyclohexyl)anilino)-2-oxo-ethyl]piperidine-4-carboxylic acid | 525.3 |
| 71 | 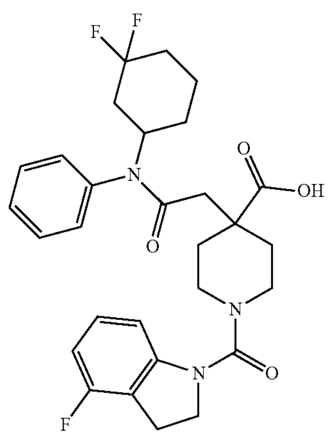 [SMILES: O=C(N1CCC(CC(=O)N(c2ccccc2)C2CCCC(F)(F)C2)(C(=O)O)CC1)N1CCc2c(F)cccc21] | 4-[2-(N-(3,3-difluorocyclohexyl)anilino)-2-oxo-ethyl]-1-(4-fluoroindoline-1-carbonyl)piperidine-4-carboxylic acid | 544.4 |
| 72 | 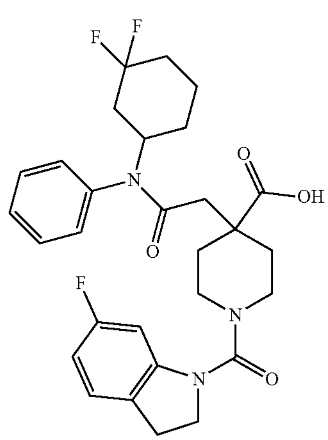 [SMILES: O=C(N1CCC(CC(=O)N(c2ccccc2)C2CCCC(F)(F)C2)(C(=O)O)CC1)N1CCc2ccc(F)cc21] | 4-[2-(N-(3,3-difluorocyclohexyl)anilino)-2-oxo-ethyl]-1-(6-fluoroindoline-1-carbonyl)piperidine-4-carboxylic acid | 544.2 |

TABLE I-continued

| Example No. | Structure | Name | ES/MS (m/z) (M + H) |
|---|---|---|---|
| 72A (isomer 1) | 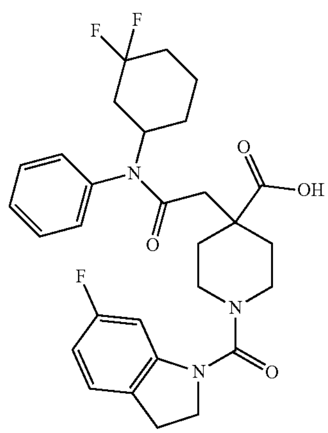 [SMILES: O=C(N1CCC(CC(=O)N(c2ccccc2)C2CCCC(F)(F)C2)(C(=O)O)CC1)N1CCc2ccc(F)cc21] | 4-[2-(N-(3,3-difluorocyclohexyl)anilino)-2-oxo-ethyl]-1-(6-fluoroindoline-1-carbonyl)piperidine-4-carboxylic acid | 544.5 |
| 72B (isomer 2) | 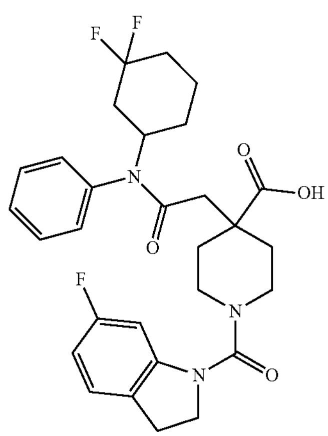 [SMILES: O=C(N1CCC(CC(=O)N(c2ccccc2)C2CCCC(F)(F)C2)(C(=O)O)CC1)N1CCc2ccc(F)cc21] | 4-[2-(N-(3,3-difluorocyclohexyl)anilino)-2-oxo-ethyl]-1-(6-fluoroindoline-1-carbonyl)piperidine-4-carboxylic acid | 544.5 |
| 73 | 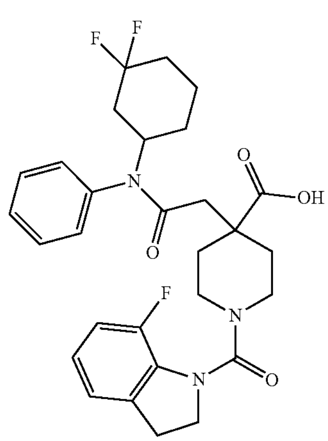 [SMILES: O=C(N1CCC(CC(=O)N(c2ccccc2)C2CCCC(F)(F)C2)(C(=O)O)CC1)N1CCc2cccc(F)c21] | 4-[2-(N-(3,3-difluorocyclohexyl)anilino)-2-oxo-ethyl]-1-(7-fluoroindoline-1-carbonyl)piperidine-4-carboxylic acid | 544.5 |

TABLE I-continued

| Example No. | Structure | Name | ES/MS (m/z) (M + H) |
|---|---|---|---|
| 74 | 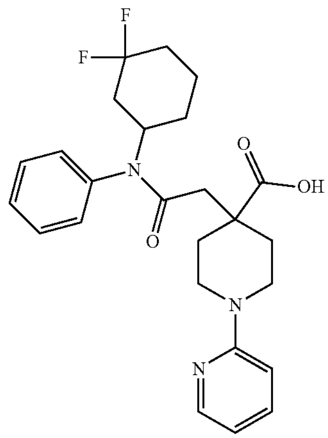 [SMILES: O=C(CC1(C(=O)O)CCN(c2ccccn2)CC1)N(c1ccccc1)C1CCCC(F)(F)C1] | 4-(2-((3,3-difluorocyclohexyl)(phenyl)amino)-2-oxoethyl)-1-(pyridin-2-yl)piperidine-4-carboxylic acid | 458.3 |
| 74A (isomer 1) | 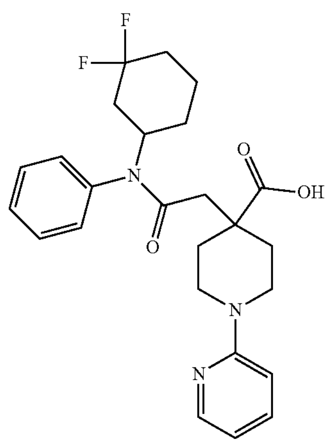 [SMILES: O=C(CC1(C(=O)O)CCN(c2ccccn2)CC1)N(c1ccccc1)C1CCCC(F)(F)C1] | 4-(2-((3,3-difluorocyclohexyl)(phenyl)amino)-2-oxoethyl)-1-(pyridin-2-yl)piperidine-4-carboxylic acid | 458.4 |
| 74B (isomer 2) | 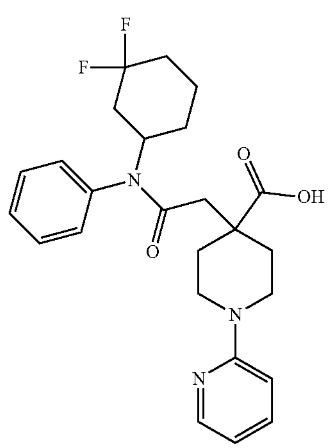 [SMILES: O=C(CC1(C(=O)O)CCN(c2ccccn2)CC1)N(c1ccccc1)C1CCCC(F)(F)C1] | 4-(2-((3,3-difluorocyclohexyl)(phenyl)amino)-2-oxoethyl)-1-(pyridin-2-yl)piperidine-4-carboxylic acid | 458.55 |

TABLE I-continued

| Example No. | Structure | Name | ES/MS (m/z) (M + H) |
|---|---|---|---|
| 75 | 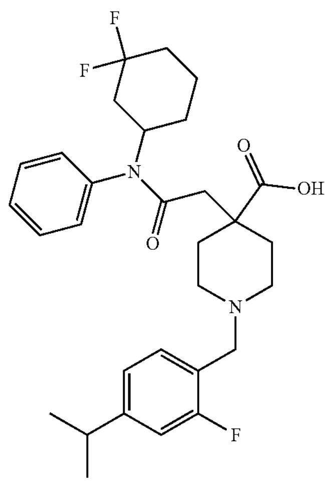 [SMILES: CC(C)c1ccc(CN2CCC(CC(=O)N(c3ccccc3)C3CCCC(F)(F)C3)(C(=O)O)CC2)c(F)c1] | 4-(2-((3,3-difluorocyclohexyl)(phenyl)amino)-2-oxoethyl)-1-(2-fluoro-4-isopropylbenzyl)piperidine-4-carboxylic acid | 531.5 |
| 75A (isomer 1) | 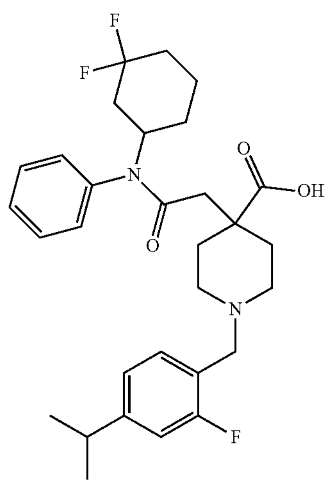 [SMILES: CC(C)c1ccc(CN2CCC(CC(=O)N(c3ccccc3)C3CCCC(F)(F)C3)(C(=O)O)CC2)c(F)c1] | 4-(2-((3,3-difluorocyclohexyl)(phenyl)amino)-2-oxoethyl)-1-(2-fluoro-4-isopropylbenzyl)piperidine-4-carboxylic acid | 531.5 |
| 75B (isomer 2) | 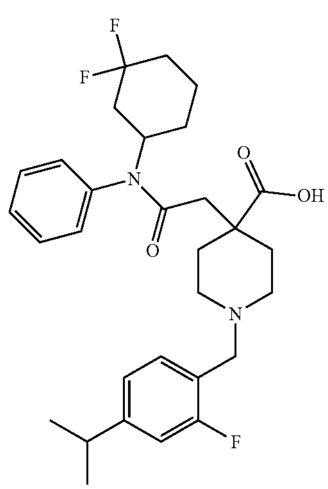 [SMILES: CC(C)c1ccc(CN2CCC(CC(=O)N(c3ccccc3)C3CCCC(F)(F)C3)(C(=O)O)CC2)c(F)c1] | 4-(2-((3,3-difluorocyclohexyl)(phenyl)amino)-2-oxoethyl)-1-(2-fluoro-4-isopropylbenzyl)piperidine-4-carboxylic acid | 531.5 |

TABLE I-continued

| Example No. | Structure | Name | ES/MS (m/z) (M + H) |
|---|---|---|---|
| 76 | 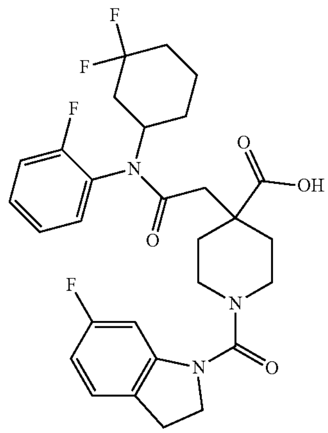 [SMILES: O=C(N1CCC(CC(=O)N(c2ccccc2F)C2CCCC(F)(F)C2)(C(=O)O)CC1)N1CCc2ccc(F)cc21] | 4-(2-((3,3-difluorocyclohexyl)(2-fluorophenyl)amino)-2-oxoethyl)-1-(6-fluoroindoline-1-carbonyl)piperidine-4-carboxylic acid | 562.5 |
| 77 | 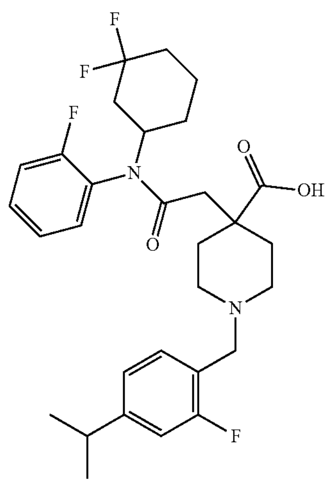 [SMILES: CC(C)c1ccc(CN2CCC(CC(=O)N(c3ccccc3F)C3CCCC(F)(F)C3)(C(=O)O)CC2)c(F)c1] | 4-(2-((3,3-difluorocyclohexy])(2-fluorophenyl)amino)-2-oxoethyl)-1-(2-fluoro-4-isopropylbenzyl)piperidine-4-carboxylic acid | 549.5 |
| 78 | 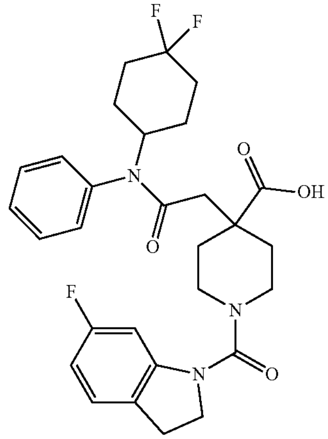 [SMILES: O=C(N1CCC(CC(=O)N(c2ccccc2)C2CCC(F)(F)CC2)(C(=O)O)CC1)N1CCc2ccc(F)cc21] | 4-(2-((4,4-difluorocyclohexyl)(phenyl)amino)-2-oxoethyl)-1-(6-fluoroindoline-1-carbonyl)piperidine-4-carboxylic acid | 544.5 |

TABLE I-continued

| Example No. | Structure | Name | ES/MS (m/z) (M + H) |
|---|---|---|---|
| 79 | 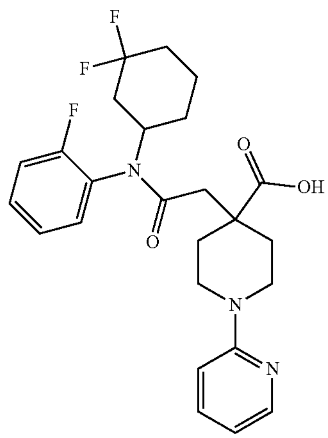 [SMILES: O=C(CC1(C(=O)O)CCN(c2ccccn2)CC1)N(c1ccccc1F)C1CCCC(F)(F)C1] | 4-(2-((3,3-difluorocyclohexyl)(2-fluorophenyl)amino)-2-oxoethyl)-1-(pyridin-2-yl)piperidine-4-carboxylic acid | 476.3 |
| 80 | 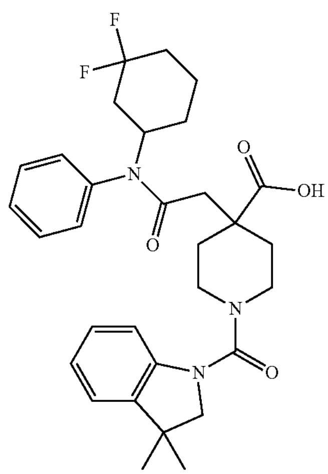 [SMILES: CC1(C)CN(C(=O)N2CCC(CC(=O)N(c3ccccc3)C3CCCC(F)(F)C3)(C(=O)O)CC2)c2ccccc21] | 4-(2-((3,3-difluorocyclohexyl)(phenyl)amino)-2-oxoethyl)-1-(3,3-dimethylindoline-1-carbonyl)piperidine-4-carboxylic acid | 554.5 |
| 80A (isomer 1) | 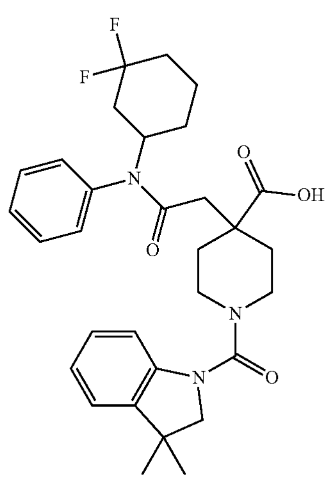 [SMILES: CC1(C)CN(C(=O)N2CCC(CC(=O)N(c3ccccc3)C3CCCC(F)(F)C3)(C(=O)O)CC2)c2ccccc21] | 4-(2-((3,3-difluorocyclohexyl)(phenyl)amino)-2-oxoethyl)-1-(3,3-dimethylindoline-1-carbonyl)piperidine-4-carboxylic acid | 554.5 |

TABLE I-continued

| Example No. | Structure | Name | ES/MS (m/z) (M + H) |
|---|---|---|---|
| 80B (isomer 2) | 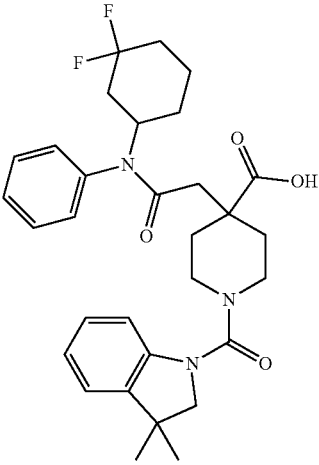 | 4-(2-((3,3-difluorocyclohexyl)(phenyl)amino)-2-oxoethyl)-1-(3,3-dimethylindoline-1-carbonyl)piperidine-4-carboxylic acid | 554.5 |
| 81 | 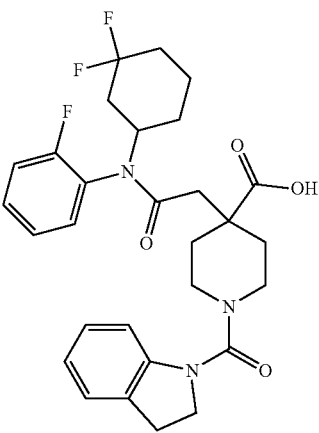 [SMILES: O=C(N1CCC(CC(=O)N(c2ccccc2F)C2CCCC(F)(F)C2)(C(=O)O)CC1)N1CCc2ccccc21] | 4-(2-((3,3-difluorocyclohexyl)(2-fluorophenyl)amino)-2-oxoethyl)-1-(indoline-1-carbonyl)piperidine-4-carboxylic acid | 544.5 |
| 82A (isomer 1) | 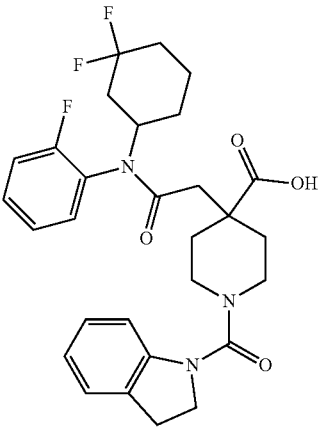 [SMILES: O=C(N1CCC(CC(=O)N(c2ccccc2F)C2CCCC(F)(F)C2)(C(=O)O)CC1)N1CCc2ccccc21] | 4-(2-((3,3-difluorocyclohexyl)(2-fluorophenyl)amino)-2-oxoethyl)-1-(indoline-1-carbonyl)piperidine-4-carboxylic acid | 544.5 |

TABLE I-continued

| Example No. | Structure | Name | ES/MS (m/z) (M + H) |
|---|---|---|---|
| 82B (isomer 2) | 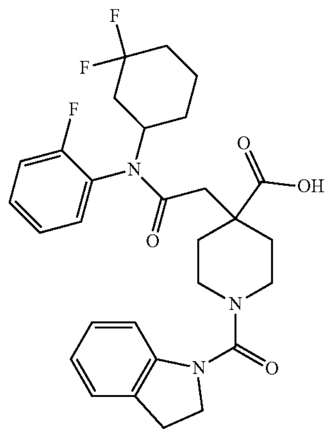 [SMILES: O=C(N1CCC(CC(=O)N(c2ccccc2F)C2CCCC(F)(F)C2)(C(=O)O)CC1)N1CCc2ccccc21] | 4-(2-((3,3-difluorocyclohexy])(2-fluorophenyl)amino)-2-oxoethyl)-1-(indoline-1-carbonyl)piperidine-4-carboxylic acid | 544.5 |
| 83 | 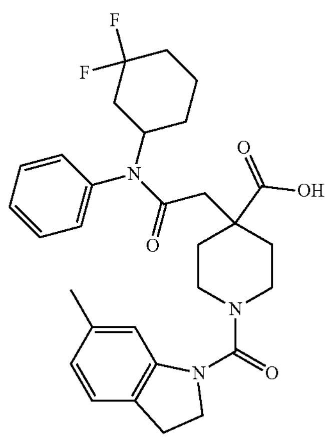 [SMILES: Cc1ccc2c(c1)N(C(=O)N1CCC(CC(=O)N(c3ccccc3)C3CCCC(F)(F)C3)(C(=O)O)CC1)CC2] | 4-(2-((3,3-difluorocyclohexyl)(phenyl)amino)-2-oxoethyl)-1-(6-methylindoline-1-carbonyl)piperidine-4-carboxylic acid | 540.3 |
| 83A (isomer 1) | 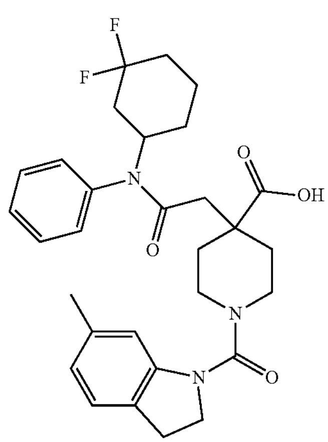 [SMILES: Cc1ccc2c(c1)N(C(=O)N1CCC(CC(=O)N(c3ccccc3)C3CCCC(F)(F)C3)(C(=O)O)CC1)CC2] | 4-(2-((3,3-difluorocyclohexyl)(phenyl)amino)-2-oxoethyl)-1-(6-methylindoline-1-carbonyl)piperidine-4-carboxylic acid | 540.2 |

TABLE I-continued

| Example No. | Structure | Name | ES/MS (m/z) (M + H) |
|---|---|---|---|
| 83B (isomer 2) | 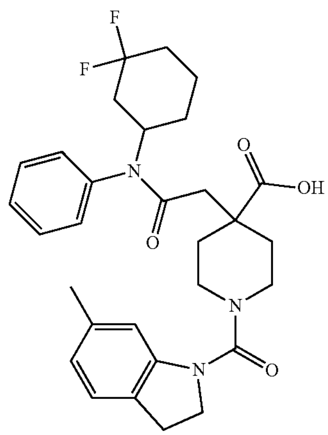 [SMILES: Cc1ccc2c(c1)N(C(=O)N1CCC(CC(=O)N(c3ccccc3)C3CCCC(F)(F)C3)(C(=O)O)CC1)CC2] | 4-(2-((3,3-difluorocyclohexyl)(phenyl)amino)-2-oxoethyl)-1-(6-methylindoline-1-carbonyl)piperidine-4-carboxylic acid | 540.2 |
| 84 | 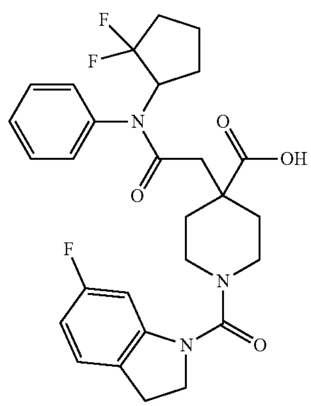 [SMILES: O=C(N1CCC(CC(=O)N(c2ccccc2)C2CCCC2(F)F)(C(=O)O)CC1)N1CCc2ccc(F)cc21] | 4-(2-((2,2-difluorocyclopentyl)(phenyl)amino)-2-oxoethyl)-1-(6-fluoroindoline-1-carbonyl)piperidine-4-carboxylic acid | 530.4 |
| 85 | 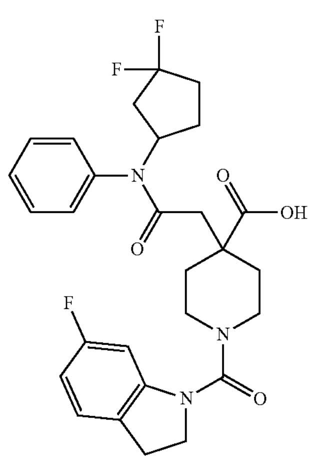 [SMILES: O=C(N1CCC(CC(=O)N(c2ccccc2)C2CCC(F)(F)C2)(C(=O)O)CC1)N1CCc2ccc(F)cc21] | 4-(2-((3,3-difluorocyclopentyl)(phenyl)amino)-2-oxoethyl)-1-(6-fluoroindoline-1-carbonyl)piperidine-4-carboxylic acid | 530.4 |

TABLE I-continued

| Example No. | Structure | Name | ES/MS (m/z) (M + H) |
|---|---|---|---|
| 86 | 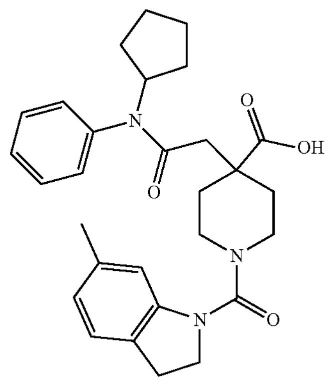 [SMILES: Cc1ccc2c(c1)N(C(=O)N1CCC(CC(=O)N(c3ccccc3)C3CCCC3)(C(=O)O)CC1)CC2] | 4-(2-(cyclopentyl(phenyl)amino)-2-oxoethyl)-1-(6-methylindoline-1-carbonyl)piperidine-4-carboxylic acid | 490.3 |
| 87 | 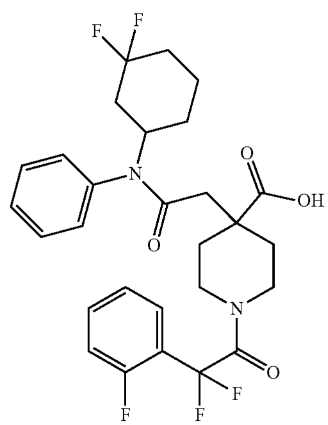 [SMILES: O=C(CC1(C(=O)O)CCN(C(=O)C(F)(F)c2ccccc2F)CC1)N(c1ccccc1)C1CCCC(F)(F)C1] | 1-(2,2-difluoro-2-(2-fluorophenyl)acetyl)-4-(2-((3,3-difluorocyclohexyl)(phenyl)amino)-2-oxoethyl)piperidine-4-carboxylic acid | 553.4 |
| 88 | 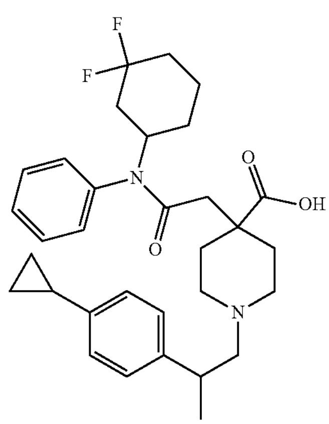 [SMILES: CC(CN1CCC(CC(=O)N(c2ccccc2)C2CCCC(F)(F)C2)(C(=O)O)CC1)c1ccc(C2CC2)cc1] | 1-(2-(4-cyclopropylphenyl)propyl)-4-(2-((3,3-difluorocyclohexyl)(phenyl)amino)-2-oxoethyl)piperidine-4-carboxylic acid | 539.4 |
| 89 | 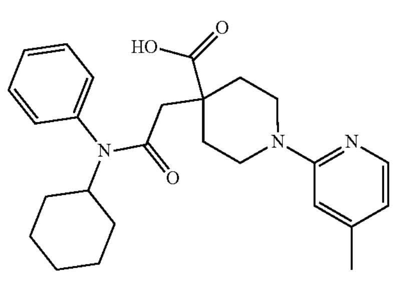 [SMILES: Cc1ccnc(N2CCC(CC(=O)N(c3ccccc3)C3CCCCC3)(C(=O)O)CC2)c1] | 4-(2-(cyclohexyl(phenyl)amino)-2-oxoethyl)-1-(4-methylpyridin-2-yl)piperidine-4-carboxylic acid | 436.2 |

TABLE I-continued

| Example No. | Structure | Name | ES/MS (m/z) (M + H) |
|---|---|---|---|
| 90 | 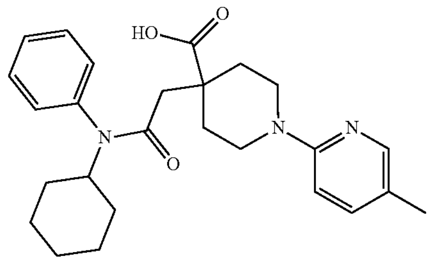 [SMILES: Cc1ccc(N2CCC(CC(=O)N(c3ccccc3)C3CCCCC3)(C(=O)O)CC2)nc1] | 4-(2-(cyclohexyl(phenyl)amino)-2-oxoethyl)-1-(5-methylpyridin-2-yl)piperidine-4-carboxylic acid | 436.2 |
| 91 | 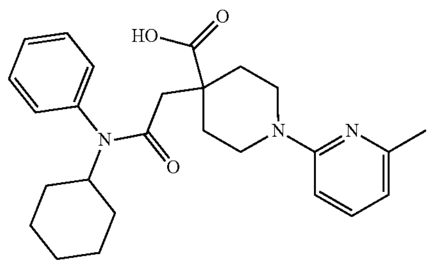 [SMILES: Cc1cccc(N2CCC(CC(=O)N(c3ccccc3)C3CCCCC3)(C(=O)O)CC2)n1] | 4-(2-(cyclohexyl(phenyl)amino)-2-oxoethyl)-1-(6-methylpyridin-2-yl)piperidine-4-carboxylic acid | 436.2 |
| 92 | 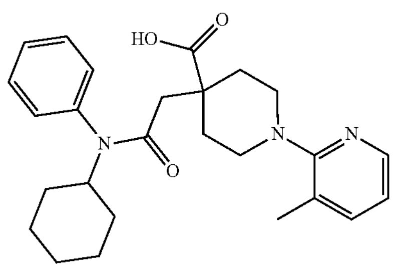 [SMILES: Cc1cccnc1N1CCC(CC(=O)N(c2ccccc2)C2CCCCC2)(C(=O)O)CC1] | 4-(2-(cyclohexyl(phenyl)amino)-2-oxoethyl)-1-(3-methylpyridin-2-yl)piperidine-4-carboxylic acid | 436.2 |
| 93 | 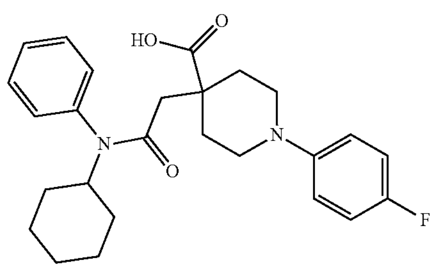 [SMILES: O=C(CC1(C(=O)O)CCN(c2ccc(F)cc2)CC1)N(c1ccccc1)C1CCCCC1] | 4-(2-(cyclohexyl(phenyl)amino)-2-oxoethyl)-1-(4-fluorophenyl)piperidine-4-carboxylic acid | 439.2 |
| 94 | 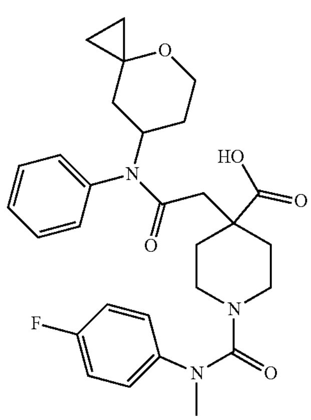 [SMILES: CN(C(=O)N1CCC(CC(=O)N(c2ccccc2)C2CCOC3(CC3)C2)(C(=O)O)CC1)c1ccc(F)cc1] | 1-((4-fluorophenyl)(methyl)carbamoyl)-4-(2-oxo-2-(phenyl(4-oxaspiro[2.5]octan-7-yl)amino)ethyl)piperidine-4-carboxylic acid | 524.5 |

TABLE I-continued

| Example No. | Structure | Name | ES/MS (m/z) (M + H) |
|---|---|---|---|
| 95 | 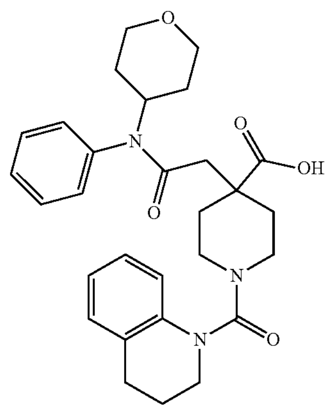 [SMILES: O=C(N1CCC(CC(=O)N(c2ccccc2)C2CCOCC2)(C(=O)O)CC1)N1CCCc2ccccc21] | 4-(2-oxo-2-(phenyl(tetrahydro-2H-pyran-4-yl)amino)ethyl)-1-(1,2,3,4-tetrahydroquinoline-1-carbonyl)piperidine-4-carboxylic acid | 506.5 |
| 96 | 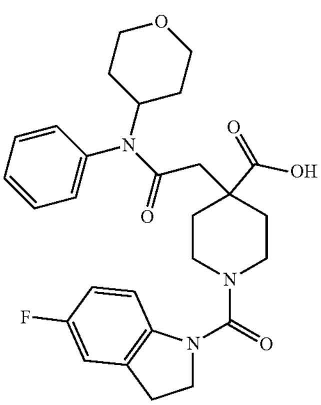 [SMILES: O=C(N1CCC(CC(=O)N(c2ccccc2)C2CCOCC2)(C(=O)O)CC1)N1CCc2cc(F)ccc21] | 1-(5-fluoroindoline-1-carbonyl)-4-(2-oxo-2-(phenyl(tetrahydro-2H-pyran-4-yl)amino)ethyl)piperidine-4-carboxylic acid | 510.2 |
| 97 | 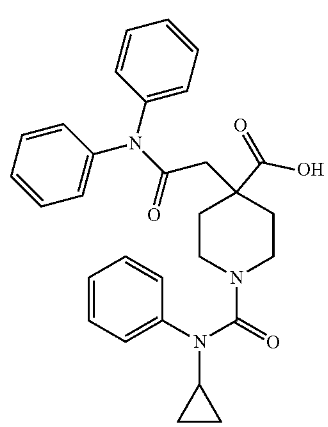 [SMILES: O=C(CC1(C(=O)O)CCN(C(=O)N(c2ccccc2)C2CC2)CC1)N(c1ccccc1)c1ccccc1] | 1-(cyclopropyl(phenyl)carbamoyl)-4-(2-(diphenylamino)-2-oxoethyl)piperidine-4-carboxylic acid | |

TABLE I-continued

| Example No. | Structure | Name | ES/MS (m/z) (M + H) |
|---|---|---|---|
| 98 | 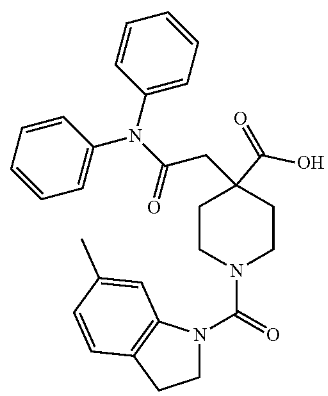 [SMILES: Cc1ccc2c(c1)N(C(=O)N1CCC(CC(=O)N(c3ccccc3)c3ccccc3)(C(=O)O)CC1)CC2] | 4-(2-(diphenylamino)-2-oxoethyl)-1-(6-methylindoline-1-carbonyl)piperidine-4-carboxylic acid | 498.4 |
| 99 | 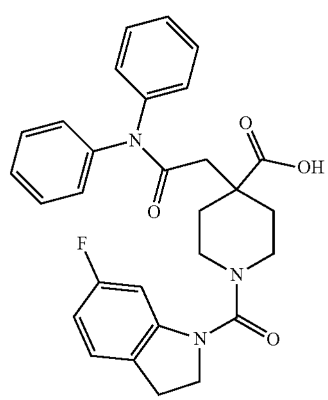 [SMILES: O=C(N1CCC(CC(=O)N(c2ccccc2)c2ccccc2)(C(=O)O)CC1)N1CCc2ccc(F)cc21] | 4-(2-(diphenylamino)-2-oxoethyl)-1-(6-fluoroindoline-1-carbonyl)piperidine-4-carboxylic acid | 502.4 |
| 100 | 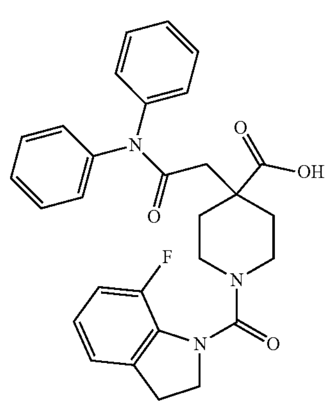 [SMILES: O=C(N1CCC(CC(=O)N(c2ccccc2)c2ccccc2)(C(=O)O)CC1)N1CCc2cccc(F)c21] | 4-(2-(diphenylamino)-2-oxoethyl)-1-(7-fluoroindoline-1-carbonyl)piperidine-4-carboxylic acid | 502.4 |

TABLE I-continued

| Example No. | Structure | Name | ES/MS (m/z) (M + H) |
|---|---|---|---|
| 101 | 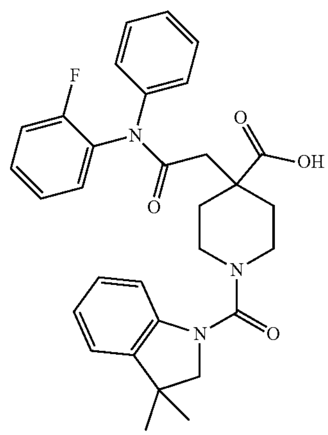 [SMILES: CC1(C)CN(C(=O)N2CCC(CC(=O)N(c3ccccc3)c3ccccc3F)(C(=O)O)CC2)c2ccccc21] | 1-(3,3-dimethylindoline-1-carbonyl)-4-(2-((2-fluorophenyl)(phenyl)amino)-2-oxoethyl)piperidine-4-carboxylic acid | 530.5 |
| 102 | 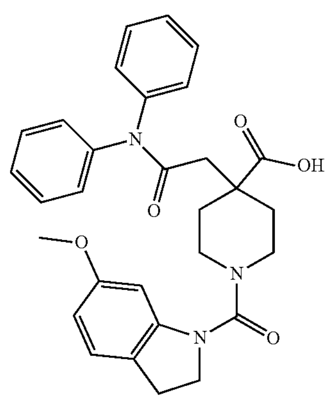 [SMILES: COc1ccc2c(c1)N(C(=O)N1CCC(CC(=O)N(c3ccccc3)c3ccccc3)(C(=O)O)CC1)CC2] | 4-(2-(diphenylamino)-2-oxoethyl)-1-(6-methoxyindoline-1-carbonyl)piperidine-4-carboxylic acid | 514.5 |
| 103 | 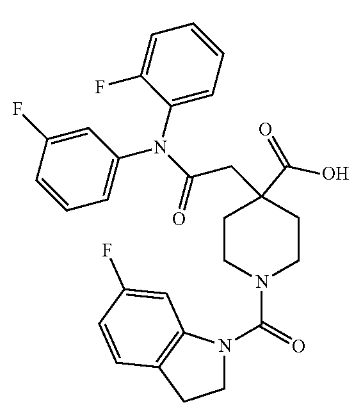 [SMILES: O=C(N1CCC(CC(=O)N(c2cccc(F)c2)c2ccccc2F)(C(=O)O)CC1)N1CCc2ccc(F)cc21] | 1-(6-fluoroindoline-1-carbonyl)-4-(2-((2-fluorophenyl)(3-fluorophenyl)amino)-2-oxoethyl)piperidine-4-carboxylic acid | 538.4 |

TABLE I-continued

| Example No. | Structure | Name | ES/MS (m/z) (M + H) |
|---|---|---|---|
| 104 | 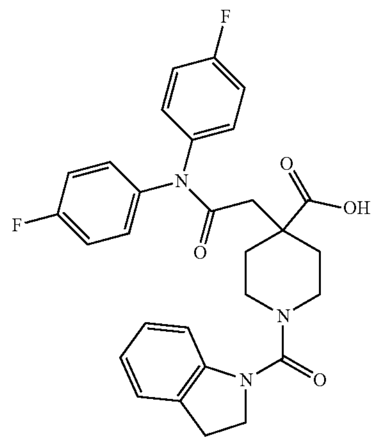 [SMILES: O=C(N1CCC(CC(=O)N(c2ccc(F)cc2)c2ccc(F)cc2)(C(=O)O)CC1)N1CCc2ccccc21] | 4-(2-(bis(4-fluorophenyl)amino)-2-oxoethyl)-1-(indoline-1-carbonyl)piperidine-4-carboxylic acid | 520.4 |
| 105 | 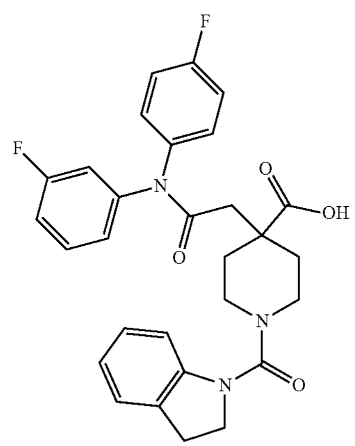 [SMILES: O=C(N1CCC(CC(=O)N(c2ccc(F)cc2)c2cccc(F)c2)(C(=O)O)CC1)N1CCc2ccccc21] | 4-(2-((3-fluorophenyl)(4-fluorophenyl)amino)-2-oxoethyl)-1-(indoline-1-carbonyl)piperidine-4-carboxylic acid | 520.4 |
| 106 | 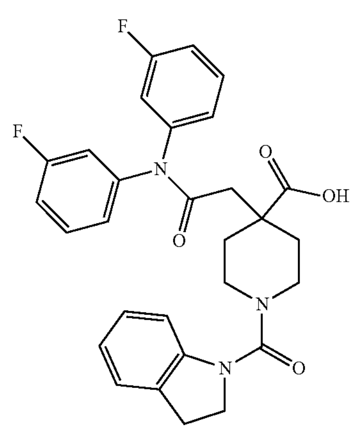 [SMILES: O=C(N1CCC(CC(=O)N(c2cccc(F)c2)c2cccc(F)c2)(C(=O)O)CC1)N1CCc2ccccc21] | 4-(2-(bis (3-fluorophenyl)amino)-2-oxoethyl)-1-(indoline-1-carbonyl)piperidine-4-carboxylic acid | 520.4 |

TABLE I-continued

| Example No. | Structure | Name | ES/MS (m/z) (M + H) |
|---|---|---|---|
| 107 | 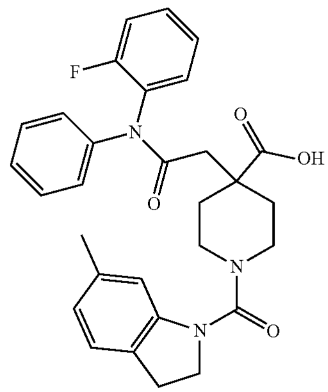 [SMILES: Cc1ccc2c(c1)N(C(=O)N1CCC(CC(=O)N(c3ccccc3)c3ccccc3F)(C(=O)O)CC1)CC2] | 4-(2-((2-fluorophenyl)(phenyl)amino)-2-oxoethyl)-1-(6-methylindoline-1-carbonyl)piperidine-4-carboxylic acid | 516.5 |
| 108 | 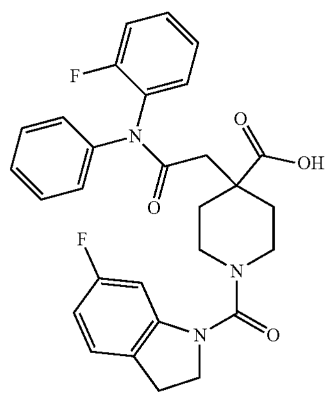 [SMILES: O=C(N1CCC(CC(=O)N(c2ccccc2)c2ccccc2F)(C(=O)O)CC1)N1CCc2ccc(F)cc21] | 1-(6-fluoroindoline-1-carbonyl)-4-(2-((2-fluorophenyl)(phenyl)amino)-2-oxoethyl)piperidine-4-carboxylic acid | 520.4 |
| 109 | 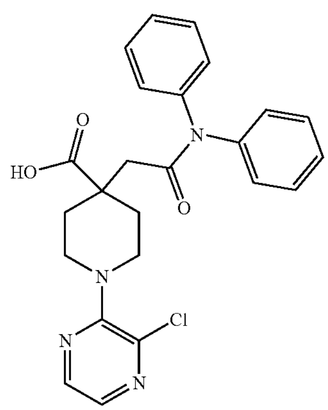 [SMILES: O=C(CC1(C(=O)O)CCN(c2nccnc2Cl)CC1)N(c1ccccc1)c1ccccc1] | 1-(3-chloropyrazin-2-yl)-4-(2-(diphenylamino)-2-oxoethyl)piperidine-4-carboxylic acid | 451.0 |
| 110 | 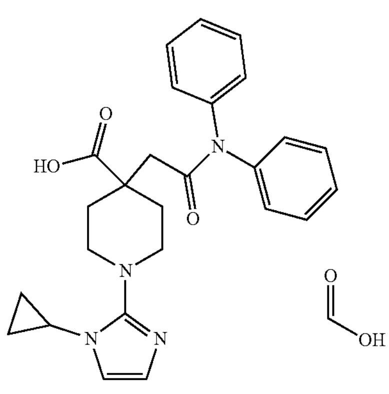 [SMILES: O=C(CC1(C(=O)O)CCN(c2nccn2C2CC2)CC1)N(c1ccccc1)c1ccccc1 ; O=CO] | 1-(1-cyclopropyl-1H-imidazol-2-yl)-4-(2-(diphenylamino)-2-oxoethyl)piperidine-4-carboxylic acid--formic acid | 445.1 (M + H − HCO2H) |

TABLE I-continued

| Example No. | Structure | Name | ES/MS (m/z) (M + H) |
|---|---|---|---|
| 111 | 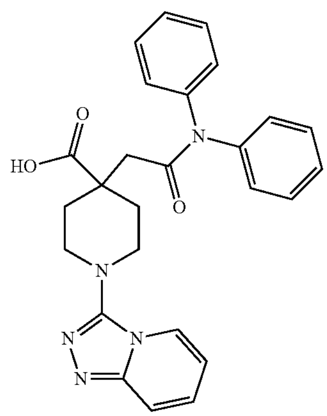 [SMILES: O=C(CC1(C(=O)O)CCN(c2nnc3ccccn23)CC1)N(c1ccccc1)c1ccccc1] | 1-([1,2,4]triazolo[4,3-a]pyridin-3-yl)-4-(2-(diphenylamino)-2-oxoethyl)piperidine-4-carboxylic acid | 456.4 |
| 112 | 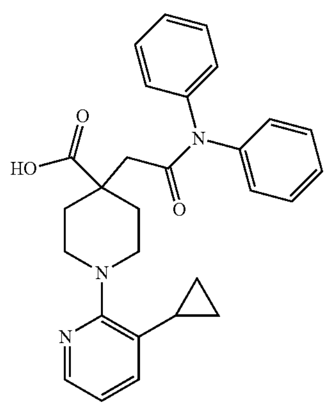 [SMILES: O=C(CC1(C(=O)O)CCN(c2ncccc2C2CC2)CC1)N(c1ccccc1)c1ccccc1] | 1-(3-cyclopropylpyridin-2-yl)-4-(2-(diphenylamino)-2-oxoethyl)piperidine-4-carboxylic acid | 456.4 |

In some embodiments, the present disclosure provides a compound being an isotopic derivative (e.g., isotopically labeled compound) of any one of the compounds disclosed herein.

In some embodiments, the compound is an isotopic derivative of any one of the compounds described in Table I and pharmaceutically acceptable salts thereof.

In some embodiments, the compound is an isotopic derivative of any one of the compounds described in Table I.

It is understood that the isotopic derivative can be prepared using any of a variety of art-recognized techniques. For example, the isotopic derivative can generally be prepared by carrying out the procedures disclosed in the schemes and/or in the examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

In some embodiments, the compound is a deuterium labeled compound of any one of the compounds described in Table I and pharmaceutically acceptable salts thereof.

In some embodiments, the compound is a deuterium labeled compound of any one of the compounds described in Table I.

It is understood that the deuterium labeled compound comprises a deuterium atom having an abundance of deuterium that is substantially greater than the natural abundance of deuterium, which is about 0.015%.

It is understood that the deuterium labeled compound can be prepared using any of a variety of art-recognized techniques. For example, the deuterium labeled compound can generally be prepared by carrying out the procedures disclosed in the schemes and/or in the examples described herein, by substituting a deuterium labeled reagent for a non-deuterium labeled reagent.

A compound of the invention or a pharmaceutically acceptable salt thereof that contains the aforementioned deuterium atom(s) is within the scope of the invention.

Further, substitution with deuterium (i.e., $^2$H) may afford certain therapeutic advantages resulting from greater metabolic stability (e.g., increased in vivo half-life or reduced dosage requirements).

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. The references cited herein are not admitted to be prior art to the claimed invention. In the case of conflict, the present specification, including definitions, will control. In addition, the materials, methods, and examples are illustrative only and are not intended to be limiting.

Other features and advantages of the disclosure will be apparent from the following detailed description and claims.

For the avoidance of doubt, it is to be understood that, where in this specification a group is qualified by "described herein", the said group encompasses the first occurring and broadest definition as well as each and all of the particular definitions for that group.

A suitable pharmaceutically acceptable salt of a compound of the disclosure is, for example, an acid addition salt with, for example, an inorganic or organic acid, for example hydrochloric, hydrobromic, sulfuric, phosphoric, trifluoroacetic, formic, citric methane sulfonate, or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine, or tris(2hydroxyethyl)amine.

It will be understood that the compounds of the present disclosure and any pharmaceutically acceptable salts thereof, comprise stereoisomers, mixtures of stereoisomers, and polymorphs of all isomeric forms of said compounds.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J. Chem. Educ. 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however because of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent, and pH. The concept of tautomers that are interconvertible by tautomerizations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are nonsuperimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the way the molecule rotates the plane of polarized light and designated as dextrorotatory or levorotatory (i.e., as (+) or (−)isomers respectively). A chiral compound can exist as either individual enantiomer or as a mixture thereof. A mixture containing equal proportions of the enantiomers is called a "racemic mixture".

The compounds of this disclosure may possess one or more asymmetric centers; such compounds can therefore be produced as individual (R) or (S) stereoisomers or as mixtures thereof. Unless indicated otherwise, the description or naming of a particular compound in the specification and claims is intended to include both individual enantiomers and mixtures, racemic or otherwise, thereof. Flat bond in chemical structures are intended to include any isomer (e.g., enantiomer or diastereomer), and mixtures thereof. The methods for the determination of stereochemistry and the separation of stereoisomers are well known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centers (E and Z isomers). It is to be understood that the present disclosure encompasses all optical, diastereoisomers and geometric isomers and mixtures thereof that possess inflammasome inhibitory activity.

Example compounds 1-112 of the present invention represent chiral compounds, and as described in the Examples herein, have been made and tested as individual stereoisomers or as racemic mixtures. (See, e.g., Examples 2-5 below). The characterization and determination of the absolute stereochemistry of the individual stereoisomers of the Examples provided herein is within the skill of the art for the ordinary artisan, and methods for such determinations are well known in medicinal chemistry literature (See e.g *Chiral Analysis* (*Second Edition*) *Advances in Spectroscopy, Chromatography and Emerging Methods,* 2018). For example, absolute configurations are commonly determined by NMR on the basis of the use of CDAs: diastereomeric derivatives involving covalent binding between the chiral auxiliary and the enantiomeric substrates adopt a preferred conformation which can be predicted on the basis of the differential shielding that is caused by an aromatic ring incorporated into the chiral discriminating reagent.

The present disclosure also encompasses compounds of the disclosure as defined herein which comprise one or more isotopic substitutions.

It is to be understood that the compounds of any formula described herein include the compounds themselves, as well as their salts, and their solvates, if applicable. A salt, for example, can be formed between an anion and a positively charged group (e.g., amino) on a substituted compound disclosed herein.

"Pharmaceutically acceptable salts" or "a pharmaceutically acceptable salt" refers to the relatively non-toxic, inorganic and organic salt or salts of the compound of the present invention. It will be understood by the skilled artisan that compounds of the present invention can form salts. The compounds of the present invention contain basic heterocycles, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts", *Journal of Pharmaceutical Sciences*, Vol 66, No. 1, January 1977.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water, the solvate formed is a hydrate; and if the solvent is alcohol, the solvate formed is an alcoholate. Hydrates are formed by the combination of one or more molecules of water with one molecule of the substance in which the water retains its molecular state as $H_2O$.

It is also to be understood that certain compounds of the present disclosure may exhibit polymorphism, and that the disclosure encompasses all such forms, or mixtures thereof. It is generally known that crystalline materials may be analyzed using techniques known to a skilled artisan such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NTR) spectroscopy, solution and/or solid state nuclear magnetic resonance spectroscopy. The water content of such crystalline materials may be determined by Karl Fischer analysis.

Compounds of the present disclosure may exist in a number of different tautomeric forms and references to compounds of the present disclosure include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

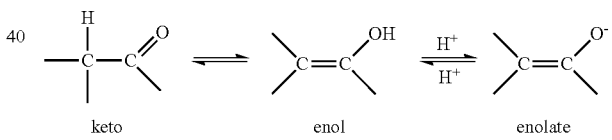

keto          enol          enolate

Compounds of the present disclosure containing an amine function may also form N-oxides. A reference herein to a compound disclosed herein that contains an amine function also includes the N-oxide. Where a compound contains several amine functions, one or more than one nitrogen atom may be oxidized to form an N-oxide. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a peracid (e.g., a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of the present disclosure may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the sulfonylurea group in a compound of the any one of the formulae disclosed herein.

Accordingly, the present disclosure includes those compounds of the present disclosure as defined hereinbefore when made available by organic synthesis and when made available within the human or animal body by way of cleavage of a prodrug thereof. Accordingly, the present disclosure includes those compounds of the present disclosure that are produced by organic synthetic means and also such compounds that are produced in the human or animal body by way of metabolism of a precursor compound, that is a compound of the present disclosure may be a synthetically produced compound or a metabolically produced compound.

A suitable pharmaceutically acceptable prodrug of a compound of the present disclosure is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of the present disclosure that possesses a hydroxy group is, for example, an in vivo cleavable ester or ether thereof. An in vivo cleavable ester or ether of a compound of the present disclosure containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N-($C_1$-$C_6$ alkyl)2carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of the present disclosure that possesses a carboxy group is, for example, an in vivo cleavable amide thereof, for example an amide formed with an amine such as ammonia, a $C_1$-$C_4$alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of the present disclosure that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl, and 4-($C_1$-$C_4$ alkyl)piperazin-1-ylmethyl.

The in vivo effects of a compound of the present disclosure may be exerted in part by one or more metabolites that are formed within the human or animal body after administration of a compound of the present disclosure. As stated hereinbefore, the in vivo effects of a compound of the present disclosure may also be exerted by way of metabolism of a precursor compound (a prodrug).

As used herein, the term "about" refers to a range covering any normal fluctuations appreciated by one of ordinary skill in the relevant art. In some embodiments, the term "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted" is understood to mean that a given chemical moiety (e.g., an alkyl group) can (but is not required to) be bonded to other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain, be bounded to a halogen atom, a hydroxyl group, or any other substituent described herein. Thus, the term "optionally substituted" means that a given chemical moiety has the potential to contain other functional groups but does not necessarily have any further functional groups. The substituents can themselves be optionally substituted.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like.

As used herein, the term "heteroaryl" is intended to include a stable 5-, 6-, or 7-membered monocyclic or 7-, 8-, 9-, 10-, 11—or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl).

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthyridine, indole, benzofuran, purine, deazapurine, indolizine.

As used herein, the term "halo" or "halogen" refers to fluoro, chloro, bromo and iodo.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups.

As used herein, the term "cyano" refers to a substituent having a carbon atom joined to a nitrogen atom by a triple bond, i.e., C≡N.

As used herein, the term "oxo" is understood to describe a carbonyl group (i.e., C(O)).

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having a disease or disorder disclosed herein. A subject in need thereof can also be one who has (e.g., is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that doesn't respond or hasn't yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the terms "treatment", "treating", or "mitigating" are intended to refer to all processes wherein there may be a slowing, interrupting, arresting, controlling, or stopping of the progression of an existing disorder and/or a reduction in symptoms thereof, but does not necessarily indicate a total elimination of all symptoms. As used herein, the term "effective amount" of a compound of formula (I) refers to an amount, that is a dosage, which is effective in inhibiting an $AT_2R$ mediated response in a subject. An "effective amount" is determined as an amount that can treat or eliminate the signs and symptoms of moderate to severe psoriasis in the subject, as compared to the subject when untreated. In determining an effective amount or dose of a compound of formula (I), a number of factors are considered, including, but not limited to the compound to be administered and its particular formulation; the subject's size, age, and general health; the degree of involvement or the severity of the disorder; the response of the individual subject; the mode of administration; and other relevant circumstances.

Compounds of the present inventions are $AT_2R$ antagonists, and upon administration to a subject in need thereof, may provide therapeutic benefits while avoiding certain problems associated with other $AT_2R$ antagonists. As such, compounds of the present invention are believed to be useful for the treatment of conditions in which $AT_2R$ is implicated, such as pain. In some embodiments, the pain in neuropathic pain.

The present disclosure provides a pharmaceutical composition comprising a compound and/or salt of formula (I), and a pharmaceutically acceptable carrier, diluent, or excipient. In some embodiments, the present disclosure provides a pharmaceutical composition comprising a compound of formula (I), and a pharmaceutically acceptable carrier, diluent, or excipient. In some embodiments, the present disclosure provides a pharmaceutical composition comprising a salt of a compound of formula (I), and a pharmaceutically acceptable carrier, diluent, or excipient. In some embodiments, the pain is neuropathic pain, inflammatory pain, nociceptive pain, mixed nociceptive and neuropathic pain, visceral pain, post-operative pain, post-herpetic pain, traumatic pain, phantom-limb pain, fibromyalgia syndrome (FMS), back pain, cancer pain, chemotherapy-induced peripheral neuropathy (CIPN), or osteoarthritic (OA) pain. In some embodiments, the neuropathic pain is diabetic peripheral neuropathic pain (DPNP). In some embodiments, the back pain is chronic low back pain (CLBP). In some embodiments, the visceral pain is pain associated with irritable bowel syndrome (IBS), bladder pain, prostate pain, or vulvodynia.

The present disclosure provides a method of treating a disease or disorder in which $AT_2R$ is implicated. In some embodiments, the present disclosure provides a method of treating pain, comprising administering to a subject in need thereof an effective amount of a compound of formula (I), or a pharmaceutically acceptable salt thereof. In some embodiments, the present disclosure provides a method of treating neuropathic pain, inflammatory pain, nociceptive pain, mixed nociceptive and neuropathic pain, visceral pain, post-operative pain, post-herpetic pain, traumatic pain, phantom-limb pain, fibromyalgia syndrome (FMS), back pain, cancer pain, chemotherapy-induced peripheral neuropathy (CIPN), or osteoarthritic (OA) pain, comprising administering to a subject in need thereof an effective amount of a compound of formula (I), or a pharmaceutically acceptable salt thereof. In some embodiments, the present disclosure provides a method of treating neuropathic pain, comprising administering to a subject in need thereof an effective amount of a compound of formula (I), or a pharmaceutically acceptable salt thereof. In some embodiments, the present disclosure provides a method of treating fibromyalgia syndrome (FMS), comprising administering to a subject in need thereof an effective amount of a compound of formula (I), or a pharmaceutically acceptable salt thereof. In some embodiments, the present disclosure provides a method of treating osteoarthritic (OA) pain, comprising administering to a subject in need thereof an effective amount of a compound of formula (I), or a pharmaceutically acceptable salt thereof. In some embodiments, the present disclosure provides a method of treating diabetic peripheral neuropathic pain (DPNP), comprising administering to a subject in need thereof an effective amount of a compound of formula (I), or a pharmaceutically acceptable salt thereof. In some embodiments, the present disclosure provides a method of treating chronic low back pain (CLBP), comprising administering to a subject in need thereof an effective amount of a compound of formula (I), or a pharmaceutically acceptable salt thereof. In some embodiments, the present disclosure provides a method of treating chemotherapy-induced peripheral neuropathy (CIPN), comprising administering to a subject in need thereof an effective amount of a compound of formula (I), or a pharmaceutically acceptable salt thereof. In some embodiments, the present disclosure provides a method of treating visceral pain (e.g., pain associated with irritable bowel syndrome (IBS), bladder pain, prostate pain, or vulvodynia), comprising administering to a subject in need thereof an effective amount of a compound of formula (I), or a pharmaceutically acceptable salt thereof. The present disclosure provides a compound of formula (I), or a pharmaceutically acceptable salt thereof, for use in treating pain. The present disclosure provides a compound of formula (I), or a pharmaceutically acceptable salt thereof, for use in treating neuropathic pain, inflammatory pain, nociceptive pain, mixed nociceptive and neuropathic pain, visceral pain, post-operative pain, post-herpetic pain, traumatic pain, phantom-limb pain, fibromyalgia syndrome (FMS), back pain, cancer pain, chemotherapy-induced peripheral neuropathy (CIPN) or osteoarthritic (OA) pain. The present disclosure provides a compound of formula (I), or a pharmaceutically acceptable salt thereof, for use in treating neuropathic pain. In some embodiments, the present disclosure provides a compound of formula (I), or a pharmaceutically acceptable salt thereof, for use in treating fibromyalgia syndrome (FMS). In some embodiments, the present disclosure provides a compound of formula (I), or a pharmaceutically acceptable salt thereof, for use in treating osteoarthritic (OA) pain. In some embodiments, the present disclosure provides a compound of formula (I), or a pharmaceutically acceptable salt thereof, for use in treating diabetic peripheral neuropathic pain (DPNP). In some embodiments, the present disclosure provides a compound of formula (I), or a pharmaceutically acceptable salt thereof, for use in treating chronic low back pain (CLBP). In some embodiments, the present disclosure provides a compound of formula (I), or a pharmaceutically acceptable salt thereof, for use in treating chemotherapy-induced peripheral neuropathy (CIPN). In some embodiments, the present disclosure provides a compound of formula (I), or a pharmaceutically acceptable salt thereof, for use in treating visceral pain (e.g., pain associated with irritable bowel syndrome (IBS), bladder pain, prostate pain, or vulvodynia).

The present disclosure provides the use of a compound of formula (I), or a pharmaceutically acceptable salt thereof, in the manufacture of a medicament for the treatment of pain. The present disclosure provides the use of a compound of formula (I), or a pharmaceutically acceptable salt thereof, in the manufacture of a medicament for the treatment of neuropathic pain, inflammatory pain, nociceptive pain, mixed nociceptive and neuropathic pain, visceral pain, post-operative pain, post-herpetic pain, traumatic pain, phantom-limb pain, fibromyalgia syndrome, back pain, cancer pain, chemotherapy-induced peripheral neuropathy (CIPN), or osteoarthritic (OA) pain. The present disclosure provides the use of a compound of formula (I), or a pharmaceutically acceptable salt thereof, in the manufacture of a medicament for the treatment of neuropathic pain. In some embodiments, the present disclosure provides the use of a compound of formula (I), or a pharmaceutically acceptable salt thereof, in the manufacture of a medicament for the treatment of fibromyalgia syndrome (FMS). In some embodiments, the present disclosure provides the use of a compound of formula (I), or a pharmaceutically acceptable salt thereof, in the manufacture of a medicament for the treatment of osteoarthritic (OA) pain. In some embodiments, the present disclosure provides the use of a compound of formula (I), or a pharmaceutically acceptable salt thereof, in the manufacture of a medicament for the treatment of diabetic peripheral neuropathic pain (DPNP). In some embodiments, the present disclosure provides the use of a compound of formula (I), or a pharmaceutically acceptable salt thereof, in the manufacture of a medicament for the treatment of chronic low back pain (CLBP). In some embodiments, the present disclosure provides the use of a compound of formula (I), or a pharmaceutically acceptable salt thereof, in the manufacture of a medicament for the treatment of chemotherapy-induced peripheral neuropathy (CIPN). In some embodiments, the present disclosure provides the use of a compound of formula (I), or a pharmaceutically acceptable salt thereof, in the manufacture of a medicament for the treatment of visceral pain (e.g., pain associated with irritable bowel syndrome (IBS), bladder pain, prostate pain, or vulvodynia).

Compositions of compounds of formula (I), or pharmaceutically acceptable salts thereof, may be formulated in a unit dosage form, each dosage containing from about 0.5 to about 1000 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient. It will be understood that the amount of the compound actually administered will be determined by a physician, in the light of the relevant circumstances, including the condition to be treated, the chosen route of administration, the actual compound administered, the age, weight, and response of the individual subject, and the severity of the subject's symptoms. It is contemplated that the compound of the invention, as for example in a pharmaceutical composition of the invention, will be used to treat pain (e.g., neuropathic pain), by chronic administration.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilized.

Moreover, by utilizing the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognize which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesized by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

Exemplified compounds were prepared as described below. Other example compounds of the present invention can be made following similar schemes as described herein.

Certain abbreviations are defined as follows:

| | |
|---|---|
| ACN and MeCN | acetonitrile |
| DCM | dichloromethane |
| DMSO | dimethyl sulfoxide |
| EA and EtOAc | ethyl acetate |
| EtOH | ethanol and ethyl alcohol |
| H and h | Hour(s) |
| HATU | 1-[Bis(dimethylamino)methylene]-1H-1,2,3-triazolo[4,5-b]pyridinium 3-oxide hexafluorophosphate |
| IPA | isopropanol and isopropyl alcohol |
| LDA | lithium diisopropylamide |
| MeOH | methanol and methyl alcohol |
| MTBE | methyl tert-butyl ether |
| $Pd_2(dba)_3$ | tris(dibenzylideneacetone)dipalladium(0) |
| $PdCl_2(dppf)$ | [1,1'-bis(diphenylphosphino)ferrocene]dichloropalladium(II) |
| PE | Petroleum ether |
| PSI | Pounds per square inch |
| RT | room temperature |
| RuPhos | 2-dicyclohexylphosphino-2',6'-diisopropoxybipheny |
| SFC | supercritical fluid chromatography |
| tBuXPhos Pd G3 | [(2-di-tert-butylphosphino-2',4',6'-triisopropyl-1,1'-biphenyl)-2-(2'-amino-1,1'-biphenyl)] palladium(II) methanesulfonate |
| TEA | triethylamine |
| TFA | trifluoroacetic acid |
| THF | tetrahydrofuran |
| Xantphos | 4,5-bis(diphenylphosphino)-9,9-dimethylxanthene |

Example 1. Synthesis of Example Nos. 1, 2, 4, 5, 13, 16, 19, 26, 33, 38, 40, 46, 56, 57, 58, 59, 61, 87, 98, 100, 101, 102, 107, 108, 109, 110, 111, and 112

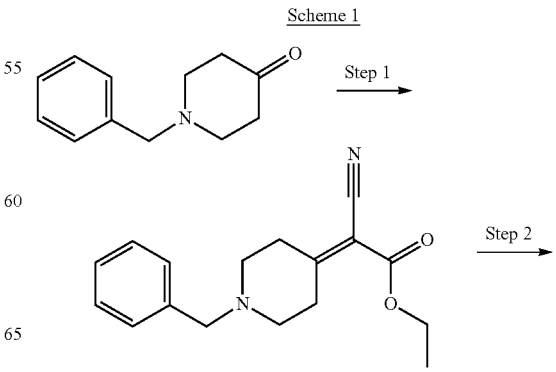

Scheme 1

123
-continued

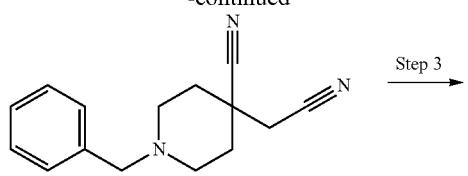

Step 3

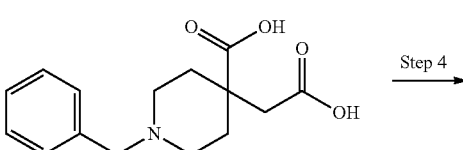

Step 4

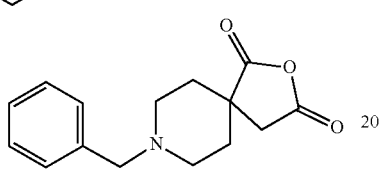

+

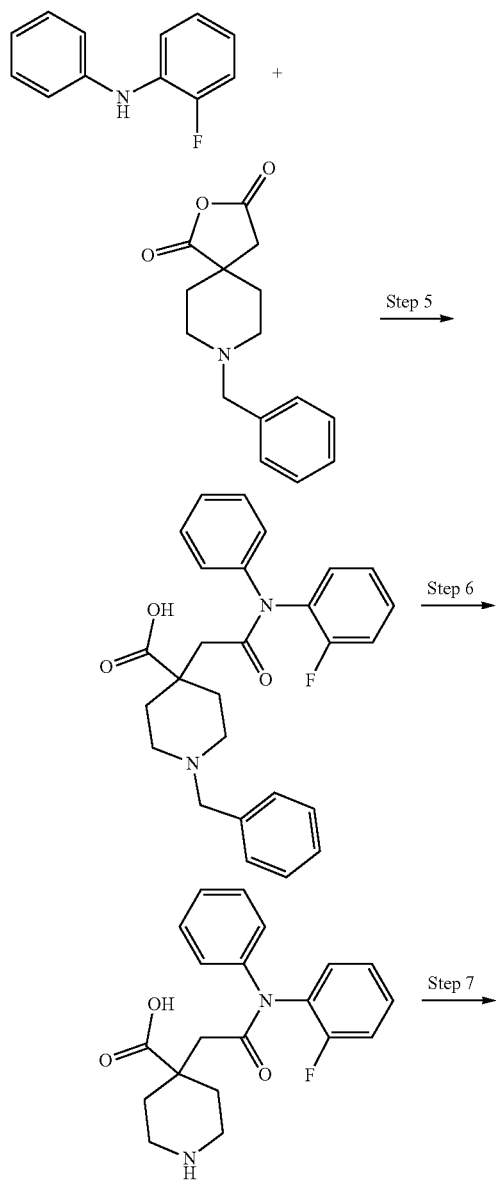

124
-continued

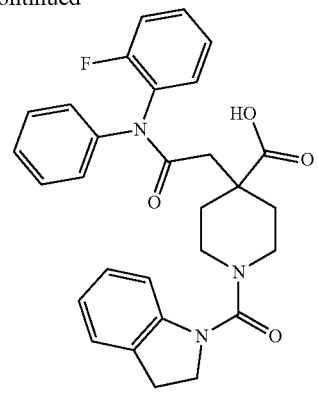

Step 1: Ethyl 2-(1-benzyl-4-piperidylidene)-2-cyano-acetate

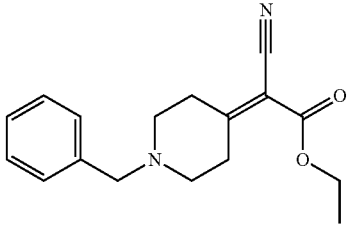 [SMILES: CCOC(=O)C(C#N)=C1CCN(Cc2ccccc2)CC1]

To a solution of 1-benzylpiperidin-4-one (3.45 kg, 18.2 mol) in toluene (10.0 L) was added ethyl 2-cyanoacetate (2.47 kg, 21.8 mol) and AcOH (875 g, 14.5 mol) in one portion at 20° C.-25° C., the reaction mixture was then heated to 110° C. After 4 h, the reaction was cooled down to RT and concentrated in vacuo directly. Water (10.0 L) was added to the above mixture and stirred for 20 mins. The mixture was extracted with ethyl acetate (10.0 L×3). Then the combined organic phase was washed with brine (10.0 L×1), dried with anhydrous $Na_2SO_4$ and concentrated in vacuo. The residue was purified by silica gel chromatography, eluting 0 to 100% ethyl acetate/petroleum ether. The appropriate fractions were combined, concentrated and afforded the title compound (4.10 kg, 79.10% yield) as the light-yellow solid. $^1H$ NMR (399.91 MHz, $CDCl_3$): 7.36-7.29 (m, 5H), 4.29 (q, J=7.2 Hz, 2H), 3.57 (s, 2H), 3.18 (t, J=5.8 Hz, 2H), 2.82 (t, J=5.7 Hz, 2H), 2.67 (t, J=5.7 Hz, 2H), 2.60 (t, J=5.8 Hz, 2H), 1.37 (t, J=7.2 Hz, 3H).

Step 2: Benzyl-4-(cyanomethyl)piperidine-4-carbonitrile

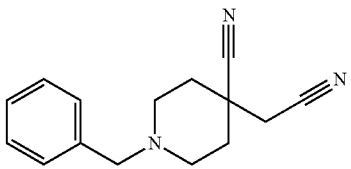 [SMILES: N#CCC1(C#N)CCN(Cc2ccccc2)CC1]

To a solution of ethyl 2-(1-benzyl-4-piperidylidene)-2-cyano-acetate (505 g, 1.78 mol) in EtOH (2.50 L) and H$_2$O (500 mL) was added KCN (145.31 g, 2.23 mol) at 20-25° C. under a nitrogen atmosphere. The reaction mixture was stirred at 80-85° C. for 4 hrs. Seven same-scale reactions were set up simultaneously. After the reactions were cooled to RT, all seven reactions were combined and concentrated in vacuo directly. To the mixture was added water (5.00 L) and was extracted with ethyl acetate (5.00 L×3), the combined organic phase was washed with brine (5.00 L), dried with anhydrous Na$_2$SO$_4$, and concentrated in vacuum. The crude product was triturated with petroleum ether: tert-butyl methyl ether=1:1 (5000 mL), filtered, and dried to afford title compound (2.38 kg, 80.0% yield) as a yellow solid. $^1$H NMR (400.13 MHz, CDCl$_3$): 7.35-7.29 (m, 5H), 3.58 (s, 2H), 2.96-2.93 (m, 2H), 2.71 (s, 2H), 2.42-2.36 (m, 2H), 2.07-2.04 (m, 2H), 1.82-1.79 (m, 2H).

Step 3:
benzyl-4-(carboxymethyl)piperidine-4-carboxylic acid

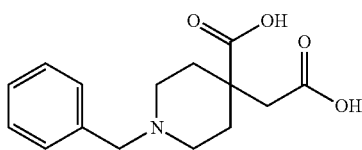 [SMILES: O=C(O)CC1(C(=O)O)CCN(Cc2ccccc2)CC1]

To a solution of KOH (540 g, 9.63 mol) in H$_2$O (1700 mL) was added 1-benzyl-4-(cyanomethyl)piperidine-4-carbonitrile (576 g, 2.41 mol). The reaction mixture was refluxed at 95° C.~100° C. for 24 hrs. Five same-scale reactions were set up simultaneously. The mixture was cooled to 20° C.~25° C., all five reactions were combined, the reaction was adjusted to pH 5~6 with HCl (12.0 M, 3.00 L) at 20° C.~25° C., the mixture was filtered to give a filter cake, the filter cake was washed with H$_2$O (6.00 L), and the cake was triturated with MeCN (4.50 L) at 25° C. for 30 mins and filtered. The product was dried in a vacuum oven for 15 hours to give the title product (2.04 kg, 61.1% yield) as a white solid. MS m/z 188.1 (M+H); $^1$H NMR (400.13 MHz, DMSO-d$_6$): 7.39-7.31 (m, 5H), 3.72 (s, 2H), 2.68-2.55 (m, 4H), 2.44 (s, 2H), 2.03-1.99 (m, 2H), 1.62-1.56 (m, 2H).

Step 4: 8-benzyl-2-oxa-8-azaspiro[4.5]decane-1,3-dione

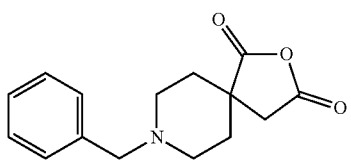 [SMILES: O=C1CC2(CCN(Cc3ccccc3)CC2)C(=O)O1]

In a 3 L flask, 1-benzyl-4-(carboxymethyl)piperidine-4-carboxylic acid (20 g, 72.12 mmol) was suspended in dichloromethane (400 mL) at 0° C. under N$_2$, to the suspension trifluoroacetic anhydride (300 mL, 2134 mmol) was added dropwise at 0° C. After addition the reaction mixture was heated to 45° C. for 16 h. The reaction was concentrated in vacuum to remove solvent, the residue was dissolved in DCM (300 mL), the solution was added slowly into 10% aqueous K$_2$HPO$_4$ (500 mL), the mixture kept at pH 8. The aqueous layer was extracted with DCM (300 mL×3), the combined organic layers were washed with brine (100 mL), dried over with Na$_2$SO$_4$, filtered, and concentrated in vacuum to give the title product (10.5 g, 40.5 mmol, 100 mass %, 56.1% Yield). $^1$H NMR (400 MHz, DMSO-d$_6$) 7.34-7.24 (m, 5H), 3.46 (s, 2H), 2.94 (s, 2H), 2.74-2.70 (m, 2H), 2.06-2.01 (m, 2H), 1.83-1.81 (m, 4H). 2-fluoro-N-phenyl-aniline

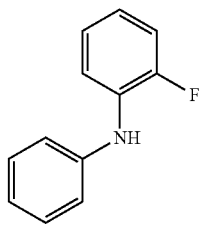 [SMILES: Fc1ccccc1Nc1ccccc1]

Under nitrogen, to a solution of 1-bromo-2-fluoro-benzene (3.0 g, 16.97 mmol), aniline (1.76 g, 18.3 mmol), sodium tert-butoxide (5.1 g, 50.9 mmol) in toluene (30.0 mL) was added tris(dibenzylideneacetone)dipalladium(0) (162 mg, 0.17 mmol) and 1,1'-bis(diphenylphosphino)ferrocene (196 mg, 0.34 mmol) under nitrogen. The mixture was stirred at 100° C. After overnight stirring at 100° C., the reaction was cooled to RT, filtered, and concentrated to give a residue. To the residue was added water (200 mL) and it was extracted with EA (200 mL×3). The combined organic layers were washed with brine (100 mL), dried over Na$_2$SO$_4$, filtered, and concentrated under reduced pressure to give a residue. The residue was purified by silica gel flash chromatography, eluting 0~7% ethyl acetate/petroleum ether to give title compound (2.83 g, 95 mass %, 84.6% yield). $^1$H NMR (400.14 MHz, DMSO-d$_6$): 7.93 (s, 1H), 7.31-7.22 (m, 4H), 7.10-7.05 (m, 1H), 7.00 (d, J=8.3 Hz, 2H), 6.94-6.91 (m, 1H), 6.85-6.81 (m, 1H).

The compounds in the table below were prepared according to the procedure described above.

| Chemical Name | Structure | $^1$H NMR (400 MHz, DMSO-d$_6$) |
|---|---|---|
| N,N-bis(2-fluorophenyl)amine | 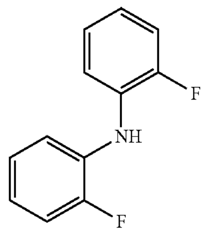 [SMILES: Fc1ccccc1Nc1ccccc1F] | $^1$H NMR (400 MHz, DMSO-d$_6$): 7.74 (s, 1H), 7.20 (m, 2H), 7.10-7.06 (m, 2H), 7.02-6.93 (m, 4H). |
| 2-fluoro-N-(3-fluorophenyl)aniline | 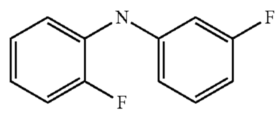 [SMILES: Fc1cccc(Nc2ccccc2F)c1] | $^1$H NMR (400 MHz, CDCl$_3$): 7.27 (dt, J = 1.6, 8.3 Hz, 1H), 7.22-7.09 (m, 1H), 7.08-6.93 (m, 2H), 6.90-6.80 (m, 1H), 6.79-6.68 (m, 2H), 6.64-6.44 (m, 1H), 5.75 (br, 1H). |
| bis(4-fluorophenyl)amine | 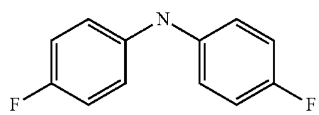 [SMILES: Fc1ccc(Nc2ccc(F)cc2)cc1] | $^1$H NMR (400 MHz, CDCl$_3$): 6.98 (d, J = 6.5 Hz, 8H). |
| 3-fluoro-N-(4-fluorophenyl)aniline | 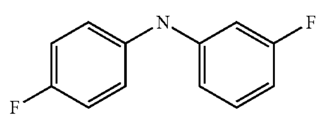 [SMILES: Fc1ccc(Nc2cccc(F)c2)cc1] | $^1$H NMR (400 MHz, DMSO-d$_6$): 8.34 (s, 1H), 7.24-7.17 (m, 1H), 7.13 (s, 2H), 7.12-7.08 (m, 2H), 6.78 (dd, J = 1.5, 8.1 Hz, 1H), 6.71 (td, J = 2.3, 12.0 Hz, 1H), 6.54 (dt, J = 2.0, 8.4 Hz, 1H) |
| 3-fluoro-N-(3-fluorophenyl)aniline | 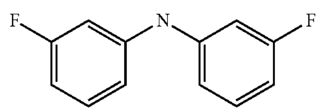 [SMILES: Fc1cccc(Nc2cccc(F)c2)c1] | $^1$H NMR (400 MHz, DMSO-d$_6$): 8.62 (s, 1H), 7.34-7.20 (m, 2H), 6.95-6.80 (m, 4H), 6.66 (dt, J = 2.2, 8.4 Hz, 2H) |

Step 5: benzyl-4-[2-(N-(2-fluorophenyl)anilino)-2-oxo-ethyl]piperidine-4-carboxylic acid

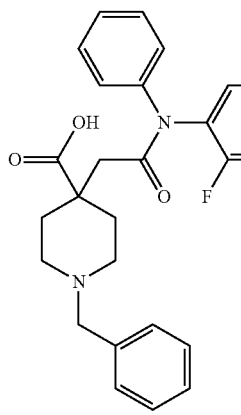

In a microwave tube, a mixture of 2-fluoro-N-phenyl-aniline (1.3 g, 6.7 mmol), 8-benzyl-2-oxa-8-azaspiro[4.5]decane-1,3-dione (1.0 g, 3.9 mmol) and trifluoroacetic acid (2.0 mL, 26.19 mmol) were dissolved in dichloromethane (5.0 mL), the reaction mixture was heated at 80° C. in microwave. After 3 h, the reaction mixture was cooled to RT and concentrated to give a crude residue. The residue was purified by revers phase prep-HPLC: Xtimate C18 column (150*40 mm*10 µm), solvent A: water (NH$_4$OH+ NH$_4$HCO$_3$), solvent B: ACN, eluting from 30% B to 70% B in min. The appropriate fractions were combined and lyophilized to give the title compound (700 mg, 40.4% Yield), MS m/z 447.1 (M+H)

1-benzyl-4-[2-(2-fluoro-N-(2-fluorophenyl)anilino)-2-oxo-ethyl]piperidine-4-carboxylic acid was prepared according to the procedure described above

| Chemical Name | Structure | ES/MS (m/z) (M + H) |
|---|---|---|
| 1-benzyl-4-[2-(2-fluoro-N-(2-fluorophenyl)anilino)-2-oxo-ethyl]piperidine-4-carboxylic acid | | 465.1 | benzyl-4-[2-oxo-2-(N-phenylanilino)ethyl]piperidine-4-carboxylic acid; formic acid

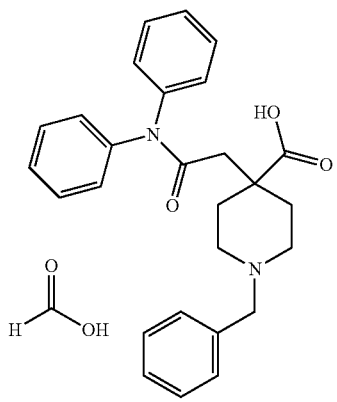

A solution of diphenylamine (6.65 g, 38.9 mmol) in tetrahydrofuran (30.0 mL) was added N-butyllithium in hexanes (16 mL, 40 mmol, 2.5 mol/L) dropwise at −78° C. under $N_2$, stirred for 15 min, 8-benzyl-2-oxa-8-azaspiro[4.5]decane-1,3-dione (6.01 g, 19.7 mmol, 85 mass %) in tetrahydrofuran (30.0 mL) was added dropwise at −78° C. The reaction was stirred at −78° C. for 2 h and then warmed to RT and stirred overnight. The reaction mixture was quenched by adding sat. $NH_4Cl$ (20 mL), concentrated in vacuo to give a brown residue. To the residue was added water (50 mL) and formic acid (10 mL). Insoluble material was collected by filtration and washed with ethyl acetate (60 mL×4), the solid was dried in vacuo to give the title compound (5.66 g, 97 mass %, 58.7% yield). MS m/z 429.0 (M+H—$HCO_2H$).

Step 6: 4-[2-(N-(2-fluorophenyl)anilino)-2-oxo-ethyl]piperidine-4-carboxylic acid hydrochloride salt

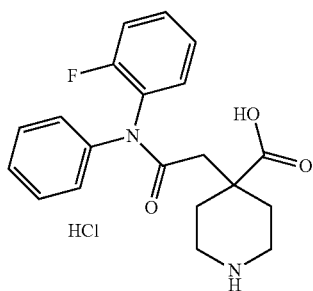 [SMILES: O=C(CC1(C(=O)O)CCNCC1)N(c1ccccc1)c1ccccc1F ; Cl]

To a solution of 1-benzyl-4-[2-(N-(2-fluorophenyl)anilino)-2-oxo-ethyl]piperidine-4-carboxylic acid (700 mg, 1.56 mmol) in tetrahydrofuran (20.0 mL), aqueous hydrochloric acid (1.0 ml, 36.5 mass %) was added in one portion and followed by Pd/C (420 mg, 0.3962 mmol, 10 mass %) at RT. The mixture was stirred at 60° C. under $H_2$ (50 psi) for 16 h. The reaction mixture was filtered through a pad of celite and washed with MeOH and dichloromethane (1:1, 40 mL×5). The filtrate was concentrated to give the crude title product (630 mg, 87.7 mass %, 90.3% yield). MS m/z 357.0 (M+H—HCl).

The compounds in the table below were prepared according to the procedure described above.

| Chemical Name | Structure | ES/MS (m/z) |
|---|---|---|
| 4-[2-(2-fluoro-N-(2-fluorophenyl)anilino)-2-oxo-ethyl]piperidine-4-carboxylic acid; hydrochloride salt | 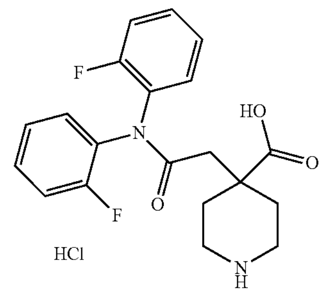 [SMILES: O=C(CC1(C(=O)O)CCNCC1)N(c1ccccc1F)c1ccccc1F ; Cl] | 375.1 (M + H − HCl) |
| 4-[2-oxo-2-(N-phenylanilino)ethyl]piperidine-4-carboxylic acid; hydrochloride | 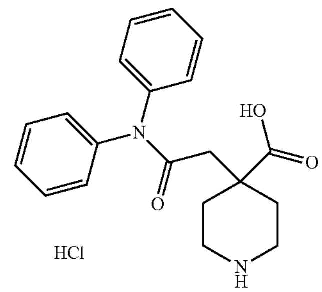 [SMILES: O=C(CC1(C(=O)O)CCNCC1)N(c1ccccc1)c1ccccc1 ; Cl] | 339.0 (M + H − HCl) |

4-[2-(2-fluoro-N-(2-fluorophenyl)anilino)-2-oxo-ethyl]piperidine-4-carboxylic acid; hydrochloride salt and 4-[2-oxo-2-(N-phenylanilino)ethyl]piperidine-4-carboxylic acid;hydrochloride were prepared according to the procedure above indoline-1-carbonyl chloride

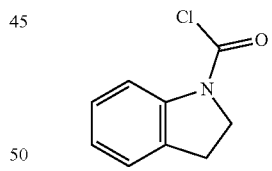

A solution of indoline (10.01 g, 83.16 mmol) and triethylamine (17.5 mL, 125 mmol) in dichloromethane (50 mL) was added dropwise into a solution of triphosgene (12.98 g, 43.30 mmol) in dichloromethane (100 mL) at 0° C. The reaction was slowly warmed up to RT and stirred for 2 h. The reaction mixture was quenched by adding $H_2O$ (100 mL) carefully and extracted with dichloromethane (80 mL×2). The combined organic layers were washed with brine (50 mL), dried over $Na_2SO_4$, filtered, and concentrated under vacuum to give title product (19.42 g, 75 mass %, 96.43% yield) as a brown solid. The crude product was used for next step directly without purification. MS m/z 182.1 (M+H).

The compounds in the table below were prepared according to the procedure described above.

| Chemical Name | Structure | ¹H NMR (400 MHz, DMSO-d$_6$) |
|---|---|---|
| N-(4-fluorophenyl)-N-methyl-carbamoyl chloride | 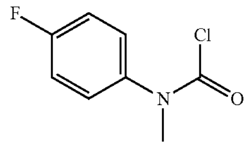 | 7.53-7.48 (m, 2H), 7.33-7.28 (m, 2H), 3.29 (s, 3H). |
| N-methyl-N-phenyl-carbamoyl chloride | 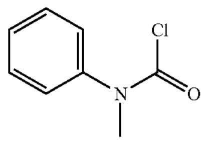 | 7.55-7.47 (m, 5H), 3.38 (s, 3H). |
| N-methyl-N-pentyl-carbamoyl chloride | 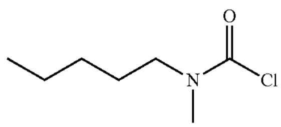 | ¹H NMR (400 MHz, CDCl$_3$): 3.51-3.37 (m, 2H), 3.17-3.01 (m, 3H), 1.69-1.57 (m, 2H), 1.44-1.23 (m, 4H), 0.98-0.87 (m, 3H). |
| 4-fluoroindoline-1-carbonyl chloride | 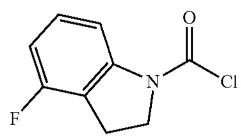 [SMILES: O=C(Cl)N1CCc2c(F)cccc21] | ¹H NMR (400 MHz, CDCl$_3$): 7.67 (d, J = 8.1 Hz, 1H), 7.22 (dt, J = 5.7, 8.2 Hz, 1H), 6.83 (t, J = 8.4 Hz, 1H), 4.32 (t, J = 8.5 Hz, 2H), 3.23 (t, J = 8.5 Hz, 2H). |
| 6-fluoroindoline-1-carbonyl chloride | 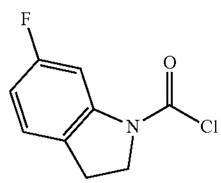 [SMILES: O=C(Cl)N1CCc2ccc(F)cc21] | ¹H NMR (400.14 MHz, DMSO-d$_6$): 7.29-7.23 (m, 1H), 6.97-6.91 (m, 1H), 6.85-6.77 (m, 1H), 4.05-3.99 (m, 2H), 3.04-2.98 (m, 2H). |
| 3,3-dimethylindoline-1-carbonyl chloride | 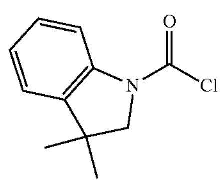 | MS m/z 209.9 (M + H) |
| 6-methylindoline-1-carbonyl chloride | 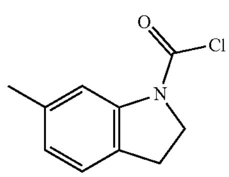 | MS m/z 196.1 (M + H) |
| 3,4-dihydro-2H-quinoline-1-carbonyl chloride | 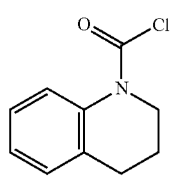 [SMILES: O=C(Cl)N1CCCc2ccccc21] | ¹H NMR (400 MHz, DMSO-d$_6$): 7.28-7.20 (m, 3H), 7.17 (d, J = 7.1 Hz, 1H), 3.33-3.30 (m, 2H), 2.81 (t, J = 6.4 Hz, 2H), 2.02-1.94 (m, 2H). |
| 5-fluoroindoline-1-carbonyl chloride | 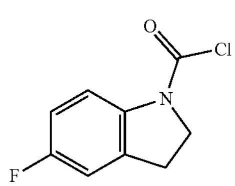 [SMILES: O=C(Cl)N1CCc2cc(F)ccc21] | ¹H NMR (400 MHz, DMSO-d$_6$): 7.68 (dd, J = 4.8, 8.9 Hz, 1H), 7.47 (dd, J = 4.6, 8.8 Hz, 1H), 7.39-7.31 (m, 1H), 4.26 (t, J = 8.4 Hz, 2H), 3.74 (t, J = 7.9 Hz, 2H) |

| Chemical Name | Structure | $^1$H NMR (400 MHz, DMSO-d$_6$) |
|---|---|---|
| 7-fluoroindoline-1-carbonyl chloride | 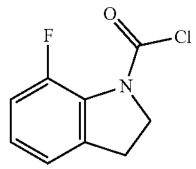 [SMILES: O=C(Cl)N1CCc2cccc(F)c21] | MS m/z 199.9 (M + H) |
| 6-methoxyindoline-1-carbonyl chloride | 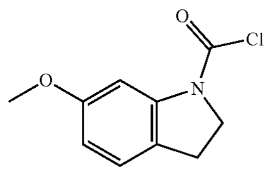 | $^1$H NMR (400 MHz, CDCl$_3$): 7.52 (d, J = 2.4 Hz, 1H), 7.08 (d, J = 8.3 Hz, 1H), 6.66 (dd, J = 2.4, 8.3 Hz, 1H), 4.31-4.25 (m, 2H), 3.80 (s, 3H), 3.16-3.10 (m, 2H). |
| N-cyclopropyl-N-phenyl-carbamoyl chloride | 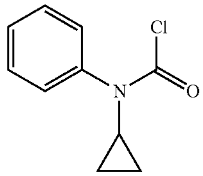 [SMILES: O=C(Cl)N(c1ccccc1)C1CC1] | 1H NMR (400 MHz, CDCl$_3$): 7.45-7.41 (m, 2H), 7.39-7.34 (m, 1H), 7.20-7.18 (m, 2H), 3.26-3.21 (m, 1H), 0.92 (q, J = 6.7 Hz, 2H), 0.72-0.68 (m, 2H). |

2,2-difluoro-2-(2-fluorophenyl)acetyl chloride

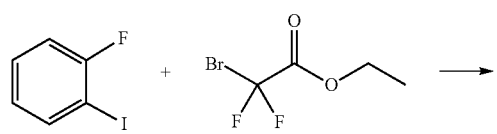

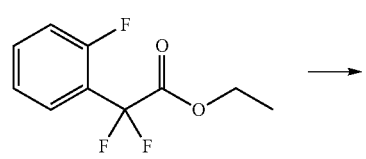

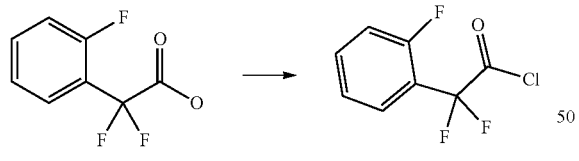 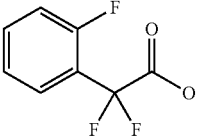

ethyl 2,2-difluoro-2-(2-fluorophenyl)acetate

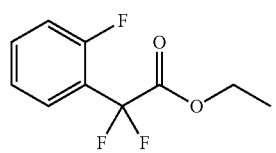

To a stirring solution of ethyl bromodifluoroacetate (5.00 g, 24.1 mmol) in DMSO (20 mL) was added 1-fluoro-2-iodobenzene (4.5 g, 19 mmol) and copper (5.1 g, 79 mmol), the resulting solution was heated at 50° C. under N$_2$ overnight. Upon completion, the reaction mixture was cooled to RT and 60 mL of water was added to the mixture. The aqueous phase was extracted with ethyl acetate (50 mL×3). Then the combined organic phase was washed with brine (60 mL×4), dried with anhydrous Na$_2$SO$_4$ and concentrated under reduced pressure. The residue was purified by flash silica gel chromatography, eluting with 0~10% ethyl acetate in petroleum ether to give the title compound (3.31 g, 95 mass %, 59.7% Yield) as a light-yellow oil. $^1$H NMR (400.13 MHz, CDCl$_3$): 7.66 (dt, J=1.5, 7.6 Hz, 1H), 7.55-7.47 (m, 1H), 7.27 (t, J=7.6 Hz, 1H), 7.15 (ddd, J=0.9, 9.0, 10.0 Hz, 1H), 4.37 (q, J=7.1 Hz, 2H), 1.33 (t, J=7.1 Hz, 3H).

2,2-difluoro-2-(2-fluorophenyl)acetic acid

To a stirring solution of ethyl 2,2-difluoro-2-(2-fluorophenyl)acetate (1.030 g, 4.485 mmol) in Tetrahydrofuran (8.0 mL, 97 mmol) and water (0.8 mL) was added lithium hydroxide (385 mg, 8.708 mmol), the resulting solution was stirred at 60° C. under N$_2$ for 3 h. Upon completion, the reaction was cooled to RT and 1N HCl (8.0 mL) was added to adjusted pH<2 and added water (30 mL), the residue was extracted with ethyl acetate (30 mL×3). Then the combined organic phase was washed with brine (30 mL), dried with anhydrous Na$_2$SO$_4$ and concentrated under reduced pressure to give the title compound (862 mg, 96 mass %, 97.05% Yield) as a purple oil. $^1$H NMR (400 MHz, CDCl$_3$): 11.36 (d, J=4.0 Hz, 1H), 7.72-7.64 (m, 1H), 7.53 (q, J=6.8 Hz, 1H), 7.32-7.25 (m, 1H), 7.21-7.12 (m, 1H).

2,2-difluoro-2-(2-fluorophenyl)acetyl chloride

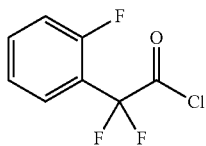 [SMILES: O=C(Cl)C(F)(F)c1ccccc1F]

To a solution of 2,2-difluoro-2-(2-fluorophenyl)acetic acid (100 mg, 0.5049 mmol, 96 mass %) in dichloromethane (1.0 mL) was added oxalyl chloride (90 μL, 1.017 mmol) followed by one drop of DMF at 0° C. The reaction mixture was stirred at RT for 1 h. Upon completion, the reaction mixture was concentrated in vacuum to give the crude compound (92 mg, 90 mass %, 78.62% yield) was obtained as a pale-yellow solid. The crude was used directly in the next step without purification.

4-[2-(N-(2-fluorophenyl)anilino)-2-oxo-ethyl]-1-(indoline-1-carbonyl)piperidine-4-carboxylic acid
(Example No. 56)

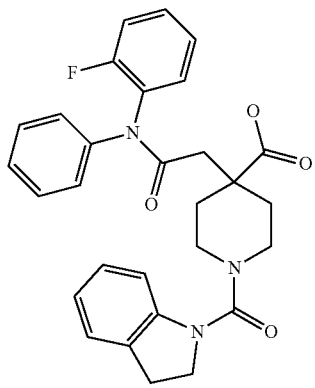 [SMILES: O=C(N1CCC(CC(=O)N(c2ccccc2)c2ccccc2F)(C(=O)O)CC1)N1CCc2ccccc21]

To a solution of 4-[2-(N-(2-fluorophenyl)anilino)-2-oxo-ethyl]piperidine-4-carboxylic acid; hydrochloride (100.0 mg, 0.223 mmol, 87.7 mass %) in tetrahydrofuran (1.0 ml) was added N,O-bis(trimethylsilyl)acetamide (0.22 ml, 0.88 mmol) and N,N-diisopropylethylamine (0.12 ml, 0.69 mmol). The mixture was stirred at RT for 1 h followed by the addition of indoline-1-carbonyl chloride (122.0 mg, 0.470 mmol, 75 mass %) to the reaction mixture, which was then stirred at RT overnight. This reaction was combined with same reaction from a smaller scale on of 4-[2-(N-(2-fluorophenyl)anilino)-2-oxo-ethyl]piperidine-4-carboxylic acid; hydrochloride (30.0 mg, 0.223 mmol, 87.7 mass %). The reaction mixture was concentrated to give a residue, and purified by reverse phase prep-HPLC (Xtimate C18 100*30 mm*10 μm), mobile phase A: water-formic acid, mobile phase B: ACN, eluting with 50-70% B in 10 min, then to 100% B. The appropriate fractions were combined and lyophilized to give title product (42.6 mg, 38.0% yield). MS m/z 502.4 (M+H); $^1$H NMR (400.21 MHz, DMSO-$d_6$): 12.40 (s, 1H), 7.53-7.46 (m, 10H), 7.11 (t, J=7.38 Hz, 1H), 6.94 (d, J=8.0 Hz, 1H), 6.86 (t, J=7.50 Hz, 1H), 3.79 (t, J=8.3 Hz, 2H), 3.35-3.17 (m, 4H), 2.97 (t, J=8.2 Hz, 2H), 2.08 (s, 2H), 2.01-1.97 (m, 2H), 1.58-1.51 (m, 2H).

Example Nos. 1, 2, 13, 16, 19, 26, 33, 38, 40, 46, 55, 57, 58, 59, 61, 87, 97, 98, 100, 101, 102, 107, and 108 were Prepared According to the Procedure Above

| Example No. | Chemical Name | Structure | ES/MS (m/z) (M + H) | $^1$H NMR (400 MHz, DMSO-$d_6$) |
|---|---|---|---|---|
| 1 | 1-[methyl(pentyl)carbamoyl]-4-[2-oxo-2-(N-phenylanilino)ethyl]piperidine-4-carboxylic acid | 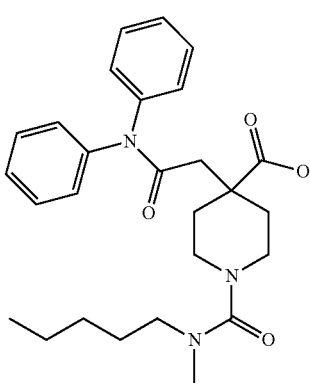 [SMILES: CCCCCN(C)C(=O)N1CCC(CC(=O)N(c2ccccc2)c2ccccc2)(C(=O)O)CC1] | 466.4 | 12.29 (br, 1H), 7.57-7.12 (m, 10H), 3.10-2.94 (m, 6H), 2.71-2.66 (m, 3H), 2.53-2.50 (m, 2H), 1.99-1.82 (m, 2H), 1.56-1.38 (m, 4H), 1.34-1.21 (m, 2H), 1.20-1.10 (m, 2H), 0.84 (t, J = 7.3 Hz, 3H) |

-continued

| Example No. | Chemical Name | Structure | ES/MS (m/z) (M + H) | $^1$H NMR (400 MHz, DMSO-$d_6$) |
|---|---|---|---|---|
| 2 | 1-[(4-fluorophenyl)-methyl-carbamoyl]-4-[2-oxo-2-(N-phenylanilino)ethyl]piperidine-4-carboxylic acid | 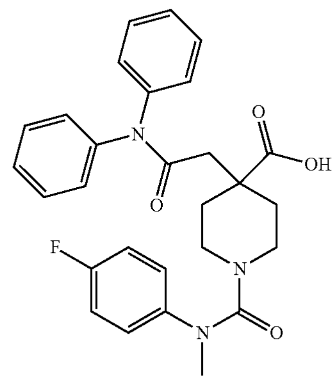 [SMILES: CN(C(=O)N1CCC(CC(=O)N(c2ccccc2)c2ccccc2)(C(=O)O)CC1)c1ccc(F)cc1] | 490.4 | 7.36-7.22 (m, 14H), 3.19-3.11 (m, 2H), 3.03 (s, 3H), 3.00-2.95 (m, 2H), 2.41 (s, 2H), 1.78-1.75 (m, 2H), 1.33-1.27 (m, 2H). |
| 13 | 4-[2-(N-cyclohexylanilino)-2-oxo-ethyl]-1-[methyl(p-tolyl)carbamoyl]piperidine-4-carboxylic acid | 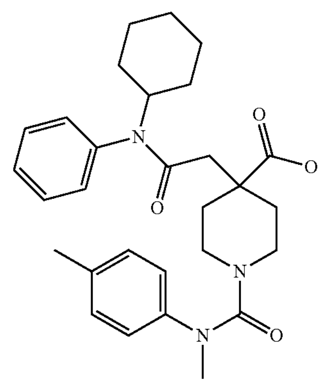 [SMILES: Cc1ccc(N(C)C(=O)N2CCC(CC(=O)N(c3ccccc3)C3CCCCC3)(C(=O)O)CC2)cc1] | 492.5 | $^1$H NMR (400 MHz, DMSO-$d_6$): 12.11 (br, 1H), 7.49-7.39 (m, 3H), 7.12 (t, J = 7.3 Hz, 4H), 6.92 (d, J = 8.3 Hz, 2H), 4.38-4.28 (m, 1H), 3.33 (s, 3H), 3.09-3.02 (m, 2H), 2.95-2.87 (m, 2H), 2.26 (s, 3H), 2.03 (s, 2H), 1.71-1.61 (m, 6H), 1.49 (d, J = 12.8 Hz, 1H), 1.25-1.20 (m, 2H), 1.19-1.13 (m, 2H), 0.96-0.76 (m, 3H) |
| 16 | 4-[2-(N-cyclohexylanilino)-2-oxo-ethyl]-1-[cyclopropyl-(4-fluorophenyl)carbamoyl]piperidine-4-carboxylic acid | 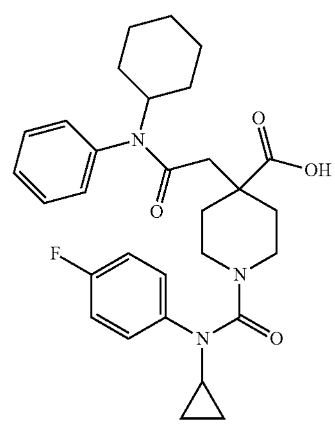 [SMILES: O=C(CC1(C(=O)O)CCN(C(=O)N(c2ccc(F)cc2)C2CC2)CC1)N(c1ccccc1)C1CCCCC1] | 522.4 | $^1$H NMR (400 MHz, DMSO-d6): 12.16 (br, 1H), 7.51-7.40 (m, 3H), 7.18-7.06 (m, 6H), 4.34 (t, J = 12.0 Hz, 1H), 3.27-3.18 (m, 2H), 3.02 (t, J = 10.0 Hz, 2H), 2.60-2.54 (m, 1H), 2.04 (s, 2H), 1.71-1.66 (m, 6H), 1.50 (d, J = 12.4 Hz, 1H), 1.28-1.25 (m, 2H), 1.17-1.05 (m, 2H), 0.97-0.81 (m, 3H), 0.76-0.68 (m, 2H), 0.58-0.52 (m, 2H) |
| 19 | 1-[methyl(phenyl)carbamoyl]-4-[2-oxo-2-(N-phenylanilino)ethyl]piperidine-4-carboxylic acid | 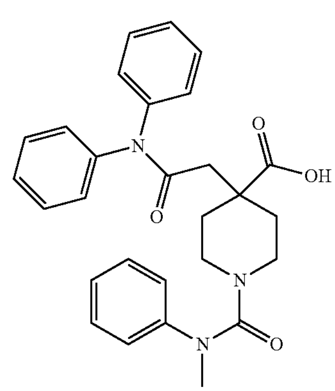 [SMILES: CN(C(=O)N1CCC(CC(=O)N(c2ccccc2)c2ccccc2)(C(=O)O)CC1)c1ccccc1] | 472.4 | 7.39-7.28 (m, 15H), 3.24-3.14 (m, 2H), 3.05 (s, 3H), 2.99-2.93 (m, 2H), 2.39 (s, 2H), 1.77-1.73 (m, 2H), 1.34-1.24 (m, 2H). |

-continued

| Example No. | Chemical Name | Structure | ES/MS (m/z) (M + H) | $^1$H NMR (400 MHz, DMSO-d$_6$) |
|---|---|---|---|---|
| 26 | 1-[(4-cyclopropylphenyl)-methyl-carbamoyl]-4-[2-oxo-2-(N-tetrahydropyran-4-ylanilino)ethyl]piperidine-4-carboxylic acid | 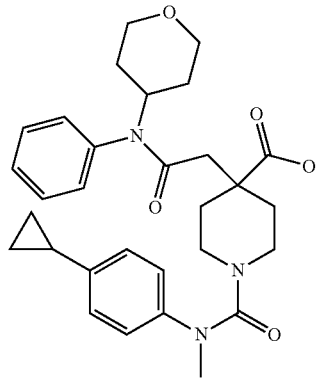 [SMILES: CN(C(=O)N1CCC(CC(=O)N(c2ccccc2)C2CCOCC2)(C(=O)O)CC1)c1ccc(C2CC2)cc1] | 520.5 | $^1$H NMR (400 MHz, DMSO-d6): 12.15 (br, 1H), 7.58-7.40 (m, 3H), 7.15 (d, J = 7.0 Hz, 2H), 7.04-6.97 (m, 2H), 6.95-6.82 (m, 2H), 4.64-4.51 (m, 1H), 3.79 (dd, J = 4.1, 11.1 Hz, 2H), 3.32-3.27 (m, 2H), 3.10-3.02 (m, 2H), 2.98 (s, 3H), 2.95-2.85 (m, 2H), 2.09-2.00 (m, 2H), 1.92-1.82 (m, 1H), 1.74-1.54 (m, 4H), 1.25-1.07 (m, 4H), 0.97-0.88 (m, 2H), 0.65-0.57 (m, 2H) |
| 33 | 1-(6-cyanoindoline-1-carbonyl)-4-[2-(N-cyclohexylanilino)-2-oxo-ethyl]piperidine-4-carboxylic acid | 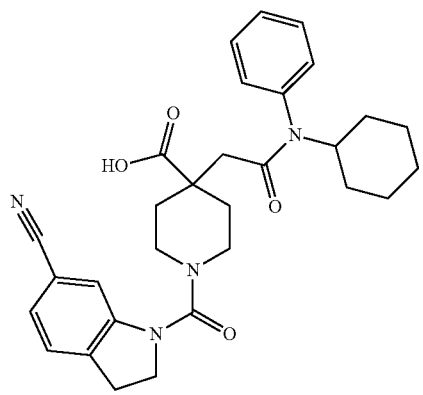 [SMILES: N#Cc1ccc2c(c1)N(C(=O)N1CCC(CC(=O)N(c3ccccc3)C3CCCCC3)(C(=O)O)CC1)CC2] | 515.5 | $^1$H NMR (400 MHz, DMSO-d6): 12.24 (br, 1H), 7.53-7.40 (m, 3H), 7.39-7.28 (m, 2H), 7.25-7.13 (m, 3H), 4.45-4.30 (m, 1H), 3.84 (t, J = 8.3 Hz, 2H), 3.30-3.13 (m, 4H), 3.07 (t, J = 8.3 Hz, 2H), 2.17 (s, 2H), 1.96-1.82 (m, 2H), 1.78-1.61 (m, 4H), 1.58-1.36 (m, 3H), 1.34-1.20 (m, 2H), 1.02-0.76 (m, 3H). |
| 38 | 4-[2-(N-(2-fluorophenyl)anilino)-2-oxo-ethyl]-1-[(4-fluorophenyl)-isopropyl-carbamoyl]piperidine-4-carboxylic acid | 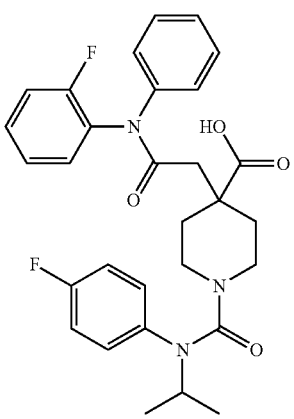 [SMILES: CC(C)N(C(=O)N1CCC(CC(=O)N(c2ccccc2)c2ccccc2F)(C(=O)O)CC1)c1ccc(F)cc1] | 536.4 | $^1$H NMR (400 MHz, DMSO-d$_6$): 12.24 (br, 1H), 7.61-7.12 (m, 11H), 7.12-7.00 (m, 2H), 4.24-4.01 (m, 1H), 3.18-3.02 (m, 2H), 2.98-2.84 (m, 2H), 2.46-2.22 (m, 2H), 1.72-1.54 (m, 2H), 1.14-1.06 (m, 2H), 1.04 (d, J = 6.8 Hz, 6H). |

-continued

| Example No. | Chemical Name | Structure | ES/MS (m/z) (M + H) | ¹H NMR (400 MHz, DMSO-d$_6$) |
|---|---|---|---|---|
| 40 | 1-[cyclopropyl-(4-fluorophenyl)carbamoyl]-4-[2-(N-(2-fluorophenyl)anilino)-2-oxo-ethyl]piperidine-4-carboxylic acid | 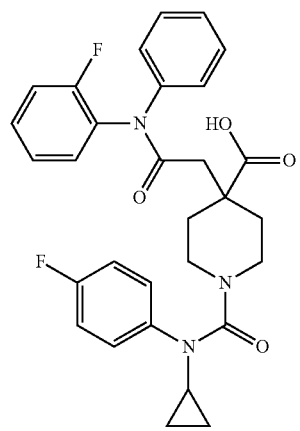 [SMILES: O=C(CC1(C(=O)O)CCN(C(=O)N(c2ccc(F)cc2)C2CC2)CC1)N(c1ccccc1)c1ccccc1F] | 534.4 | ¹H NMR (400 MHz, DMSO-d6): 7.60-7.25 (m, 8H), 7.22-7.15 (m, 3H), 7.10 (s, 2H), 3.32 (s, 2H), 3.08-3.01 (m, 2H), 2.56 (tt, J = 3.6, 6.7 Hz, 1H), 2.45 (s, 2H), 1.76 (d, J = 12.5 Hz, 2H), 1.32-1.23 (m, 2H), 0.76-0.70 (m, 2H), 0.59-0.53 (m, 2H) |
| 46 | 4-[2-(2-fluoro-N-(2-fluorophenyl)anilino]-2-oxo-ethyl]-1-[methyl(phenyl)carbamoyl]piperidine-4-carboxylic acid | 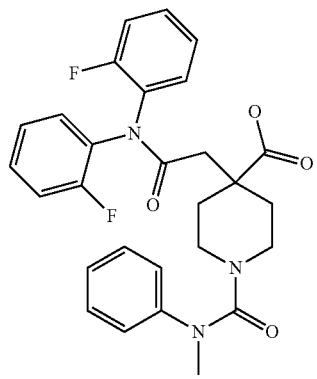 [SMILES: CN(C(=O)N1CCC(CC(=O)N(c2ccccc2F)c2ccccc2F)(C(=O)O)CC1)c1ccccc1] | 508.5 | ¹H NMR (400 MHz, DMSO-d6): 7.56-7.50 (m, 1H), 7.49-7.43 (m, 1H), 7.43-7.37 (m, 1H), 7.34-7.28 (m, 4H), 7.27-7.20 (m, 2H), 7.19-7.15 (m, 1H), 7.09 (d, J = 7.2 Hz, 1H), 7.05 (d, J = 7.6 Hz, 2H), 3.23-3.18 (m, 2H), 3.05 (s, 3H), 2.94 (t, J = 10.1 Hz, 2H), 2.47-2.37 (m, 2H), 1.73-1.71 (m, 2H), 1.30 (t, J = 9.8 Hz, 2H) |
| 55 | 1-[dicyclopropylmethyl(methyl)carbamoyl]-4-[2-(N-(2-fluorophenyl)anilino)-2-oxo-ethyl]piperidine-4-carboxylic acid | 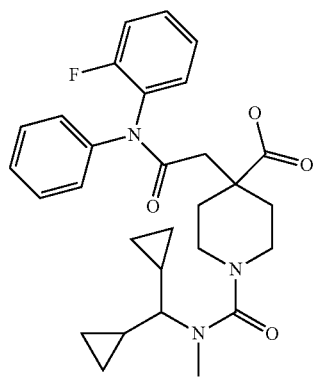 [SMILES: CN(C(=O)N1CCC(CC(=O)N(c2ccccc2)c2ccccc2F)(C(=O)O)CC1)C(C1CC1)C1CC1] | 508.2 | ¹H NMR (400 MHz, DMSO-d$_6$): 7.54-7.13 (m, 9H), 3.07-2.89 (m, 4H), 2.82 (s, 3H), 2.55-2.51 (m, 3H), 1.95-1.83 (m, 2H), 1.55-1.41 (m, 2H), 1.08-0.95 (m, 2H), 0.58-0.48 (m, 2H), 0.40-0.24 (m, 4H), 0.18-0.07 (m, 2H) |

-continued

| Example No. | Chemical Name | Structure | ES/MS (m/z) (M + H) | ¹H NMR (400 MHz, DMSO-d$_6$) |
|---|---|---|---|---|
| 57 | 4-[2-(N-(3-fluorophenyl)anilino)-2-oxo-ethyl]-1-(indoline-1-carbonyl)piperidine-4-carboxylic acid | 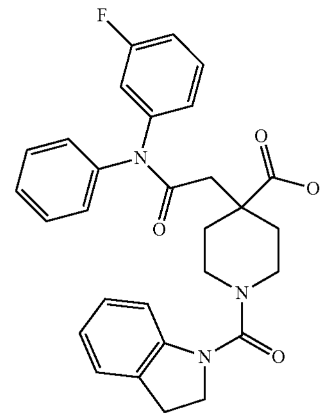 [SMILES: O=C(N1CCC(CC(=O)N(c2ccccc2)c2cccc(F)c2)(C(=O)O)CC1)N1CCc2ccccc21] | 502.4 | ¹H NMR (400 MHz, DMSO-d$_6$): 12.43 (br, 1H), 7.43 (s, 7H), 7.18 (d, J = 7.3 Hz, 2H), 7.10 (t, J = 7.6 Hz, 2H), 6.94 (d, J = 8.0 Hz, 1H), 6.88-6.82 (m, 1H), 3.78 (t, J = 8.3 Hz, 2H), 3.30-3.15 (m, 4H), 2.96 (t, J = 8.1 Hz, 2H), 2.56 (s, 2H), 2.02-1.89 (m, 2H), 1.63-1.48 (m, 2H) |
| 58 | 4-[2-(N-(4-fluorophenyl)anilino)-2-oxo-ethyl]-1-(indoline-1-carbonyl)piperidine-4-carboxylic acid | 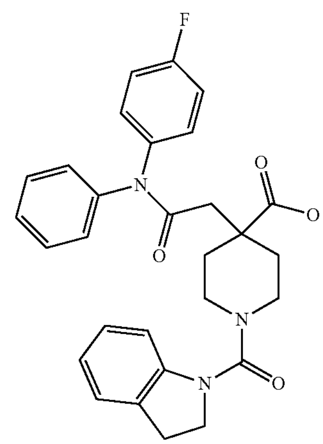 [SMILES: O=C(N1CCC(CC(=O)N(c2ccccc2)c2ccc(F)cc2)(C(=O)O)CC1)N1CCc2ccccc21] | 502.4 | ¹H NMR (400 MHz, DMSO-d$_6$): 12.08 (br, 1H), 7.63-7.14 (m, 10H), 7.10 (t, J = 7.6 Hz, 1H), 6.93 (d, J = 7.9 Hz, 1H), 6.89-6.80 (m, 1H), 3.78 (t, J = 8.2 Hz, 2H), 3.29-3.15 (m, 4H), 2.96 (t, J = 8.1 Hz, 2H), 2.53 (s, 2H), 2.04-1.88 (m, 2H), 1.55 (t, J = 9.2 Hz, 2H) |
| 59 | 4-[2-(2-fluoro-N-(2-fluorophenyl)anilino)-2-oxo-ethyl]-1-(indoline-1-carbonyl)piperidine-4-carboxylic acid | 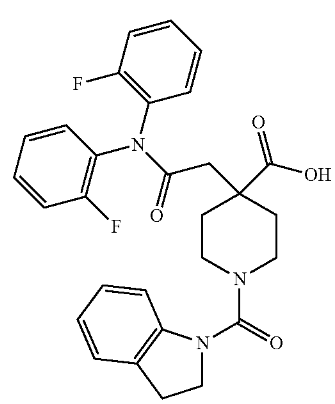 [SMILES: O=C(N1CCC(CC(=O)N(c2ccccc2F)c2ccccc2F)(C(=O)O)CC1)N1CCc2ccccc21] | 520.3 | 12.40 (br, 1H), 7.63-7.55 (m, 1H), 7.50-7.39 (m, 8H), 7.14-7.08 (m, 1H), 6.95 (d, J = 8.0 Hz, 1H), 6.85 (t, J = 7.3 Hz, 1H), 3.79 (t, J = 8.3 Hz, 2H), 3.34-3.31 (m, 2H), 3.27-3.17 (m, 2H), 2.97 (t, J = 8.1 Hz, 2H), 2.71-2.68 (m, 2H), 2.07-1.95 (m, 2H), 1.58-1.52 (m, 2H). |

| Example No. | Chemical Name | Structure | ES/MS (m/z) (M + H) | ¹H NMR (400 MHz, DMSO-d₆) |
|---|---|---|---|---|
| 61 | 4-[2-(4-fluoro-N-(2-fluorophenyl)anilino)-2-oxo-ethyl]-1-(indoline-1-carbonyl)piperidine-4-carboxylic acid | 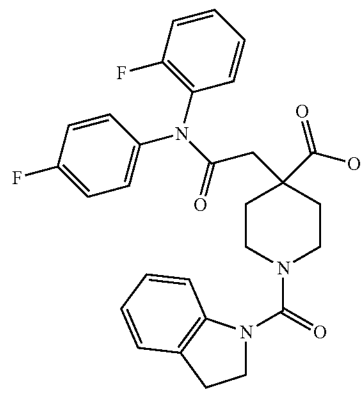 [SMILES: O=C(N1CCC(CC(=O)N(c2ccc(F)cc2)c2ccccc2F)(C(=O)O)CC1)N1CCc2ccccc21] | 520.4 | ¹H NMR (400 MHz, DMSO-d₆): 7.70-7.45 (m, 2H), 7.40-7.23 (m, 5H), 7.23-7.15 (m, 2H), 7.13-7.06 (m, 1H), 6.93 (d, J = 8.0 Hz, 1H), 6.88-6.81 (m, 1H), 3.78 (t, J = 8.3 Hz, 2H), 3.41-3.33 (m, 2H), 3.24-3.15 (m, 2H), 2.96 (t, J = 8.2 Hz, 2H), 2.57 (s, 2H), 1.96 (d, J = 12.5 Hz, 2H), 1.57 (d, J = 5.5 Hz, 2H) |
| 87 | 4-[2-(N-[(racemic)-3,3-difluorocyclohexyl]anilino)-2-oxo-ethyl]-1-[2,2-difluoro-2-(2-fluorophenyl)acetyl]piperidine-4-carboxylic acid | 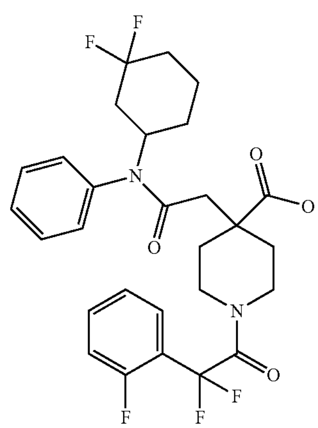 [SMILES: O=C(CC1(C(=O)O)CCN(C(=O)C(F)(F)c2ccccc2F)CC1)N(c1ccccc1)C1CCCC(F)(F)C1] | 553.4 | ¹H NMR (400 MHz, DMSO-d6): 12.33 (br, 1H), 7.68-7.58 (m, 2H), 7.52-7.43 (m, 3H), 7.40-7.32 (m, 2H), 7.22 (d, J = 6.9 Hz, 2H), 4.59 (t, J = 12.4 Hz, 1H), 3.80-3.62 (m, 1H), 3.48-3.39 (m, 1H), 3.30-3.20 (m, 2H), 2.27-2.19 (m, 1H), 2.18-2.06 (m, 2H), 1.96-1.85 (m, 2H), 1.80 (d, J = 13.5 Hz, 1H), 1.73 (d, J = 11.5 Hz, 2H), 1.65-1.44 (m, 2H), 1.42-1.32 (m, 2H), 1.27-1.17 (m, 1H), 1.08-0.95 (m, 1H) |
| 98 | 1-(6-methylindoline-1-carbonyl)-4-[2-oxo-2-(N-phenylanilino)ethyl]piperidine-4-carboxylic acid | 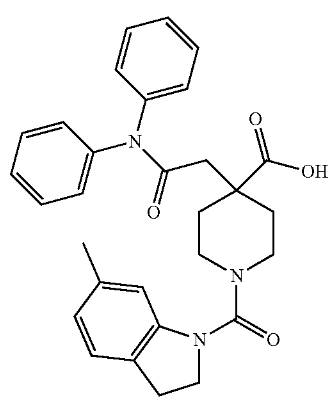 [SMILES: Cc1ccc2c(c1)N(C(=O)N1CCC(CC(=O)N(c3ccccc3)c3ccccc3)(C(=O)O)CC1)CC2] | 498.4 | ¹H NMR (400 MHz, DMSO-d₆): 7.59-7.10 (m, 10H), 7.04 (d, J = 7.5 Hz, 1H), 6.75 (s, 1H), 6.66 (d, J = 7.4 Hz, 1H), 3.76 (t, J = 8.2 Hz, 2H), 3.33-3.15 (m, 4H), 2.90 (t, J = 8.1 Hz, 2H), 2.53 (s, 2H), 2.24 (s, 3H), 2.02-1.89 (m, 2H), 1.63-1.47 (m, 2H) |

-continued

| Example No. | Chemical Name | Structure | ES/MS (m/z) (M + H) | ¹H NMR (400 MHz, DMSO-d$_6$) |
|---|---|---|---|---|
| 100 | 1-(7-fluoroindoline-1-carbonyl)-4-[2-oxo-2-(N-phenylanilino)ethyl]piperidine-4-carboxylic acid | 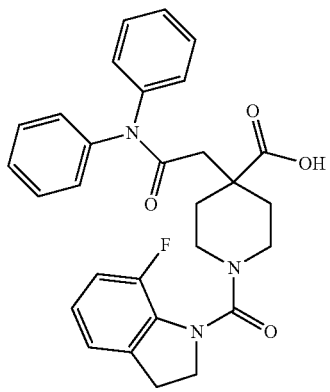 [SMILES: O=C(N1CCC(CC(=O)N(c2ccccc2)c2ccccc2)(C(=O)O)CC1)N1CCc2cccc(F)c21] | 502.4 | ¹H NMR (400 MHz, DMSO-d$_6$): 12.43 (br, 1H), 7.93-7.09 (m, 10H), 7.06-6.99 (m, 1H), 6.97-6.90 (m, 2H), 3.98-3.73 (m, 2H), 3.45-3.38 (m, 2H), 3.29-3.21 (m, 2H), 3.15-2.99 (m, 2H), 2.55 (s, 2H), 2.03-1.90 (m, 2H), 1.60-1.45 (m, 2H) |
| 101 | 1-(3,3-dimethylindoline-1-carbonyl)-4-[2-(N-(2-fluorophenyl)anilino)-2-oxo-ethyl]piperidine-4-carboxylic acid | 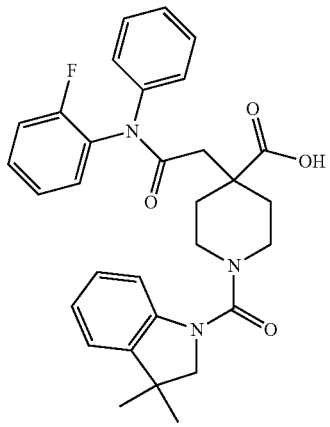 [SMILES: CC1(C)CN(C(=O)N2CCC(CC(=O)N(c3ccccc3)c3ccccc3F)(C(=O)O)CC2)c2ccccc21] | 530.5 | ¹H NMR (400 MHz, DMSO-d$_6$): 12.41 (br, 1H), 7.60-7.22 (m, 9H), 7.17-7.08 (m, 2H), 6.96-6.91 (m, 1H), 6.91-6.86 (m, 1H), 3.53 (s, 2H), 3.28-3.17 (m, 4H), 2.59 (d, J = 11.0 Hz, 2H), 2.02-1.92 (m, 2H), 1.63-1.47 (m, 2H), 1.26-1.20 (m, 6H) |
| 102 | 1-(6-methoxyindoline-1-carbonyl)-4-[2-oxo-2-(N-phenylanilino)ethyl]piperidine-4-carboxylic acid | 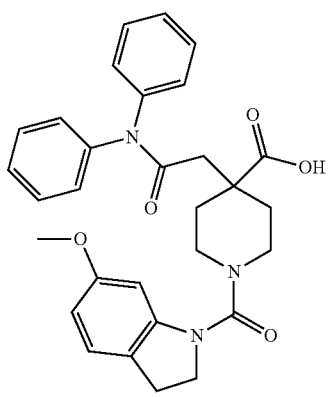 [SMILES: COc1ccc2c(c1)N(C(=O)N1CCC(CC(=O)N(c3ccccc3)c3ccccc3)(C(=O)O)CC1)CC2] | 514.5 | ¹H NMR (400 MHz, DMSO-d$_6$): 12.38 (br, 1H), 7.58-7.12 (m, 10H), 7.06 (d, J = 1.0 Hz, 1H), 6.53-6.50 (m, 1H), 6.42 (dd, J = 2.2, 8.1 Hz, 1H), 3.78 (t, J = 8.1 Hz, 2H), 3.68 (s, 3H), 3.27-3.17 (m, 4H), 2.88 (t, J = 8.1 Hz, 2H), 2.55 (s, 2H), 2.02-1.91 (m, 2H), 1.60-1.50 (m, 2H) |

| Example No. | Chemical Name | Structure | ES/MS (m/z) (M + H) | $^1$H NMR (400 MHz, DMSO-d$_6$) |
|---|---|---|---|---|
| 107 | 4-[2-(N-(2-fluorophenyl)anilino)-2-oxo-ethyl]-1-(6-methylindoline-1-carbonyl)piperidine-4-carboxylic acid | 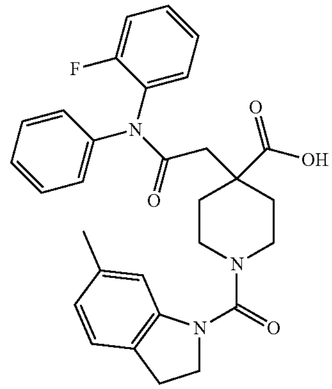 [SMILES: Cc1ccc2c(c1)N(C(=O)N1CCC(CC(=O)N(c3ccccc3)c3ccccc3F)(C(=O)O)CC1)CC2] | 516.5 | $^1$H NMR (400 MHz, DMSO-d$_6$): 12.40 (br, 1H), 7.69-7.11 (m, 9H), 7.08-6.99 (m, 1H), 6.77 (s, 1H), 6.66 (d, J = 7.5 Hz, 1H), 3.77 (t, J = 8.2 Hz, 2H), 3.29-3.10 (m, 4H), 2.90 (t, J = 8.1 Hz, 2H), 2.66-2.61 (m, 2H), 2.24 (s, 3H), 1.97 (d, J = 13.3 Hz, 2H), 1.65-1.45 (m, 2H) |
| 108 | 1-(6-fluoroindoline-1-carbonyl)-4-[2-(N-(2-fluorophenyl)anilino)-2-oxo-ethyl]piperidine-4-carboxylic acid | 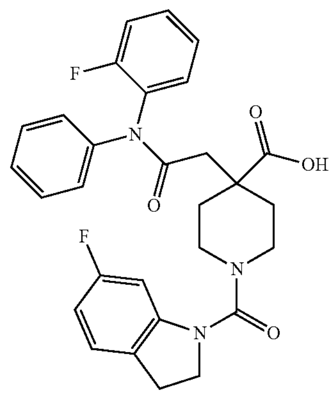 [SMILES: O=C(N1CCC(CC(=O)N(c2ccccc2)c2ccccc2F)(C(=O)O)CC1)N1CCc2ccc(F)cc21] | 520.4 | $^1$H NMR (400 MHz, DMSO-d$_6$): 7.75-7.07 (m, 10H), 6.79-6.68 (m, 1H), 6.68-6.58 (m, 1H), 3.84 (t, J = 8.3 Hz, 2H), 3.25-3.07 (m, 4H), 2.94 (t, J = 8.1 Hz, 2H), 2.58 (s, 2H), 1.95 (d, J = 12.4 Hz, 2H), 1.56 (t, J = 9.6 Hz, 2H) |

1-(5-bromo-4-pentyl-1,2,4-triazol-3-yl)-4-[2-oxo-2-(N-phenylanilino)ethyl]piperidine-4-carboxylic acid (Example No. 4)

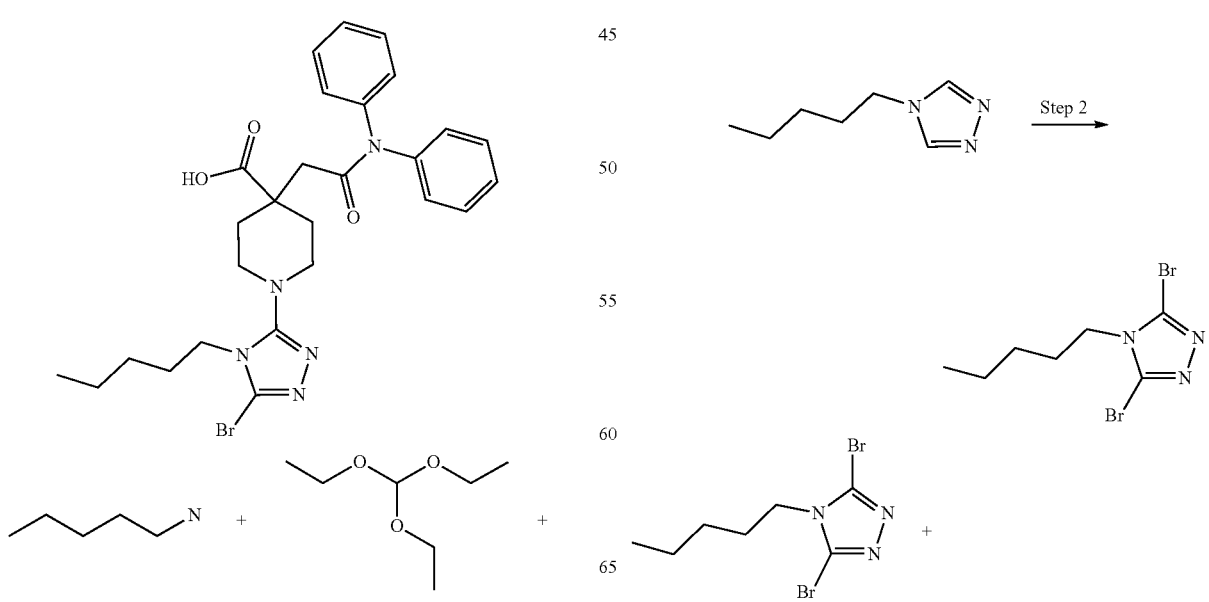

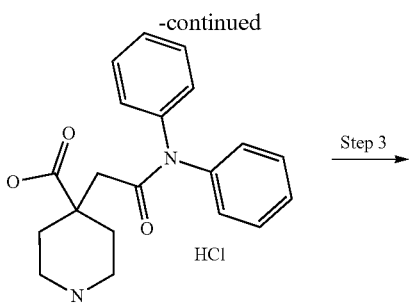

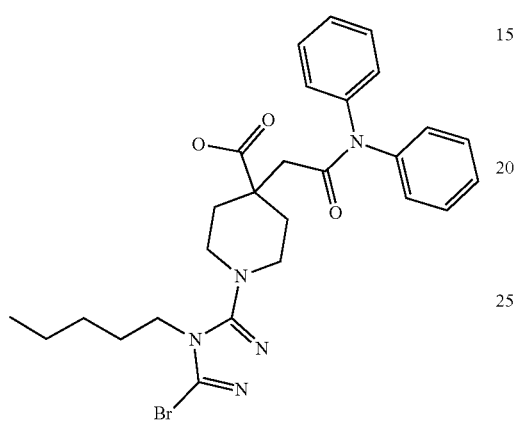

Step 1: To a solution of diethoxymethoxyethane (5 g, 33.7 mmol, 100 mass %) and formohydrazide (1.4 g, 23 mmol, 98 mass %) in was added methanol (50 mL) at 20° C. The mixture was stirred at 60° C. for 3 h. After cooling to 40° C., the mixture was added pentan-1-amine (2 g, 22.7 mmol) and stirred overnight at 60° C. The mixture was cooled to RT and concentrated under reduced pressure. The reaction mixture was added water 20 mL, then extracted with dichloromethane (20 mL×4). The combined organic layers were washed with brine (20 mL), dried over $Na_2SO_4$ and concentrated in vacuo. The residue was purified by flash silica gel chromatography, eluting with 0~3% methanol/dichloromethane to give 4-pentyl-1,2,4-triazole (2.55 g, 90 mass %, 72.6% yield) as a yellow oil.

$^1$H NMR (400.13 MHz, DMSO-$d_6$): 8.52 (s, 2H), 4.01 (t, J=7.2 Hz, 2H), 1.71 (td, J=7.4, 14.8 Hz, 2H), 1.34-1.22 (m, 2H), 1.22-1.09 (m, 2H), 0.84 (t, J=7.3 Hz, 3H)

Step 2: To a solution of 4-pentyl-1,2,4-triazole (2.5 g, 16.0 mmol, 90 mass %) in DMF (10 mL) was added N-bromosuccinimide (7 g, 38.5 mmol) at 20° C. The reaction was stirred at 60° C. for 3 h. The reaction mixture was cooled to RT, diluted with water (30 mL) and extracted with ethyl acetate (30 mL×3). The combined organic layers were washed with brine (30 mL), dried over anhydrous $Na_2SO_4$ and concentrated in vacuo. The residue was purified by flash silica gel chromatography, eluting with 0-33% ethyl acetate in petroleum ether to give 3,5-dibromo-4-pentyl-4H-1,2,4-triazole (3.1 g, 95 mass %, 61% yield) as a colorless oil. $^1$H NMR (400 MHz, DMSO-$d_6$): 3.98 (t, J=7.4 Hz, 2H), 1.67 (m, J=7.3 Hz, 2H), 1.38-1.20 (m, 4H), 0.87 (t, J=7.1 Hz, 3H)

Step 3: To the solution of 4-[2-oxo-2-(N-phenylanilino)ethyl]piperidine-4-carboxylic acid; hydrochloride (202 mg, 0.512 mmol, 95 mass %), 3,5-dibromo-4-pentyl-1,2,4-triazole (170 mg, 0.544 mmol) and cesium carbonate (470 mg, 1.44 mmol) in 2-methyl-2-butanol (4.0 mL) was added [(2-di-tert-butylphosphino-2',4',6'-triisopropyl-1,1'-biphenyl)-2-(2'-amino-1,1'-biphenyl)] palladium(II) methanesulfonate (43 mg, 0.05 mmol). The flask was flushed with nitrogen. The resulting mixture was stirred under nitrogen at 120° C. overnight. Upon completion, the reaction mixture was cooled to RT, concentrated in vacuum and adjusted pH to 7 with 1N HCl and filtrated off the solid. The filtrate was concentrated in vacuum. The residue was purified by prep-HPLC (Column: Xtimate C18 100*30 mm*10 um; mobile phase A: water-formic acid, mobile phase B: ACN, eluting with 50-80% B in 10 min, then to 100% B. The appropriate fractions were combined and lyophilized to give title product (75.6 mg, 25.0% yield). MS m/z 554.2, 556.2 (M+H); $^1$H NMR (400.13 MHz, DMSO-$d_6$): 7.60-7.02 (m, 10H), 3.75 (t, J=7.4 Hz, 2H), 3.03 (d, J=8.9 Hz, 1H), 2.98 (d, J=5.5 Hz, 2H), 2.55 (s, 2H), 2.14-2.00 (m, 2H), 1.71-1.54 (m, 4H), 1.34-1.23 (m, 2H), 1.21-1.12 (m, 2H), 0.83 (t, J=7.3 Hz, 3H).

1-(5-cyclopropylpyrimidin-4-yl)-4-(2-(diphenylamino)-2-oxoethyl)piperidine-4-carboxylic acid
(Example No. 5)

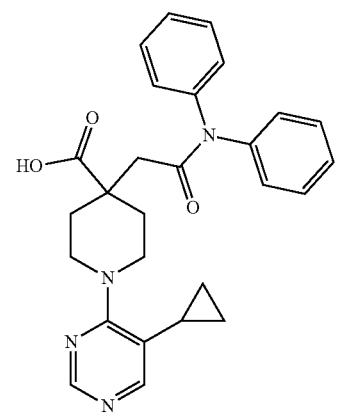

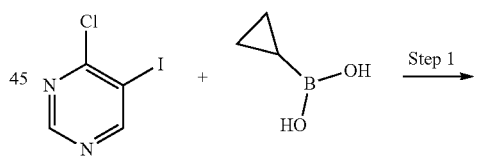

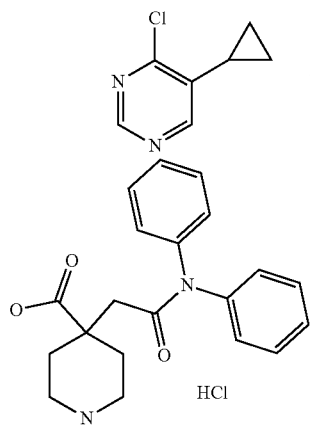

-continued

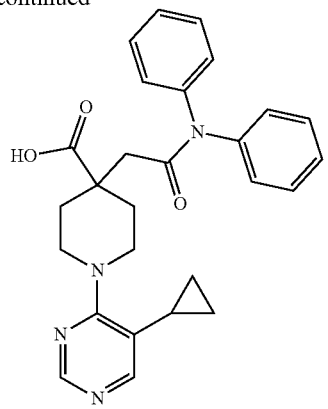

Step 1: A flask was charged with cyclopropylboronic acid (345 mg, 4.016 mmol), cesium carbonate (2.603 g, 7.988 mmol), 4-chloro-5-iodopyrimidine (1.011 g, 4.037 mmol), 1,4-Dioxane (24 mL) and water (6.0 mL) under nitrogen. To the suspension was then added [1,1'-bis(diphenylphosphino)ferrocene]dichloropalladium(II) (312 mg, 0.405 mmol). The reaction mixture was stirred at 95° C. under $N_2$ for 6 h. Upon completion, the reaction was cooled to RT, poured into water (50 mL) and extracted with DCM (40 mL×3). Then the combined organic phase was washed with brine (50 mL), dried with anhydrous $Na_2SO_4$ and concentrated in vacuum. The residue was purified by normal silica gel chromatography (PE:EtOAc=1:0 to 3:1) to 4-chloro-5-cyclopropylpyrimidine (284 mg, 91 mass %, 41.4% yield) as a colorless oil. MS m/z 154.9 (M+H);

Step 2: To a solution of 4-[2-oxo-2-(N-phenylanilino)ethyl]piperidine-4-carboxylic acid;hydrochloride (151 mg, 0.362 mmol, 90 mass %) in N,N-dimethylacetamide (1.5 mL) was added 4-chloro-5-cyclopropyl-pyrimidine (105 mg, 0.618 mmol, 91 mass %) and potassium carbonate (245 mg, 1.77 mmol). The mixture was stirred at 110° C. for 5 h under nitrogen. Upon completion, the reaction mixture was cooled to RT, combined with pilot batch, adjusted pH to 5 by adding 1N HCl. Then the mixture was extracted with ethyl acetate (40 mL×3). Then the combined organic phase was dried with anhydrous $Na_2SO_4$ and concentrated in vacuum. The residue was purified by prep-HPLC, Column: Xtimate C18 100*30 mm*10 um; mobile phase A: water-formic acid, mobile phase B: ACN, eluting with 25-55% B in 14 min, then to 100% B. The appropriate fractions were combined and lyophilized to give 1-(5-cyclopropylpyrimidin-4-yl)-4-(2-(diphenylamino)-2-oxoethyl)piperidine-4-carboxylic acid (16.4 mg, 5.56% yield) as a yellow solid. MS m/z 457.4 (M+H); $^1$H NMR (400 MHz, DMSO-$d_6$): 12.48 (br, 1H), 8.47 (s, 1H), 8.04 (s, 1H), 7.52-7.16 (m, 10H), 3.88 (d, J=14.4 Hz, 2H), 3.59-3.50 (m, 1H), 2.56 (s, 2H), 2.47 (s, 1H), 2.08 (d, J=13.5 Hz, 2H), 1.88-1.79 (m, 1H), 1.67-1.57 (m, 2H), 0.99-0.89 (m, 2H), 0.74-0.67 (m, 2H)

1-(3-chloropyrazin-2-yl)-4-[2-oxo-2-(N-phenylanilino)ethyl]piperidine-4-carboxylic acid (Example No. 109)

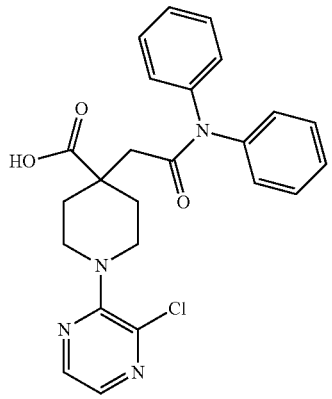 [SMILES: O=C(CC1(C(=O)O)CCN(c2nccnc2Cl)CC1)N(c1ccccc1)c1ccccc1]

To a solution of 4-[2-oxo-2-(N-phenylanilino)ethyl]piperidine-4-carboxylic acid; hydrochloride (300 mg, 0.7202 mmol, 90 mass %) in N,N-dimethylacetamide (4.0 mL) was added 2,3-dichloropyrazine (361 mg, 2.40 mmol) and potassium carbonate (332 mg, 2.40 mmol). The mixture was stirred at 110° C. for 5 h under $N_2$. The mixture was filtered and the filtrate was concentrated under reduced pressure. The residue was purified by prep-HPLC (Instrument PREP-WI, Column C18-6 100*30 mm*5 um, mobile phase A: water-0.225% formic acid, mobile phase B: ACN, eluting with B 45-75% in 15 min, then to 100% B, flow rate 25 mL/min). The appropriate fractions were combined and lyophilized to give title product (45 mg, 99.3 mass %, 13.8% yield) as a white solid. MS m/z 451.0 (M+H); $^1$H NMR (400.15 MHz, DMSO-$d_6$): 12.37 (br, 1H), 8.22 (d, J=2.5 Hz, 1H), 7.95 (d, J=2.5 Hz, 1H), 7.68-7.06 (m, 10H), 3.30-3.22 (m, 4H), 2.56 (s, 2H), 2.18-2.03 (m, 2H), 1.73-1.58 (m, 2H).

1-(1-cyclopropylimidazol-2-yl)-4-[2-oxo-2-(N-phenylanilino)ethyl]piperidine-4-carboxylic acid, formic acid (Example No. 110)

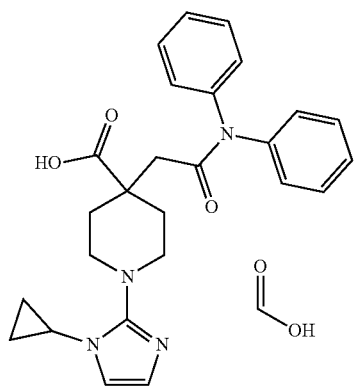

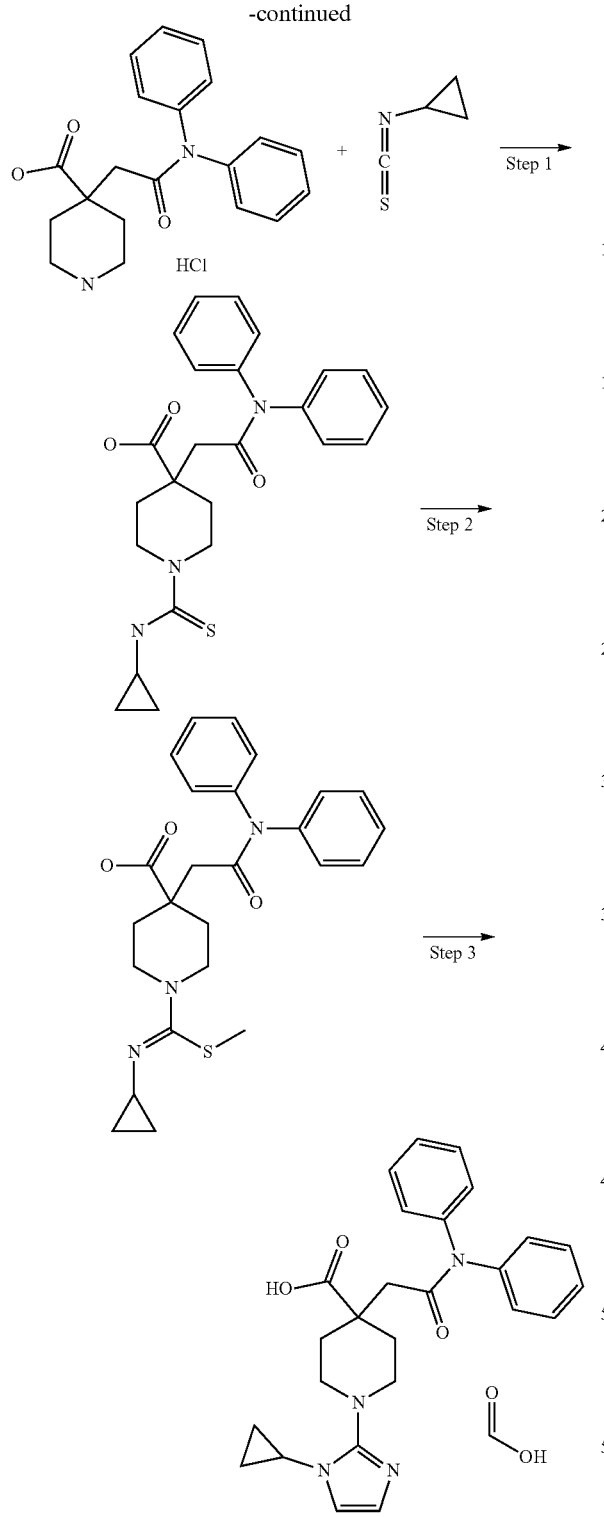

Phenomenex C18 75*30 mm*3 um; mobile phase A: water (10 mM NH₄HCO₃), mobile phase B: ACN, eluting with 10-80% B, then to 100% B. The appropriate fractions were combined and lyophilized to give 1-(cyclopropylcarbamothioyl)-4-[2-oxo-2-(N-phenylanilino)ethyl]piperidine-4-carboxylic acid (250 mg, 90 mass %, 49.7% yield) as a white solid. MS m/z 438.1 (M+H).

Step 2: To a solution of 1-(cyclopropylcarbamothioyl)-4-[2-oxo-2-(N-phenylanilino)ethyl]piperidine-4-carboxylic acid (250 mg, 0.54 mmol) in acetone (4.0 mL) was added iodomethane (60 μL, 0.94 mmol). The mixture was stirred at RT for 4 h under N₂. The reaction was concentrated to get 1-[(Z)—N-cyclopropyl-C-methylsulfanyl-carbonimidoyl]-4-[2-oxo-2-(N-phenylanilino)ethyl]piperidine-4-carboxylic acid;hydroiodide (300 mg, 90 mass %, 85.8% yield) as a white solid. The crude product was used for next step directly.

Step 3: To a solution of 1-[(Z)—N-cyclopropyl-C-methylsulfanyl-carbonimidoyl]-4-[2-oxo-2-(N-phenylanilino) ethyl]piperidine-4-carboxylic acid, hydroiodide (300 mg, 0.46 mmol, 90 mass %) and 2,2-dimethoxyethan-1-amine (136 mg, 1.27 mmol) in acetonitrile (4 mL) was added pyridine (0.08 mL, 1 mmol). The reaction was stirred at RT overnight. 4.0 N HCl (4.0 mL) was added and the mixture was stirred at RT 16 h. Upon completion, the reaction was neutralized with sat. Na₂CO₃ to pH to 6 and extract with ethyl acetate (10 mL×2), the organic layer was further washed with brine (20 mL×2), dried over Na₂SO₄, filtered, and concentrated under reduced pressure to give a residue. The residue was purified by prep-HPLC (column: Xtimate C18 100*30 mm*10 um; mobile phase A: water-0.225% formic acid, mobile phase B: ACN, eluting with 15-45% B in 4 min, then to 100% B). The appropriate fractions were combined and lyophilized to give the product 1-(1-cyclopropylimidazol-2-yl)-4-[2-oxo-2-(N-phenylanilino)ethyl] piperidine-4-carboxylic acid, formic acid (37.0 mg, 97.5 mass %, 15.8% Yield). MS m/z 445.1 (M+H—HCO₂H); H NMR (400.13 MHz, DMSO-d₆): 8.24 (s, 1H), 7.52-7.17 (m, 10H), 6.73 (d, J=1.4 Hz, 1H), 6.47 (d, J=1.3 Hz, 1H), 3.23-3.17 (m, 1H), 3.10-2.94 (m, 4H), 2.55 (s, 2H), 2.10-2.00 (m, 2H), 1.63 (dt, J=3.9, 8.6 Hz, 2H), 0.96-0.81 (m, 4H).

4-[2-oxo-2-(N-phenylanilino)ethyl]-1-([1,2,4]triazolo[4,3-a]pyridin-3-yl)piperidine-4-carboxylic acid (Example No. 111)

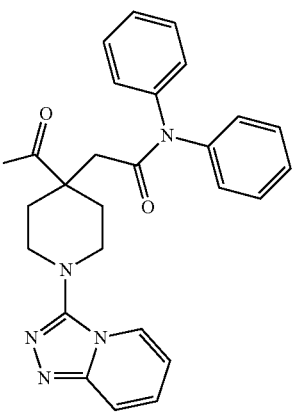

Step 1: To a solution of 4-[2-oxo-2-(N-phenylanilino) ethyl]piperidine-4-carboxylic acid, hydrochloride (400 mg, 1.1 mmol) in tetrahydrofuran (5.0 mL) was added N,O-bis (trimethylsilyl)acetamide (1.3 mL, 5.2 mmol). The mixture was stirred at RT for 0.5 h, then isothiocyanatocyclopropane (222 mg, 2.2 mmol) was added. The mixture was stirred at 50° C. for 2 h. Upon completion, the reaction was concentrated. The residue was purified by prep-HPLC (column:

To a mixture of 3-chloro-[1,2,4]triazolo[4,3-a]pyridine (96 mg, 0.61 mmol), 4-[2-oxo-2-(N-phenylanilino)ethyl]piperidine-4-carboxylic acid, hydrochloride (85 mg, 0.20 mmol, 90 mass %) in 2-methyl-2-butanol (1.0 mL) was added tBuXPhos Pd G3 (30 mg, 0.036 mmol) and cesium carbonate (200 mg, 0.61 mmol), the mixture was stirred at 120° C. overnight under $N_2$. Upon completion, the mixture was cooled to RT, the crude was purified by prep-HPLC (Instrument NCX, Column: Phenomenex Gemini-NX C18 100*30 mm*3 um, mobile phase A: water-0.225% formic acid, mobile phase B: ACN, eluting with 10-70% B in 15 min, then to 100% B, flow rate: 25 mL/min). The appropriate fractions were combined and lyophilized to give title product (44.2 mg, 99.6 mass %, 47.4% yield). MS m/z 456.4 (M+H); $^1$H NMR (400 MHz, DMSO-$d_6$): 8.10 (d, J=7.0 Hz, 1H), 7.59 (d, J=9.3 Hz, 1H), 7.55-7.08 (m, 11H), 6.85 (t, J=6.7 Hz, 1H), 3.19-3.09 (m, 4H), 2.59 (s, 2H), 2.23-2.08 (m, 2H), 1.83-1.65 (m, 2H).

1-(3-cyclopropyl-2-pyridyl)-4-[2-oxo-2-(N-phenylanilino)ethyl]piperidine-4-carboxylic acid (Example No. 112)

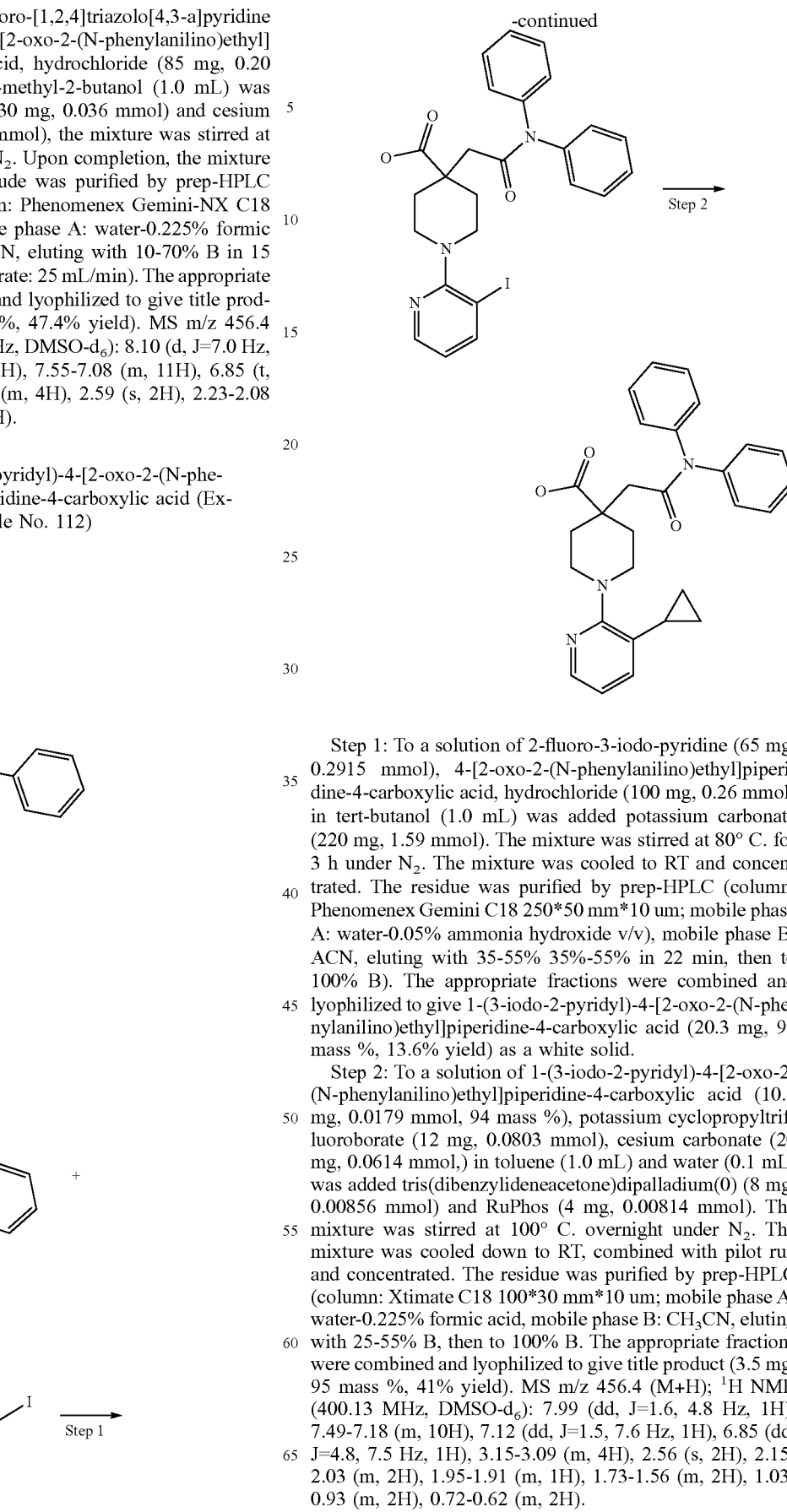

Step 1: To a solution of 2-fluoro-3-iodo-pyridine (65 mg, 0.2915 mmol), 4-[2-oxo-2-(N-phenylanilino)ethyl]piperidine-4-carboxylic acid, hydrochloride (100 mg, 0.26 mmol) in tert-butanol (1.0 mL) was added potassium carbonate (220 mg, 1.59 mmol). The mixture was stirred at 80° C. for 3 h under $N_2$. The mixture was cooled to RT and concentrated. The residue was purified by prep-HPLC (column: Phenomenex Gemini C18 250*50 mm*10 um; mobile phase A: water-0.05% ammonia hydroxide v/v), mobile phase B: ACN, eluting with 35-55% 35%-55% in 22 min, then to 100% B). The appropriate fractions were combined and lyophilized to give 1-(3-iodo-2-pyridyl)-4-[2-oxo-2-(N-phenylanilino)ethyl]piperidine-4-carboxylic acid (20.3 mg, 94 mass %, 13.6% yield) as a white solid.

Step 2: To a solution of 1-(3-iodo-2-pyridyl)-4-[2-oxo-2-(N-phenylanilino)ethyl]piperidine-4-carboxylic acid (10.3 mg, 0.0179 mmol, 94 mass %), potassium cyclopropyltrifluoroborate (12 mg, 0.0803 mmol), cesium carbonate (20 mg, 0.0614 mmol,) in toluene (1.0 mL) and water (0.1 mL) was added tris(dibenzylideneacetone)dipalladium(0) (8 mg, 0.00856 mmol) and RuPhos (4 mg, 0.00814 mmol). The mixture was stirred at 100° C. overnight under $N_2$. The mixture was cooled down to RT, combined with pilot run and concentrated. The residue was purified by prep-HPLC (column: Xtimate C18 100*30 mm*10 um; mobile phase A: water-0.225% formic acid, mobile phase B: $CH_3CN$, eluting with 25-55% B, then to 100% B. The appropriate fractions were combined and lyophilized to give title product (3.5 mg, 95 mass %, 41% yield). MS m/z 456.4 (M+H); $^1$H NMR (400.13 MHz, DMSO-$d_6$): 7.99 (dd, J=1.6, 4.8 Hz, 1H), 7.49-7.18 (m, 10H), 7.12 (dd, J=1.5, 7.6 Hz, 1H), 6.85 (dd, J=4.8, 7.5 Hz, 1H), 3.15-3.09 (m, 4H), 2.56 (s, 2H), 2.15-2.03 (m, 2H), 1.95-1.91 (m, 1H), 1.73-1.56 (m, 2H), 1.03-0.93 (m, 2H), 0.72-0.62 (m, 2H).

Example Nos. 35, 35A, 35B, 52, 60, 76, 77, 78, 80, 80A, 80B, 81, 82A, 82B, 83, 83A, 83B, 84, 85, 94, 99, 103, 104, 105 and 106 were Prepared According to Scheme 2
Scheme 2
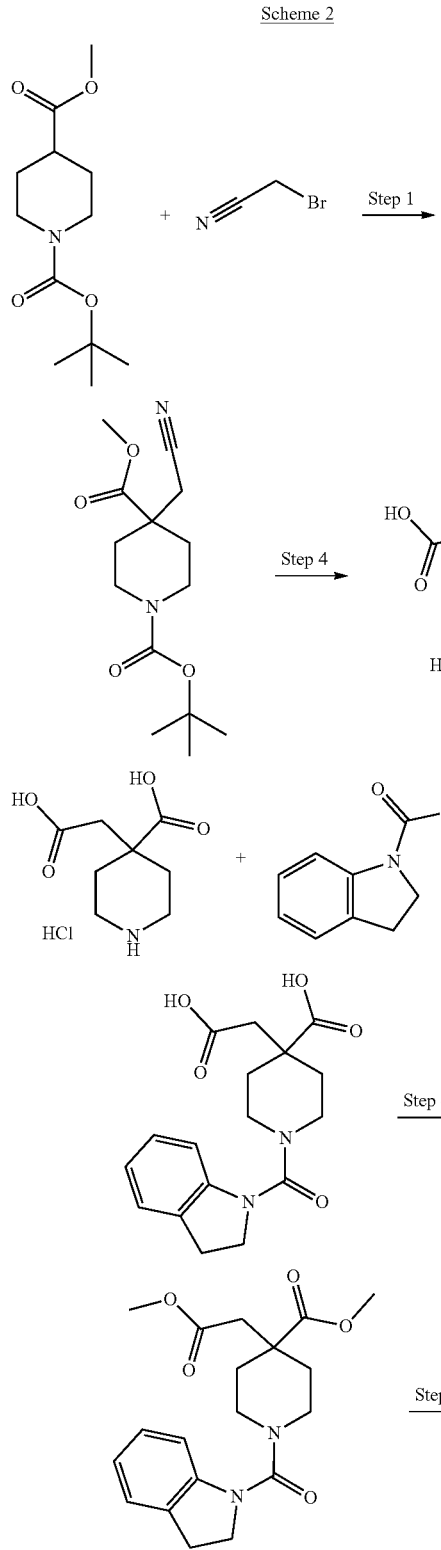
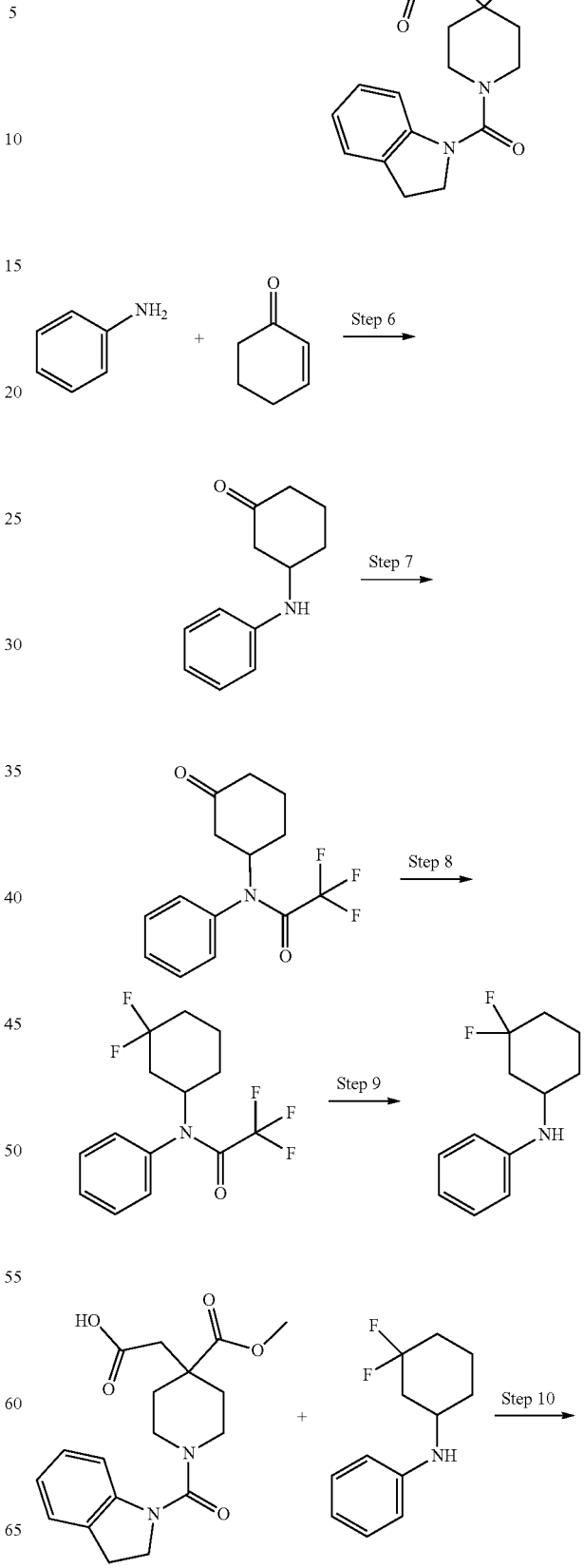

-continued

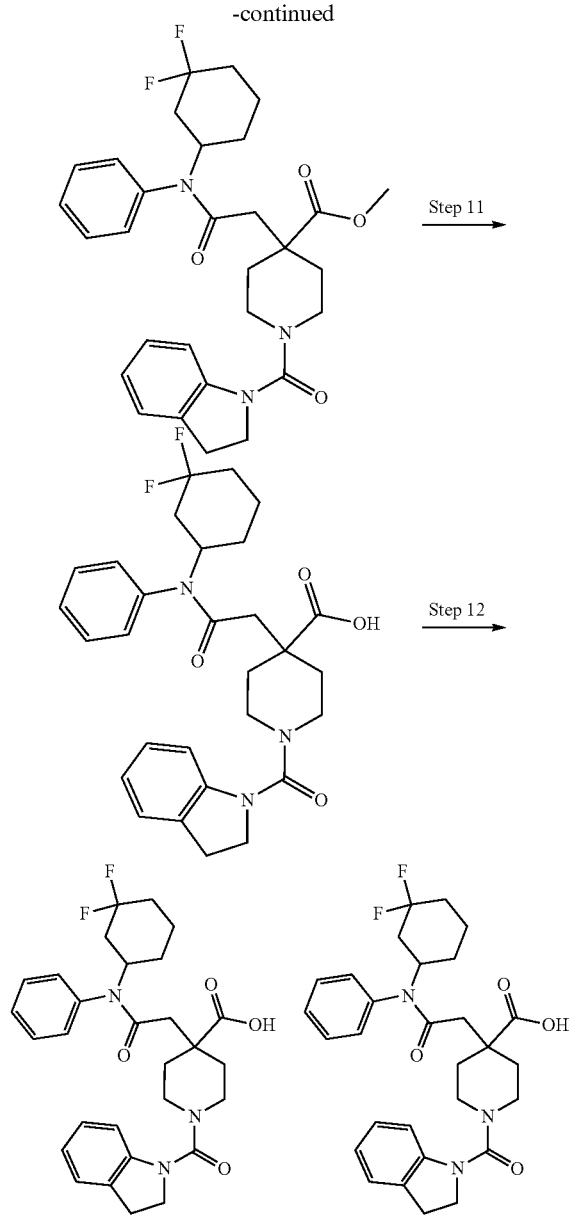

Step 1: O1-tert-butyl O4-methyl 4-(cyanomethyl)piperidine-1,4-dicarboxylate

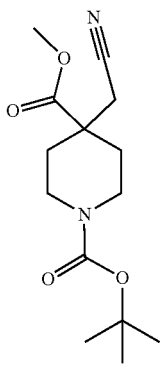 [SMILES: COC(=O)C1(CC#N)CCN(C(=O)OC(C)(C)C)CC1]

To a solution of 1-tert-butyl 4-methyl piperidine-1,4-dicarboxylate (15 g, 60.41 mmol) in tetrahydrofuran (150.0 ml) was added a solution of diisopropylamino lithium in THF/hexane (45.0 ml, 90.0 mmol, 2.0 mol/L) dropwise at −65° c. under $N_2$. After the mixture was stirred 1 h, the bromoacetonitrile (6.4 ml, 91 mmol) was added dropwise at −65° C. The reaction mixture was then slowly warmed up to RT and stirred overnight under $N_2$. The reaction was quenched by adding sat. $NH_4Cl$ (200.0 mL) and extracted with EtOAc (200.0 mL×3). The combined organic layers were washed with brine (100 mL), dried over $Na_2SO_4$, filtered, and concentrated in vacuo to give a residue. The residue was purified by silica gel flash chromatography, eluting 0~27% ethyl acetate/petroleum ether to give the title compound (8.2 g, 95 mass %, 45.9% yield). $^1$H NMR (400.21 MHz, DMSO-$d_6$): 3.77 (s, 3H), 3.67 (dt, J=14.1, 4.6 Hz, 2H), 2.96 (s, 2H), 2.57-2.56 (m, 1H), 2.05-1.99 (m, 2H), 1.61-1.52 (m, 2H), 1.46-1.45 (m, 10H).

Step 2: 4-(carboxymethyl)piperidine-4-carboxylic acid;hydrochloride

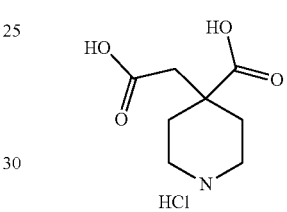

O1-tert-butyl O4-methyl 4-(cyanomethyl)piperidine-1,4-dicarboxylate (8.25 g, 27.75 mmol, 95 mass %) was treated with hydrochloric acid (60 mL, 36%), the reaction mixture was heated to 100° C. and stirred overnight. The reaction was cooled down to RT and concentrated in vacuo to give crude title compound (7.48 g, 80 mass %, 96.4% yield), which was used directly in the next step without purification. $^1$H NMR (400.13 MHz, DMSO-$d_6$): 9.31 (br, 1H), 9.18 (br, 1H), 3.26-3.17 (m, 2H), 3.02-2.91 (m, 2H), 2.63 (s, 2H), 2.20-2.14 (m, 2H), 1.88-1.81 (m, 2H).

Step 3: 4-(carboxymethyl)-1-(indoline-1-carbonyl)piperidine-4-carboxylic acid

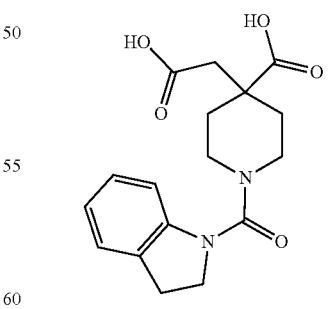

To a solution of 4-(carboxymethyl)piperidine-4-carboxylic acid; hydrochloride (9.6 g, 34 mmol, 80 mass %) in tetrahydrofuran (100.0 mL) was added N,O-bis(trimethylsilyl)acetamide (35 mL, 141 mmol, 99 mass %). After stirring half an hour at RT, the reaction mixture was cooled on ice bath, N,N-diisopropylethylamine (12 mL, 68.7 mmol) was added, followed by indoline-1-carbonyl chloride (12.01 g, 49.60 mmol, 75 mass %). The reaction mixture was warm up to RT and stirred overnight. Water was added to the reaction (150 ml) and was adjusted pH to 4 with 1.0 sat. NH$_4$Cl aq. and extracted with ethyl acetate (100 mL×3). The combined organic layers were washed with brine (100 mL), dried over Na$_2$SO$_4$, filtered and concentrated under vacuo to give a residue. The residue was purified by silica gel flash chromatography eluting DCM to 10% MeOH/DCM to give the title compound (8.4 g, 90 mass %, 66% yield). MS m/z 313.1 (M+H).

The compounds in the table below were prepared as described above.

| Chemical Name | Structure | ES/MS m/z (M + H) |
|---|---|---|
| 4-(carboxymethyl)-1-(6-fluoroindoline-1-carbonyl)piperidine-4-carboxylic acid | 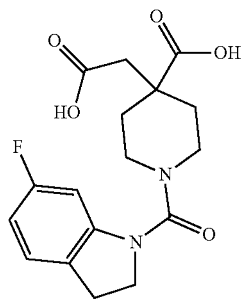 [SMILES: O=C(O)CC1(C(=O)O)CCN(C(=O)N2CCc3ccc(F)cc32)CC1] | 351.1 |
| 4-(carboxymethyl)-1-(6-methylindoline-1-carbonyl)piperidine-4-carboxylic acid | 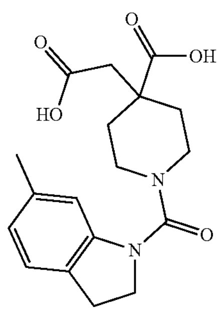 [SMILES: Cc1ccc2c(c1)N(C(=O)N1CCC(CC(=O)O)(C(=O)O)CC1)CC2] | 347.0 |

Step 4: Methyl 1-(indoline-1-carbonyl)-4-(2-methoxy-2-oxo-ethyl)piperidine-4-carboxylate

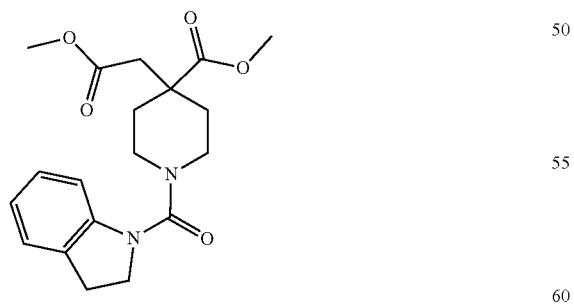

To a solution of 4-(carboxymethyl)-1-(indoline-1-carbonyl)piperidine-4-carboxylic acid (3.2 g, 8.7 mmol, 90 mass %) in methanol (6.0 mL) and acetonitrile (60.0 mL), cooled on ice, was added (diazomethyl)trimethylsilane (2.0 mol/L) in hexanes (17.0 mL, 34 mmol, 2.0 mol/L) dropwise, followed by N,N-diisopropylethylamine (3.0 mL, 17.17 mmol). The mixture was warmed up to RT and stirred overnight. The mixture was quenched by adding water (80 ml) and extracted with ethyl acetate (50 mL×2). The combined organic layers were washed with brine (80 mL), dried over Na$_2$SO$_4$, filtered, and concentrated to give a residue. The residue was purified by silica gel flash chromatography, eluting 0-56% ethyl acetate/petroleum ether to give title compound (2.88 g, 90 mass %, 83% yield). MS m/z 361.0 (M+H).

The compounds in the table below were prepared as described above.

| Chemical Name | Structure | ES/MS (m/z) (M + H) |
|---|---|---|
| methyl 1-(6-fluoroindoline-1-carbonyl)-4-(2-methoxy-2-oxo-ethyl)piperidine-4-carboxylate | | 379.2 |
| methyl 4-(2-methoxy-2-oxo-ethyl)-1-(6-methylindoline-1-carbonyl)piperidine-4-carboxylate | | 375.5 | ethyl 1-[(2-fluoro-4-isopropyl-phenyl)methyl]-4-(2-methoxy-2-oxo-ethyl)piperidine-4-carboxylate

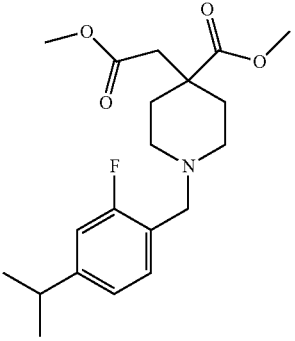 [SMILES: COC(=O)CC1(C(=O)OC)CCN(Cc2ccc(C(C)C)cc2F)CC1]

To a mixture of methyl 4-(2-methoxy-2-oxo-ethyl)piperidine-4-carboxylate: acetic acid (1.0 g, 3.3 mmol, 90 mass %), trimethylamine (1.0 mL, 7.0 mmol) and 2-fluoro-4-isopropyl-benzaldehyde (700 mg, 4.00 mmol) in 1,2-dichloroethane (60.0 mL) was added titanium (IV) isopropoxide (4.0 mL, 13 mmol). The mixture was stirred at 80° C. for 2 hours. After the reaction was cooled to RT, Sodium triacetoxyborohydride (2.1 g, 9.6 mmol) was added. The mixture was stirred at room temperature for 1 hour. Upon completion, the mixture was quenched with water (5 mL), extracted with EtOAc (10 ml×3), the combined the organic layers was dried with $Na_2SO_4$, filtered, and concentrated to hive a residue. The residue was purified by prep-HPLC (YMC-Triart Prep C 18 250×50 mm×10 um, mobile phase A: water-0.225% formic acid, mobile phase B: ACN, eluting 10-50% B in 20 min, then to 100% B, Flowrate: 110 mL/min). The eluent was concentrated, the residue aqueous solution was basified with $NaHCO_3$ to pH>7. The mixture was extracted with DCM (30 mL×3). The combined phase was dried over $Na_2SO_4$; filtered and evaporated under vacuum to give the title compound (760 mg, 90 mass %, 57% Yield). MS m/z 366.2 (M+H);

Step 5: 2-[1-(indoline-1-carbonyl)-4-methoxycarbonyl-4-piperidyl]acetic acid

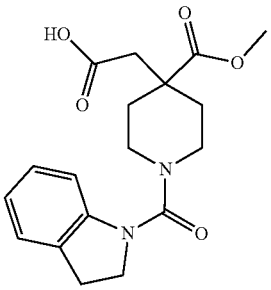 [SMILES: COC(=O)C1(CC(=O)O)CCN(C(=O)N2CCc3ccccc32)CC1]

To a mixture of methyl 1-(indoline-1-carbonyl)-4-(2-methoxy-2-oxo-ethyl)piperidine-4-carboxylate (2.88 g, 7.19 mmol, 90 mass %) in methanol (8.0 mL), water (8.0 mL), and tetrahydrofuran (8.0 mL) was added lithium hydroxide (0.36 g, 14.72 mmol) in one portion at RT, the mixture was stirred overnight at RT. Upon monitoring the reaction by LCMS, additional lithium hydroxide (0.202 g, 8.27 mmol) was added and the reaction was stirred at RT overnight. The reaction mixture was adjusted to pH 4 with 1.0 N HCl and extracted with ethyl acetate (18 mL×3). The combined organic layers were washed with brine (30 mL), dried over $Na_2SO_4$, filtered, and concentrated under vacuo to give a residue. The residue was purified by silica gel flash eluting 0-6% MeOH/DCM to give the title compound (1.52 g, 95 mass %, 58.0% yield). MS m/z 347 (M+H).

The compounds in the table below were prepared as described above.

| Chemical Name | Structure | ES/MS (m/z) (M + H) | $^1$H NMR (400 MHz, DMSO-$d_6$) |
|---|---|---|---|
| 2-[4-methoxycarbonyl-1-[methyl(phenyl)carbamoyl]-4-piperidyl]acetic acid | 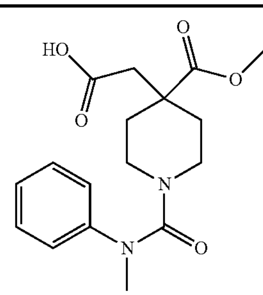 | 335.1 | |
| 2-[1-[(2-fluoro-4-isopropyl-phenyl)methyl]-4-methoxycarbonyl-4-piperidyl]acetic acid | 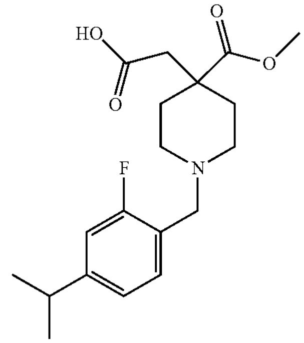 [SMILES: COC(=O)C1(CC(=O)O)CCN(Cc2ccc(C(C)C)cc2F)CC1] | / | $^1$H NMR (400 MHz, CDCl$_3$): 11.04 (br, 1H), 7.72 (t, J = 8.0 Hz, 1H), 7.12 (d, J = 8.0 Hz, 1H), 6.95 (d, J = 7.2 Hz, 1H), 4.26 (s, 2H), 3.62 (s, 3H), 3.53-3.51 (m, 2H), 2.95-2.90 (m, 3H), 2.82 (s, 2H), 2.26-2.20 (m, 4H), 1.24 (d, J = 6.8 Hz, 6H). |

| Chemical Name | Structure | ES/MS (m/z) (M + H) | $^1$H NMR (400 MHz, DMSO-$d_6$) |
|---|---|---|---|
| 2-[1-(6-fluoroindoline-1-carbonyl)-4-methoxycarbonyl-4-piperidyl]acetic acid | 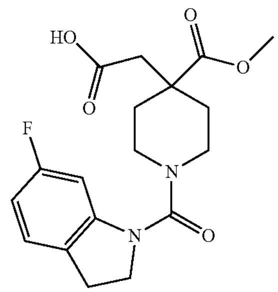 [SMILES: COC(=O)C1(CC(=O)O)CCN(C(=O)N2CCc3ccc(F)cc32)CC1] | 365.2 | |
| 2-[4-methoxycarbonyl-1-(6-methylindoline-1-carbonyl)-4-piperidyl]acetic acid | 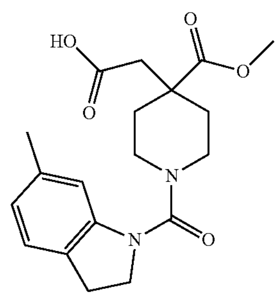 [SMILES: COC(=O)C1(CC(=O)O)CCN(C(=O)N2CCc3ccc(C)cc32)CC1] | / | $^1$H NMR (400 MHz, CDCl$_3$): 7.05 (d, J = 7.5 Hz, 1H), 6.81 (s, 1H), 6.72 (d, J = 7.5 Hz, 1H), 3.91 (t, J = 8.2 Hz, 2H), 3.76 (s, 3H), 3.58 (td, J = 4.3, 13.9 Hz, 2H), 3.28 (ddd, J = 3.0, 10.5, 13.5 Hz, 2H), 2.97 (t, J = 8.1 Hz, 2H), 2.71 (s, 2H), 2.32 (s, 3H), 2.23-2.15 (m, 2H), 1.68 (ddd, J = 3.9, 10.2, 13.9 Hz, 2H). |

Step 6: rac-3-anilinocyclohexanone

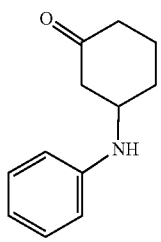 [SMILES: O=C1CCCC(Nc2ccccc2)C1]

To a mixture of aniline (20.0 g, 208.3 mmol) in 2-cyclohexen-1-one (31.0 ml, 310 mmol) was added 4-dimethylaminopyridine (7.8 g, 62 mmol, 97 mass %) at RT. The mixture was stirred at room temperature for three days to give a red solution. The reaction mixture was directly purified by silica gel flash chromatography, eluting 0-15% EA/petroleum to give the title compound (31.7 g, 68.3% yield, 85% purity by $^1$H NMR). $^1$H NMR (400.14 MHz, CDCl$_3$): 7.15-7.11 (m, 2H), 6.70 (t, J=7.3 Hz, 1H), 6.59 (d, J=8.0 Hz, 2H), 3.74-3.67 (m, 1H), 2.79-2.74 (m, 1H), 2.38-2.30 (m, 3H), 2.19-2.12 (m, 1H), 2.03-1.95 (m, 1H), 1.72-1.65 (m, 2H).

| Chemical Name | Structure | ES/MS (m/z) (M + H) |
|---|---|---|
| racemic)-3-anilinocyclopentanone | 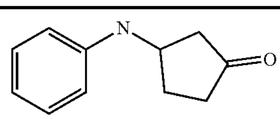 | 176.2 |

Step 7: 2,2,2-trifluoro-N-phenyl-N-[rac-3-oxocyclohexyl]acetamide

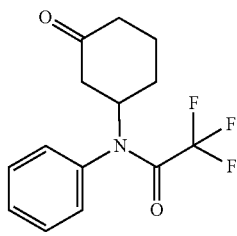 [SMILES: O=C1CCCC(N(C(=O)C(F)(F)F)c2ccccc2)C1]

To a solution of rac-3-anilinocyclohexanone (15.0 g, 67.3 mmol, 85 mass %) and triethylamine (19.0 ml, 134 mmol) in dichloromethane (150.0 ml), (2,2,2-trifluoroacetyl) 2,2,2-trifluoroacetate (14.0 ml, 99.6 mmol) was added dropwise at 0° C. The mixture was slowly warmed up to RT and stirred overnight. the reaction mixture was concentrated under reduced pressure to give the crude product (10.4 g, 90 mass %, 48.7% yield), the material was used directly in the next step without further purification. $^1$H NMR (400.21 MHz, CDCl$_3$): 7.50-7.45 (m, 3H), 7.25 (d, J=6.3 Hz, 1H), 7.15 (d, J=6.8 Hz, 1H), 4.84-4.76 (m, 1H), 2.67-2.62 (m, 1H), 2.41-2.36 (m, 1H), 2.27 (t, J=13.3 Hz, 1H), 2.18-2.07 (m, 3H), 1.76-1.70 (m, 2H).

Step 8: 2,2,2-trifluoro-N-phenyl-N-[rac-3,3-difluorocyclohexyl]acetamide

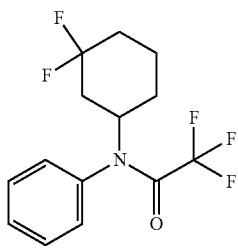 [SMILES: O=C(N(c1ccccc1)C1CCCC(F)(F)C1)C(F)(F)F]

To a solution of 2,2,2-trifluoro-N-[(rac)-3-oxocyclohexyl]-N-phenyl-acetamide, (10.4 g, 32.8 mmol, 90 mass %) in dichloromethane (100.0 ml) cooled on ice, was added diethylaminosulfur trifluoride (9.0 ml, 66.65 mmol). the mixture was warmed up to RT after stirred at RT for 2 h, the reaction was quenched by adding sat. NaHCO₃ (100.0 ml), the mixture was extracted with dichloromethane (150 ml×2). The combined organic layers were washed with brine (100.0 ml), dried over Na₂SO₄ and concentrated in vacuo to give a residue. The residue was purified by silica gel flash chromatography, eluting with 0~40% dichloromethane/petroleum ether to give the title compound, (6.5 g, 95 mass %, 61% yield). ¹H NMR (400.14 MHz, CDCl₃): 7.41-7.35 (m, 3H), 7.09 (t, J=7.6 Hz, 2H), 4.68-4.62 (m, 1H), 2.30-2.26 (m, 1H), 2.02-1.96 (m, 2H), 1.84-1.82 (m, 1H), 1.62-1.52 (m, 3H), 1.23-1.14 (m, 1H).

Step 9: N-[rac-3,3-difluorocyclohexyl]aniline

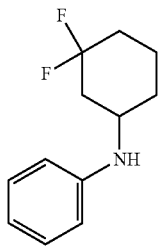 [SMILES: FC1(F)CCCC(Nc2ccccc2)C1]

To a solution of 2,2,2-trifluoro-n-phenyl-n-[rac-3,3-difluorocyclohexyl]acetamide (6.5 g, 20 mmol, 95 mass %) in methanol (100.0 ml) and water (10.0 ml) was added potassium carbonate (8.6 g, 61 mmol) portion wise at RT. The reaction mixture was heated to 65° C., after 4 h, the reaction was cooled to RT and water was added (100.0 mL). The mixture was extracted with ethyl acetate (200 mL×3). The combined organic layers were washed with brine (20.0 ml), dried over Na₂SO₄, and concentrated in vacuo to give a residue. The residue was purified by silica gel flash chromatography, eluting 0~22% ethyl acetate/petroleum ether to give the title compound (3.54 g, 90 mass %, 75% yield). MS m/z 212.2 (M+H). ¹H NMR (400.13 MHz, CDCl₃): 7.14-7.09 (m, 2H), 6.67 (t, J=7.3 Hz, 1H), 6.57 (d, J=7.8 Hz, 2H), 3.60-3.53 (m, 1H), 2.49-2.44 (m, 1H), 2.03-1.95 (m, 2H), 1.80-1.71 (m, 4H), 1.28-1.15 (m, 1H).

The compounds in the table below were prepared as described above.

| Chemical Name | Structure | ES/MS (m/z) (M + H) |
|---|---|---|
| N-[(racemic)-3,3-difluorocyclohexyl]-2-fluoro-aniline | 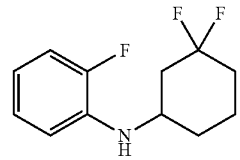 [SMILES: Fc1ccccc1NC1CCCC(F)(F)C1] | 229.9 |
| N-[(racemic)-3,3-difluorocyclohexyl]-3-fluoro-aniline | 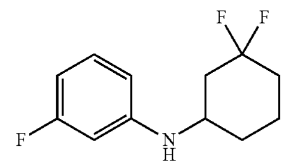 [SMILES: Fc1cccc(NC2CCCC(F)(F)C2)c1] | 230.1 |
| N-((racemic)-3,3-difluorocyclohexyl)-4-fluoro-aniline | 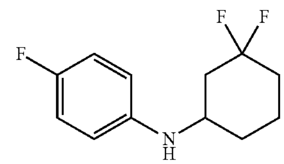 [SMILES: Fc1ccc(NC2CCCC(F)(F)C2)cc1] | 230.1 |

N-cyclopentylaniline

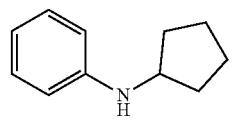 [SMILES: c1ccc(NC2CCCC2)cc1]

To a solution of cyclopentanone (3.05 g, 35.5 mmol) in dichloromethane (35 mL) was added aniline (3.35 g, 35.6 mmol) and sodium triacetoxyborohydride (9.4 g, 43.0 mmol), then the mixture was stirred at RT overnight. Upon completion, the reaction was diluted with water (50 mL) and extracted with dichloromethane (30 mL×3). The combined organic layers were washed with brine (50 mL), dried over Na₂SO₄ and concentrated in vacuo to give a residue. The residue was purified by flash silica gel chromatography, eluting 0~8% Ethyl acetate/Petroleum ether to give the title compound (5.1 g, 95 mass %, 85% yield). MS m/z=162.0 (M+H).

N-phenyl-4-oxaspiro[2.5]octan-7-amine

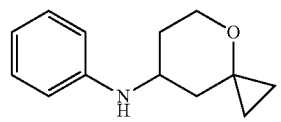 [SMILES: c1ccc(NC2CCOC3(CC3)C2)cc1]

To a solution of 4-oxaspiro[2.5]octan-7-one (116 mg, 0.83 mmol, 90 mass %) and aniline (83 mg, 0.87 mmol) in methanol (1.5 mL) were added acetic acid (0.03 mL, 0.5 mmol) and sodium cyanoborohydride (85 mg, 1.34 mmol). The mixture was stirred at room temperature overnight. Upon completion, the mixture was quenched with 1N HCl (0.5 mL) and evaporated under vacuum. The residue was dissolved in EtOAc (10 mL×2) and washed with brine (3 mL×2). The organic layer was dried over Na₂SO₄; filtered and evaporated under vacuum. The residue was purified by flash silica gel chromatography, eluting with 0~20% ethyl acetate in petroleum ether to give the title compound (80 mg, 95 mass %, 45.17% yield). ¹H NMR (400 MHz, CDCl₃): 7.22-7.18 (m, 2H), 6.79-6.76 (m, 1H), 6.72-6.70 (m, 2H), 3.92-3.88 (m, 1H), 3.69-3.64 (m, 1H), 3.62-3.59 (m, 1H), 2.11-2.07 (m, 1H), 1.92-1.87 (m, 1H), 1.66-1.61 (m, 2H), 0.89-0.87 (m, 1H), 0.72-0.71 (m, 1H), 0.52-0.51 (m, 1H), 0.44-0.42 (m, 1H).

N-phenyltetrahydropyran-4-amine was prepared according to the procedure above.

| Chemical Name | Structure | ¹H NMR (400 MHz, DMSO-d₆) |
|---|---|---|
| N-phenyl-tetrahydro pyran-4-amine | 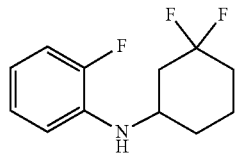 [SMILES: Fc1ccccc1NC1CCCC(F)(F)C1] | 7.05 (t, J = 7.7 Hz, 2H), 6.58 (d, J = 7.8 Hz, 2H), 6.49 (t, J = 7.2 Hz, 1H), 5.44 (d, J = 7.9 Hz, 1H), 3.85 (d, J = 11.4 Hz, 2H), 3.47-3.35 (m, 3H), 1.86 (d, J = 12.6 Hz, 2H), 1.43-1.26 (m, 2H) |

Isolation of isomers (2-fluoro-N-[3,3-difluorocyclo-hexyl]aniline

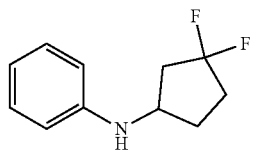

N-[(racemic)-3,3-difluorocyclohexyl]-2-fluoro-aniline (9.0 g) was dissolved in minimal MeOH, the solution was separated by SFC: DAICEL CHIRALPAK AD (250 mm*50 mm, 10 um); mobile phase A: CO2 B: 0.1% NH3H2O MEOH; eluting with 5% B, Flowrate: 140 mL/min.

The eluent of first peak was collected and lyophilized to give the title compound (2.99 g, 35% yield, ee: 98.5%). MS m/z 230.1 (M+H).

The eluent with major second peak (80%) was collected and lyophilized. Then it was re-purified by SFC: DAICEL CHIRALCEL OD (250 mm*30 mm, 10 um); mobile phase A: CO2 B: 0.10% NH3H2O isopropanol; eluting with 15% B, Flowrate 60 mL/min) to give the title compound as the second enantiomer (1.2 g, 14% yield, ee: 99.9%). MS m/z 230.1 (M+H).

N-[(racemic)-2,2-difluorocyclopentyl]aniline

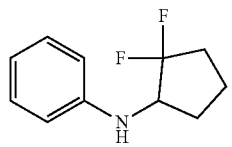 [SMILES: FC1(F)CCCC1Nc1ccccc1]

To a 50 mL flask was charged chlorobenzene (645 mg, 5.67 mmol), (racemic)-2,2-difluorocyclopentanamine, hydrochloride (1.0 g, 6.28 mmol), BrettPhos Pd G3 (592 mg, 0.640 mmol), potassium tert-butoxide (1.456 g, 12.72 mmol) and 1,4-dioxane (18.0 mL), the mixture was stirred at 60° C. for 5 h under N₂. Upon completion, the reaction mixture was cooled down to RT and concentrated under reduced pressure. The residue was purified by flash silica gel chromatography, eluting 0-12% ethyl acetate in petroleum ether to give the title compound (285 mg, 97 mass %, 22.3% yield). MS m/z 198.1 (M+H).

N-[(racemic)-3,3-difluorocyclopentyl]aniline

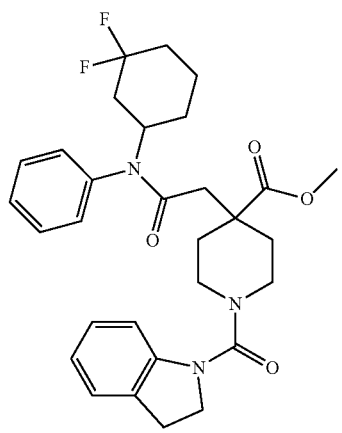 [SMILES: COC(=O)C1(CC(=O)N(c2ccccc2)C2CCCC(F)(F)C2)CCN(C(=O)N2CCc3ccccc32)CC1]

To a solution of (racemic)-3-anilinocyclopentanone (1.015 g, 5.503 mmol, 95 mass %) in dichloromethane (10 mL) was added (diethylamino)sulfur trifluoride (1.9 mL, 14 mmol) at 0° C. The mixture was stirred at room temperature overnight. Upon completion, the mixture was quenched with 1N NaHCO₃ to pH>7, then the reaction mixture was added water (50 mL), the residue was extracted with ethyl acetate (50 mL×4). Then the combined organic phase was washed with brine (50 mL), dried with anhydrous Na₂SO₄ and concentrated under reduced pressure. The residue was purified by normal silica gel chromatography, eluting 15% ethyl acetate in petroleum ether to give the title compound (256 mg, 90 mass %, 21.23% yield). MS m/z 198.2 (M+H).

Step 10: Methyl 4-[2-(N-[(rac)-3,3-difluorocyclo-hexyl]anilino)-2-oxo-ethyl]-1-(indoline-1-carbonyl) piperidine-4-carboxylate To a solution of 2-[1-(indoline-1-carbonyl)-4-methoxy-carbonyl-4-piperidyl]acetic acid (1.2 g, 3.3 mmol), N-[rac-3,3-difluorocyclohexyl]aniline (770 mg, 3.2 mmol, 90 mass %) in pyridine (12.0 mL) was added phosphoryl chloride (460 μL, 4.90 mmol) at RT under N₂. The mixture was heated to 100° C., after 5 h heating, the reaction was cooled down to RT, 50 mL of water was carefully added to the reaction and the mixture was extracted with ethyl acetate (50 mL×3). The combined organic layers were washed with brine (40 mL), dried over $Na_2SO_4$ and concentrated in vacuo to give a residue. The residue was purified by silica gel flash chromatography, eluting 0~43% ethyl acetate/petroleum ether to give the title compound (1.25 g, 98 mass %, 69% yield). MS m/z 540.4 (M+H).

The compounds in the table below were prepared as described above.

| Chemical Name | Structure | ES/MS (m/z) (M + H) | $^1$H NMR (400 MHz, DMSO-$d_6$) |
|---|---|---|---|
| methyl 4-[2-(3-fluoro-N-(2-fluorophenyl)anilino)-2-oxo-ethyl]-1-(indoline-1-carbonyl)piperidine-4-carboxylate | | 534.2 | |
| Isomer 2: methyl 4-[2-(N-(3,3-difluorocyclohexyl)-2-fluoro-anilino)-2-oxo-ethyl]-1-(6-fluoroindoline-1-carbonyl)piperidine-4-carboxylate | | 576.2 | |
| Isomer 2: methyl 4-[2-(N-(3,3-difluorocyclohexyl)-2-fluoro-anilino)-2-oxo-ethyl]-1-[(2-fluoro-4-isopropyl-phenyl)methyl]piperidine-4-carboxylate | | 563.3 | |

-continued

| Chemical Name | Structure | ES/MS (m/z) (M + H) | $^1$H NMR (400 MHz, DMSO-$d_6$) |
|---|---|---|---|
| methyl 4-[2-(N-(4,4-difluorocyclohexyl)-2-fluoroanilino)-2-oxo-ethyl]-1-(6-fluoroindoline-1-carbonyl)piperidine-4-carboxylate | 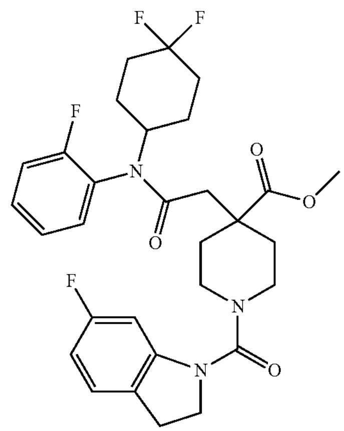 [SMILES: COC(=O)C1(CC(=O)N(c2ccccc2F)C2CCC(F)(F)CC2)CCN(C(=O)N2CCc3ccc(F)cc32)CC1] | 558.7 | |
| Isomer 1: methyl 4-[2-(N-(3,3-difluorocyclohexyl)-2-fluoroanilino)-2-oxo-ethyl]-1-(indoline-1-carbonyl)piperidine-4-carboxylate | 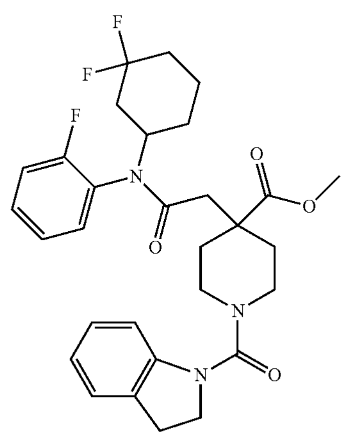 [SMILES: COC(=O)C1(CC(=O)N(c2ccccc2F)C2CCCC(F)(F)C2)CCN(C(=O)N2CCc3ccccc32)CC1] | 558.3 | |
| Racemic methyl 4-[2-(N-[3,3-difluorocyclohexyl]anilino)-2-oxo-ethyl]-1-(6-methylindoline-1-carbonyl)piperidine-4-carboxylate | 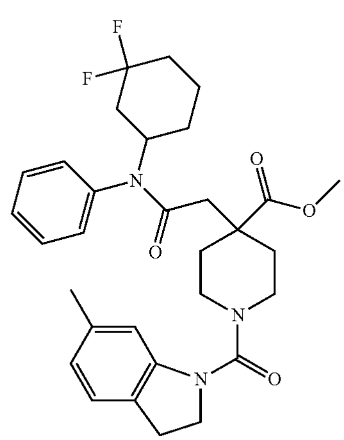 [SMILES: COC(=O)C1(CC(=O)N(c2ccccc2)C2CCCC(F)(F)C2)CCN(C(=O)N2CCc3ccc(C)cc32)CC1] | 554.4 | |

-continued

| Chemical Name | Structure | ES/MS (m/z) (M + H) | ¹H NMR (400 MHz, DMSO-d₆) |
|---|---|---|---|
| Racemic methyl 4-[2-(N-[2,2-difluorocyclopentyl]anilino)-2-oxo-ethyl]-1-(6-fluoroindoline-1-carbonyl)piperidine-4-carboxylate | | 544.3 | |
| Racemis, methyl 4-[2-(N-[3,3-difluorocyclopentyl]anilino)-2-oxo-ethyl]-1-(6-fluoroindoline-1-carbonyl)piperidine-4-carboxylate | | 544.1 | |
| methyl 1-[(4-fluorophenyl)-methyl-carbamoyl]-4-[2-(N-[(racemic)-4-oxaspiro[2.5]octan-7-yl]anilino)-2-oxo-ethyl]piperidine-4-carboxylate | | | ¹H NMR (400.14 MHz, DMSO-d₆): 7.61-7.42 (m, 3H), 7.26-7.02 (m, 6H), 4.79-4.57 (m, 1H), 3.69 (dd, J = 3.9, 10.9 Hz, 1H), 3.55 (s, 3H), 3.41 (t, J = 11.1 Hz, 1H), 3.15-3.03 (m, 2H), 3.00 (s, 3H), 2.91 (dd, J = 4.6, 8.8 Hz, 2H), 2.11 (s, 2H), 1.73-1.58 (m, 4H), 1.32-1.20 (m, 2H), 1.15-1.09 (m, 2H), 0.70-0.59 (m, 1H), 0.58-0.48 (m, 1H), 0.46-0.39 (m, 1H), 0.38-0.30 (m, 1H). ¹⁹F NMR (377 MHz, DMSO-d₆): −118.72. |

-continued

| Chemical Name | Structure | ES/MS (m/z) (M + H) | $^1$H NMR (400 MHz, DMSO-$d_6$) |
|---|---|---|---|
| methyl 1-(6-fluoroindoline-1-carbonyl)-4-[2-oxo-2-(N-phenylanilino)ethyl]piperidine-4-carboxylate | 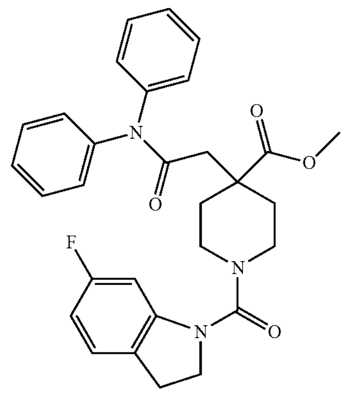 [SMILES: COC(=O)C1(CC(=O)N(c2ccccc2)c2ccccc2)CCN(C(=O)N2CCc3ccc(F)cc32)CC1] | 516.3 | |
| methyl 4-[2-(3-fluoro-N-(2-fluorophenyl)anilino)-2-oxo-ethyl]-1-(6-fluoroindoline-1-carbonyl)piperidine-4-carboxylate | 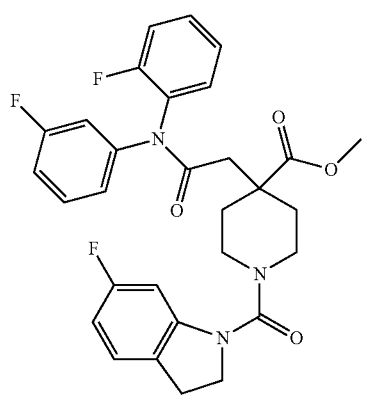 [SMILES: COC(=O)C1(CC(=O)N(c2cccc(F)c2)c2ccccc2F)CCN(C(=O)N2CCc3ccc(F)cc32)CC1] | 552.5 | |
| methyl 4-[2-(4-fluoro-N-(4-fluorophenyl)anilino)-2-oxo-ethyl]-1-(indoline-1-carbonyl)piperidine-4-carboxylate | 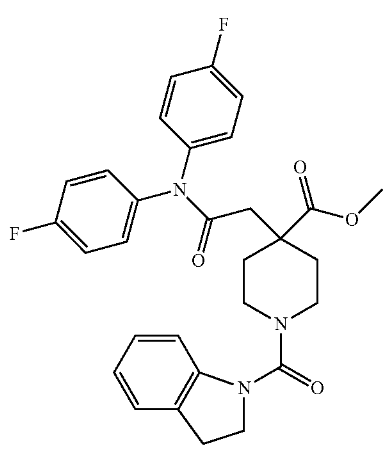 [SMILES: COC(=O)C1(CC(=O)N(c2ccc(F)cc2)c2ccc(F)cc2)CCN(C(=O)N2CCc3ccccc32)CC1] | 534.1 | |

| Chemical Name | Structure | ES/MS (m/z) (M + H) | ¹H NMR (400 MHz, DMSO-d₆) |
|---|---|---|---|
| methyl 4-[2-(4-fluoro-N-(3-fluorophenyl)anilino)-2-oxo-ethyl]-1-(indoline-1-carbonyl)piperidine-4-carboxylate | 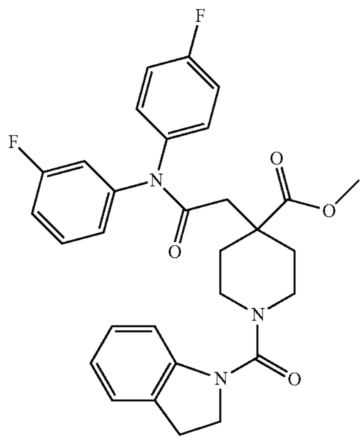 [SMILES: COC(=O)C1(CC(=O)N(c2ccc(F)cc2)c2cccc(F)c2)CCN(C(=O)N2CCc3ccccc32)CC1] | 534.9 | |
| methyl 4-[2-(3-fluoro-N-(3-fluorophenyl)anilino)-2-oxo-ethyl]-1-(indoline-1-carbonyl)piperidine-4-carboxylate | 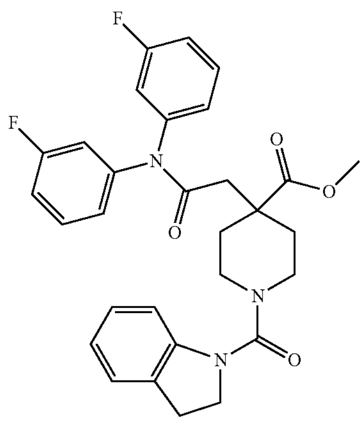 [SMILES: COC(=O)C1(CC(=O)N(c2cccc(F)c2)c2cccc(F)c2)CCN(C(=O)N2CCc3ccccc32)CC1] | | ¹H NMR (400 MHz, DMSO-d₆): 8.64-8.53 (m, 1H), 7.88-7.70 (m, 1H), 7.57-7.42 (m, 2H), 7.41-7.34 (m, 2H), 7.18 (d, J = 7.3 Hz, 2H), 7.10 (t, J = 7.6 Hz, 2H), 6.93 (d, J = 7.9 Hz, 1H), 6.89-6.80 (m, 1H), 3.78 (t, J = 8.2 Hz, 2H), 3.65 (s, 3H), 3.31-3.26 (m, 1H), 3.24-3.13 (m, 2H), 3.02-2.91 (m, 2H), 2.62 (s, 2H), 1.99 (s, 1H), 2.03-1.90 (m, 2H), 1.64-1.49 (m, 2H) |

Step 11: Racemic, 4-[2-(N-[-3,3-difluorocyclohexyl]anilino)-2-oxo-ethyl]-1-(indoline-1-carbonyl)piperidine-4-carboxylic acid (Example No. 35)

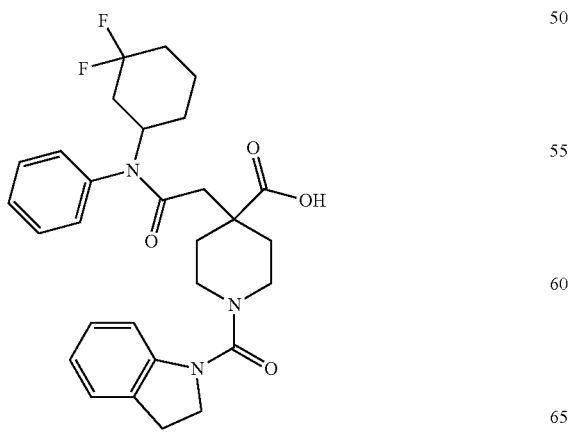

To a solution of methyl 4-[2-(N-[(racemic)-3,3-difluorocyclohexyl]anilino)-2-oxo-ethyl]-1-(indoline-1-carbonyl)piperidine-4-carboxylate (1.25 g, 2.27 mmol, 98 mass %) in 1,4-dioxane (10.0 mL) was added 1.0 M potassium hydroxide in water (4.5 mL, 4.5 mmol) at RT. The mixture was heated to 100° C. After stirring for 5 h, the reaction was cooled down to RT, 1.0 ml of formic acid was added and the reaction mixture was concentrated under reduced pressure to give a residue. The residue was purified by reverse phase prep-HPLC (Xtimate C18 150*40 mm*10 μm), mobile phase A: water (NH13H2O+NH4HCO3), phase B: CH₃CN, eluting 15%-55% B in 10 min. The appropriate fractions were collected and lyophilized to give title compound (0.7 g, 97 mass %, 60.00 yield). MS m/z 526.2 (M+H).

Example Nos. 52, 60, 80, 81, 83, 94, 103 and 104 were Prepared According to the Procedure Above

| Example No. | Chemical Name | Structure | ES/MS (m/z) (M + H) | $^1$H NMR (400 MHz, DMSO-$d_6$) |
|---|---|---|---|---|
| 52 | Racemic 4-[2-(N-[3,3-difluorocyclohexyl]-2-fluoro-anilino)-2-oxo-ethyl]-1-[methyl(phenyl)carbamoyl]piperidine-4-carboxylic acid | 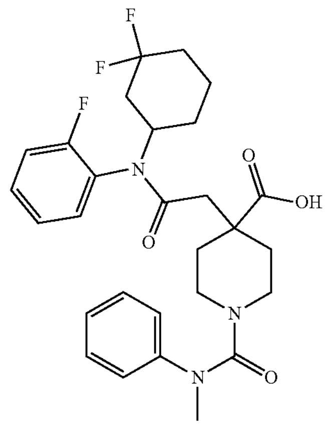 [SMILES: CN(C(=O)N1CCC(CC(=O)N(c2ccccc2F)C2CCCC(F)(F)C2)(C(=O)O)CC1)c1ccccc1] | 532.5 | $^1$H NMR (400 MHz, DMSO-$d_6$): 12.20 (br, 1H), 7.60-7.49 (m, 1H), 7.48-7.39 (m, 1H), 7.39-7.22 (m, 4H), 7.15-7.01 (m, 3H), 5.42-5.17 (m, 1H), 4.72-4.35 (m, 1H), 3.18-3.07 (m, 2H), 3.04 (s, 3H), 3.00-2.89 (m, 2H), 2.35-1.98 (m, 3H), 1.90 (s, 1H), 1.82-1.29 (m, 6H), 1.26-0.86 (m, 3H) |
| 60 | 4-[2-(3-fluoro-N-(2-fluorophenyl)anilino)-2-oxo-ethyl]-1-(indoline-1-carbonyl)piperidine-4-carboxylic acid | 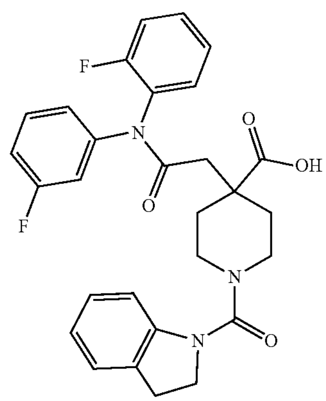 [SMILES: O=C(N1CCC(CC(=O)N(c2cccc(F)c2)c2ccccc2F)(C(=O)O)CC1)N1CCc2ccccc21] | 520.4 | $^1$H NMR (400 MHz, DMSO-$d_6$): 7.71-6.96 (m, 10H), 6.93 (d, J = 7.9 Hz, 1H), 6.84 (t, J = 7.4 Hz, 1H), 3.78 (t, J = 8.3 Hz, 2H), 3.35-3.28 (m, 2H), 3.25-3.14 (m, 2H), 2.96 (t, J = 8.2 Hz, 2H), 2.59 (s, 2H), 2.02-1.89 (m, 2H), 1.56 (t, J = 9.4 Hz, 2H) |
| 80 | Racemic 4-[2-(N-3,3-difluorocyclohexyl]anilino)-2-oxo-ethyl]-1-(3,3-dimethylindoline-1-carbonyl)piperidine-4-carboxylic acid | 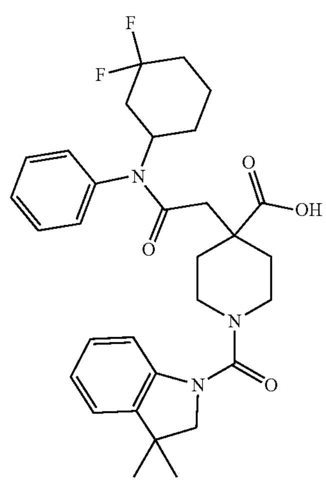 [SMILES: CC1(C)CN(C(=O)N2CCC(CC(=O)N(c3ccccc3)C3CCCC(F)(F)C3)(C(=O)O)CC2)c2ccccc21] | 554.5 | $^1$H NMR (400 MHz, DMSO-$d_6$): 12.25 (s, 1H), 7.65-7.43 (m, 3H), 7.26 (d, J = 5.8 Hz, 2H), 7.16 (d, J = 7.3 Hz, 1H), 7.13-7.07 (m, 1H), 6.93-6.83 (m, 2H), 4.62 (t, J = 12.3 Hz, 1H), 3.50 (s, 2H), 3.25-3.14 (m, 4H), 2.30-2.12 (m, 3H), 1.99-1.84 (m, 3H), 1.81-1.66 (m, 2H), 1.63-1.33 (m, 5H), 1.29-1.16 (m, 6H), 1.14-0.95 (m, 1H) |

-continued

| Example No. | Chemical Name | Structure | ES/MS (m/z) (M + H) | ¹H NMR (400 MHz, DMSO-d₆) |
|---|---|---|---|---|
| 81 | Racemic 4-[2-(N-[3,3-difluorocyclohexyl]-2-fluoro-anilino)-2-oxo-ethyl]-1-(indoline-1-carbonyl)piperidine-4-carboxylic acid | 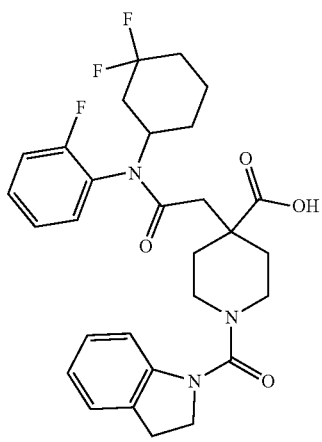 [SMILES: O=C(N1CCC(CC(=O)N(c2ccccc2F)C2CCCC(F)(F)C2)(C(=O)O)CC1)N1CCc2ccccc21] | 544.5 | ¹H NMR (400 MHz, DMSO-d₆): 7.59-7.50 (m, 1H), 7.48-7.39 (m, 2H), 7.39-7.31 (m, 1H), 7.17 (d, J = 7.4 Hz, 1H), 7.12-7.05 (m, 1H), 6.91 (d, J = 8.0 Hz, 1H), 6.84 (dt, J = 0.7, 7.4 Hz, 1H), 4.62 (dt, J = 3.3, 12.3 Hz, 1H), 3.76 (t, J = 8.3 Hz, 2H), 3.29-3.23 (m, 2H), 3.21-3.10 (m, 2H), 2.95 (t, J = 8.2 Hz, 2H), 2.34-2.07 (m, 3H), 1.97-1.83 (m, 3H), 1.82-1.59 (m, 3H), 1.58-1.50 (m, 1H), 1.49-1.34 (m, 3H), 1.19-0.88 (m, 1H) |
| 83 | Racemic 4-[2-(N-[3,3-difluorocyclohexyl]anilino)-2-oxo-ethyl]-1-(6-methylindoline-1-carbonyl)piperidine-4-carboxylic acid | 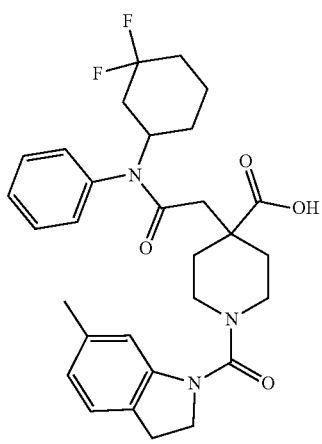 [SMILES: Cc1ccc2c(c1)N(C(=O)N1CCC(CC(=O)N(c3ccccc3)C3CCCC(F)(F)C3)(C(=O)O)CC1)CC2] | 540.3 | ¹H NMR (400 MHz, DMSO-d₆): 7.61-7.47 (m, 3H), 7.32 (d, J = 6.3 Hz, 2H), 7.10 (d, J = 7.5 Hz, 1H), 6.80 (s, 1H), 6.72 (d, J = 7.5 Hz, 1H), 4.69 (t, J = 12.4 Hz, 1H), 3.81 (t, J = 8.2 Hz, 2H), 3.32-3.20 (m, 4H), 2.95 (t, J = 8.1 Hz, 2H), 2.33-2.28 (m, 4H), 2.23 (s, 2H), 1.96 (d, J = 13.3 Hz, 3H), 1.80 (s, 2H), 1.71-1.5-1.39 (m, 5H), 1.16-1.01 (m, 1H) |
| 94 | Racemic 1-[(4-fluorophenyl)-methyl-carbamoyl]-4-[2-(N-[4-oxaspiro[2.5]octan-7-yl]anilino)-2-oxo-ethyl]piperidine-4-carboxylic acid | 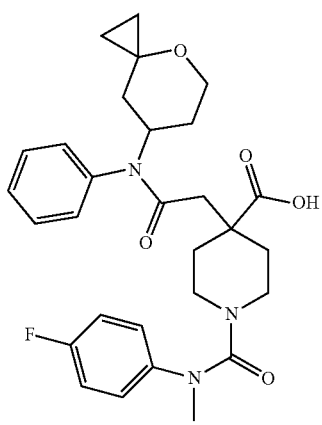 [SMILES: CN(C(=O)N1CCC(CC(=O)N(c2ccccc2)C2CCOC3(CC3)C2)(C(=O)O)CC1)c1ccc(F)cc1] | 524.5 | ¹H NMR (400 MHz, DMSO-d₆): 7.56-7.53 (m, 3H), 7.22-7.05 (m, 6H), 4.78-4.67 (m, 1H), 3.73-3.66 (m, 1H), 3.42 (t, J = 10.9 Hz, 1H), 3.13-3.04 (m, 2H), 3.03-2.98 (m, 3H), 2.97-2.87 (m, 2H), 2.09-2.04 (m, 2H), 1.72-1.59 (m, 4H), 1.29-1.21 (m, 1H), 1.20-1.11 (m, 3H), 0.69-0.61 (m, 1H), 0.59-0.50 (m, 1H), 0.47-0.39 (m, 1H), 0.39-0.32 (m, 1H) |

| Example No. | Chemical Name | Structure | ES/MS (m/z) (M + H) | $^1$H NMR (400 MHz, DMSO-d$_6$) |
|---|---|---|---|---|
| 103 | 4-[2-(3-fluoro-N-(2-fluorophenyl)anilino)-2-oxo-ethyl]-1-(6-fluoroindoline-1-carbonyl)piperidine-4-carboxylic acid | 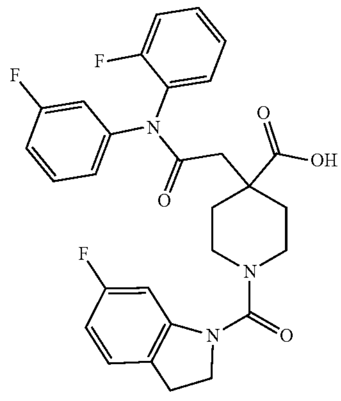 [SMILES: O=C(N1CCC(CC(=O)N(c2cccc(F)c2)c2ccccc2F)(C(=O)O)CC1)N1CCc2ccc(F)cc21] | 538.4 | $^1$H NMR (400 MHz, DMSO-d$_6$): 12.42 (s, 1H), 7.67-6.96 (m, 9H), 6.73 (dd, J = 2.3, 10.6 Hz, 1H), 6.68-6.61 (m, 1H), 3.85 (t, J = 8.3 Hz, 2H), 3.31-3.16 (m, 4H), 2.94 (t, J = 8.2 Hz, 2H), 2.62 (s, 2H), 1.96 (d, J = 13.6 Hz, 2H), 1.56 (t, J = 9.3 Hz, 2H) |
| 104 | 4-[2-(4-fluoro-N-(4-fluorophenyl)anilino)-2-oxo-ethyl]-1-(indoline-1-carbonyl)piperidine-4-carboxylic acid | 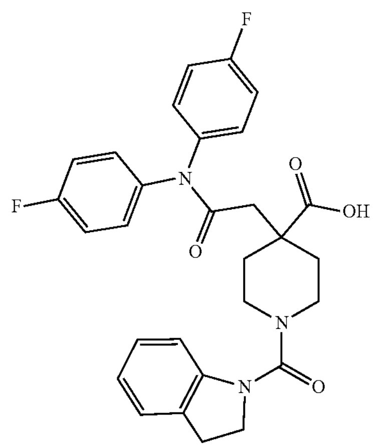 [SMILES: O=C(N1CCC(CC(=O)N(c2ccc(F)cc2)c2ccc(F)cc2)(C(=O)O)CC1)N1CCc2ccccc21] | 520.4 | $^1$H NMR (400 MHz, DMSO-d$_6$): 7.51 (s, 2H), 7.39-7.13 (m, 7H), 7.13-7.06 (m, 1H), 6.93 (d, J = 7.9 Hz, 1H), 6.85 (t, J = 7.4 Hz, 1H), 3.78 (t, J = 8.3 Hz, 2H), 3.28-3.15 (m, 6H), 2.96 (t, J = 8.1 Hz, 2H), 2.03-1.89 (m, 2H), 1.57-1.54 (m, 2H) |

Isomer 2, 1-(6-fluoroindoline-1-carbonyl)-4-[2-(2-fluoro-N-[rel-(chiral)-3,3-difluorocyclohexyl]anilino)-2-oxo-ethyl]piperidine-4-carboxylic acid (Example No. 76)

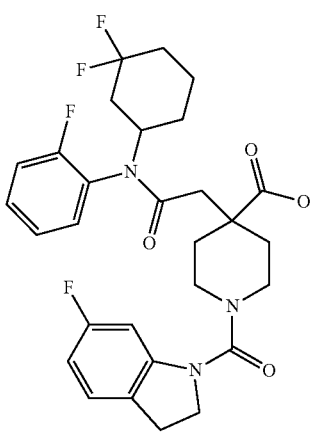 [SMILES: O=C(N1CCC(CC(=O)N(c2ccccc2F)C2CCCC(F)(F)C2)(C(=O)O)CC1)N1CCc2ccc(F)cc21]

To a mixture of isomer 2-methyl 1-(6-fluoroindoline-1-carbonyl)-4-[2-(2-fluoro-N-[3,3-difluorocyclohexyl]anilino)-2-oxo-ethyl]piperidine-4-carboxylate (109 mg, 0.1704 mmol, 90 mass %) in 2-propanol (3.0 mL, 39 mmol, 100 mass %) was added sodium hydroxide (190 µL, 0.95 mmol, 5 mol/L in H$_2$O), then the mixture was stirred at 50° C. overnight. Upon completion, the mixture was cooled down to RT and 3 mL of water was added. Then the mixture was adjusted pH about 4 with 1 N HCl, extracted with Ethyl acetate (5 mL×3). The combined organic layers were washed with brine (10 mL), dried over Na$_2$SO$_4$, filtered and concentrated under vacuum. The residue was purified by prep-HPLC (column: Xtimate C18 100*30 mm*10 um; mobile phase A: water −0.225% formic acid, mobile phase B: ACN, eluting with 65%-95% in 2 min, then to 100% B to give the product (34 mg, 100 mass %, 35.5% yield) as a yellow solid. MS m/z 562.5 (M+H), $^1$H NMR (400 MHz, DMSO-d$_6$) 12.27 (br, 1H), 7.58-7.51 (m, 1H), 7.48-7.39 (m, 2H), 7.39-7.32 (m, 1H), 7.15 (dd, J=6.1, 7.8 Hz, 1H), 6.71 (dd, J=2.2, 10.6 Hz, 1H), 6.67-6.60 (m, 1H), 4.61 (dt, J=3.1, 12.3 Hz, 1H), 3.83 (t, J=8.3 Hz, 2H), 3.29-3.14 (m, 4H), 2.93 (t, J=8.1 Hz, 2H), 2.35-2.24 (m, 1H), 2.23-2.17 (m, 2H), 1.91 (s, 3H), 1.83-1.49 (m, 4H), 1.43 (d, J=8.8 Hz, 3H), 1.18-0.91 (m, 1H).

Example Nos. 77, 78, 82b, 82a, 84, 85, 99, 105 and 106 were Prepared According to the Procedure Above

| Example No. | Chemical Name | Structure | ES/MS (m/z) (M + H) | ¹H NMR (400 MHz, DMSO-d6) |
|---|---|---|---|---|
| 77 | Isomer 2,4-[2-(N-(3,3-difluorocyclohexyl)-2-fluoroanilino)-2-oxo-ethyl]-1-[(4-ethyl-2-fluorophenyl)methyl]piperidine-4-carboxylic acid | 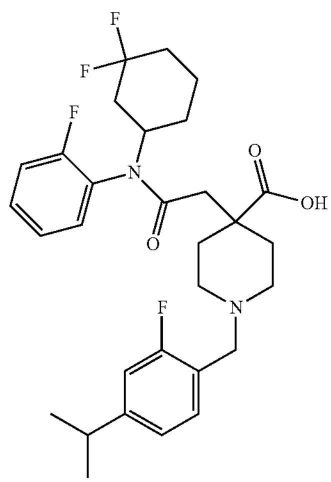 [SMILES: CC(C)c1ccc(CN2CCC(CC(=O)N(c3ccccc3F)C3CCCC(F)(F)C3)(C(=O)O)CC2)c(F)c1] | 549.5 | ¹H NMR (400 MHz, DMSO-d$_6$): 12.08 (br, 1H), 7.55-7.49 (m, 1H), 7.46-7.30 (m, 3H), 7.24-7.20 (m, 1H), 7.03-6.97 (m, 2H), 4.63-4.56 (m, 1H), 2.92-2.82 (m, 1H), 2.36-2.21 (m, 3H), 2.20-2.09 (m, 4H), 1.91-1.77 1.55 (m, 8H), 1.53-1.27 (m, 4H), 1.18 (d, J = 6.9 Hz, 6H), 1.12-0.91 (m, 1H) |
| 78 | 4-[2-(N-(4,4-difluorocyclohexyl)anilino)-2-oxo-ethyl]-1-(6-fluoroindoline-1-carbonyl)piperidine-4-carboxylic acid | 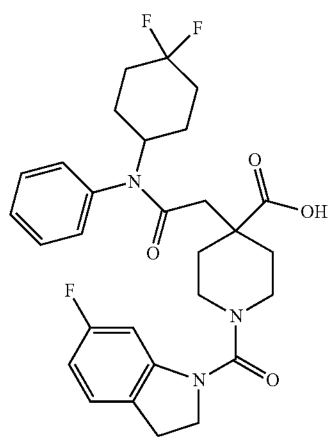 [SMILES: O=C(N1CCC(CC(=O)N(c2ccccc2)C2CCC(F)(F)CC2)(C(=O)O)CC1)N1CCc2ccc(F)cc21] | 544.5 | ¹H NMR (400 MHz, DMSO-d$_6$): 7.52-7.42 (m, 3H), 7.25-7.19 (m, 2H), 7.17-7.12 (m, 1H), 6.72-6.60 (m, 2H), 4.56 (t, J = 12.1 Hz, 1H), 3.82 (t, J = 8.3 Hz, 2H), 3.27-3.21 (m, 2H), 3.20-3.11 (m, 2H), 2.93 (t, J = 8.3 Hz, 2H), 2.16 (s, 2H), 2.03-1.85 (m, 6H), 1.79 (d, J = 12.4 Hz, 2H), 1.50-1.40 (m, 2H), 1.25-1.14 (m, 2H) |
| 82b | Isomer 2,4-[2-(N-(3,3-difluorocyclohexyl)-2-fluoroanilino)-2-oxo-ethyl]-1-(indoline-1-carbonyl)piperidine-4-carboxylic acid | 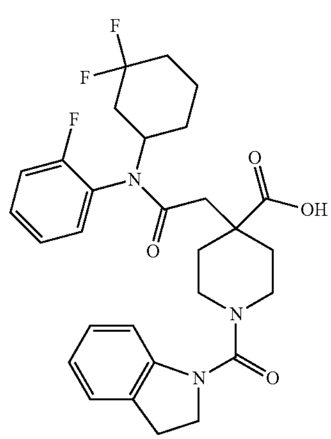 [SMILES: O=C(N1CCC(CC(=O)N(c2ccccc2F)C2CCCC(F)(F)C2)(C(=O)O)CC1)N1CCc2ccccc21] | 544.5 | ¹H NMR (400 MHz, DMSO-d$_6$): 12.26 (br, 1H), 7.59-7.51 (m, 1H), 7.49-7.32 (m, 3H), 7.17 (d, J = 7.4 Hz, 1H), 7.13-7.06 (m, 1H), 6.91 (d, J = 8.0 Hz, 1H), 6.87-6.81 (m, 1H), 4.61 (dt, J = 3.1, 12.3 Hz, 1H), 3.76 (t, J = 8.3 Hz, 2H), 3.28-3.12 (m, 4H), 2.95 (t, J = 8.2 Hz, 2H), 2.35-2.11 (m, 3H), 1.91 (d, J = 2.8 Hz, 3H), 1.84-1.49 (m, 4H), 1.48-1.33 (m, 3H), 1.18-0.90 (m, 1H). |

| Example No. | Chemical Name | Structure | ES/MS (m/z) (M + H) | $^1$H NMR (400 MHz, DMSO-d6) |
|---|---|---|---|---|
| 82a | Isomer 1,4-[2-(N-(3,3-difluorocyclohexyl)-2-fluoroanilino)-2-oxo-ethyl]-1-(indoline-1-carbonyl)piperidine-4-carboxylic acid | 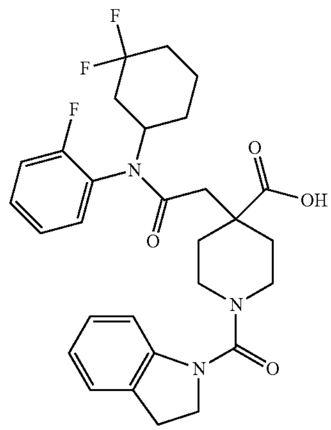 [SMILES: O=C(N1CCC(CC(=O)N(c2ccccc2F)C2CCCC(F)(F)C2)(C(=O)O)CC1)N1CCc2ccccc21] | 544.5 | $^1$H NMR (400 MHz, DMSO-d$_6$): 12.28 (br, 1H), 7.59-7.51 (m, 1H), 7.49-7.39 (m, 2H), 7.39-7.32 (m, 1H), 7.17 (d, J = 7.3 Hz, 1H), 7.12-7.06 (m, 1H), 6.92 (d, J = 7.9 Hz, 1H), 6.84 (t, J = 7.3 Hz, 1H), 4.66-4.56 (m, 1H), 3.76 (t, J = 8.2 Hz, 2H), 3.28-3.12 (m, 4H), 2.95 (t, J = 8.1 Hz, 2H), 2.34-2.24 (m, 1H), 2.22-2.17 (m, 2H), 1.96-1.85 (m, 3H), 1.83-1.51 (m, 4H), 1.48-1.37 (m, 3H), 1.17-0.91 (m, 1H) |
| 84 | Racemic 4-[2-(N-[2,2-difluorocyclopentyl]anilino)-2-oxo-ethyl]-1-(6-fluoroindoline-1-carbonyl)piperidine-4-carboxylic acid | 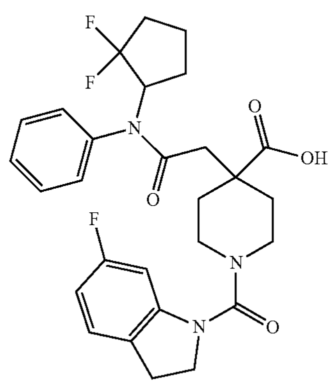 [SMILES: O=C(N1CCC(CC(=O)N(c2ccccc2)C2CCCC2(F)F)(C(=O)O)CC1)N1CCc2ccc(F)cc21] | 530.4 | $^1$H NMR (400 MHz, DMSO-d$_6$): 7.54-7.39 (m, 3H), 7.25 (d, J = 7.1 Hz, 2H), 7.19-7.11 (m, 1H), 6.74-6.59 (m, 2H), 5.06-4.91 (m, 1H), 3.82 (t, J = 8.3 Hz, 2H), 3.45-3.11 (m, 4H), 2.93 (t, J = 8.1 Hz, 2H), 2.22 (s, 2H), 2.16-2.04 (m, 1H), 1.96-1.75 (m, 4H), 1.64-1.52-1.34 (m, 5H) |
| 85 | Racemic 4-[2-(N-[3,3-difluorocyclopentyl]anilino)-2-oxo-ethyl]-1-(6-fluoroindoline-1-carbonyl)piperidine-4-carboxylic acid | 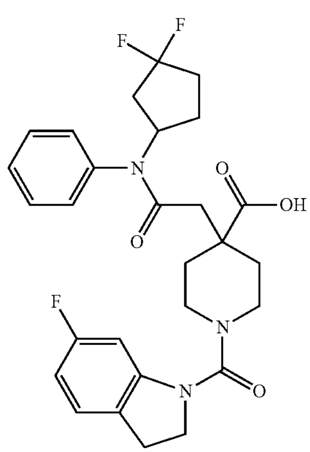 [SMILES: O=C(N1CCC(CC(=O)N(c2ccccc2)C2CCC(F)(F)C2)(C(=O)O)CC1)N1CCc2ccc(F)cc21] | 530.4 | $^1$H NMR (400 MHz, DMSO-d$_6$): 7.58-7.42 (m, 3H), 7.26 (d, J = 7.3 Hz, 2H), 7.15 (t, J = 6.9 Hz, 1H), 6.70 (d, J = 10.3 Hz, 1H), 6.64 (t, J = 8.7 Hz, 1H), 5.00-4.85 (m, 1H), 3.82 (t, J = 8.1 Hz, 2H), 3.26-3.17 (m, 4H), 2.93 (t, J = 7.8 Hz, 2H), 2.47-2.34 (m, 1H), 2.21 (s, 2H), 2.09-1.94 (m, 3H), 1.94-1.78 (m, 3H), 1.53-1.35 (m, 3H) |

-continued

| Example No. | Chemical Name | Structure | ES/MS (m/z) (M + H) | $^1$H NMR (400 MHz, DMSO-d6) |
|---|---|---|---|---|
| 99 | 1-(6-fluoroindoline-1-carbonyl)-4-[2-oxo-2-(N-phenylanilino)ethyl]piperidine-4-carboxylic acid | 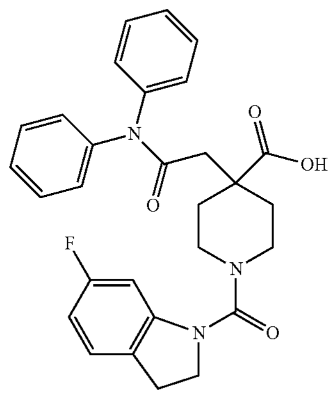 [SMILES: O=C(N1CCC(CC(=O)N(c2ccccc2)c2ccccc2)(C(=O)O)CC1)N1CCc2ccc(F)cc21] | 502.4 | $^1$H NMR (400 MHz, DMSO-d$_6$): 7.57-7.19 (m, 10H), 7.16 (dd, J = 6.1, 7.9 Hz, 1H), 6.73 (dd, J = 2.3, 10.6 Hz, 1H), 6.69-6.58 (m, 1H), 3.85 (t, J = 8.3 Hz, 2H), 3.26-3.12 (m, 4H), 2.95 (t, J = 8.1 Hz, 2H), 2.56 (s, 2H), 2.04-1.89 (m, 2H), 1.62-1.45 (m, 2H) |
| 105 | 4-[2-(4-fluoro-N-(3-fluorophenyl)anilino)-2-oxo-ethyl]-1-(indoline-1-carbonyl)piperidine-4-carboxylic acid | 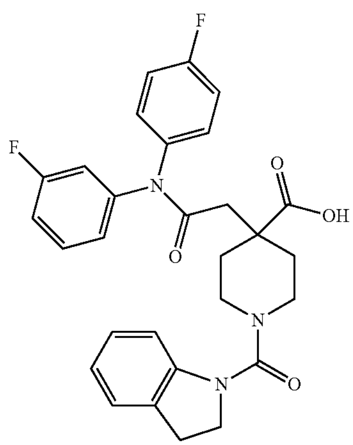 [SMILES: O=C(N1CCC(CC(=O)N(c2ccc(F)cc2)c2cccc(F)c2)(C(=O)O)CC1)N1CCc2ccccc21] | 520.4 | $^1$H NMR (400 MHz, DMSO-d$_6$): 7.61-7.09 (m, 10H), 6.93 (d, J = 7.9 Hz, 1H), 6.84 (t, J = 7.4 Hz, 1H), 3.78 (t, J = 8.2 Hz, 2H), 3.34-3.26 (m, 2H), 3.25-3.16 (m, 2H), 2.96 (t, J = 8.1 Hz, 2H), 2.50-2.49 (m, 2H), 2.00-1.92 (m, 2H), 1.60-1.51 (m, 2H) |
| 106 | 4-[2-(3-fluoro-N-(3-fluorophenyl)anilino)-2-oxo-ethyl]-1-(indoline-1-carbonyl)piperidine-4-carboxylic acid | 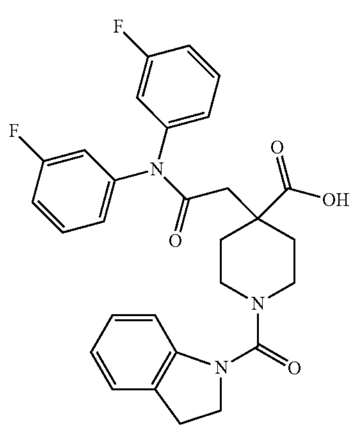 [SMILES: O=C(N1CCC(CC(=O)N(c2cccc(F)c2)c2cccc(F)c2)(C(=O)O)CC1)N1CCc2ccccc21] | 520.4 | $^1$H NMR (400 MHz, DMSO-d$_6$): 12.41 (br, 1H), 7.64-6.98 (m, 10H), 6.93 (d, J = 8.0 Hz, 1H), 6.88-6.80 (m, 1H), 3.78 (t, J = 8.3 Hz, 2H), 3.30-3.26 (m, 2H), 3.24-3.17 (m, 2H), 2.96 (t, J = 8.1 Hz, 2H), 2.57 (s, 2H), 2.02-1.87 (m, 2H), 1.62-1.50 (m, 2H) |

Step 12: Isolation of isomers (Example Nos. 35A and 35B)

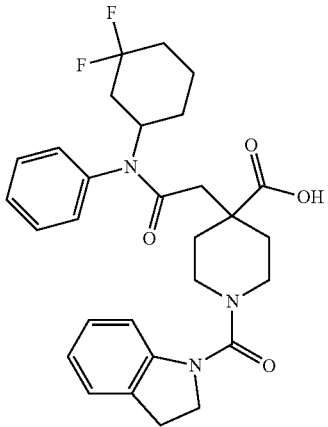 [SMILES: O=C(N1CCC(CC(=O)N(c2ccccc2)C2CCCC(F)(F)C2)(C(=O)O)CC1)N1CCc2ccccc21]

Racemic 4-[2-(N-[-3,3-difluorocyclohexyl]anilino)-2-oxo-ethyl]-1-(indoline-1-carbonyl)piperidine-4-carboxylic acid (700.0 mg) was dissolved in minimal MeOH, the solution was purified by SFC-80 (column: DAICEL CHIRALPAK IE (250 mm*30 mm, 10 μm), mobile phase A: CO2, B: 0.1% NH₄OH in EtOH; eluting with 60% of B, flow rate: 80 mL/min.

The eluent of first peak was collected and lyophilized to give the title compound (275.3 mg, 40.5% yield, ee: 100%). MS m/z 526.2 (M+H). ¹H NMR (400.14 MHz, DMSO-d₆): 12.12 (br, OH), 7.59-7.51 (m, 3H), 7.32 (d, J=6.0 Hz, 2H), 7.27-7.22 (m, 1H), 7.15 (t, J=7.6 Hz, 1H), 6.98-6.88 (m, 2H), 4.68 (t, J=12.4 Hz, 1H), 3.82 (t, J=8.2 Hz, 2H), 3.33-3.20 (m, 4H), 3.01 (t, J=8.1 Hz, 2H), 2.28-2.25 (m, 3H), 2.04-1.94 (m, 3H), 1.82-1.78 (m, 2H), 1.69-1.43 (m, 5H), 1.16-1.05 (m, 1H).

The eluent of second peak was collected and lyophilized to give the title compound as the second enantiomer (284.7 mg, 41.9% yield, ee: 98.6%). MS m/z 526.2 (M+H). ¹H NMR (400.14 MHz, DMSO-d₆): 12.11 (br, OH), 7.53-7.45 (m, 3H), 7.26 (d, J=6.4 Hz, 2H), 7.17 (d, J=7.3 Hz, 1H), 7.09 (t, J=7.6 Hz, 1H), 6.91 (d, J=7.9 Hz, 1H), 6.84 (t, J=7.3 Hz, 1H), 4.62 (t, J=12.4 Hz, 1H), 3.76 (t, J=8.2 Hz, 2H), 3.24-3.14 (m, 4H), 2.95 (t, J=8.1 Hz, 2H), 2.23-2.18 (m, 3H), 1.92-1.88 (m, 3H), 1.75-1.73 (m, 2H), 1.63-1.46 (m, 5H), 1.10-0.99 (m, 1H).

Example Nos. 80b, 80a, were Prepared According to the Procedure Above

The racemate was separated by SFC-80 (column: Daicel ChiralPak IG (250*30 mm, 10 um); mobile phase: A: CO2 B:0.10% NH3H2O EtOH; eluting 4000, flow rate: 80 mL/min) to give 80b and 80a.

The racemate was separated by SFC-80, column: DAICEL CHTRALPAK AD (250 mm*30 mm, 10 um) mobile phase: A: CO2; B: 0.1% NH3H2O TPA; B %: 35%, flow rate: 80 mL/min)) to give 3b and 83a.

| Example No. | Chemical Name | Structure | ES/MS (m/z) (M + H) | 1H NMR (400 MHz, DMSO-d6) |
|---|---|---|---|---|
| 80b | Isomer 2,4-[2-(N-(3,3-difluorocyclohexyl)anilino)-2-oxo-ethyl]-1-(3,3-dimethylindoline-1-carbonyl)piperidine-4-carboxylic acid | 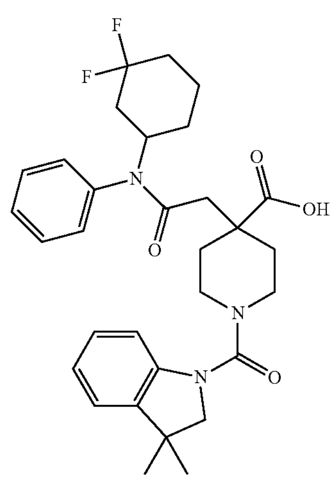 [SMILES: CC1(C)CN(C(=O)N2CCC(CC(=O)N(c3ccccc3)C3CCCC(F)(F)C3)(C(=O)O)CC2)c2ccccc21] | 554.5 | ¹H NMR (400 MHz, DMSO-d₆): 7.56-7.41 (m, 3H), 7.26 (d, J = 6.3 Hz, 2H), 7.19-7.03 (m, 2H), 6.94-6.82 (m, 2H), 4.70-4.53 (m, 1H), 3.50 (s, 2H), 3.23-3.13 (m, 4H), 2.29-2.20 (m, 1H), 2.17 (s, 2H), 1.90 (d, J = 13.0 Hz, 3H), 1.79-1.68 (m, 2H), 1.65-1.33 (m, 5H), 1.23 (s, 6H), 1.02 (dd, J = 3.1, 12.7 Hz, 1H) |

| Example No. | Chemical Name | Structure | ES/MS (m/z) (M + H) | 1H NMR (400 MHz, DMSO-d6) |
|---|---|---|---|---|
| 80a | Isomer 1,4-[2-(N-(3,3-difluorocyclohexyl)anilino)-2-oxo-ethyl]-1-(3,3-dimethylindoline-1-carbonyl)piperidine-4-carboxylic acid | 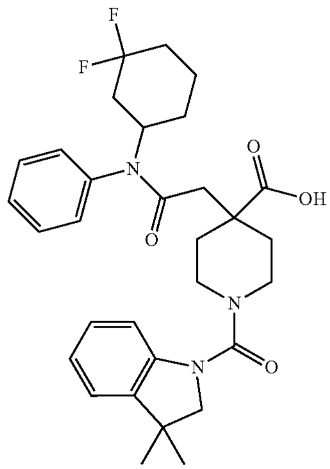 [SMILES: CC1(C)CN(C(=O)N2CCC(CC(=O)N(c3ccccc3)C3CCCC(F)(F)C3)(C(=O)O)CC2)c2ccccc21] | 554.5 | ¹H NMR (400 MHz, DMSO-d₆): 7.61-7.40 (m, 3H), 7.25 (d, J = 5.9 Hz, 2H), 7.19-7.03 (m, 2H), 6.96-6.80 (m, 2H), 4.74-4.51 (m, 1H), 3.50 (s, 2H), 3.24-3.13 (m, 4H), 2.29-2.19 (m, 1H), 2.16 (s, 2H), 1.89 (d, J = 12.9 Hz, 3H), 1.81-1.66 (m, 2H), 1.64-1.36 (m, 5H), 1.23 (s, 6H), 1.10-0.99 (m, 1H) |
| 83b | Isomer 2,4-[2-(N-(3,3-difluorocyclohexyl)anilino)-2-oxo-ethyl]-1-(6-methylindoline-1-carbonyl)piperidine-4-carboxylic acid | 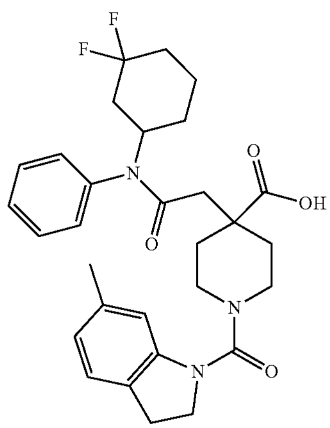 [SMILES: Cc1ccc2c(c1)N(C(=O)N1CCC(CC(=O)N(c3ccccc3)C3CCCC(F)(F)C3)(C(=O)O)CC1)CC2] | 540.2 | ¹H NMR (400 MHz, DMSO-d₆): 12.27 (br, 1H), 7.58-7.40 (m, 3H), 7.26 (d, J = 6.0 Hz, 2H), 7.03 (d, J = 7.4 Hz, 1H), 6.74 (s, 1H), 6.65 (d, J = 7.5 Hz, 1H), 4.63 (t, J = 12.4 Hz, 1H), 3.75 (t, J = 8.2 Hz, 2H), 3.27-3.08 (m, 4H), 2.89 (t, J = 8.1 Hz, 2H), 2.23 (s, 4H), 2.20-2.11 (m, 2H), 1.90 (dd, J = 3.9, 9.0 Hz, 3H), 1.74 (s, 2H), 1.65-1.50 (m, 1H), 1.49-1.29 (m, 4H), 1.06-1.00 (m, 1H) |
| 83a | Isomer 1,4-[2-(N-(3,3-difluorocyclohexyl)anilino)-2-oxo-ethyl]-1-(6-methylindoline-1-carbonyl)piperidine-4-carboxylic acid | 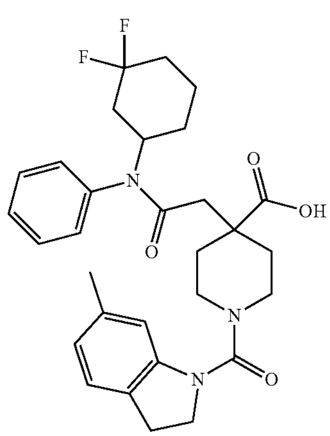 [SMILES: Cc1ccc2c(c1)N(C(=O)N1CCC(CC(=O)N(c3ccccc3)C3CCCC(F)(F)C3)(C(=O)O)CC1)CC2] | 540.2 | ¹H NMR (400 MHz, DMSO-d₆): 12.25 (br, 1H), 7.61-7.40 (m, 3H), 7.26 (d, J = 5.9 Hz, 2H), 7.03 (d, J = 7.5 Hz, 1H), 6.74 (s, 1H), 6.65 (d, J = 7.4 Hz, 1H), 4.63 (t, J = 12.4 Hz, 1H), 3.75 (t, J = 8.2 Hz, 2H), 3.27-3.08 (m, 4H), 2.89 (t, J = 8.1 Hz, 2H), 2.23 (s, 4H), 2.19 (s, 2H), 1.90 (dd, J = 4.1, 9.0 Hz, 3H), 1.74 (s, 2H), 1.65-1.51 (m, 1H), 1.51-1.32 (m, 4H), 1.11-0.93 (m, 1H) |

Example Nos. 6, 8, 9, 10, 11, 12, 14, 15, 17, 18, 34, 36, 37, 39, 41, 41A, 41IB, 43, 43A 431B, 45, 45A, 451B, 47, 53, 54, 86, 95 and 96 were Prepared According to the Procedure Above
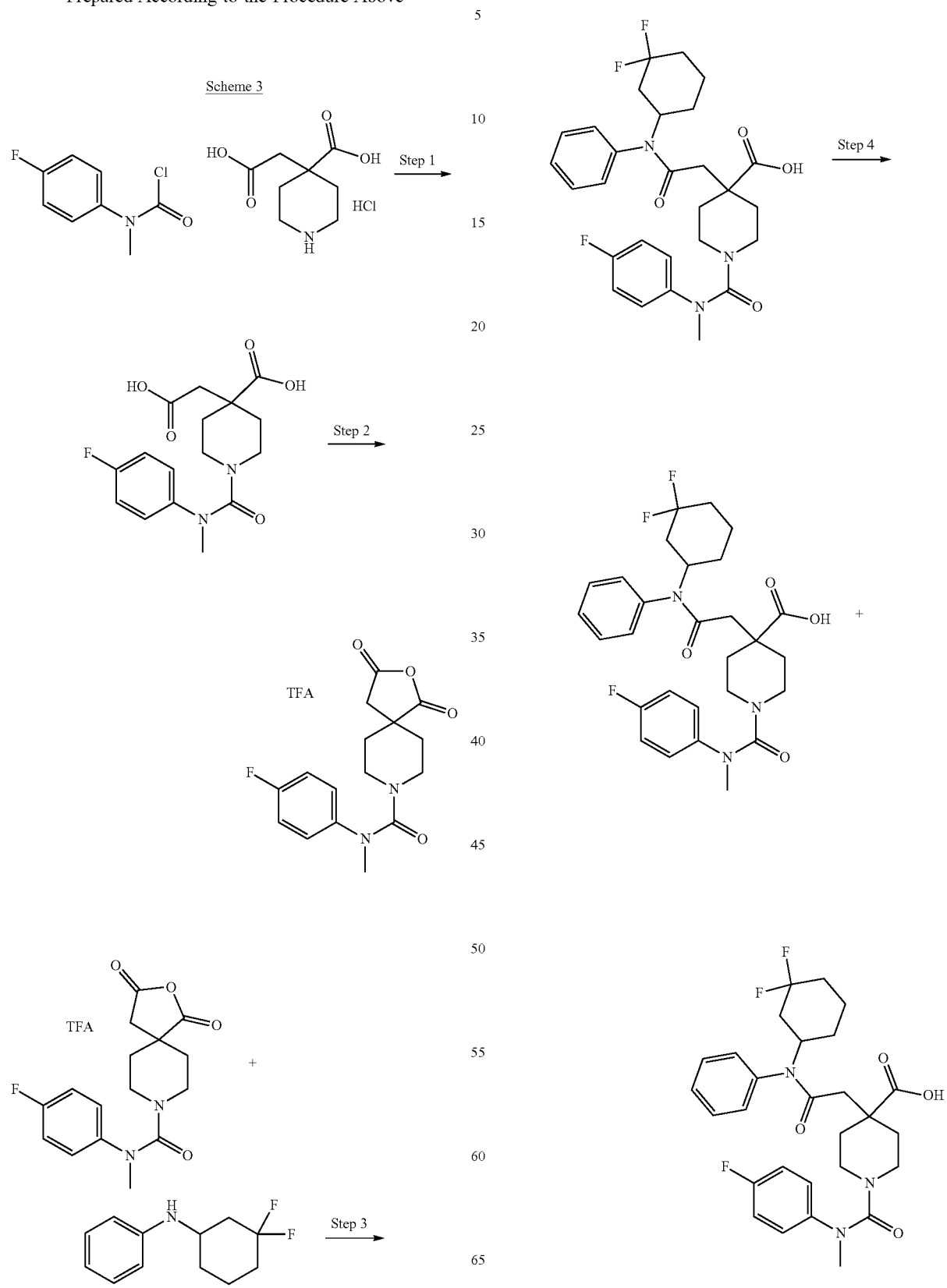

Example Nos. 44, 44A, and 44B were Prepared According to Scheme 3

Step 1: 4-(carboxymethyl)-1-[(4-fluorophenyl)-methyl-carbamoyl]piperidine-4-carboxylic acid

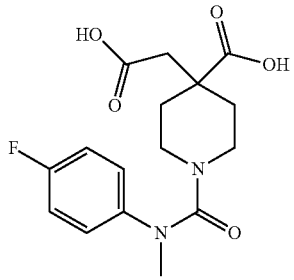 [SMILES: CN(C(=O)N1CCC(CC(=O)O)(C(=O)O)CC1)c1ccc(F)cc1]

To a mixture of N-(4-fluorophenyl)-N-methyl-carbamoyl chloride (5.91 g, 25.2 mmol, 80 mass %) and 4-(carboxymethyl)piperidine-4-carboxylic acid;hydrochloride (6.98 g, 25.0 mmol, 80 mass %) in tetrahydrofuran (100 mL) was added N,O-bis(trimethylsilyl)acetamide (25 mL, 100 mmol) dropwise, followed by N,N-diisopropylethylamine (13.5 mL, 77.3 mmol) at 0° C. The mixture was warmed up to RT and stirred overnight. The reaction was quenched by adding water (50 mL) and the pH was adjusted to 3 with 1.0 N HCl and extracted with EtOAc (60 mL×3). The combined organic layers were washed with brine (30 mL), dried over $Na_2SO_4$, filtered and concentrated in vacuo to give a residue. The residue was purified by silica gel flash eluting petroleum ether to 0 to 100% ethyl acetate (0.1% formic acid)/petroleum ether to give the title compound (6.11 g, 95 mass %, 68.7% yield). MS m/z 339.3 (M+H).

| Example No. | Chemical Name | Structure | ES/MS (m/z) (M + H) | 1H NMR (400 MHz, DMSO-d6) |
|---|---|---|---|---|
| | 4-(carboxymethyl)-1-(6-methylindoline-1-carbonyl)piperidine-4-carboxylic acid | | 347.0 | |
| | 4-(carboxymethyl)-1-(3,4-dihydro-2H-quinoline-1-carbonyl)piperidine-4-carboxylic acid | | | $^1$H NMR (400.15 MHz, DMSO-d$_6$): 12.31 (br, 2H), 7.14-6.98 (m, 2H), 6.89 (d, J = 8.0 Hz, 1H), 6.84 (dt, J = 1.1, 7.3 Hz, 1H), 3.48-3.40 (m, 4H), 3.19-3.07 (m, 2H), 2.72 (t, J = 6.6 Hz, 2H), 2.52 (d, J = 3.4 Hz, 2H), 1.94-1.78 (m, 4H), 1.52 (ddd, J = 3.6, 9.3, 13.3 Hz, 2H). |
| | 4-(carboxymethyl)-1-(5-fluoroindoline-1-carbonyl)piperidine-4-carboxylic acid | | 351.1 | |

Step 2: N-(4-fluorophenyl)-N-methyl-1,3-dioxo-2-oxa-8-azaspiro[4.5]decane-8-carboxamide; 2,2,2-trifluoroacetic acid

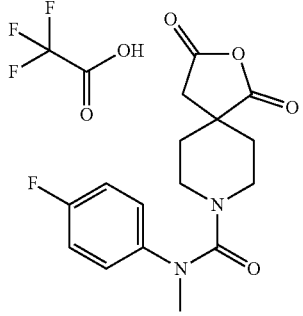

To a solution of 4-(carboxymethyl)-1-[(4-fluorophenyl)-menthyl-carbamoyl]piperidine-4-carboxylic acid (0.5 g, 1 mmol, 95 mass %) in DCM (5.0 mL) was added 2,2,2-trifluoroacetic acid anhydride (0.5 mL, 4 mmol, 99 mass %0) at RT, the reaction mixture was stirred overnight. The reaction mixture was concentrated in vacuo, toluene (5 mL) was added to the residue and concentrated in vacuo (repeated 3 times) to give crude title product (600 mg, 90 mass %, 90% yield) which used directly in the next step.

Step 3: racemic 4-[2-(N-[-3,3-difluorocyclohexyl]anilino)-2-oxo-ethyl]-1-[(4-fluorophenyl)-methyl-carbamoyl]piperidine-4-carboxylic acid (Example No. 44)

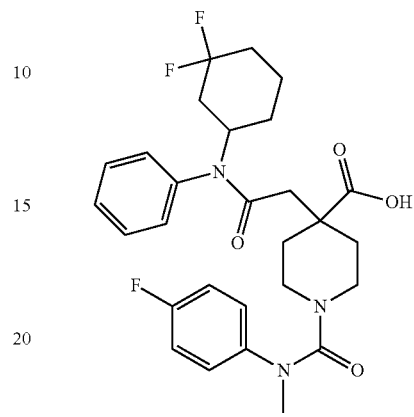

A mixture of racemic N-[3,3-difluorocyclohexyl]aniline (0.5 g, 2.0 mmol, 90 mass %), N-(4-fluorophenyl)-N-methyl-1,3-dioxo-2-oxa-8-azaspiro[4.5]decane-8-carboxamide; 2,2,2-trifluoroacetic acid (0.6 g, 2.0 mmol, 90 mass %) in dichloromethane (5 mL, 99.5 mass %) was placed in a microwave tube, the reaction was heated in a microwave at 80° C. for 4 h. The mixture was concentrated to give as a residue. The crude product was purified by reverse phase prep-HPLC, using Welch Xtimate C18 100*30 mm*5 μm column, mobile phase A: water (0.225% formic acid), B:

| Chemical Name | Structure | ES/MS (m/z) (M + H) | 1H NMR (400 MHz, DMSO-d6) |
|---|---|---|---|
| 8-(6-methylindoline-1-carbonyl)-2-oxa-8-azaspiro[4.5]decane-1,3-dione | 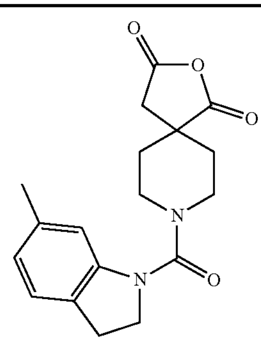 | 329.0 | |
| 8-(3,4-dihydro-2H-quinoline-1-carbonyl)-2-oxa-8-azaspiro[4.5]decane-1,3-dione | 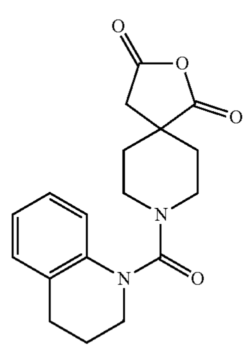 [SMILES: O=C1CC2(CCN(C(=O)N3CCCc4ccccc43)CC2)C(=O)O1] | | $^1$H NMR (400 MHz, DMSO-d$_6$): 7.10-7.04 (m, 2H), 7.02-6.94 (m, 1H), 6.90-6.82 (m, 1H), 3.64-3.54 (m, 4H), 3.48-3.40 (m, 2H), 3.02-2.90 (m, 2H), 2.74-2.70 (m, 2H), 1.88-1.76 (m, 6H). |

CH₃CN, eluting 45% B to 75% B. The appropriate fractions were collected and lyophilized to give the title compound (170 mg, 99 mass %, 20% yield). MS m/z 532.4 (M+H). $^1$H NMR (400.14 MHz, DMSO-d$_6$): 12.16 (br, 1H), 7.52-7.43 (m, 3H), 7.20-7.08 (m, 6H), 4.61-4.55 (m, 1H), 3.18-3.05 (m, 2H), 3.01 (s, 3H), 2.96-2.90 (m, 2H), 2.35-2.26 (m, 1H), 2.05 (s, 2H), 1.97-1.92 (m, 1H), 1.73-1.61 (m, 4H), 1.59-1.53 (m, 3H), 1.18-1.13 (m, 2H), 1.08-0.99 (m, 1H).

Example Nos. 10, 14, 15, 17, 18, 34, 36, 37, 39, 41, 45, 53, 54, 86, 95 and 96 were Prepared According to the Procedure Above

| Example No. | Chemical Name | Structure | ES/MS (m/z) (M + H) | 1H NMR (400 MHz, DMSO-d6) |
|---|---|---|---|---|
| 10 | Racemic, 4-[2-(N-[2,2-difluorocyclohexyl]anilino)-2-oxo-ethyl]-1-[(4-fluorophenyl)-methyl-carbamoyl]piperidine-4-carboxylic acid | 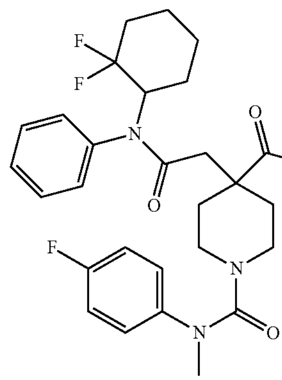 | 532.4 | $^1$H NMR (400 MHz, DMSO-d$_6$): 12.12 (br, 1H), 7.50-7.38 (m, 3H), 7.28-7.22 (m, 1H), 7.21-7.05 (m, 5H), 5.06-4.91 (m, 1H), 3.11-3.02 (m, 2H), 3.01 (s, 3H), 2.93 (dddd, J = 3.2, 9.7, 13.1, 16.5 Hz, 2H), 2.14-2.02 (m, 2H), 2.01-1.92 (m, 1H), 1.90-1.74 (m, 2H), 1.66 (t, J = 13.8 Hz, 4H), 1.50-1.35 (m, 1H), 1.28-1.06 (m, 4H) |
| 14 | 4-[2-(N-cyclohexylanilino)-2-oxo-ethyl]-1-[(4-methoxyphenyl)-methyl-carbamoyl]piperidine-4-carboxylic acid | 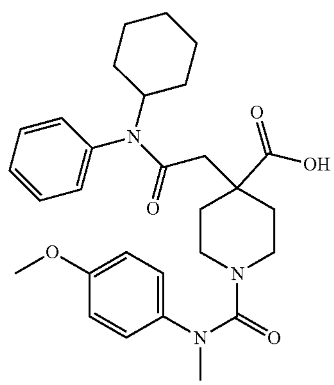 [SMILES: COc1ccc(N(C)C(=O)N2CCC(CC(=O)N(c3ccccc3)C3CCCCC3)(C(=O)O)CC2)cc1] | 508.5 | $^1$H NMR (400 MHz, DMSO-d$_6$) 12.07 (br, 1H), 7.50-7.39 (m, 3H), 7.12 (d, J = 7.0 Hz, 2H), 7.01-6.95 (m, 2H), 6.87 (d, J = 8.9 Hz, 2H), 4.38-4.28 (m, 1H), 3.73 (s, 3H), 3.09-3.00 (m, 2H), 2.96 (s, 3H), 2.94-2.85 (m, 2H), 2.02 (s, 2H), 1.72-1.59 (m, 6H), 1.49 (d, J = 12.8 Hz, 1H), 1.33-1.18 (m, 2H), 1.10 (ddd, J = 3.6, 9.3, 13.1 Hz, 2H), 0.95-0.80 (m, 3H) |
| 15 | 4-(2-(cyclohexyl(phenyl)amino)-2-oxoethyl)-1-(ethyl(4-fluorophenyl)carbamoyl)piperidine-4-carboxylic acid | 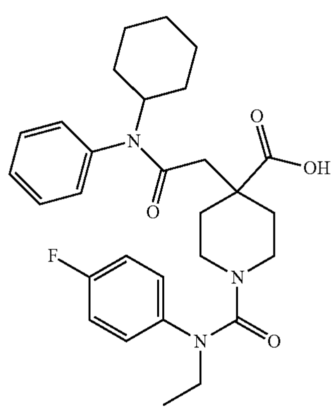 [SMILES: CCN(C(=O)N1CCC(CC(=O)N(c2ccccc2)C2CCCCC2)(C(=O)O)CC1)c1ccc(F)cc1] | 510.5 | $^1$H NMR (400 MHz, DMSO-d$_6$): 12.07 (br, 1H), 7.54-7.36 (m, 3H), 7.22-7.04 (m, 6H), 4.43-4.25 (m, 1H), 3.50-3.48 (m, 2H), 3.12-2.96 (m, 2H), 2.93-2.83 (m, 2H), 2.02 (s, 2H), 1.72-1.59 (m, 6H), 1.49 (d, J = 12.8 Hz, 1H), 1.33-1.19 (m, 2H), 1.10 (ddd, J = 3.6, 9.3, 13.2 Hz, 2H), 0.96 (t, J = 7.0 Hz, 3H), 0.92-0.75 (m, 3H) |

| Example No. | Chemical Name | Structure | ES/MS (m/z) (M + H) | 1H NMR (400 MHz, DMSO-d6) |
|---|---|---|---|---|
| 17 | Racemic, 4-[2-(N-[1-cyclopropylpropyl]anilino)-2-oxo-ethyl]-1-[(4-fluorophenyl)-methyl-carbamoyl]piperidine-4-carboxylic acid | 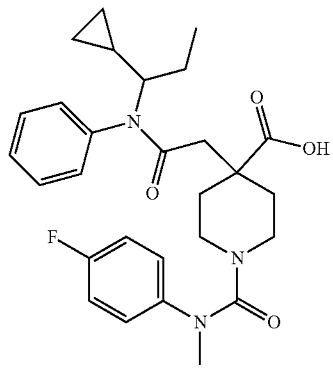 [SMILES: CCC(C1CC1)N(C(=O)CC1(C(=O)O)CCN(C(=O)N(C)c2ccc(F)cc2)CC1)c1ccccc1] | 496.2 | $^1$H NMR (400 MHz, DMSO-d$_6$): 12.09 (br, 1H), 7.54-7.40 (m, 3H), 7.36-7.25 (m, 1H), 7.20-7.06 (m, 5H), 3.80-3.69 (m, 1H), 3.14-3.04 (m, 2H), 3.00 (s, 3H), 2.96-2.87 (m, 2H), 2.09 (s, 2H), 1.72-1.61 (m, 2H), 1.51-1.33 (m, 2H), 1.12 (m, 2H), 0.89 (t, J = 7.4 Hz, 3H), 0.60-0.50 (m, 1H), 0.43-0.27 (m, 3H), 0.24-0.15 (m, 1H) |
| 18 | 4-[2-[N-(dicyclopropylmethyl)anilino]-2-oxo-ethyl]-1-[(4-fluorophenyl)-methyl-carbamoyl]piperidine-4-carboxylic acid | 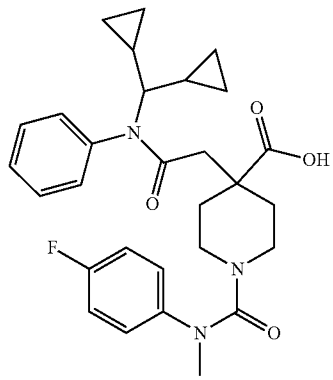 [SMILES: CN(C(=O)N1CCC(CC(=O)N(c2ccccc2)C(C2CC2)C2CC2)(C(=O)O)CC1)c1ccc(F)cc1] | 508.5 | $^1$H NMR (400 MHz, DMSO-d$_6$): 11.90 (br, 1H), 7.35-7.22 (m, 3H), 7.10 (d, J = 7.1 Hz, 2H), 7.00-6.87 (m, 4H), 3.17-3.13 (m, 1H), 2.97-2.88 (m, 2H), 2.81 (s, 3H), 2.77-2.66 (m, 2H), 1.90 (s, 2H), 1.53-1.42 (m, 2H), 0.99-0.87 (m, 2H), 0.48-0.37 (m, 2H), 0.37-0.29 (m, 2H), 0.23-0.10 (m, 4H), 0.04--0.06 (m, 2H) |
| 34 | Racemic 4-[2-(N-[1,2-dimethylpropyl]anilino)-2-oxo-ethyl]-1-[(4-fluorophenyl)-methyl-carbamoyl]piperidine-4-carboxylic acid | 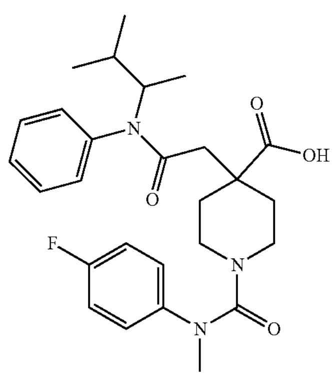 [SMILES: CC(C)C(C)N(C(=O)CC1(C(=O)O)CCN(C(=O)N(C)c2ccc(F)cc2)CC1)c1ccccc1] | 484.4 | $^1$H NMR (400 MHz, DMSO-d$_6$): 7.50-7.39 (m, 3H), 7.19-7.06 (m, 6H), 4.31-4.23 (m, 1H), 3.13-3.06 (m, 2H), 3.00 (s, 3H), 2.96-2.86 (m, 2H), 2.07 (q, J = 16 Hz, 2H), 1.71-1.61 (m, 2H), 1.56-1.46 (m, 1H), 1.22-1.10 (m, 2H), 0.92 (t, J = 6.3 Hz, 6H), 0.79 (d, J = 6.6 Hz, 3H) |
| 36 | Racemic, 4-[2-(N-[3,3-difluoro-1-methyl-propyl]anilino)-2-oxo-ethyl]-1-[(4-fluorophenyl)-methyl-carbamoyl]piperidine-4-carboxylic acid | 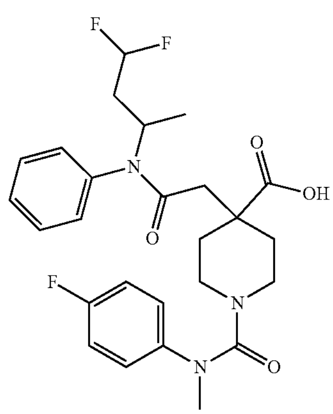 [SMILES: CC(CC(F)F)N(C(=O)CC1(C(=O)O)CCN(C(=O)N(C)c2ccc(F)cc2)CC1)c1ccccc1] | 506.4 | $^1$H NMR (400 MHz, DMSO-d$_6$): 12.20 (br, 1H), 7.57-7.38 (m, 3H), 7.21 (d, J = 7.1 Hz, 2H), 7.18-7.05 (m, 4H), 6.35-5.85 (m, 1H), 4.85-4.59 (m, 1H), 3.11-3.02 (m, 2H), 3.00 (s, 3H), 2.98-2.88 (m, 2H), 2.07 (s, 2H), 2.12-1.96 (m, 1H), 1.87-1.71 (m, 1H), 1.71-1.58 (m, 2H), 1.22-1.09 (m, 2H), 1.01 (d, J = 6.9 Hz, 3H) |

| Example No. | Chemical Name | Structure | ES/MS (m/z) (M + H) | 1H NMR (400 MHz, DMSO-d6) |
|---|---|---|---|---|
| 37 | 1-[(4-fluorophenyl)-methyl-carbamoyl]-4-[2-[N-(o-tolyl)anilino]-2-oxo-ethyl]piperidine-4-carboxylic acid | 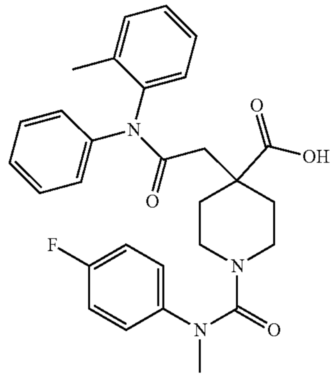 [SMILES: Cc1ccccc1N(C(=O)CC1(C(=O)O)CCN(C(=O)N(C)c2ccc(F)cc2)CC1)c1ccccc1] | 504.4 | ¹H NMR (400 MHz, DMSO-d₆): 12.26 (br, 1H), 7.35 (s, 6H), 7.19-7.04 (m, 7H), 3.21-3.06 (m, 2H), 3.02 (s, 3H), 3.00-2.89 (m, 2H), 2.46-2.34 (m, 1H), 2.29-2.02 (m, 4H), 1.88-1.63 (m, 2H), 1.37-1.18 (m, 2H). |
| 39 | 1-(cyclopropyl(4-fluorophenyl)carbamoyl)-4-(2-(diphenylamino)-2-oxoethyl)piperidine-4-carboxylic acid | 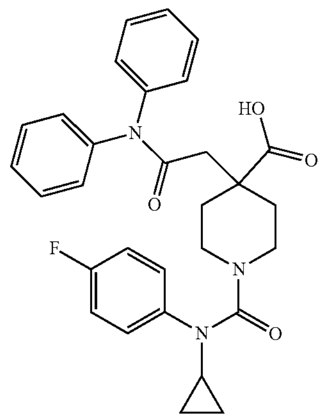 [SMILES: O=C(CC1(C(=O)O)CCN(C(=O)N(c2ccc(F)cc2)C2CC2)CC1)N(c1ccccc1)c1ccccc1] | 516.3 | ¹H NMR (400 MHz, DMSO-d₆): 7.50-7.17 (m, 9H), 7.29-7.16 (m, 1H), 7.15-7.03 (m, 4H), 3.39-3.28 (m, 2H), 3.05 (t, J = 10.1 Hz, 2H), 2.56 (td, J = 3.2, 6.7 Hz, 1H), 2.38 (s, 2H), 1.83-1.70 (m, 2H), 1.36-1.24 (m, 2H), 0.77-0.70 (m, 2H), 0.59-0.52 (m, 2H) |
| 41 | 1-[(4-fluorophenyl)-methyl-carbamoyl]-4-[2-oxo-2-(N-[(racemic)-tetrahydropyran-3-yl]anilino)ethyl]piperidine-4-carboxylic acid | 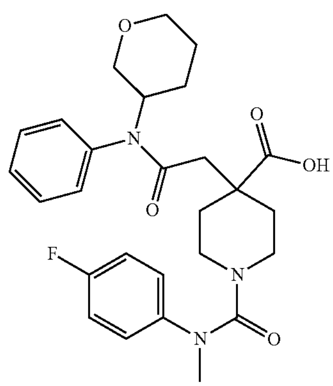 [SMILES: CN(C(=O)N1CCC(CC(=O)N(c2ccccc2)C2CCCOC2)(C(=O)O)CC1)c1ccc(F)cc1] | 498.4 | ¹H NMR (400 MHz, DMSO-d₆): 7.50-7.40 (m, 3H), 7.21-7.12 (m, 3H), 7.12-7.07 (m, 3H), 4.44-4.35 (m, 1H), 3.81 (dd, J = 1.9, 10.4 Hz, 1H), 3.67 (d, J = 10.8 Hz, 1H), 3.10-3.03 (m, 2H), 3.00 (s, 3H), 2.97-2.88 (m, 4H), 2.04 (dd, J = 16.4 Hz, 2H), 1.75 (d, J = 11.8 Hz, 1H), 1.71-1.62 (m, 2H), 1.58-1.50 (m, 2H), 1.20-1.09 (m, 2H), 1.07-0.96 (m, 1H) |
| 43 | Racemic 1,4-[2-[N-(1-cyclopropylethyl)anilino]-2-oxo-ethyl]-1-[(4-fluorophenyl)-methyl-carbamoyl]piperidine-4-carboxylic acid | 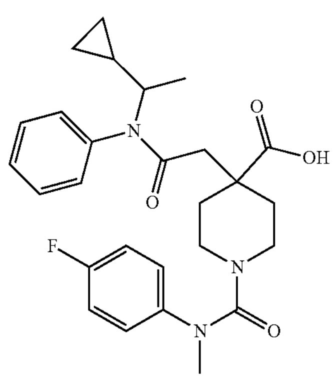 [SMILES: CC(C1CC1)N(C(=O)CC1(C(=O)O)CCN(C(=O)N(C)c2ccc(F)cc2)CC1)c1ccccc1] | 482.4 | ¹H NMR (400 MHz, DMSO-d₆): 12.11 (br, 1H), 7.54-7.38 (m, 3H), 7.33-7.05 (m, 6H), 3.90 (dd, J = 7.1, 8.3 Hz, 1H), 3.13-3.04 (m, 2H), 3.00 (s, 3H), 2.97-2.86 (m, 2H), 2.13-2.00 (m, 2H), 1.74-1.59 (m, 2H), 1.20-1.08 (m, 2H), 1.03 (d, J = 6.8 Hz, 3H), 0.51-0.32 (m, 3H), 0.24 (d, J = 3.9 Hz, 2H) |

-continued

| Example No. | Chemical Name | Structure | ES/MS (m/z) (M + H) | 1H NMR (400 MHz, DMSO-d6) |
|---|---|---|---|---|
| 45 | Racemic, 1-[(4-cyclopropylphenyl)-methyl-carbamoyl]-4-[2-oxo-2-(N-tetrahydropyran-3-yl]anilino)ethyl]piperidine-4-carboxylic acid | 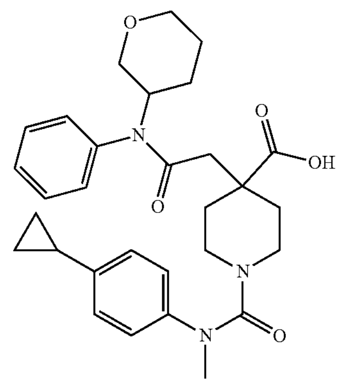 [SMILES: CN(C(=O)N1CCC(CC(=O)N(c2ccccc2)C2CCCOC2)(C(=O)O)CC1)c1ccc(C2CC2)cc1] | 520.5 | $^1$H NMR (400 MHz, DMSO-d$_6$): 12.15 (s, 1H), 7.53-7.42 (m, 3H), 7.21-7.10 (m, 2H), 7.00 (d, J = 9.2 Hz, 2H), 6.91 (d, J = 8.4 Hz, 2H), 4.43-4.35 (m, 1H), 3.84-3.79 (m, 1H), 3.67 (d, J = 11.1 Hz, 1H), 3.08-3.01 (m, 2H), 2.98 (s, 3H), 2.96-2.87 (m, 4H), 2.03 (dd, J = 16.4 Hz, 2H), 1.91-1.84 (m, 1H), 1.75 (d, J = 11.8 Hz, 1H), 1.68-1.60 (m, 2H), 1.57-1.51 (m, 2H), 1.17-1.07 (m, 2H), 1.06-0.99 (m, 1H), 0.95-0.89 (m, 2H), 0.64-0.59 (m, 2H) |
| 47 | Racemic, 1-(6-cyanoindoline-1-carbonyl)-4-[2-(N-[3,3-difluorocyclohexyl]anilino)-2-oxo-ethyl]piperidine-4-carboxylic acid | 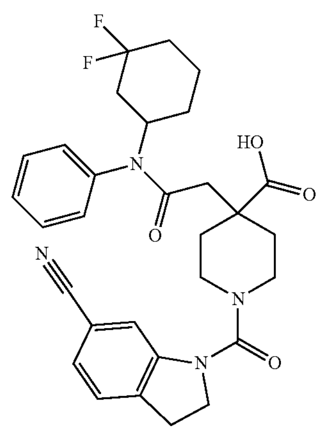 [SMILES: N#Cc1ccc2c(c1)N(C(=O)N1CCC(CC(=O)N(c3ccccc3)C3CCCC(F)(F)C3)(C(=O)O)CC1)CC2] | 551.5 | $^1$H NMR (400 MHz, DMSO-d$_6$): 12.27 (br, 1H), 7.55-7.43 (m, 3H), 7.35 (d, J = 7.6 Hz, 1H), 7.31 (d, J = 8.0 Hz, 1H), 7.26 (d, J = 6.8 Hz, 2H), 7.22 (s, 1H), 4.62 (t, J = 12.3 Hz, 1H), 3.85 (t, J = 8.3 Hz, 2H), 3.27-3.17 (m, 4H), 3.07 (t, J = 8.3 Hz, 2H), 2.22-2.18 (m, 3H), 1.95-1.86 (m, 3H), 1.79-1.71 (m, 2H), 1.62-1.37 (m, 5H), 1.09-0.97 (m, 1H) |
| 53 | Racemic, 4-[2-(N-[3,3-difluorocyclohexyl]-3-fluoro-anilino)-2-oxo-ethyl]-1-[methyl(phenyl)carbamoyl]piperidine-4-carboxylic acid | 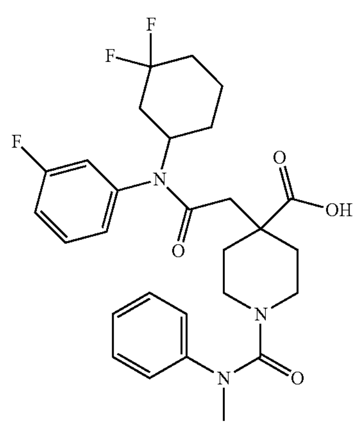 [SMILES: CN(C(=O)N1CCC(CC(=O)N(c2cccc(F)c2)C2CCCC(F)(F)C2)(C(=O)O)CC1)c1ccccc1] | 532.5 | $^1$H NMR (400 MHz, DMSO-d$_6$): 12.12 (br, 1H), 7.58-7.44 (m, 1H), 7.36-7.25 (m, 3H), 7.19 (s, 1H), 7.13-6.98 (m, 4H), 4.55 (t, J = 12.1 Hz, 1H), 3.12-3.08 (m, 2H), 3.04 (s, 3H), 3.00-2.89 (m, 2H), 2.22-2.20 (m, 1H), 2.09 (s, 2H), 1.90-1.88 (m, 1H), 1.81-1.60 (m, 5H), 1.58-1.32 (m, 2H), 1.23-1.21 (m, 2H), 1.07-0.96 (m, 1H) |

-continued

| Example No. | Chemical Name | Structure | ES/MS (m/z) (M + H) | 1H NMR (400 MHz, DMSO-d6) |
|---|---|---|---|---|
| 54 | Racemic, 4-[2-(N-(3,3-difluorocyclohexyl)-4-fluoro-anilino)-2-oxo-ethyl]-1-[methyl(phenyl)carbamoyl]piperidine-4-carboxylic acid | 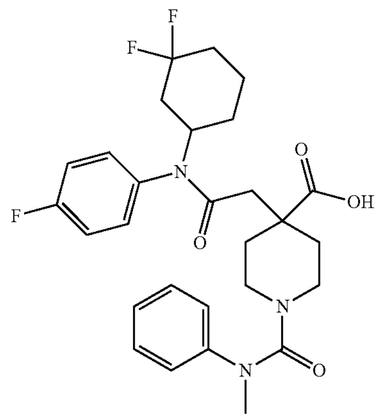 [SMILES: CN(C(=O)N1CCC(CC(=O)N(c2ccc(F)cc2)C2CCCC(F)(F)C2)(C(=O)O)CC1)c1ccccc1] | 532.5 | $^1$H NMR (400 MHz, DMSO-d$_6$): 7.36-7.20 (m, 6H), 7.10-7.01 (m, 3H), 4.58 (t, J = 12.4 Hz, 1H), 3.12 (d, J = 13.4 Hz, 2H), 3.04 (s, 3H), 2.93 (t, J = 9.9 Hz, 2H), 2.20-2,18 (m, 1H), 2.03 (s, 2H), 1.90-1.88 (m, 1H), 1.77-1.61 (m, 4H), 1.60-1.34 (m, 3H), 1.27-1.15 (m, 2H), 1.05-0.90 (m, 1H) |
| 86 | 4-[2-(N-cyclopentylanilino)-2-oxo-ethyl]-1-(6-methylindoline-1-carbonyl)piperidine-4-carboxylic acid | 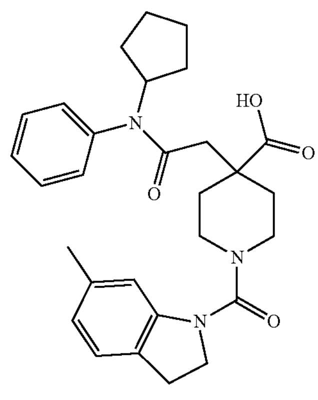 [SMILES: Cc1ccc2c(c1)N(C(=O)N1CCC(CC(=O)N(c3ccccc3)C3CCCC3)(C(=O)O)CC1)CC2] | 490.3 | $^1$H NMR (400 MHz, DMSO-d$_6$): 12.21 (br, 1H), 7.52-7.46 (m, 2H), 7.46-7.41 (m, 1H), 7.21 (d, J = 7.3 Hz, 2H), 7.03 (d, J = 7.4 Hz, 1H), 6.74 (s, 1H), 6.66 (d, J = 7.5 Hz, 1H), 4.75-4.72 (m, 1H), 3.75 (t, J = 8.1 Hz, 2H), 3.25-3.12 (m, 4H), 2.89 (t, J = 8.0 Hz, 2H), 2.23 (s, 3H), 2.19 (s, 2H), 1.94-1.86 (m, 2H), 1.82-1.72 (m, 2H), 1.46-1.36 (m, 6H), 1.25-1.16 (m, 2H) |
| 95 | 1-(3,4-dihydro-2H-quinoline-1-carbonyl)-4-[2-oxo-2-(N-tetrahydropyran-4-ylanilino)ethyl]piperidine-4-carboxylic acid | 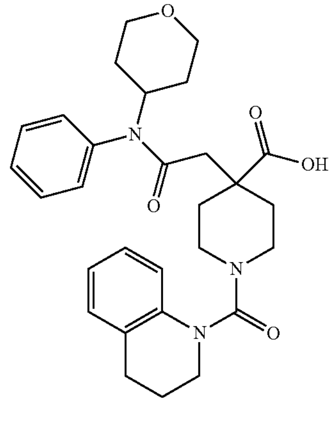 [SMILES: O=C(N1CCC(CC(=O)N(c2ccccc2)C2CCOCC2)(C(=O)O)CC1)N1CCCc2ccccc21] | 506.5 | $^1$H NMR (400 MHz, DMSO-d$_6$): 12.19 (br, 1H), 7.54-7.42 (m, 3H), 7.22-7.15 (m, 2H), 7.09-6.98 (m, 2H), 6.87-6.78 (m, 2H), 4.66-4.53 (m, 1H), 3.80 (dd, J = 4.1, 11.1 Hz, 2H), 3.42-3.37 (m, 2H), 3.25-3.18 (m, 2H), 3.14-3.03 (m, 2H), 2.72-2.68 (m, 2H), 2.33-2.31 (m, 2H), 2.15 (s, 2H), 1.89-1.74 (m, 4H), 1.61 (dd, J = 2.1, 12.4 Hz, 2H), 1.35 (ddd, J = 3.9, 9.5, 13.3 Hz, 2H), 1.25-1.12 (m, 2H) |

-continued

| Example No. | Chemical Name | Structure | ES/MS (m/z) (M + H) | 1H NMR (400 MHz, DMSO-d6) |
|---|---|---|---|---|
| 96 | 1-(5-(fluoroindoline-1-carbonyl)-4-[2-oxo-2-(N-tetrahydropyran-4-ylanilino)ethyl]piperidine-4-carboxylic acid | 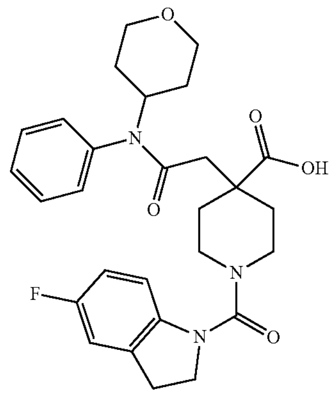 [SMILES: O=C(N1CCC(CC(=O)N(c2ccccc2)C2CCOCC2)(C(=O)O)CC1)N1CCc2cc(F)ccc21] | 510.2 | $^1$H NMR (400 MHz, DMSO-d$_6$): 7.56-7.42 (m, 3H), 7.23-7.18 (t, 2H), 7.04 (d, J = 8.0 Hz, 1H), 6.94-6.86 (m, 2H), 4.68-4.55 (m, 1H), 3.80 (m, J = 8.1 Hz, 4H), 3.31 (m, 1H), 3.26-3.04 (m, 5H), 2.97 (t, J = 8.1 Hz, 2H), 2.19 (s, 2H), 1.97-1.84 (m, 2H), 1.62 (dd, J = 2.1, 12.2 Hz, 2H), 1.42 (ddd, J = 3.9, 9.1, 13.3 Hz, 2H), 1.27-1.13 (m, 2H) |

4-[2-(N-cyclohexylanilino)-2-oxo-ethyl]-1-(indoline-1-carbonyl)piperidine-4-carboxylic acid (Example No. 6

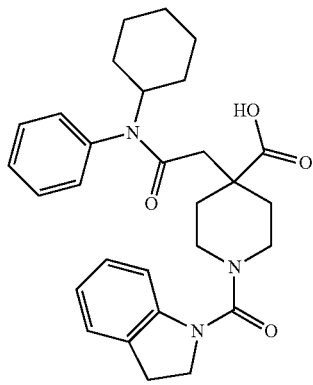 [SMILES: O=C(N1CCC(CC(=O)N(c2ccccc2)C2CCCCC2)(C(=O)O)CC1)N1CCc2ccccc21]

To a solution of N-cyclohexylaniline (115 mg, 0.643 mmol) in tetrahydrofuran (2 mL) was added n-butyllithium (0.3 mL, 0.80 mmol, 2.5 M in hexanes) at −78° C. under nitrogen and stirred at −78° C. for 15 min, then the solution of 8-(indoline-1-carbonyl)-2-oxa-8-azaspiro[4.5]decane-1,3-dione (170 mg, 0.433 mmol, 80 mass %) in tetrahydrofuran (2 mL) was added at −78° C. under N, then the reaction mixture was stirred at −78° C. under N$_2$ and slowly warmed up to RT for 1 h. The reaction was quenched by sat. Nap$_4$C (3.0 ml) and concentrated. The residue was purified by reverse phase prep-HPLC, using Xtimate C18 100*30 mm*10 um, mobile phase A: water-0.225% oformic acid, mobile phasefB: ACN, eluting with 58-88% B in 10 min then to 100% B. The appropriate fractions were combined and lyophilized to give title product (31.7 mg, 97.4 mass %, 14.6% yield) as white solid. MS m/z 490.4 (M+H); $^1$H NMR (400.13 MHz, DMSO-d$_6$): 12.18 (br, 1H), 7.54-7.39 (m, 3H), 7.22-7.13 (m, 3H), 7.09 (t, J=7.5 Hz, 1H), 6.90 (d, J=8.0 Hz, 1H), 6.87-6.80 (m, 1H), 4.37 (t, J=11.9 Hz, 1H), 3.76 (t, J=8.1 Hz, 2H), 3.26-3.10 (m, 4H), 2.95 (t, J=8.1 Hz, 2H), 2.16 (s, 2H), 1.89 (d, J=13.8 Hz, 2H), 1.77-1.61 (m, 4H), 1.51 (d, J=12.6 Hz, 1H), 1.41 (t, J=9.1 Hz, 2H), 1.34-1.19 (m, 2H), 1.00-0.75 (m, 3H)

Example Nos. 8, 9, 11 and 12 were Prepared According to the Procedure Above

| Example No. | Chemical Name | Structure | ES/MS (m/z) (M + H) | $^1$H NMR (400 MHz, DMSO-d$_6$) |
|---|---|---|---|---|
| 7 | 4-[2-(N-cyclohexylanilino)-2-oxo-ethyl]-1-[(4-fluorophenyl)-methyl-carbamoyl]piperidine-4-carboxylic acid | 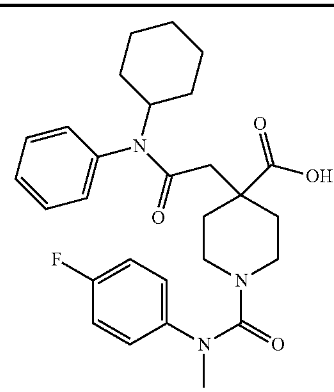 | 496.4 | 1H NMR (399.80 MHz, DMSO): 12.11 (s, 1H), 7.50-7.41 (m, 3H), 7.17-7.10 (m, 6H), 4.38-4.30 (m, 1H), 3.30-3.28 (m, 1H), 3.10-3.05 (m, 2H), 3.01 (s, 3H), 2.96-2.90 (m, 2H), 2.04 (s, 2H), 1.68-1.66 (m, 6H), 1.54-1.48 (m, 1H), 1.31-1.17 (m, 4H), 0.95-0.85 (m, 3H). |

| Example No. | Chemical Name | Structure | ES/MS (m/z) (M + H) | $^1$H NMR (400 MHz, DMSO-d$_6$) |
|---|---|---|---|---|
| 8 | 4-[2-(N-(4,4-difluorocyclohexyl)anilino)-2-oxo-ethyl]-1-[(4-fluorophenyl)-methyl-carbamoyl]piperidine-4-carboxylic acid | 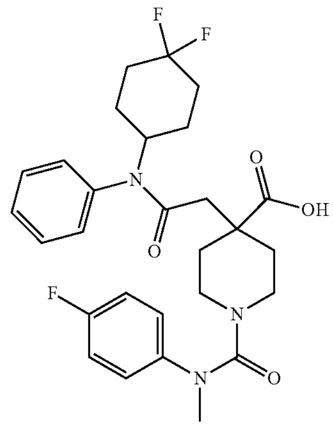 [SMILES: CN(C(=O)N1CCC(CC(=O)N(c2ccccc2)C2CCC(F)(F)CC2)(C(=O)O)CC1)c1ccc(F)cc1] | 532.4 | $^1$H NMR (400 MHz, DMSO-d$_6$): 12.14 (br, 1H), 7.54-7.40 (m, 3H), 7.23-7.13 (m, 3H), 7.13-7.05 (m, 3H), 4.51 (t, J = 12.1 Hz, 1H), 3.13-3.04 (m, 2H), 3.00 (s, 3H), 2.97-2.87 (m, 2H), 2.06 (s, 2H), 2.01-1.83 (m, 4H), 1.76 (d, J = 11.9 Hz, 2H), 1.71-1.62 (m, 2H), 1.25-1.08 (m, 4H) |
| 9 | 4-(2-(cyclopentyl(phenyl)amino)-2-oxoethyl)-1-((4-fluorophenyl)(methyl)carbamoyl)piperidine-4-carboxylic acid | 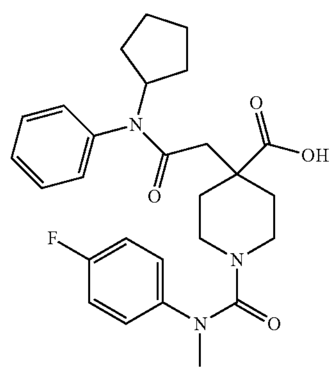 [SMILES: CN(C(=O)N1CCC(CC(=O)N(c2ccccc2)C2CCCC2)(C(=O)O)CC1)c1ccc(F)cc1] | 482.2 | $^1$H NMR (400 MHz, CD$_3$OD-d$_4$): 7.54-7.41 (m, 3H), 7.20-7.04 (m, 6H), 4.80-4.69 (m, 1H), 3.31-3.30 (m, 2H), 3.11 (s, 3H), 3.07-2.97 (m, 2H), 2.20 (s, 2H), 1.91-1.77 (m, 4H), 1.56-1.43 (m, 4H), 1.34-1.17 (m, 4H), |
| 11 | 4-[2-(N-cyclohexylanilino)-2-oxo-ethyl]-1-[(3-fluorophenyl)-methyl-carbamoyl]piperidine-4-carboxylic acid | 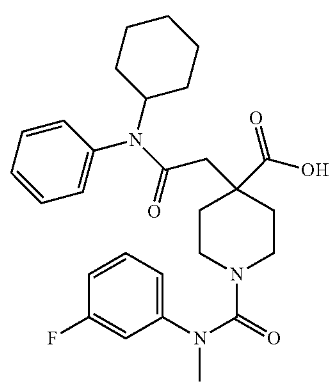 [SMILES: CN(C(=O)N1CCC(CC(=O)N(c2ccccc2)C2CCCCC2)(C(=O)O)CC1)c1cccc(F)c1] | 496.5 | $^1$H NMR (400 MHz, DMSO-d$_6$): 12.14 (br, 1H), 7.52-7.38 (m, 3H), 7.35-7.26 (m, 1H), 7.20-7.06 (m, 2H), 6.97-6.76 (m, 3H), 4.49-4.15 (m, 1H), 3.18-3.10 (m, 2H), 3.05 (s, 3H), 3.03-2.94 (m, 2H), 2.07 (s, 2H), 1.80-1.59 (m, 6H), 1.50 (d, J = 12.6 Hz, 1H), 1.35-1.16 (m, 4H), 0.99-0.74 (m, 3H) |
| 12 | 4-[2-(N-cyclohexylanilino)-2-oxo-ethyl]-1-[(2-fluorophenyl)-methyl-carbamoyl]piperidine-4-carboxylic acid | 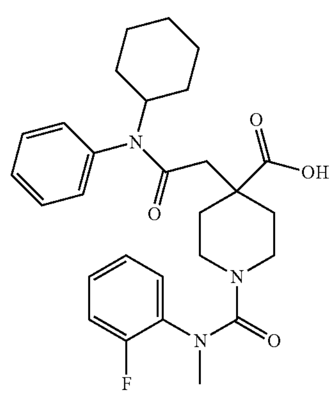 [SMILES: CN(C(=O)N1CCC(CC(=O)N(c2ccccc2)C2CCCCC2)(C(=O)O)CC1)c1ccccc1F] | 496.5 | $^1$H NMR (400 MHz, DMSO-d$_6$): 7.50-7.40 (m, 3H), 7.26-7.20 (m, 3H), 7.19-7.16 (m, 1H), 7.11 (d, J = 6.9 Hz, 2H), 4.37-4.28 (m, 1H), 3.08-3.00 (m, 2H), 2.96 (s, 3H), 2.94-2.87 (m, 2H), 2.01 (s, 2H), 1.71-1.59 (m, 6H), 1.49 (d, J = 12.6 Hz, 1H), 1.31-1.19 (m, 2H), 1.11-1.02 (m, 2H), 0.94-0.79 (m, 3H) |

Step 4: Isolation of isomers (Example Nos. 44A and 44B3)

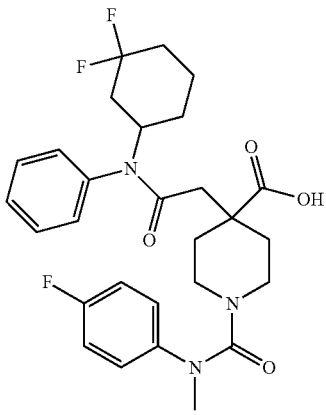 [SMILES: CN(C(=O)N1CCC(CC(=O)N(c2ccccc2)C2CCCC(F)(F)C2)(C(=O)O)CC1)c1ccc(F)cc1]

Racemic 4-[2-(N-[-3,3-difluorocyclohexyl]anilino)-2-oxo-ethyl]-1-[(4-fluorophenyl)-methyl-carbamoyl]piperidine-4-carboxylic acid 485 mg was purified by SFC-80, Daicel ChiralPak IG (250*30 mm, 10 μm), mobile phase A: CO2, B: 0.1% NH4OH in EtOH, eluting 40% of B, flow rate: 80 mL/min.

The eluent of first peak was collected and lyophilized to give the title compound (225.3 mg, 0.4153 mmol, 45.98% yield, ee: 98.7%). MS m/z 532.4 (M+H). $^1$H NMR (400.13 MHz, DMSO-$d_6$): 12.08 (br, 1H), 7.58-7.49 (m, 3H), 7.26-7.14 (m, 6H), 4.64 (t, J=12.4 Hz, 1H), 3.15-3.11 (m, 2H), 3.07 (s, 3H), 3.02-2.96 (m, 2H), 2.30-2.22 (m, 1H), 2.11 (s, 2H), 1.99-1.92 (m, 1H), 1.79 1.71 (m, 4H) 1.64-1.42 (m, 3H), 1.24-1.19 (m, 2H), 1.13-1.02 ((m, 1H).

The eluent of the second peak was collected and lyophilized to give the title compound (223.0 mg, 0.4153 mmol, 45.98% yield, ee: 99.4). MS m/z 532.5 (m+b). $^1$H NMR (400.13 MHz, DMSO-$d_6$): 12.08 (br, 1H), 7.57-7.49 (m, 3H), 7.26-7.16 (m, 6H), 4.64 (t, J=12.1 Hz, 1H), 3.15-3.09 (m, 2H), 3.07 (s, 3H), 3.02-2.97 (m, 2H), 2.35-2.26 (m, 1H), 2.11 (s, 2H), 2.04-1.88 (m, 1H), 1.79-1.68 (m, 4H), 1.64-1.40 (m, 3H), 1.29-1.19 (m, 2H), 1.13-1.02 (m, 1H).

Example Nos. 41a, 41b, 43a, 43b, 45a and 45b were Prepared According to the Procedure Above

| Example No. | Chemical Name | Structure | ES/MS (m/z) (M + H) | $^1$H NMR (400 MHz, DMSO-$d_6$) |
|---|---|---|---|---|
| 41a | Isomer 1,1-[(4-fluorophenyl)-methyl-carbamoyl]-4-[2-oxo-2-(N-tetrahydropyran-3-ylanilino)ethyl]piperidine-4-carboxylic acid | 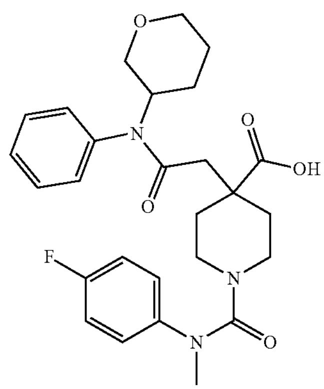 [SMILES: CN(C(=O)N1CCC(CC(=O)N(c2ccccc2)C2CCCOC2)(C(=O)O)CC1)c1ccc(F)cc1] | 498.4 | $^1$H NMR (400 MHz, DMSO-$d_6$): 12.15 (br, 1H), 7.51-7.41 (m, 3H), 7.20-7.07 (m, 6H), 4.45-4.33 (m, 1H), 3.82 (d, J = 9.4 Hz, 1H), 3.67 (d, J = 10.9 Hz, 1H), 3.10-3.03 (m, 2H), 3.00 (s, 3H), 2.97-2.88 (m, 4H), 2.04 (dd, J = 16.4 Hz, 2H), 1.75 (d, J = 12.0 Hz, 1H), 1.71-1.61 (m, 2H), 1.58-1.52 (m, 2H), 1.19-1.09 (m, 2H), 1.07-0.99 (m, 1H) |
| 41b | Isomer 2,1-[(4-fluorophenyl)-methyl-carbamoyl]-4-[2-oxo-2-(N-tetrahydropyran-3-ylanilino)ethyl]piperidine-4-carboxylic acid | 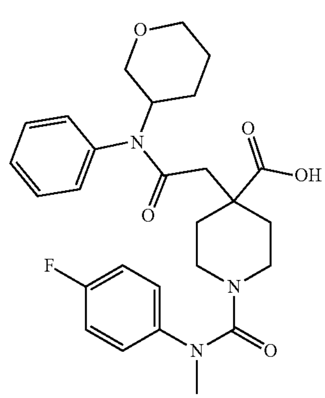 [SMILES: CN(C(=O)N1CCC(CC(=O)N(c2ccccc2)C2CCCOC2)(C(=O)O)CC1)c1ccc(F)cc1] | 498.4 | $^1$H NMR (400 MHz, DMSO-$d_6$): 12.15 (br, 1H), 7.52-7.41 (m, 3H), 7.19-7.07 (m, 6H), 4.39 (t, J = 11.3 Hz, 1H), 3.82 (d, J = 9.3 Hz, 1H), 3.67 (d, J = 10.9 Hz, 1H), 3.11-3.03 (m, 2H), 3.00 (s, 3H), 2.97-2.88 (m, 4H), 2.04 (dd, J = 16.4 Hz, 2H), 1.75 (d, J = 11.5 Hz, 1H), 1.70-1.62 (m, 2H), 1.59-1.51 (m, 2H), 1.20-1.09 (m, 2H), 1.08-0.97 (m, 1H) |

| Example No. | Chemical Name | Structure | ES/MS (m/z) (M + H) | $^1$H NMR (400 MHz, DMSO-$d_6$) |
|---|---|---|---|---|
| 43a | Isomer 1,4-[2-[N-(1-cyclopropylethyl)anilino]-2-oxo-ethyl]-1-[(4-fluorophenyl)-methyl-carbamoyl]piperidine-4-carboxylic acid | 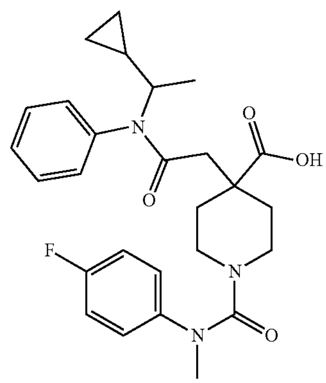 [SMILES: CC(C1CC1)N(C(=O)CC1(C(=O)O)CCN(C(=O)N(C)c2ccc(F)cc2)CC1)c1ccccc1] | 482.5 | $^1$H NMR (400 MHz, DMSO-$d_6$): 12.09 (br, 1H), 7.52-7.40 (m, 3H), 7.34-7.17 (m, 2H), 7.17-7.07 (m, 4H), 3.96-3.83 (m, 1H), 3.15-3.05 (m, 2H), 3.00 (s, 3H), 2.96-2.85 (m, 2H), 2.14-1.99 (m, 2H), 1.72-1.61 (m, 2H), 1.20-1.07 (m, 2H), 1.03 (d, J = 6.8 Hz, 3H), 0.49-0.41 (m, 3H), 0.27-0.22 (m, 2H) |
| 43b | Isomer 2,4-[2-[N-(1-cyclopropylethyl)anilino]-2-oxo-ethyl]-1-[(4-fluorophenyl)-methyl-carbamoyl]piperidine-4-carboxylic acid | 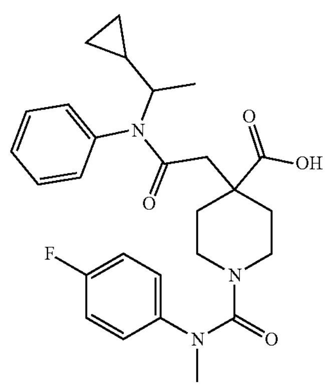 [SMILES: CC(C1CC1)N(C(=O)CC1(C(=O)O)CCN(C(=O)N(C)c2ccc(F)cc2)CC1)c1ccccc1] | 482.5 | $^1$H NMR (400 MHz, DMSO-$d_6$): 12.11 (br, 1H), 7.54-7.38 (m, 3H), 7.33-7.18 (m, 2H), 7.17-7.06 (m, 4H), 3.91 (dd, J = 7.1, 8.4 Hz, 1H), 3.15-3.05 (m, 2H), 3.00 (s, 3H), 2.98-2.85 (m, 2H), 2.12-2.00 (m, 2H), 1.72-1.61 (m, 2H), 1.19-1.07 (m, 2H), 1.03 (d, J = 6.9 Hz, 3H), 0.50-0.33 (m, 3H), 0.27-0.20 (m, 2H) |
| 45a | Isomer 1,1-[(4-cyclopropylphenyl)-methyl-carbamoyl]-4-[2-oxo-2-(N-tetrahydropyran-3-ylanilino)ethyl]piperidine-4-carboxylic acid | 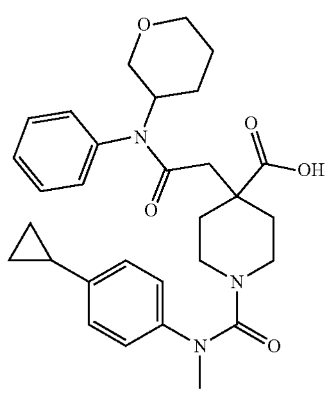 [SMILES: CN(C(=O)N1CCC(CC(=O)N(c2ccccc2)C2CCCOC2)(C(=O)O)CC1)c1ccc(C2CC2)cc1] | 520.3 | $^1$H NMR (400 MHz, DMSO-$d_6$): 12.13 (br, 1H), 7.52-7.40 (m, 3H), 7.21-7.09 (m, 2H), 7.00 (d, J = 8.4 Hz, 2H), 6.93-6.88 (m, 2H), 4.45-4.33 (m, 1H), 3.82 (dd, J = 2.1, 10.2 Hz, 1H), 3.67 (d, J = 10.8 Hz, 1H), 3.04 (d, J = 12.9 Hz, 2H), 2.98 (s, 3H), 2.95-2.87 (m, 4H), 2.04 (d, J = 5.1 Hz, 2H), 1.92-1.83 (m, 1H), 1.79-1.71 (m, 1H), 1.69-1.60 (m, 2H), 1.57-1.50 (m, 2H), 1.18-1.07 (m, 2H), 1.07-0.97 (m, 1H), 0.95-0.89 (m, 2H), 0.64-0.58 (m, 2H) |

-continued
| Example No. | Chemical Name | Structure | ES/MS (m/z) (M + H) | $^1$H NMR (400 MHz, DMSO-$d_6$) |
|---|---|---|---|---|
| 45b | Isomer 2,1-[(4-cyclopropylphenyl)-methyl-carbamoyl]-4-[2-oxo-2-(N-tetrahydropyran-3-ylanilino)ethyl]piperidine-4-carboxylic acid | 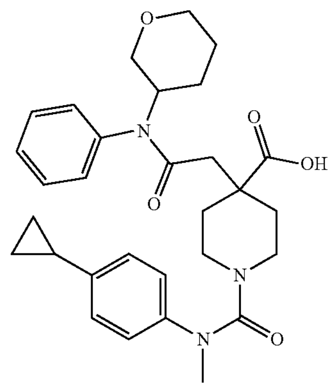 [SMILES: CN(C(=O)N1CCC(CC(=O)N(c2ccccc2)C2CCCOC2)(C(=O)O)CC1)c1ccc(C2CC2)cc1] | 520.3 | $^1$H NMR (400 MHz, DMSO-$d_6$): 12.13 (br, 1H), 7.53-7.40 (m, 3H), 7.22-7.08 (m, 2H), 7.00 (d, J = 8.5 Hz, 2H), 6.91 (d, J = 8.5 Hz, 2H), 4.44-4.34 (m, 1H), 3.82 (dd, J = 2.1, 10.2 Hz, 1H), 3.67 (d, J = 10.6 Hz, 1H), 3.09-3.01 (m, 2H), 3.00-2.96 (m, 3H), 2.96-2.87 (m, 4H), 2.09-1.98 (m, 2H), 1.91-1.83 (m, 1H), 1.79-1.72 (m, 1H), 1.64 (td, J = 3.2, 6.4 Hz, 2H), 1.54 (d, J = 8.5 Hz, 2H), 1.18-1.07 (m, 2H), 1.07-0.97 (m, 1H), 0.95-0.89 (m, 2H), 0.64-0.58 (m, 2H) |
Example No. 3 was Prepared According to Scheme 4
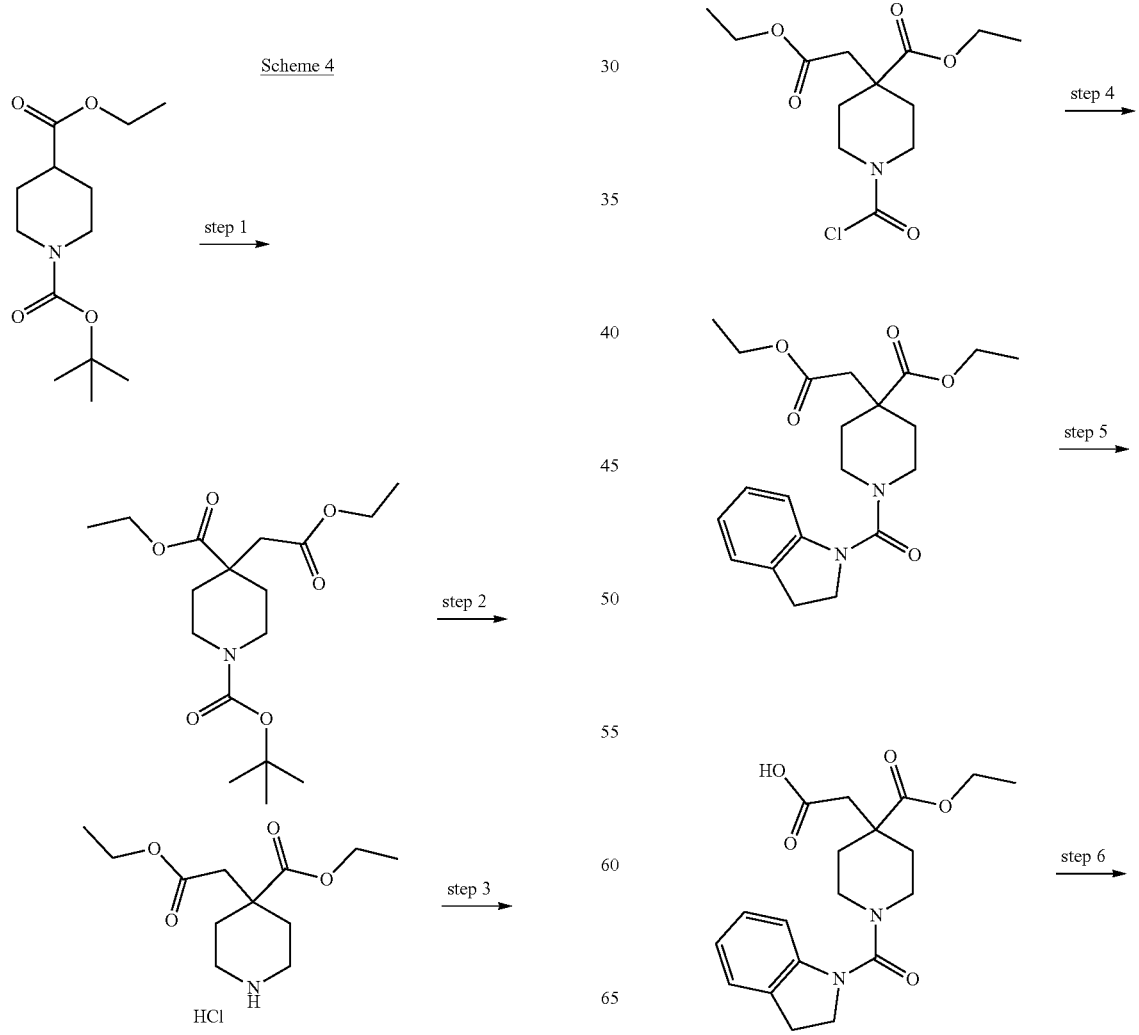

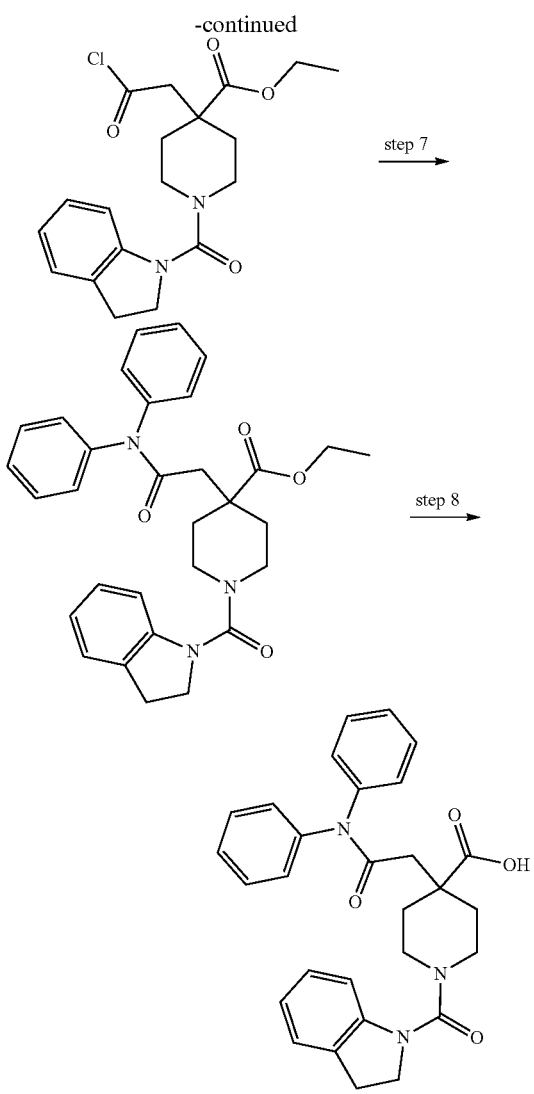

C. and stirred. After one hour, the reaction mixture was gradually warmed to 0° C. After one-hour, saturated ammonium chloride was added, and the mixture was concentrated under reduced pressure. The residue was extracted with ethyl acetate. The organic layers were combined, dried over MgSO$_4$, filtered, and concentrated under reduced pressure to give a residue. The residue was purified by silica gel flash chromatography, eluting with hexane:methyl tert butyl ether (60:40] to give the title compound (8.90 g. 57% yield). MS m/z 244.2 (M+H-BOC).

Step 2: ethyl 4-(2-ethoxy-2-oxo-ethyl)piperidine-4-carboxylate;hydrochloride

Hydrochloric acid (68 mL, 274 mmol, 4.0M in dioxane) was added to a solution of O1-tert-butyl O4-ethyl 4-(2-ethoxy-2-oxo-ethyl)piperidine-1,4-dicarboxylate (8.62 g, 25.1 mmol) and 1, 4-dioxane (40 mL) at 0° C. and stirred. The reaction mixture was gradually warmed to ambient temperature. After 30 minutes, the solvent was concentrated under reduced pressure to give the title compound (7.02 g, 99% yield). MS m/z 244.0 (M+H).

methyl 4-(2-methoxy-2-oxo-ethyl)piperidine-4-carboxylate, acetic acid

Step 1: O1-tert-butyl O4-ethyl 4-(2-ethoxy--2-oxo-ethyl)piperidine-1,4-dicarboxylate O1-tert-butyl O4-ethyl piperidine-1,4-dicarboxylate (11.0 g, 41.4 mmol) in tetrahydrofuran (60 mL) was dropwise added to a solution of LDA (41 mL, 82.0 mmol) in tetrahydrofuran (138 mL) at −78° C. under nitrogen. The addition was completed after 45 minutes and stirred below −70° C. After 65 minutes, ethyl 2-bromoacetate (8 mL, 72.1 mmol,) in tetrahydrofuran (60 mL) was added below −68°

To a solution of methyl 1-benzyl-4-(2-methoxy-2-oxo-ethyl)piperidine-4-carboxylate (2.0 g, 6.2 mmol, 95 mass %) in tetrahydrofuran (30.0 mL), acetic acid (0.72 mL, 13 mmol) was added in one portion, followed by Pd/C (1.55 g, 1.46 mmol, 10 mass %) at RT. The mixture was stirred at 60° C. under hydrogen (50 psi) for 16 h. The reaction mixture was cooled down to RT, filtered through a pad of celite and washed with methanol and dichloromethane (1:1, 100 mL×6). The filtrate was concentrated under reduced pressure to give the title compound (1.9 g).

Step 3 and 4: ethyl 4-(2-ethoxy-2-oxo-ethyl)-1-(indoline-1-carbonyl)piperidine-4-carboxylate

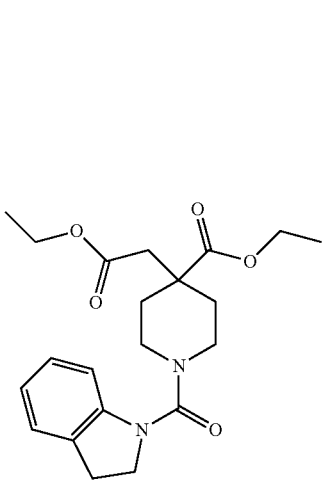 [SMILES: CCOC(=O)CC1(C(=O)OCC)CCN(C(=O)N2CCc3ccccc32)CC1]

Pyridine (17 mL) was added to ethyl 4-(2-ethoxy-2-oxo-ethyl)piperidine-4-carboxylate;hydrochloride (5.91 g, 21.1 mmol,) in dichloromethane (100 mL) at 0° C. and stirred. Triphosgene was added (3.84 g, 12.7 mmol) in a small portion while keeping the temperature 0° C. The reaction mixture was gradually warmed to 40° C. and stirred. After 1 hour, the reaction mixture was concentrated under reduced pressure. Brine was added to the mixture and was extracted with dichloromethane. The organic layers were combined and extracted with saturated sodium bicarbonate, brine, dried over MgSO$_4$, filtered, and concentrated under reduced pressure to give ethyl 1-chlorocarbonyl-4-(2-ethoxy-2-oxo-ethyl)piperidine-4-carboxylate (5.75 g, 18.8 mmol).

Ethyl 1-chlorocarbonyl-4-(2-ethoxy-2-oxo-ethyl)piperidine-4-carboxylate (5.75 g, 18.8 mmol) in acetonitrile (62 mL) was added at 0° C. to indoline (3.16 mL, 28.2 mmol) in acetonitrile (50 mL) at 0° C. Potassium carbonate (17.5 g, 126.8 mmol) was added and stirred at 76° C. After 18 hours, the solvent was concentrated under reduced pressure and the mixture was extracted with DCM. The organic layers were combined, extracted with brine, dried over MgSO$_4$, filtered, and concentrated under reduced pressure to give a residue. The residue was purified by silica gel flash chromatography, eluting with 1-80% of EtOAc/hexane to give the title compound (3.75 g, 51% yield). MS m/z 389.0 (M+H).

Step 5: 2-[4-ethoxycarbonyl-1-(indoline-1-carbonyl)-4-piperidyl]acetic acid

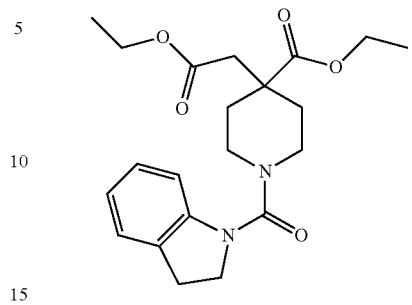

Potassium carbonate (1.97 g, 14.3 mmol) was added to ethyl 4-(2-ethoxy-2-oxo-ethyl)-1-(indoline-1-carbonyl)piperidine-4-carboxylate (3.25 g, 8.37 mmol) in methanol (35 mL), water (3 mL) and stirred at 50° C. After 18 hours, the reaction was cooled, 5 N aqueous HCl was added until pH 3.0 and the mixture was extracted with DCM. The organic layers were combined; dried over MgSO$_4$; filtered and concentrated under reduced pressure to give a residue. The residue was purified by silica gel flash chromatography, eluting with dichloromethane to 60% of (MeOH: DCM (10:90)) to give the title compound (2.71 g, 78% yield). MS m/z 361.0 (M+H).

| Chemical Name | Structure | ES/MS (m/z) (M + H) | $^1$H NMR (400 MHz, DMSO-d$_6$) |
|---|---|---|---|
| 2-[1-[(4-fluorophenyl)-methyl-carbamoyl]-4-methoxycarbonyl-4-piperidyl]acetic acid | 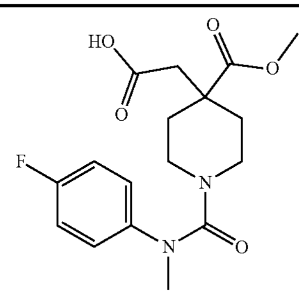 | | $^1$H NMR (400.21 MHz, DMSO-d$_6$): 12.28 (br, 1H), 7.30-7.08 (m, 4H), 3.57 (s, 3H), 3.32-3.23 (m, 4H), 3.04 (s, 3H), 3.01-2.90 (m, 2H), 1.86-1.70 (m, 2H), 1.46-1.32 (m, 2H). |

Step 6 and 7: ethyl 1-(indoline-1-carbonyl)-4-[2-oxo-2-(N-phenylanilino)ethyl]piperidine-4-carboxylate

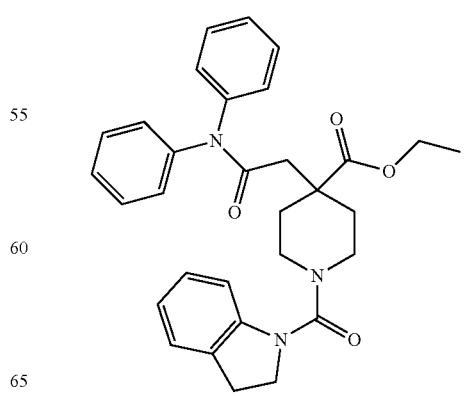

Thionyl chloride (17.90 mL, 35.8 mmol, 2.00 M in dichloromethane) was added to a solution of 2-[4-ethoxy-carbonyl-1-(indoline-1-carbonyl)-4-piperidyl]acetic acid (2.58 g, 7.12 mmol) in dichloromethane (172 m), tetrahydrofuran (42 mL) and stirred at ambient temperature. After 15 minutes, concentrated under reduced pressure to give ethyl 4-(2-chloro-2-oxo-ethyl)-1-(indoline-1-carbonyl)piperidine-4-carboxylate (2.71 g, 99% yield)

N-phenylaniline (17.0 mL, 7.00 mmol, 4.0M in dichloromethane) in pyridine (0.20 mL, 2.47 mmol) was added to a solution of ethyl 4-(2-chloro-2-oxo-ethyl)-1-(indoline-1-carbonyl)piperidine-4-carboxylate (2.71 g, 7.16 mmol) in dichloromethane (170 mL) and stirred at ambient temperature. After 3 hours, the reaction mixture was extracted with dichloromethane. The organic layers were combined and extracted with brine, dried over MgSO$_4$, filtered, and concentrated under reduced pressure to give a residue. The residue was purified by silica gel flash chromatography, eluting with EtOAc: hexane (50:50) to give the title compound (2.46 g, 67% yield). MS m/z 512.2 (M+H).

Step 8: 1-(indoline-1-carbonyl)-4-[2-oxo-2-(N-phenylanilino)ethyl]piperidine-4-carboxylic acid (Example No. 3)

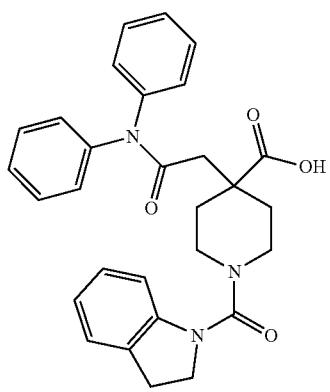 [SMILES: O=C(N1CCC(CC(=O)N(c2ccccc2)c2ccccc2)(C(=O)O)CC1)N1CCc2ccccc21]

5 N aqueous sodium hydroxide (4.8 mL, 24.1 mmol) was added to a solution of ethyl 1-(indoline-1-carbonyl)-4-[2-oxo-2-(N-phenylanilino)ethyl]piperidine-4-carboxylate (2.46 g, 4.81 mmol) in ethanol (30 mL) at ambient temperature and stirred at 50° C. After 18 hours, the reaction mixture was concentrated under reduced pressure to give a residue. 5 N aqueous HCl was added, and the mixture was extracted with DCM. The organic layers were combined, dried over MgSO$_4$, filtered, and concentrated under reduced pressure to give a residue. The residue was purified by silica gel flash chromatography, eluting with DCM: [MeOH:DCM (10:90)] to give the title compound (1.97 g, 84% yield). MS m/z 484.4 (M+H); $^1$H NMR (DMSO-d$_6$) δ 12.38 (s, 1H), 7.40-7.29 (m, 11H), 7.11 (t, J=7.7 Hz, 1H), 6.94 (d, J=8.0 Hz, 1H), 6.86 (t, J=7.4 Hz, 1H), 3.79 (t, J=8.2 Hz, 2H), 3.35-3.18 (m, 4H), 2.97 (t, J=8.2 Hz, 2H), 2.56 (s, 2H), 2.00-1.96 (m, 2H), 1.59-1.52 (m, 2H).

Example No. 48, 49, 50, 51, 62, 63, 64, 65, 66, 67, 68, 68A, 68B, 69, 70, 71, 72, 72A, 72B, 73, 74, 74A, 74B, 75, 75A, 75B, 79, 88, 89, 90, 91, 92, and 93 were Prepared According to Scheme 5

Scheme 5

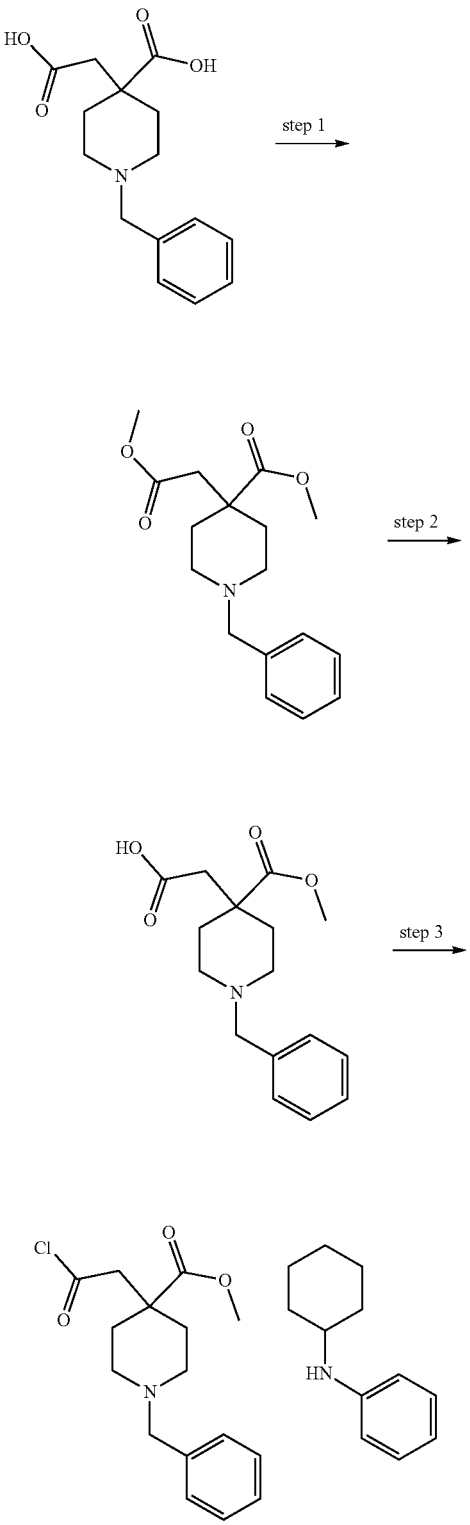

231
-continued

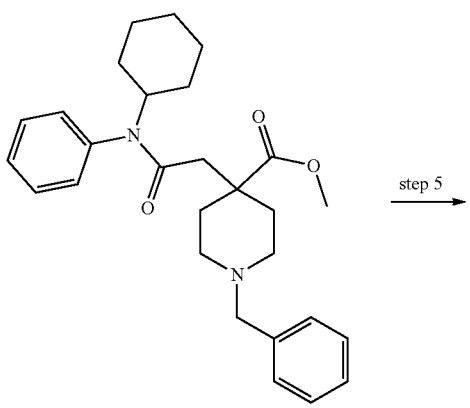

step 5 →

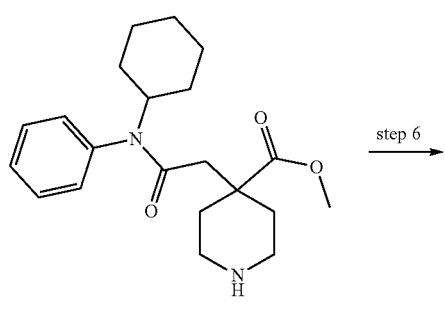

step 6 →

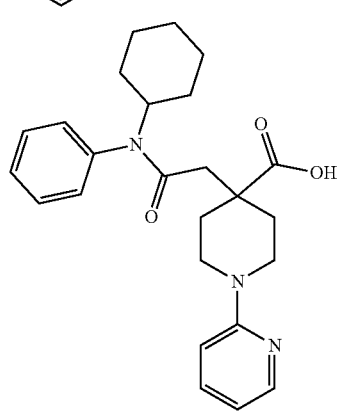

step 7 →

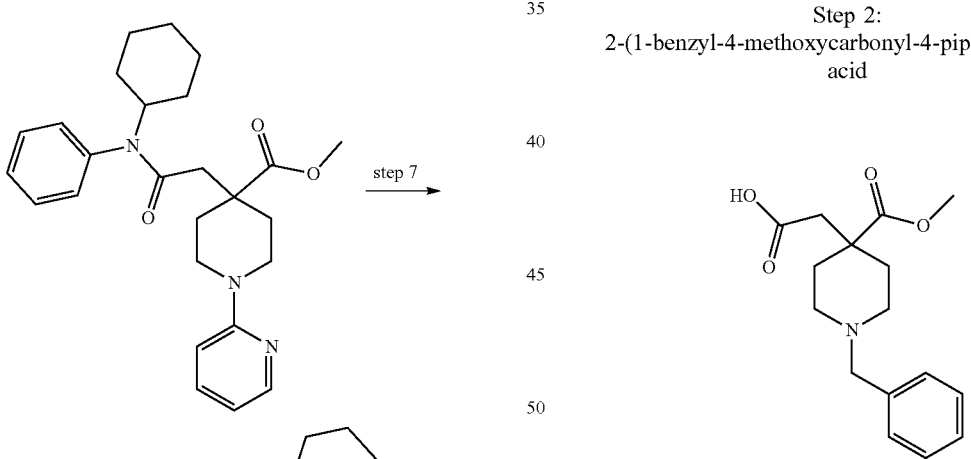

232

Step 1: methyl 1-benzyl-4-(2-methoxy-2-oxo-ethyl)piperidine-4-carboxylate

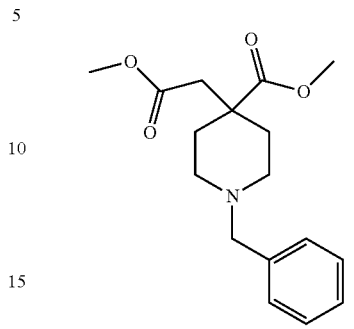

Thionyl chloride (2.0 M solution in DCM) (24.00 mL, 329.4 mmol) was added drop wise to a solution of 1-benzyl-4-(carboxymethyl)piperidine-4-carboxylic acid (10.00 g, 36.06 mmol) in methanol (400 mL) and stirred at 60° C. After 18 hours, the reaction mixture was concentrated under reduced pressure. The residue was diluted with dichloromethane and washed with saturated sodium bicarbonate. The organic layers were combined, dried over MgSO$_4$, filtered, and evaporated. The residue was dissolved in DCM and loaded onto silica gel and purified on a 120 g silica column using 10%-10% methanol in dichloromethane. Fractions were combined and evaporated. The residue was then dried under vacuum to give the title compound (9.46 g, 85.9% yield). MS m/z 306.0 (M+H).

Step 2: 2-(1-benzyl-4-methoxycarbonyl-4-piperidyl)acetic acid

Potassium carbonate (8.50 g, 61.5 mmol) was added to methyl 1-benzyl-4-(2-methoxy-2-oxo-ethyl)piperidine-4-carboxylate (11.06 g, 36.21 mmol) in methanol (120 mL), water (5.50 mL) and stirred at 60° C. After 18 hours, the reaction was cooled, and concentrated under reduced pressure. The residue was diluted with ice cold water and washed with methyl tert butyl ether and organic layer was discarded. The aqueous layer was cooled at 0° C. and acidified with 1.0M HCl until pH ~7.0 while temperature was kept below 10° C. white precipitate were formed and stirred at room temperature for one hour, filtered, collected precipitate, dried to give the title compound (8.48 g, 80.4% yield). MS m/z 292.1 (M+H).

233

Step 3 and Step 4: methyl 1-benzyl-4-[2-(N-cyclohexylanilino)-2-oxo-ethyl]piperidine-4-carboxylate

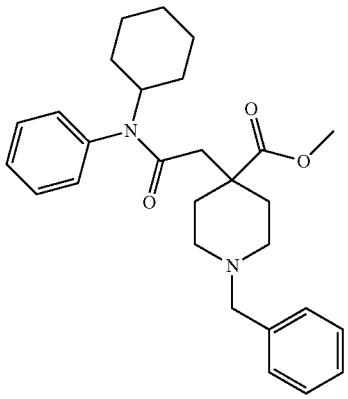 [SMILES: COC(=O)C1(CC(=O)N(c2ccccc2)C2CCCCC2)CCN(Cc2ccccc2)CC1]

Thionyl chloride (29.0 mL, 398.7 mmol) was added was added to a solution 2-(1-benzyl-4-methoxycarbonyl-4-piperidyl)acetic acid (8.46 g, 29.0 mmol) in chloroform (100 mL) and tetrahydrofuran (100 mL) and stirred at ambient temperature. After 15 minutes, concentrated under reduced pressure to give methyl 1-benzyl-4-(2-chloro-2-oxo-ethyl)piperidine-4-carboxylate (9.0 g, 99% yield).

N-cyclohexylaniline (4.50 mL, 26.09, mmol) in DCM (100.0 mL) and pyridine (10.00 mL, 124.0 mmol) was added to a solution of methyl 1-benzyl-4-(2-chloro-2-oxo-ethyl)piperidine-4-carboxylate (7.40 g, 23.90 mmol in DCM (100 mL), toluene (50 mL) and 4-dimethylaminopyridine (0.150 g, 1.21 mmol) and stirred at 70° C. After 18 hours, the reaction mixture was quenched with brine and was extracted with DCM. The organic layers were combined, dried over MgSO$_4$, filtered, and concentrated under reduced pressure to give a residue. The residue was purified by silica gel flash chromatography, eluting with EtOAc: hexane (90:10) to give the title compound (8.00 g, 74.7% yield). MS m/z 449.4 (M+H).

Methyl 1-benzyl-4-[2-(N-[(racemic)-3,3-difluorocyclohexyl]anilino)-2-oxo-ethyl]piperidine-4-carboxylate

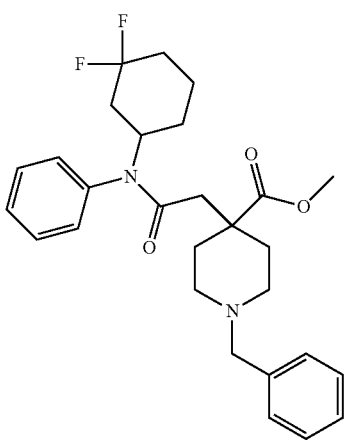 [SMILES: COC(=O)C1(CC(=O)N(c2ccccc2)C2CCCC(F)(F)C2)CCN(Cc2ccccc2)CC1]

234

Under N$_2$, to a solution of 2-(1-benzyl-4-methoxycarbonyl-4-piperidyl)acetic acid (7.5 g, 24 mmol, 95 mass %) and N-[(racemic)-3,3-difluorocyclohexyl]aniline (6.5 g, 28 mmol, 90 mass %) in pyridine (70.0 mL) was added phosphoryl chloride (4.6 mL, 49 mmol, 99 mass %) dropwise at RT, after addition the mixture was heated to 100° C. and stirred for 5 h, then cooled to RT and concentrated under reduced pressure. The residue was diluted with water (400 mL) cautiously and extracted with ethyl acetate (400 mL×3). The combined organic layers were washed with brine (200 mL), dried over Na$_2$SO$_4$ and concentrated in vacuo to give crude product, which was purified by flash silica gel chromatography, eluting with 0~8% MeOH/DCM to give title product (8.1 g, 90 mass %, 62% Yield). MS m/z 485.2 (M+H).

The compounds in the table below were prepared similar to the procedures described above.

| Chemical Name | Structure | ES/MS (m/z) (M + H) |
|---|---|---|
| Isomer 2, methyl 1-benzyl-4-[2-(N-(3,3-difluorocyclohexyl)-2-fluoro-anilino)-2-oxo-ethyl]piperidine-4-carboxylate | 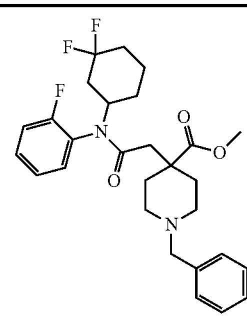 | 503.1 |
| methyl 1-benzyl-4-[2-oxo-2-(N-phenylanilino)ethyl]piperidine-4-carboxylate | 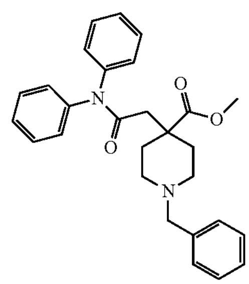 [SMILES: COC(=O)C1(CC(=O)N(c2ccccc2)c2ccccc2)CCN(Cc2ccccc2)CC1] | 433.0 |

Step 5: methyl 4-[2-(N-cyclohexylanilino)-2-oxo-ethyl]piperidine-4-carboxylate

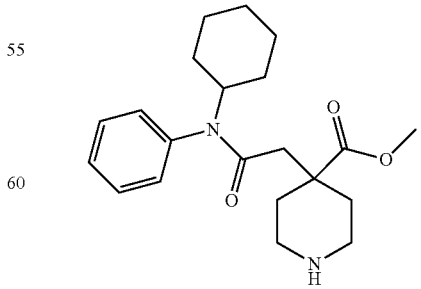

10% Pd/C (3.201 g, 29.74, mmol) in methanol (50.0 mL) was added to a solution of methyl 1-benzyl-4-[2-(N-cyclohexylanilino)-2-oxo-ethyl]piperidine-4-carboxylate (7.98 g, 17.80 mmol in methanol (325 mL), sealed, purged with nitrogen, hydrogen, pressurized with hydrogen and shaked on the shaker at 50° C., 10 PSI. After 10 hours, the reaction mixture was filtered through celite pad, and concentrated under reduced pressure to give the title compound (5.53 g, 86.700 yield). MS m/z 359.0 (M+H).

The compounds in the table below were prepared according to the procedures above.

| Chemical Name | Structure | ES/MS (m/z) (M + H) |
|---|---|---|
| Racemic, methyl 4-[2-(N-[3,3-difluorocyclohexyl]anilino)-2-oxo-ethyl]piperidine-4-carboxylate | 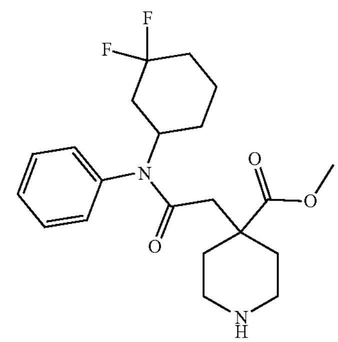 [SMILES: COC(=O)C1(CC(=O)N(c2ccccc2)C2CCCC(F)(F)C2)CCNCC1] | 395.0 |
| Isomer 2, methyl 4-[2-(N-(3,3-difluorocyclohexyl)-2-fluoro-anilino)-2-oxo-ethyl]piperidine-4-carboxylate | 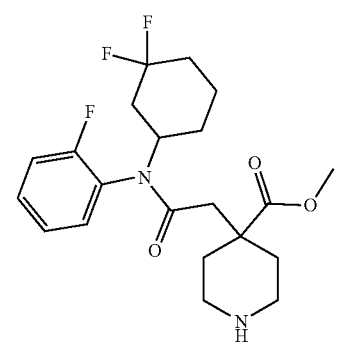 [SMILES: COC(=O)C1(CC(=O)N(c2ccccc2F)C2CCCC(F)(F)C2)CCNCC1] | 413.0 |
| methyl 4-[2-oxo-2-(N-phenylanilino)ethyl]piperidine-4-carboxylate | 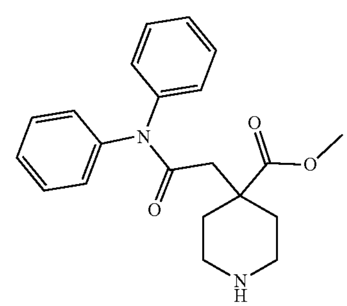 [SMILES: COC(=O)C1(CC(=O)N(c2ccccc2)c2ccccc2)CCNCC1] | 353.0 |

Step 6 methyl 4-[2-(N-[(racemic)-3,3-difluorocyclo-hexyl]anilino)-2-oxo-ethyl]-1-(2-pyridyl)piperidine-4-carboxylate

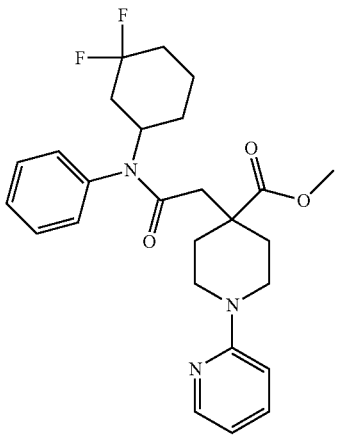 [SMILES: COC(=O)C1(CC(=O)N(c2ccccc2)C2CCCC(F)(F)C2)CCN(c2ccccn2)CC1]

Under N₂, to a mixture of methyl 4-[2-(N-[(racemic)-3,3-difluorocyclohexyl]anilino)-2-oxo-ethyl]piperidine-4-carboxylate (3.0 g, 6.5 mmol, 85 mass %) and 2-bromopyridine (3.2 g, 19 mmol, 95 mass %) in toluene (30.0 mL), tris(dibenzylideneacetone)dipalladium(0) (310 mg, 0.3 mmol, 95 mass %), RuPhos (640 mg, 1.3 mmol, 95 mass %) and sodium tert-butoxide (1.3 g, 13 mmol, 97 mass %) were added. The mixture was stirred at 100° C. for 4 hours. The reaction was cooled to RT and the solvent was removed under vacuum, the residue was dissolved in DCM (50 mL) and washed with water (20 mL), the organic layer was dried over Na₂SO₄, filtered and concentrated under vacuum. The residue was purified by flash silica gel chromatography, eluting 0% to 40% EtOAc/petroleum ether to give the title product (1.38 g, 2.63 mmol, 90 mass %, 41% yield). MS m/z 472.3 (M+H).

Methyl 4-[2-(N-(3,3-difluorocyclohexyl)-2-fluoro-anilino)-2-oxo-ethyl]-1-(2-pyridyl)piperidine-4-carboxylate was prepared according to the procedures above

| Chemical Name | Structure | ES/MS (m/z) (M + H) |
|---|---|---|
| Isomer 2, methyl 4-[2-(N-(3,3-difluoro-cyclohexyl)-2-fluoro-anilino)-2-oxo-ethyl]-1-(2-pyridyl)piperidine-4-carboxylate | 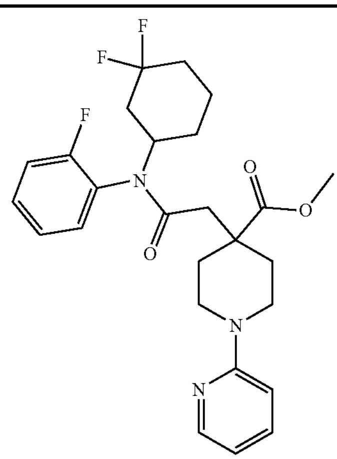 | 490.4 |

Racemic, methyl 4-[2-(N-[(racemic)-3,3-difluorocyclohexyl]anilino)-2-oxo-ethyl]-1-[(4-isopropylphenyl)methyl]piperidine-4-carboxylate

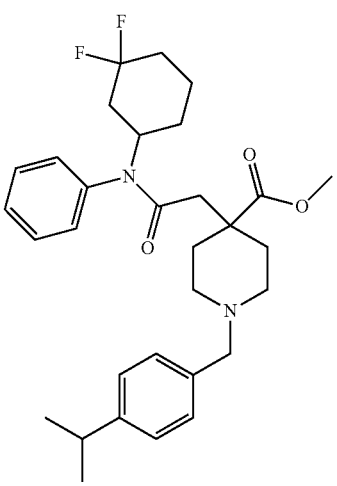 [SMILES: COC(=O)C1(CC(=O)N(c2ccccc2)C2CCCC(F)(F)C2)CCN(Cc2ccc(C(C)C)cc2)CC1]

To a mixture of racemic, methyl 4-[2-(N-[3,3-difluorocyclohexyl]anilino)-2-oxo-ethyl]piperidine-4-carboxylate (200 mg, 0.46 mmol, 90 mass %) and 4-isopropylbenzaldehyde (140 mg, 0.93 mmol) in 1,2-dichloroethane (5.0 mL) was added titanium(IV) isopropoxide (0.46 mL, 1.3 mmol, 85 mass %). After the mixture was stirred at 80° C. for 1 hour, sodium triacetoxyborohydride (300 mg, 1.373 mmol) was added, the mixture was stirred at room temperature for 1 hour. The mixture was quenched with water (5 mL) and concentrated. The residue was dissolved into MeOH (5.0 mL) and filtered off solid. The filtrate was concentrated and purified by prep-HPLC (Phenomenex C18 100*30 mm*10 um, mobile phase A: water-formic acid, mobile phase B: acetonitrile, eluting with 22-52% B, then to 100% B). The appropriate fractions were combined and lyophilized to give title product as formic acid salt, 60 mg, 95 mass %, 23.7% yield). ¹H NMR (400 MHz, DMSO-d₆): 8.15 (s, 2H), 7.60-7.42 (m, 3H), 7.34-7.06 (m, 6H), 4.58 (t, J=12.5 Hz, 1H), 3.58 (s, 3H), 2.84 (td, J=6.9, 13.8 Hz, 1H), 2.35-2.15 (m, 6H), 1.87 (br d, J=4.5 Hz, 3H), 1.73 (d, J=10.0 Hz, 2H), 1.65-1.26 (m, 6H), 1.17 (d, J=6.9 Hz, 6H), 1.09-0.92 (m, 1H).

Intermediates in the table below were prepared according to the procedure above.

| Chemical Name | Structure | ES/MS (m/z) (M + H) | $^1$H NMR (400 MHz, DMSO-d$_6$) |
|---|---|---|---|
| Racemic, methyl 1-[(4-cyclopropylphenyl)methyl]-4-[2-(N-[3,3-difluorocyclohexyl]anilino)-2-oxo-ethyl]piperidine-4-carboxylate | 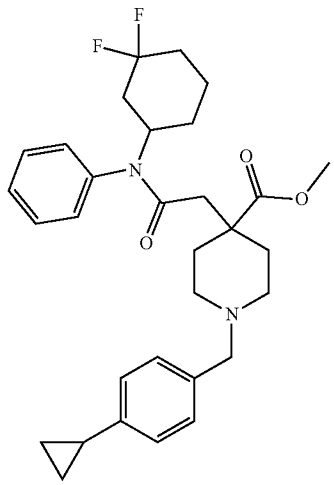 [SMILES: COC(=O)C1(CC(=O)N(c2ccccc2)C2CCCC(F)(F)C2)CCN(Cc2ccc(C3CC3)cc2)CC1] | / | $^1$H NMR (400 MHz, DMSO-d$_6$): 7.57-7.39 (m, 3H), 7.23 7.21 (m, 2H), 7.07 (d, J = 8.0 Hz, 2H), 6.97 (d, J = 8.0 Hz, 2H), 4.57 (t, J = 12.2 Hz, 1H), 3.57 (s, 3H), 3.26 (s, 2H), 2.29-2.08 (m, 6H), 1.96-1.78 (m, 4H), 1.73 (d, J = 10.3 Hz, 2H), 1.64-1.23 (m, 6H), 1.08-0.98 (m, 1H), 0.97-0.86 (m, 2H), 0.66-0.56 (m, 2H). $^{19}$F NMR (377 MHz, DMSO-d$_6$) δ = −85.24 (d, J = 235.8 Hz, 1F), −97.96 (d, J = 237.6 Hz, 1F). |
| Racemic, methyl 4-[2-(N-[3,3-difluorocyclohexyl]anilino)-2-oxo-ethyl]-1-[(2-fluoro-4-isopropyl-phenyl)methyl]piperidine-4-carboxylate | 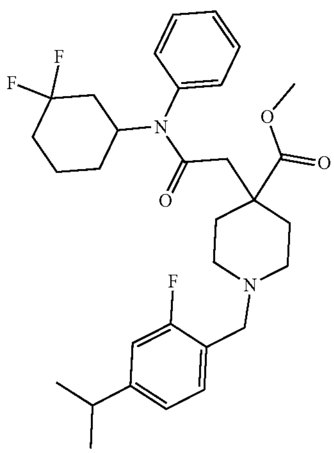 [SMILES: COC(=O)C1(CC(=O)N(c2ccccc2)C2CCCC(F)(F)C2)CCN(Cc2ccc(C(C)C)cc2F)CC1] | 545.4 | |
| Racemic, methyl 1-[2-(4-cyclopropylphenyl)propyl]-4-[2-(N-[3,3-difluorocyclohexyl]anilino)-2-oxo-ethyl]piperidine-4-carboxylate | 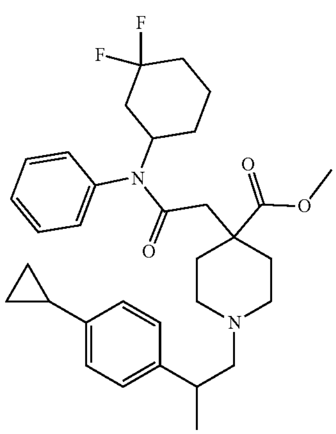 [SMILES: COC(=O)C1(CC(=O)N(c2ccccc2)C2CCCC(F)(F)C2)CCN(CC(C)c2ccc(C3CC3)cc2)CC1] | 553.5 | |

Racemic, methyl 4-[2-(N-[3,3-difluorocyclohexyl]anilino)-2-oxo-ethyl]-1-[2-(4-fluorophenyl)propanoyl]piperidine-4-carboxylate

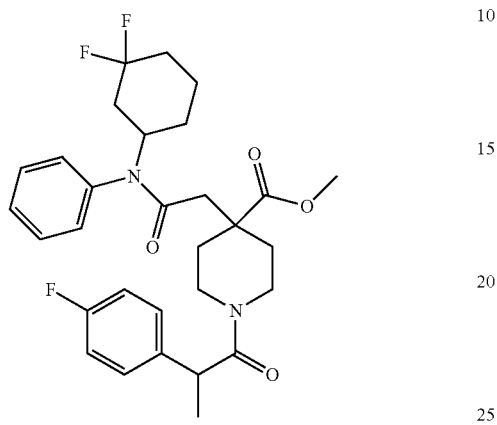

To a solution of racemic, methyl 4-[2-(N-[3,3-difluorocyclohexyl]anilino)-2-oxo-ethyl]piperidine-4-carboxylate (201 mg, 0.48 mmol, 94 mass) and racemic, 2-(4-fluorophenyl)propanoic acid (97 mg, 0.57 mmol) in DCM (3.0 mL) was added N,N-Diisopropyl ethyl amine (0.165 mL, 0.94 mmol) and HATU (270 mg, 0.69 mmol), then the mixture was stirred at room temperature overnight. The mixture was quenched by water (10 mL) and extracted with DCM (5 mL×3). The combined organic layers were washed with brine (5 mL), dried over $Na_2SO_4$ and concentrated in vacuo. The residue was purified by flash silica gel chromatography, eluting with 0~7% MeOH/DCM) to give the title compound (305 mg, 68 mass %, 79.5% yield) as a brown oil. MS m/z 545.3. (M+H).

| Chemical Name | Structure | ES/MS (m/z) (M + H) | $^1$H NMR (400 MHz, DMSO-$d_6$) |
|---|---|---|---|
| Racemic methyl 4-[2-(N-[3,3-difluorocyclohexyl]anilino)-2-oxo-ethyl]-1-[2-(3-fluorophenyl)propanoyl]piperidine-4-carboxylate | 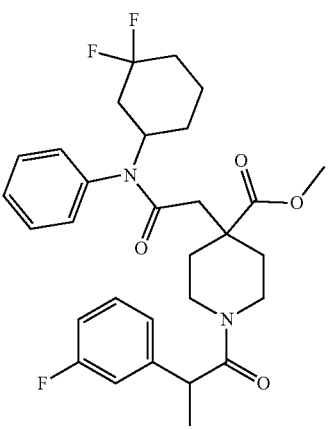 [SMILES: COC(=O)C1(CC(=O)N(c2ccccc2)C2CCCC(F)(F)C2)CCN(C(=O)C(C)c2cccc(F)c2)CC1] | 545.2 | |

| Chemical Name | Structure | ES/MS (m/z) (M + H) | ¹H NMR (400 MHz, DMSO-d₆) |
|---|---|---|---|
| Racemic, methyl 4-[2-(N-[3,3-difluorocyclohexyl]anilino)-2-oxo-ethyl]-1-[2-(2-fluorophenyl)acetyl]piperidine-4-carboxylate | 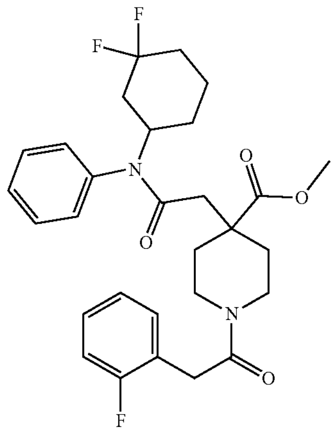 [SMILES: COC(=O)C1(CC(=O)N(c2ccccc2)C2CCCC(F)(F)C2)CCN(C(=O)Cc2ccccc2F)CC1] | 531.2 | |
| Racemic, methyl 4-[2-(N-[-3,3-difluorocyclohexyl]anilino)-2-oxo-ethyl]-1-[1-(2-fluorophenyl)cyclopropanecarbonyl]piperidine-4-carboxylate | | | ¹H NMR (400 MHz, CDCl₃): 7.49-7.42 (m, 3H), 7.24-7.18 (m, 2H), 7.11-7.06 (m, 1H), 7.06-6.93 (m, 3H), 4.75 (t, J = 12.6 Hz, 1H), 3.91-3.63 (m, 5H), 3.49 (s, 2H), 3.28-3.02 (m, 2H), 2.26-2.07 (m, 3H), 2.05-2.03 (m, 1H), 1.91-1.86 (m, 3H), 1.79-1.70 (m, 1H), 1.57-1.44 (m, 2H), 1.41 (d, J = 1.9 Hz, 2H), 1.23-1.06 (m, 4H). |
| Racemic, methyl 4-[2-(N-[3,3-difluorocyclohexyl]anilino)-2-oxo-ethyl]-1-(2-fluoro-4-isopropyl-benzoyl)piperidine-4-carboxylate | 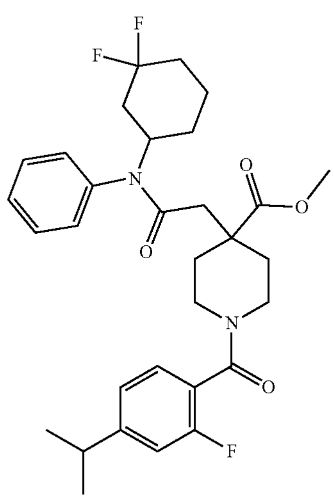 [SMILES: COC(=O)C1(CC(=O)N(c2ccccc2)C2CCCC(F)(F)C2)CCN(C(=O)c2ccc(C(C)C)cc2F)CC1] | | ¹H NMR (400 MHz, CDCl₃): 7.48-7.46 (m, 3H), 7.22 (t, J = 7.2 Hz, 1H), 7.08-7.03 (m, 3H), 6.92 (d, J = 10.8 Hz, 1H), 4.80-4.78 (m, 1H), 4.18-4.14 (m, 1H), 3.78 (s, 3H), 3.37-3.27 (m, 3H), 2.96-2.89 (m, 1H), 2.36-1.74 (m, 8H), 1.57-1.37 (m, 5H), 1.24 (d, J = 6.8 Hz, 6H), 1.20-1.18 (m, 1H). |

Racemic, methyl 4-[2-(N-[3,3-difluorocyclohexyl]anilino)-2-oxo-ethyl]-1-[2-(2-fluorophenyl)propanoyl]piperidine-4-carboxylate

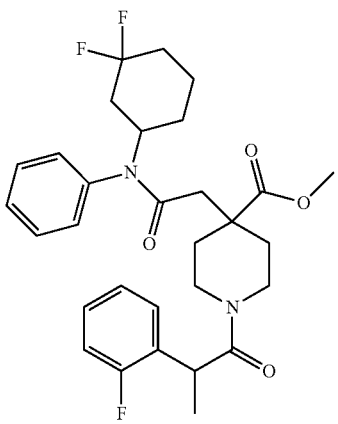 [SMILES: COC(=O)C1(CC(=O)N(c2ccccc2)C2CCCC(F)(F)C2)CCN(C(=O)C(C)c2ccccc2F)CC1]

To a solution of (racemic)-2-(2-fluorophenyl)propanoic acid (200 mg, 1.07 mmol, 90 mass %) in DCM (3.0 mL) was added oxalyl chloride (0.190 mL, 2.15 mmol) followed by a drop of DMF at 0° C. The reaction mixture was stirred at RT for 2 h. Upon completion, the reaction mixture was concentrated in vacuum to give the (racemic)-2-(2-fluorophenyl)propanoyl chloride (230 mg, 85 mass %).

Then to a solution of racemic methyl 4-[2-(N-[3,3-difluorocyclohexyl]anilino)-2-oxo-ethyl]piperidine-4-carboxylate (200 mg, 0.47 mmol, 93 mass %) and triethylamine (0.17 mL, 1.2 mmol) in DCM (4.0 mL) was added the prepared acid chloride (207 mg, 0.943 mmol, 85 mass %). The mixture was stirred at 40° C. overnight. The reaction mixture was cooled down to RT and concentrated. The residue was purified by normal silica gel chromatography, eluting with 50–58% EtOAc:petroleum ether) to give the title compound (140 mg, 90 mass %, 49.07% yield). MS m/z 545.2 (M+H).

| Chemical Name | Structure | ES/MS (m/z) (M + H) | $^1$H NMR (400 MHz, DMSO-$d_6$) |
|---|---|---|---|
| Racemic, methyl 4-[2-(N-[(racemic)-3,3-difluorocyclohexyl]anilino)-2-oxo-ethyl]-1-[2-(2-fluorophenyl)-2-methyl-propanoyl]piperidine-4-carboxylate | 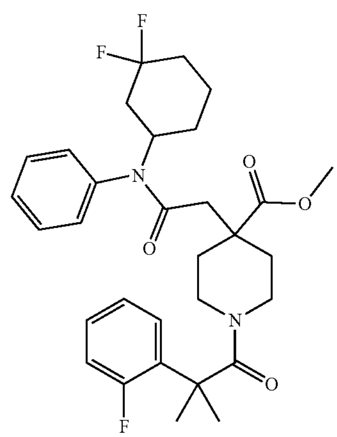 [SMILES: COC(=O)C1(CC(=O)N(c2ccccc2)C2CCCC(F)(F)C2)CCN(C(=O)C(C)(C)c2ccccc2F)CC1] | | $^1$H NMR (400.14 MHz, DMSO-$d_6$): 7.55-7.44 (m, 3H), 7.40 (t, J = 7.8 Hz, 1H), 7.36-7.29 (m, 1H), 7.27-7.13 (m, 3H), 7.08 (dd, J = 8.4, 11.6 Hz, 1H), 4.53 (t, J = 12.3 Hz, 1H), 3.55 (s, 3H), 3.50-3.40 (m, 1H), 3.07-3.04 (m, 1H), 3.01-2.80 (m, 2H), 2.25-21.71 (m, 5H), 1.62-1.41 (m, 4H), 1.39 (s, 6H), 1.30 (s, 3H), 1.07-0.93 (m, 1H), 0.88-0.68 (m, 1H). $^{19}$F NMR (377 MHz, DMSO-$d_6$): −85.27 (d, J = 235.8 Hz, 1F), −97.98 (d, J = 235.8 Hz, 1F), −114.63 (s, 1F). |
| Racemic, methyl 4-[2-(N-[3,3-difluorocyclohexyl]anilino)-2-oxo-ethyl]-1-(4-isopropylbenzoyl)piperidine-4-carboxylate | 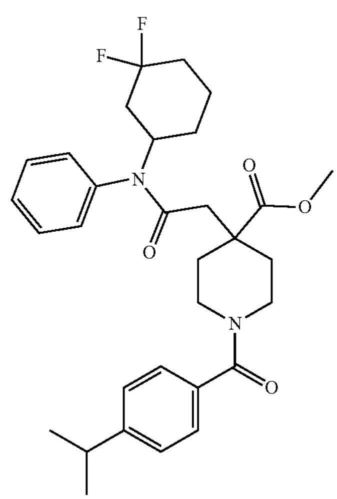 [SMILES: COC(=O)C1(CC(=O)N(c2ccccc2)C2CCCC(F)(F)C2)CCN(C(=O)c2ccc(C(C)C)cc2)CC1] | 541.3 | |

| Chemical Name | Structure | ES/MS (m/z) (M + H) | 1H NMR (400 MHz, DMSO-d6) |
|---|---|---|---|
| Racemic, methyl 1-(4-cyclopropylbenzoyl)-4-[2-(N-(3,3-difluorocyclohexyl)anilino)-2-oxo-ethyl]piperidine-4-carboxylate | 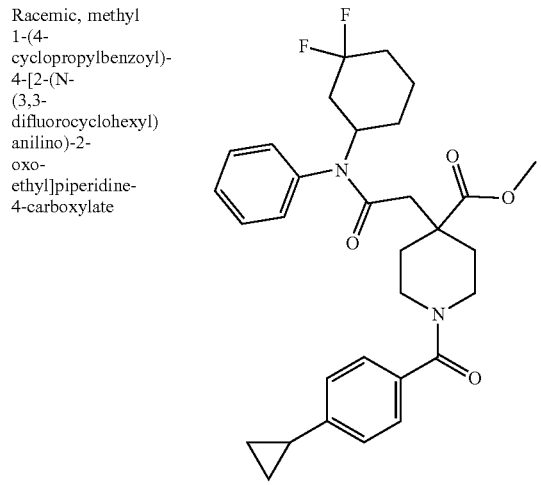 | 539.4 | |

Racemic, methyl 4-[2-(N-[3,3-difluorocyclohexyl]anilino)-2-oxo-ethyl]-1-(4-fluoroindoline-1-carbonyl)piperidine-4-carboxylate

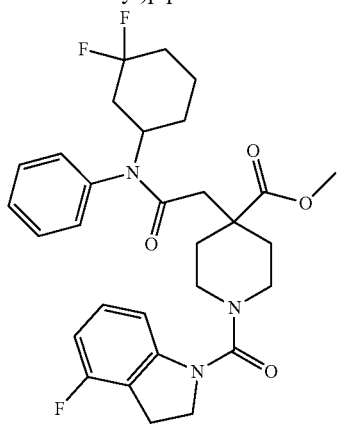

To a solution of racemic, methyl 4-[2-(N-[3,3-difluorocyclohexyl]anilino)-2-oxo-ethyl]piperidine-4-carboxylate (220 mg, 0.45 mmol, 80 mass %) and N,N-diisopropylethylamine (0.16 mL, 0.92 mmol) in DCM (4.0 mL) was added 4-fluoroindoline-1-carbonyl chloride (130 mg, 0.55 mmol, 85 mass %) at RT. The mixture was stirred at RT for 2 h to give a colorless solution. Upon completion, the reaction was added water (10 mL) and extracted with EtOAc (10 mL×2). The combined organic layers were washed with brine (20 mL×2), dried over Na$_2$SO$_4$, and concentrated under reduce pressure. The residue was purified by flash silica gel chromatography (eluting with 0~65% EtOAc/petroleum ether) to give the title compound (120 mg, 95 mass %, 45.8% yield). MS m/z 558.2 (M+H).

| Chemical Name | Structure | ES/MS (m/z) (M + H) |
|---|---|---|
| Racemic, methyl 4-[2-(N-(3,3-difluorocyclohexyl)anilino)-2-oxo-ethyl]-1-(6-fluoroindoline-1-carbonyl)piperidine-4-carboxylate | 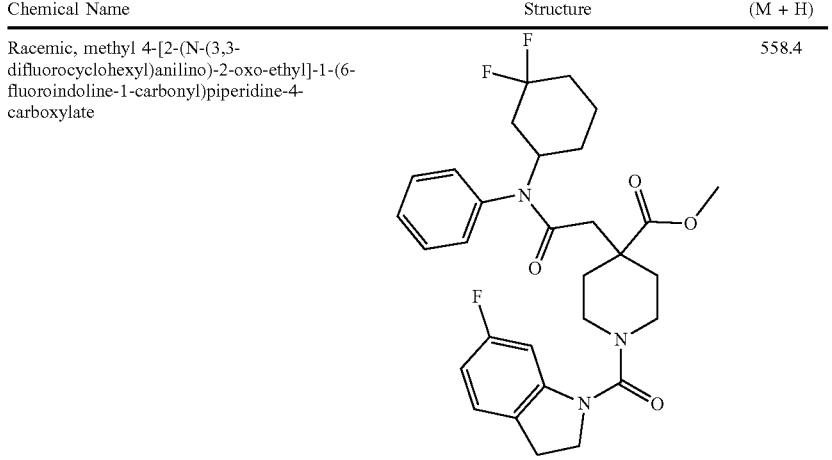 | 558.4 |

| Chemical Name | Structure | ES/MS (m/z) (M + H) |
|---|---|---|
| Racemic, methyl 4-[2-(N-[-3,3-difluorocyclohexyl]anilino)-2-oxo-ethyl]-1-(6-methylindoline-1-carbonyl)piperidine-4-carboxylate | 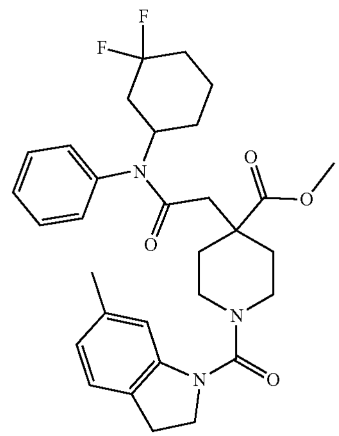 [SMILES: COC(=O)C1(CC(=O)N(c2ccccc2)C2CCCC(F)(F)C2)CCN(C(=O)N2CCc3ccc(C)cc32)CC1] | 554.4 |

Methyl 1-[cyclopropyl(phenyl)carbamoyl]-4-[2-oxo-2-(N-phenylanilino)ethyl]piperidine-4-carboxylate

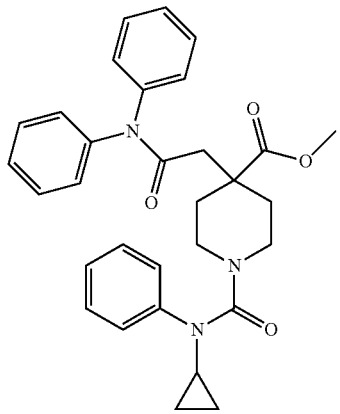 [SMILES: COC(=O)C1(CC(=O)N(c2ccccc2)c2ccccc2)CCN(C(=O)N(c2ccccc2)C2CC2)CC1]

At 0° C., to a mixture of methyl 4-[2-oxo-2-(N-phenylanilino)ethyl]piperidine-4-carboxylate (380 mg, 1.08 mmol) and potassium carbonate (448 mg, 3.24 mmol) in acetonitrile (50 mL) was added N-cyclopropyl-N-phenylcarbamoyl chloride (0.261 g, 1.33 mmol) and the resultant mixture was warmed to rt and stirred under nitrogen for 90 minutes. The reaction was diluted with EtOAc and water and extracted 2× with EtOAc. The organic layers were combined; dried over MgSO₄; filtered and concentrated under reduced pressure to give a residue. The residue was purified over 40 g silica gel with a 20 minute 0% to 100% EtOAc in hexanes gradient to afford 476 mg (86%) of the titled product. MS m/z 512 [M+H].

Step 7 4-[2-(N-[(racemic)-3,3-difluorocyclohexyl]anilino)-2-oxo-ethyl]-1-(2-pyridyl)piperidine-4-carboxylic acid (Example Nos. 74)

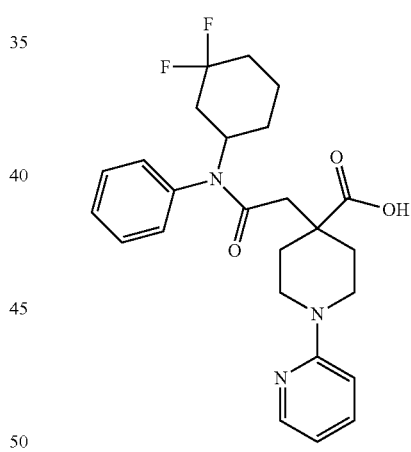

To a solution of methyl 4-[2-(N-[(racemic)-3,3-difluorocyclohexyl]anilino)-2-oxo-ethyl]-1-(2-pyridyl)piperidine-4-carboxylate (1.38 g, 2.63 mmol, 90 mass %) in 2-propanol (16.0 mL, 98 mass %) was added aq. NaOH (2.6 mL, 13 mmol, 5 mol/L), the mixture was heated to 50° C. and stirred overnight. After cooled to RT, the mixture was acidified with aqueous KHSO₄ to pH<4, the mixture was extracted with EtOAc (20 mL×3). The combined organic phases were washed with 10 mL brine, dried over Na₂SO₄, filtered and concentrated under vacuum. The residue was purified by prep-HPLC (Welch Xtimate Prep C 18 250×50 mm×10 um, condition: water (10 mM NH₄HCO₃)/MeCN from 5% to 35%, to give the title product (0.89 g, 97 mass %, 71.6% yield), MS m/z 458.3 (M+H).

Example No. 75 was Prepared According to the Procedure Above

| Example No. | Chemical Name | Structure | ES/MS (m/z) (M + H) | $^1$H NMR (400 MHz, DMSO-$d_6$) |
|---|---|---|---|---|
| 75 | Racemic, 4-[2-(N-[3,3-difluorocyclohexyl]anilino)-2-oxo-ethyl]-1-[(2-fluoro-4-isopropyl-phenyl)methyl]piperidine-4-carboxylic acid | 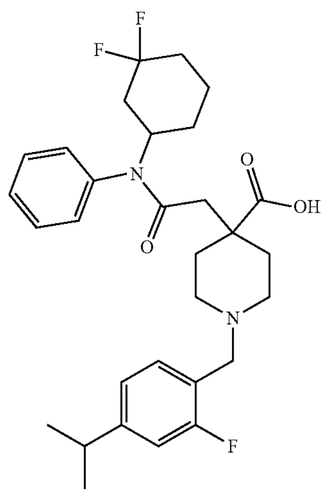 [SMILES: CC(C)c1ccc(CN2CCC(CC(=O)N(c3ccccc3)C3CCCC(F)(F)C3)(C(=O)O)CC2)c(F)c1] | 531.5 | $^1$H NMR (400 MHz, DMSO-$d_6$): 12.01 (br, 1H), 7.54-7.40 (m, 3H), 7.28-7.16 (m, 3H), 7.05-6.95 (m, 2H), 4.61 (t, J = 12.4 Hz, 1H), 2.92-2.83 (m, 1H), 2.36-2.14 (m, 6H), 2.10 (s, 2H), 1.94-1.79 (m, 3H), 1.77-1.67 (m, 2H), 1.64-1.29 (m, 6H), 1.19 (s, 3H), 1.17 (s, 3H), 1.09-0.95 (m, 1H) |

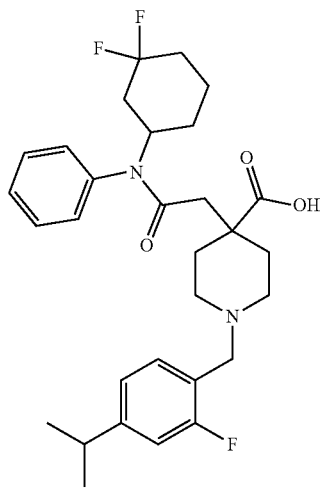

Racemic, 4-[2-(N-[3,3-difluorocyclohexyl]anilino)-2-oxo-ethyl]-1-[(4-isopropylphenyl)methyl]piperidine-4-carboxylic acid (Example No. 51)

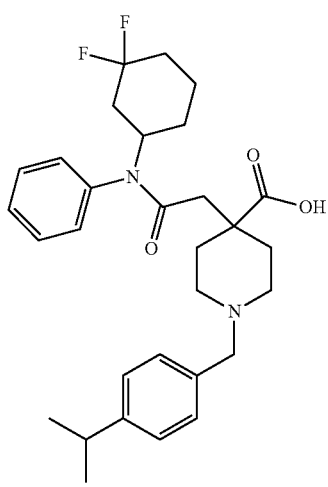 [SMILES: CC(C)c1ccc(CN2CCC(CC(=O)N(c3ccccc3)C3CCCC(F)(F)C3)(C(=O)O)CC2)cc1]

To a solution of racemic, methyl 4-[2-(N-[3,3-difluorocyclohexyl]anilino)-2-oxo-ethyl]-1-[(4-isopropylphenyl)methyl]piperidine-4-carboxylate (50 mg, 0.090 mmol, 95 mass %) in 1,4-dioxane (1.0 mL) and water (0.5 mL) was added potassium hydroxide (24 mg, 0.428 mmol) at RT. The mixture was stirred at 100° C. for 5 h. The mixture was cooled to RT, combined, the pH was adjusted to around 7 by adding formic acid and concentrated. The residue was purified by prep-HPLC (Phenomenex C18 150*30 mm*5 um, mobile phase A: water (0.04% NH$_3$H$_2$O+10 mM NH4HCO3), mobile phase B: ACN, eluting with 20-60% B in 12 min, then to 1000B. The appropriate fractions were combined and lyophilized to give title product (13.4 mg, 100 mass %, 29.0% yield) as a white solid. MS m/z 513.5 (M+H); $^1$H NMR (400.13 MHz, DMSO-$d_6$): 12.10 (br, 1H), 7.57-7.40 (m, 3H), 7.25-7.23 (m, 2H), 7.17-7.10 (m, 4H), 4.66-4.56 (m, 1H), 3.28 (s, 2H), 2.87-2.84 (m, 1H), 2.25-2.15 (m, 4H), 2.13 (s, 2H), 1.94-1.80 (m, 3H), 1.73 (d, J=10.9 Hz, 2H), 1.64-1.29 (m, 6H), 1.17 (d, J=7.0 Hz, 6H), 1.09-0.95 (m, 1H)

Example Nos. 50, 62, 63, 64, 65, 66, 67, 68, 69, 70, 71, 72, 73, 79 and 88 were Prepared According to the Procedure Above

| Example No. | Chemical Name | Structure | ES/MS (m/z) (M + H) | ¹H NMR (400 MHz, DMSO-d₆) |
|---|---|---|---|---|
| 50 | Racemic, 1-[(4-cyclopropyl-phenyl)methyl]-4-[2-(N-[3,3-difluorocyclo-hexyl]anilino)-2-oxo-ethyl]piperidine-4-carboxylic acid | 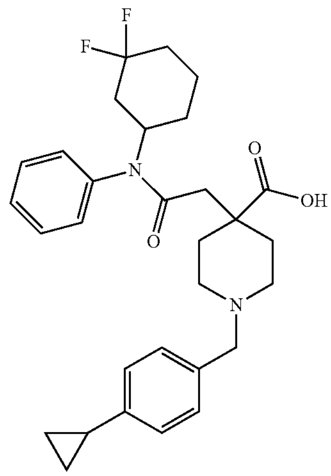 [SMILES: O=C(CC1(C(=O)O)CCN(Cc2ccc(C3CC3)cc2)CC1)N(c1ccccc1)C1CCCC(F)(F)C1] | 511.5 | ¹H NMR (400 MHz, DMSO-d₆): 12.10 (br, 1H), 7.54 (dd, J = 2.0, 5.8 Hz, 3H), 7.22 (dd, J = 1.3, 2.0 Hz, 2H), 7.10-7.06 (m, 2H), 7.00-6.95 (m, 2H), 4.66-4.55 (m, 1H), 3.27 (s, 2H), 2.27-2.18 (m, 3H), 2.17-2.07 (m, 3H), 1.96-1.78 (m, 4H), 1.73 (d, J = 11.0 Hz, 2H), 1.62-1.23 (m, 6H), 1.09-0.96 (m, 1H), 0.94-0.88 (m, 2H), 0.65-0.59 (m, 2H) |
| 62 | Racemic, 4-[2-(N-[3,3-difluorocyclo-hexyl]anilino)-2-oxo-ethyl]-1-[(racemic)-2-(4-fluorophenyl) propanoyl] piperidine-4-carboxylic acid | 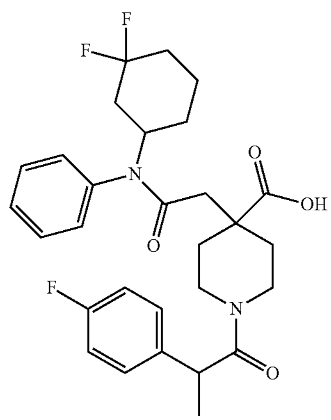 [SMILES: CC(C(=O)N1CCC(CC(=O)N(c2ccccc2)C2CCCC(F)(F)C2)(C(=O)O)CC1)c1ccc(F)cc1] | 531.5 | ¹H NMR (400 MHz, DMSO-d₆): 7.53-7.42 (m, 3H), 7.27-7.19 (m, 3H), 7.16-7.05 (m, 3H), 4.66-4.52 (m, 1H), 4.10-4.03 (m, 1H), 3.75-3.52 (m, 2H), 3.13-2.97 (m, 2H), 2.25-2.10 (m, 2H), 1.99-1.83 (m, 2H), 1.78-1.64 (m, 4H), 1.59-1.25 (m, 4H), 1.21 (d, J = 6.6 Hz, 3H), 1.09-0.96 (m, 1H) |
| 63 | Racemic, 4-[2-(N-[3,3-difluorocyclo-hexyl]anilino)-2-oxo-ethyl]-1-[(racemic)-2-(3-fluorophenyl) propanoyl] piperidine-4-carboxylic acid | 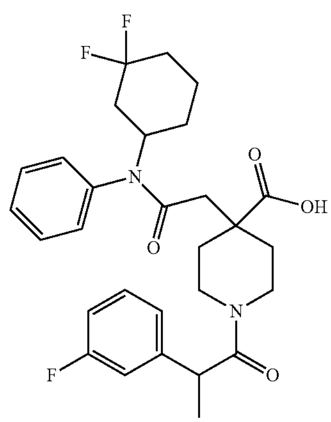 [SMILES: CC(C(=O)N1CCC(CC(=O)N(c2ccccc2)C2CCCC(F)(F)C2)(C(=O)O)CC1)c1cccc(F)c1] | 531.4 | ¹H NMR (400 MHz, DMSO-d₆): 12.23 (br, 1H), 7.53-7.39 (m, 3H), 7.38-7.27 (m, 1H), 7.26-6.98 (m, 5H), 4.72-4.46 (m, 1H), 4.15-3.96 (m, 1H), 3.72-3.41 (m, 2H), 3.25-2.90 (m, 2H), 2.28-2.06 (m, 2H), 2.04-1.83 (m, 2H), 1.79-1.63 (m, 4H), 1.61-1.27 (m, 4H), 1.23 (d, J = 6.8 Hz, 3H), 1.07-0.91 (m, 2H) |

| Example No. | Chemical Name | Structure | ES/MS (m/z) (M + H) | ¹H NMR (400 MHz, DMSO-d₆) |
|---|---|---|---|---|
| 64 | Racemic, methyl 4-[2-(N-[3,3-difluorocyclohexyl]anilino)-2-oxo-ethyl]-1-[2-(2-fluorophenyl)propanoyl]piperidine-4-carboxylate | 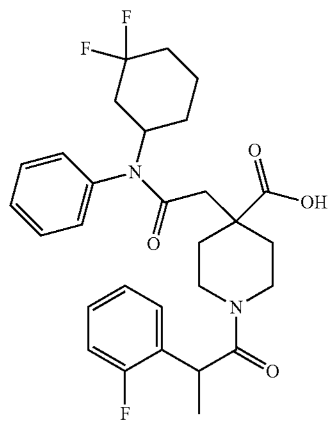 [SMILES: CC(C(=O)N1CCC(CC(=O)N(c2ccccc2)C2CCCC(F)(F)C2)(C(=O)O)CC1)c1ccccc1F] | 531.5 | ¹H NMR (400 MHz, DMSO-d₆): 7.60-7.46 (m, 3H), 7.39-7.27 (m, 2H), 7.26-7.10 (m, 4H), 4.73-4.58 (m, 1H), 4.32-4.23 (m, 1H), 3.90-3.80 (m, 1H), 3.64-3.60 (m, 2H), 3.23-3.14 (m, 1H), 3.13-2.97 (m, 2H), 2.33-2.19 (m, 1H), 2.06-1.89 (m, 2H), 1.87-1.73 (m, 3H), 1.71-1.28 (m, 8H), 1.24-1.01 (m, 1H) |
| 65 | Racemic, 4-[2-(N-[3,3-difluorocyclohexyl]anilino)-2-oxo-ethyl]-1-[2-(2-fluorophenyl)acetyl]piperidine-4-carboxylic acid | 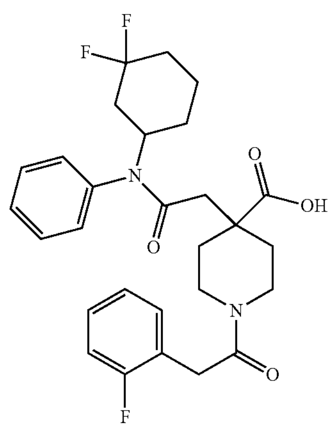 [SMILES: O=C(Cc1ccccc1F)N1CCC(CC(=O)N(c2ccccc2)C2CCCC(F)(F)C2)(C(=O)O)CC1] | 517.4 | ¹H NMR (400 MHz, DMSO-d₆): 12.28 (br, 1H), 7.55-7.42 (m, 3H), 7.32-7.16 (m, 4H), 7.15-7.07 (m, 2H), 4.62 (t, J = 12.4 Hz, 1H), 3.66 (s, 2H), 3.63-3.39 (m, 3H), 3.14 (t, J = 10.5 Hz, 1H), 2.22-2.14 (m, 1H), 2.15 (s, 2H), 1.91-1.88 (m, 2H), 1.84-1.68 (m, 3H), 1.63-1.23 (m, 5H), 1.17-0.93 (m, 1H) |
| 66 | Racemic, 4-[2-(N-[3,3-difluorocyclohexyl]anilino)-2-oxo-ethyl]-1-[1-(2-fluorophenyl)cyclopropanecarbonyl]piperidine-4-carboxylic acid | 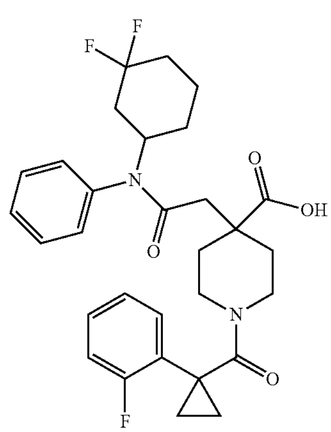 [SMILES: O=C(CC1(C(=O)O)CCN(C(=O)C2(c3ccccc3F)CC2)CC1)N(c1ccccc1)C1CCCC(F)(F)C1] | 543.4 | ¹H NMR (400 MHz, DMSO-d₆): 7.52-7.39 (m, 3H), 7.36-7.24 (m, 2H), 7.21-7.02 (m, 4H), 4.57 (t, J = 12.3 Hz, 1H), 3.46-3.25 (m, 2H), 3.15-3.08 (m, 2H), 2.23-2.18 (m, 1H), 2.01 (s, 2H), 1.91-1.88 (m, 1H), 1.75 1.30 (m, 6H), 1.27 (s, 2H), 1.12 (s, 2H), 1.06-0.93 (m, 4H) |

| Example No. | Chemical Name | Structure | ES/MS (m/z) (M + H) | ¹H NMR (400 MHz, DMSO-d₆) |
|---|---|---|---|---|
| 67 | Racemic, 4-[2-(N-[3,3-difluorocyclohexyl]anilino)-2-oxo-ethyl]-1-[2-(2-fluorophenyl)-2-methyl-propanoyl] piperidine-4-carboxylic acid | 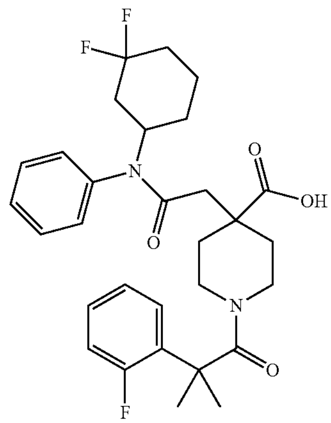 [SMILES: CC(C)(C(=O)N1CCC(CC(=O)N(c2ccccc2)C2CCCC(F)(F)C2)(C(=O)O)CC1)c1ccccc1F] | 545.6 | ¹H NMR (400 MHz, DMSO-d₆): 7.53-7.37 (m, 4H), 7.34-7.27 (m, 1H), 7.25-7.05 (m, 4H), 4.57 (t, J = 12.6 Hz, 1H), 3.71-3.58 (m, 1H), 3.14-2.97 (m, 2H), 2.92-2.78 (m, 2H), 2.21-2.18 (m, 1H), 2.07-1.86 (m, 3H), 1.72-1.70 (m, 3H), 1.63-1.42 (m, 3H), 1.39 (s, 6H), 1.27-1.17 (m, 1H), 0.99 (dt, J = 9.1, 12.3 Hz, 1H), 0.87-0.72 (m, 1H) |
| 68 | Racemic, 4-[2-(N-[3,3-difluorocyclohexyl]anilino)-2-oxo-ethyl]-1-(2-fluoro-4-isopropyl-benzoyl) piperidine-4-carboxylic acid | 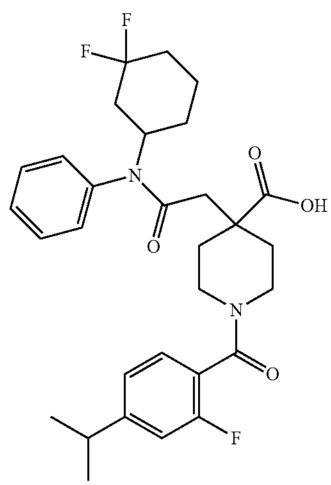 [SMILES: CC(C)c1ccc(C(=O)N2CCC(CC(=O)N(c3ccccc3)C3CCCC(F)(F)C3)(C(=O)O)CC2)c(F)c1] | 545.5 | ¹H NMR (400 MHz, DMSO-d₆): 7.55-7.41 (m, 3H), 7.30-7.21 (m, 3H), 7.18-7.10 (m, 2H), 4.65-4.59 (m, 1H), 3.83-3.81 (m, 1H), 3.30-3.18 (m, 2H), 3.13-3.06 (m, 1H), 2.97-2.87 (m, 1H), 2.23-2.21 (m, 1H), 2.13-2.12 (m, 2H)), 1.93-1.90 (m, 2H), 1.84-1.80 (m, 1H), 1.74-1.73 (m, 2H), 1.65-1.34 (m, 5H), 1.19 (d, J = 6.9 Hz, 6H), 1.08-0.95 (m, 1H) |
| 69 | Racemic, 4-[2-(N-[3,3-difluorocyclohexyl]anilino)-2-oxo-ethyl]-1-(4-isopropylbenzoyl) piperidine-4-carboxylic acid | 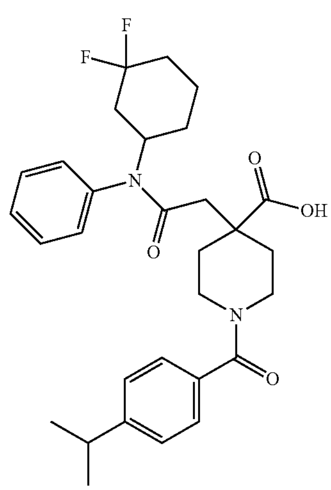 [SMILES: CC(C)c1ccc(C(=O)N2CCC(CC(=O)N(c3ccccc3)C3CCCC(F)(F)C3)(C(=O)O)CC2)cc1] | 527.3 | ¹H NMR (400 MHz, DMSO-d₆): 7.54-7.40 (m, 3H), 7.33-7.11 (m, 6H), 4.62 (t, J = 12.4 Hz, 1H), 3.7-80-3.75 (m, 1H), 3.36-3.28 (m, 3H), 2.90 (td, J = 6.9, 13.8 Hz, 1H), 2.24-2.20 (m, 3H), 1.96-1.79 (m, 3H), 1.78-1.68 (m, 2H), 1.65-1.30 (m, 5H), 1.20 (d, J = 6.9 Hz, 6H), 1.08-0.94 (m, 1H) |

-continued

| Example No. | Chemical Name | Structure | ES/MS (m/z) (M + H) | $^1$H NMR (400 MHz, DMSO-$d_6$) |
|---|---|---|---|---|
| 70 | Racemic, 1-(4-cyclopropyl-benzoyl)-4-[2-(N-[3,3-difluorocyclo-hexyl]anilino)-2-oxo-ethyl]piperidine-4-carboxylic acid | 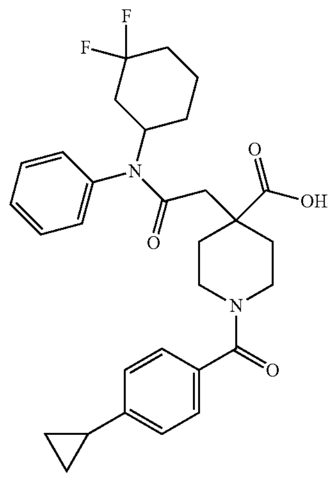 [SMILES: O=C(c1ccc(C2CC2)cc1)N1CCC(CC(=O)N(c2ccccc2)C2CCCC(F)(F)C2)(C(=O)O)CC1] | 525.4 | $^1$H NMR (400 MHz, DMSO-$d_6$): 7.53-7.41 (m, 3H), 7.30-7.17 (m, 4H), 7.09 (d, J = 8.3 Hz, 2H), 4.62 (t, J = 12.5 Hz, 1H), 3.87-3.68 (m, 1H), 3.27-3.14 (m, 3H), 2.24-2.21(m, 1H), 2.14 (s, 2H), 1.99-1.79 (m, 4H), 1.74 (d, J = 10.3 Hz, 2H), 1.64-1.45 (m, 5H), 1.08-0.94 (m, 3H), 0.72-0.65 (m, 2H) |
| 71 | Racemic, 4-[2-(N-[3,3-difluorocyclo-hexyl]anilino)-2-oxo-ethyl]-1-(4-fluoroindoline-1-carbonyl) piperidine-4-carboxylic acid | 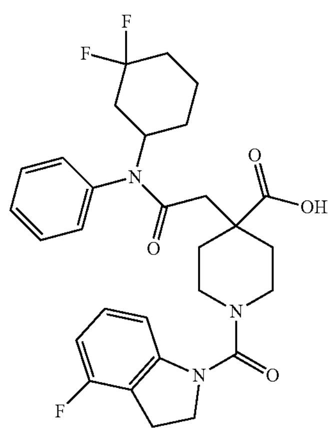 [SMILES: O=C(N1CCC(CC(=O)N(c2ccccc2)C2CCCC(F)(F)C2)(C(=O)O)CC1)N1CCc2c(F)cccc21] | 544.4 | $^1$H NMR (400 MHz, DMSO-$d_6$): 7.58-7.42 (m, 3H), 7.26 (d, J = 5.9 Hz, 2H), 7.19-7.09 (m, 1H), 6.75 (d, J = 7.9 Hz, 1H), 6.68 (t, J = 8.5 Hz, 1H), 4.63 (t, J = 12.5 Hz, 1H), 3.84 (t, J = 8.3 Hz, 2H), 3.30-3.13 (m, 4H), 2.99 (t, J = 8.3 Hz, 2H), 2.24-2.22 (m, 1H), 2.16 (s, 2H), 1.90 (d, J = 13.1 Hz, 3H), 1.81-1.68 (m, 2H), 1.66-1.33 (m, 5H), 1.11-0.96 (m, 1H) |
| 72 | Racemic, 4-[2-(N-(3,3-difluorocyclo-hexyl)anilino)-2-oxo-ethyl]-1-(6-fluoroindoline-1-carbonyl) piperidine-4-carboxylic acid | 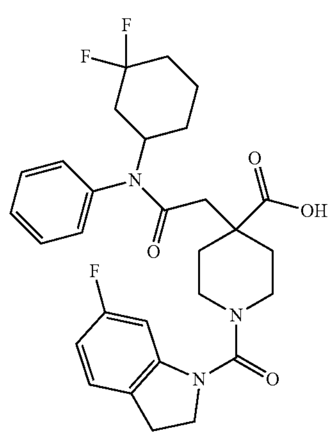 | 544.4 | $^1$H NMR (400 MHz, DMSO-$d_6$): 7.55-7.41 (m, 3H), 7.25 (d, J = 6.9 Hz, 2H), 7.15 (dd, J = 6.1, 7.8 Hz, 1H), 6.73-6.59 (m, 2H), 4.63 (t, J = 12.3 Hz, 1H), 3.83 (t, J = 8.3 Hz, 2H), 3.45-3.24 (m, m 4H), 2.94 (t, J = 8.1 Hz, 2H), 2.22-2.20 (m, 1H), 2.15 (s, 2H), 1.90-1.87 (m, 3H), 1.75-1.72 (m, 2H), 1.65-1.33 (m, 5H), 1.03 (dq, J = 3.6, 12.6 Hz, 1H) |

-continued

| Example No. | Chemical Name | Structure | ES/MS (m/z) (M + H) | $^1$H NMR (400 MHz, DMSO-$d_6$) |
|---|---|---|---|---|
| 73 | Racemic, 4-[2-(N-[3,3-difluorocyclohexyl]anilino)-2-oxo-ethyl]-1-(7-fluoroindoline-1-carbonyl)piperidine-4-carboxylic acid | 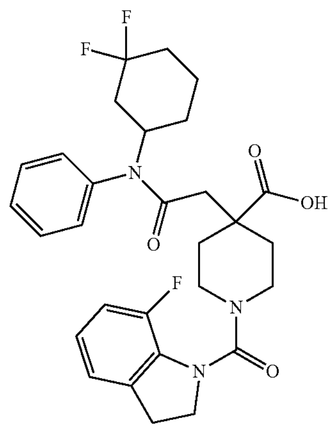 [SMILES: O=C(N1CCC(CC(=O)N(c2ccccc2)C2CCCC(F)(F)C2)(C(=O)O)CC1)N1CCc2cccc(F)c21] | 544.5 | $^1$H NMR (400 MHz, DMSO-$d_6$): 7.55-7.44 (m, 3H), 7.26 (d, J = 6.8 Hz, 2H), 7.04-6.99 (m, 1H), 6.97-6.90 (m, 2H), 4.63 (t, J = 12.4 Hz, 1H), 3.85 (t, J = 8.1 Hz, 2H), 3.40-3.35 (m, 2H), 3.26-3.18 (m, 2H), 3.06 (t, J = 8.1 Hz, 2H), 2.24-2.22 (m, 1H), 2.17 (s, 2H), 1.90 (d, J = 12.9 Hz, 3H), 1.79-1.70 (m, 2H), 1.61-1.46 (m, 2H), 1.46-1.37 (m, 3H), 1.10-0.98 (m, 1H) |
| 79 | Isomer 2, 4-[2-(N-(3,3-difluorocyclohexyl)-2-fluoroanilino)-2-oxo-ethyl]-1-(2-pyridyl)piperidine-4-carboxylic acid | 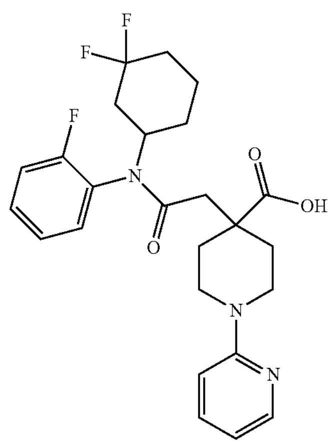 [SMILES: O=C(CC1(C(=O)O)CCN(c2ccccn2)CC1)N(c1ccccc1F)C1CCCC(F)(F)C1] | 476.3 | $^1$H NMR (400 MHz, DMSO-$d_6$): 12.26 (br, 1H), 8.05 (dd, J = 1.6, 4.8 Hz, 1H), 7.57-7.36 (m, 4H), 7.35-7.25 (m, 1H), 6.74 (d, J = 8.6 Hz, 1H), 6.57 (dd, J = 5.0, 6.9 Hz, 1H), 4.72-4.53 (t, J = 12.4 Hz, 1H), 3.56-3.46 (m, 3H), 2.35-2.23 (m, 1H), 2.22-2.11 (m, 2H), 1.97-1.85 (m, 3H), 1.83-1.63 (m, 3H), 1.63-1.52 (m, 1H), 1.42-1.38 (m, 4H), 1.19-0.91 (m, 1H) |
| 88 | 1-[(racemic)-2-(4-cyclopropylphenyl)propyl]-4-[2-(N-[(racemic)-3,3-difluorocyclohexyl]anilino)-2-oxo-ethyl]piperidine-4-carboxylic acid | 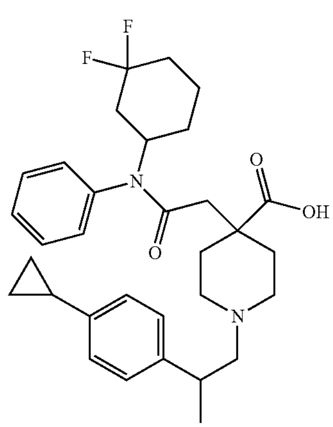 [SMILES: CC(CN1CCC(CC(=O)N(c2ccccc2)C2CCCC(F)(F)C2)(C(=O)O)CC1)c1ccc(C2CC2)cc1] | 539.4 | $_1$H NMR (400 MHz, DMSO-$d_6$): 7.54-7.37 (m, 3H), 7.23-7.21 (m, 2H), 7.04 (d, J = 7.8 Hz, 2H), 6.95 (d, J = 7.9 Hz, 2H), 4.63 (t, J = 12.1 Hz, 1H), 2.80 (dd, J = 7.1, 13.6 Hz, 1H), 2.25-2.12 (m, 6H), 2.02 (s, 2H), 1.92-1.68 (m, 6H), 1.58-1.23 (m, 6H), 1.09 (d, J = 6.6 Hz, 3H), 1.05-1.03 (m, 1H), 0.89 (d, J = 6.6 Hz, 2H), 0.60 (d, J = 3.8 Hz, 2H) |

Example 97

1-[cyclopropyl(phenyl)carbamoyl]-4-[2-oxo-2-(N-phenylanilino)ethyl]piperidine-4-carboxylic acid

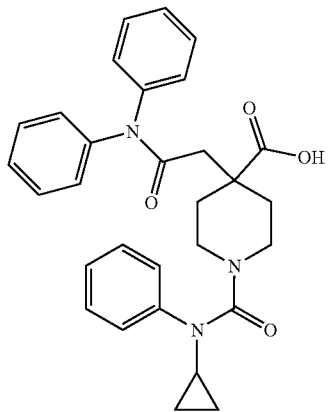 [SMILES: O=C(CC1(C(=O)O)CCN(C(=O)N(c2ccccc2)C2CC2)CC1)N(c1ccccc1)c1ccccc1]

A solution of lithium hydroxide (131 mg, 5.47 mmol) in water (2 mL) was added to a solution of methyl 1-[cyclopropyl(phenyl)carbamoyl]-4-[2-oxo-2-(N-phenylanilino)ethyl]piperidine-4-carboxylate (475 mg, 0.928 mmol) in ethanol (2 mL) and THF (2 mL) at room temperature and the reaction was stirred at 50° C. overnight. The reaction was cooled, diluted with water and dichloromethane and acidified with 5.0 M aqueous HCl until pH~2.0 (~1 mL). The mixture was extracted 3× with DCM. The organic layers were combined; dried over $Na_2SO_4$; filtered and concentrated under reduced pressure to afford crude product that was purified over 40 g silica gel with a 30 minute 0.5% to 10% MeOH in DCM gradient to afford 355 mg (77%) of the titled product. MS (m/z): 498 [M+H]. $^1$H NMR (400.13 MHz, $CDCl_3$): 7.54-7.46 (m, 3H), 7.31 (dd, J=1.6, 6.9 Hz, 3H), 7.24 (m, 6H), 7.13-7.09 (m, 3H), 3.50 (dt, J=14.0, 4.2 Hz, 2H), 3.21-3.14 (m, 2H), 2.74-2.69 (m, 1H), 2.54 (s, 2H), 2.02 (dd, J=3.3, 10.6 Hz, 2H), 0.92-0.84 (m, 4H), 0.70-0.66 (m, 2H).

Isolation of Isomers (Example Nos. 74A and 74B1)

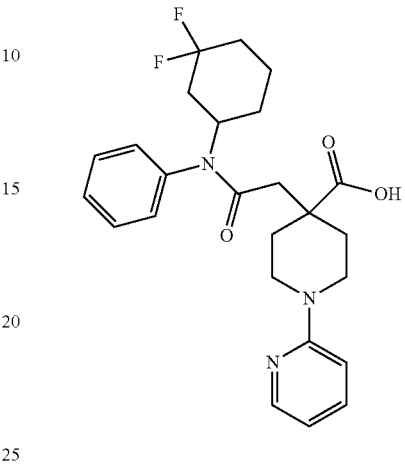

The racemic 4-[2-(N-[(racemic)-3,3-difluorocyclohexyl]anilino)-2-oxo-ethyl]-1-(2-pyridyl)piperidine-4-carboxylic acid 1.62 g was purified by SFC-80, Daicel ChiralCel IG (250 mm*50 mm, 10 um); mobile phase: A: CO2; B: 0.1% $NH_3H_2O$ in EtOH, eluting with 40%, flow rate: 80 mL/min The eluent of first peak was collected and lyophilized to give the isomer 1 of title compound (546.5 mg, 33.9% yield, ee: 100%). MS m/z 458.4 (M+H). $^1$H NMR (400.13 MHz, DMSO-$d_6$): 12.0 (brs, 1H), 8.03 (dd, J=1.2, 4.8 Hz, 1H), 7.49-7.45 (m, 4H), 7.24-7.22 (m, 2H), 6.73 (d, J=8.8 Hz, 1H), 6.57 (m, 1H), 4.65-4.59 (m, 1H), 3.53-3.31 (m, 4H), 2.23-2.19 (m, 3H), 1.90-1.87 (m, 3H), 1.76-1.73 (m, 2H), 1.62-1.39 (m, 5H), 1.04-1.01 (m, 1H).

The eluent of the second peak was collected and lyophilized to give isomer 2 of the title compound (586.6 mg, 36.5% yield, ee: 99.8%). MS m/z 458.5 (M+H). $^1$H NMR (400.13 MHz, DMSO-$d_6$): 12.18 (brs, 1H), 8.06 (dd, J=1.4, 4.9 Hz, 1H), 7.51-7.45 (m, 4H), 7.25-7.24 (m, 2H), 6.74 (d, J=8.7 Hz, 1H), 6.57 (dd, J=5.1, 6.9 Hz, 1H), 4.66-4.60 (m, 1H), 3.51-3.47 (m, 2H), 3.37-3.35 (m, 2H), 2.25-2.23 (m, 3H), 1.95-1.90 (m, 3H), 1.77-1.74 (m, 2H), 1.62-1.57 (m, 5H), 1.11-1.06 (m, 1H).

Example Nos. 72a, 72b, 75b, 75a, 68b and 68a were Prepared According to the Procedure Above The racemate 72 was separated by SFC, Daicel ChiralPak IG (250*30 mm, 10 um); mobile phase: A: $CO_2$; B: 0.10% $NH_3H_2O$ in EtOH; eluting with 40% of B, flow rate: 80 mL/min to give 72a and 72b.

The racemate 75 was separated by SFC, column: DAICEL CHIRALCEL IG (250 mm*50 mm, 10 um); mobile phase: A: $CO_2$; B: 0.1% $NH_3H_2O$ in EtOH; eluting with 35% of B, flow rate: 140 mL/min to give the 75a and 75b.

The racemate 68 was separated by SFC (column: DAICEL CHIRALCEL IG (250 mm*30 mm, 10 um); mobile phase: A: $CO_2$, B: 0.10% $NH_3H_2O$ in EtOH; eluting with 3000 of B, flow rate: 70 mL/min to give the 68a and 68b.

| Example No. | Chemical Name | Structure | ES/MS (m/z) (M + H) | ¹H NMR (400 MHz, DMSO-d₆) |
|---|---|---|---|---|
| 72a | 4-[2-(N-[(1R)-3,3-difluorocyclohexyl]anilino)-2-oxo-ethyl]-1-(6-fluoroindoline-1-carbonyl)piperidine-4-carboxylic acid | Chiral | 544.4 | ¹H NMR (400 MHz, DMSO-d₆): 7.56-7.42 (m, 3H), 7.25 (d, J = 5.8 Hz, 2H), 7.20-7.10 (m, 1H), 6.75-6.58 (m, 2H), 4.63 (t, J = 12.4 Hz, 1H), 3.82 (t, J = 8.3 Hz, 2H), 3.27-3.14 (m, 4H), 2.93 (t, J = 8.1 Hz, 2H), 2.24-2.22 (m, 1H), 2.15 (s, 2H), 1.92-1.89 (m, 3H), 1.76-1.73 (m, 2H), 1.64-1.33 (m, 5H), 1.09-0.96 (m, 1H) |
| 72b | 4-[2-(N-[(1S)-3,3-difluorocyclohexyl]anilino)-2-oxo-ethyl]-1-(6-fluoroindoline-1-carbonyl)piperidine-4-carboxylic acid | Chiral | 544.5 | ¹H NMR (400 MHz, DMSO-d₆): 7.56-7.41 (m, 3H), 7.25 (d, J = 6.4 Hz, 2H), 7.18-7.11 (m, 1H), 6.75-6.58 (m, 2H), 4.63 (t, J = 12.4 Hz, 1H), 3.82 (t, J = 8.3 Hz, 2H), 3.27-3.18 (m, 4H), 2.93 (t, J = 8.1 Hz, 2H), 2.23-2.21 (s, 1H), 2.16 (s, 2H), 1.91-1.89 (m, 3H), 1.74 (s, 2H), 1.63-1.34 (m, 5H), 1.09-0.96 (m, 1H). |
| 75a | Isomer 1,4-[2-(N-(3,3-difluorocyclohexyl)anilino)-2-oxo-ethyl]-1-[(2-fluoro-4-isopropyl-phenyl)methyl]piperidine-4-carboxylic acid | 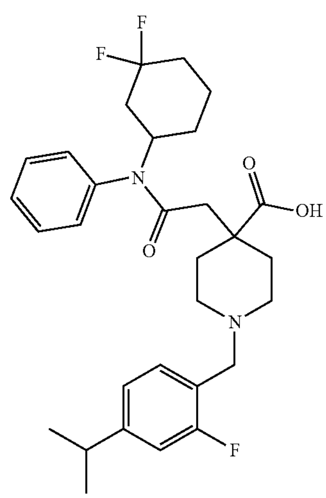 [SMILES: CC(C)c1ccc(CN2CCC(CC(=O)N(c3ccccc3)C3CCCC(F)(F)C3)(C(=O)O)CC2)c(F)c1] | 531.5 | ¹H NMR (400 MHz, DMSO-d₆): 12.03 (br, 1H), 7.54-7.40 (m, 3H), 7.24-7.20 (m, 3H), 7.02 (s, 1H), 6.99 (d, J = 6.6 Hz, 1H), 4.64-4.55 (m, 1H), 2.94-2.80 (m, 1H), 2.32-2.14 (m, 5H), 2.10 (s, 2H), 1.96-1.80 (m, 3H), 1.75-1.72 (m, 2H), 1.65-1.32 (m, 5H), 1.18 (d, J = 6.9 Hz, 6H), 1.09-0.94 (m, 1H) |

| Example No. | Chemical Name | Structure | ES/MS (m/z) (M + H) | ¹H NMR (400 MHz, DMSO-$d_6$) |
|---|---|---|---|---|
| 75b | Isomer 2,4-[2-(N-(3,3-difluorocyclohexyl)anilino)-2-oxo-ethyl]-1-[(2-fluoro-4-isopropyl-phenyl)methyl]piperidine-4-carboxylic acid | 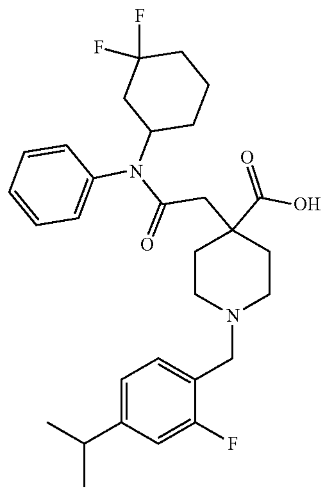 [SMILES: CC(C)c1ccc(CN2CCC(CC(=O)N(c3ccccc3)C3CCCC(F)(F)C3)(C(=O)O)CC2)c(F)c1] | 531.5 | ¹H NMR (400 MHz, DMSO-$d_6$): 12.03 (br, 1H), 7.53-7.42 (m, 3H), 7.24-7.20 (m, 3H), 7.02 (s, 1H), 6.99 (d, J = 6.6 Hz, 1H), 4.64-4.55 (m, 1H), 2.94-2.80 (m, 1H), 2.32-2.14 (m, 5H), 2.10 (s, 2H), 1.96-1.80 (m, 3H), 1.75-1.72 (m, 2H), 1.65-1.32 (m, 5H), 1.18 (d, J = 6.9 Hz, 6H), 1.09-0.94 (m, 1H) |
| 68a | Isomer 1,4-[2-(N-(3,3-difluorocyclohexyl)anilino)-2-oxo-ethyl]-1-(2-fluoro-4-isopropyl-benzoyl)piperidine-4-carboxylic acid | 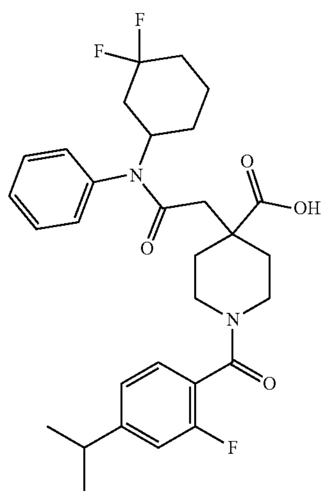 [SMILES: CC(C)c1ccc(C(=O)N2CCC(CC(=O)N(c3ccccc3)C3CCCC(F)(F)C3)(C(=O)O)CC2)c(F)c1] | 545.5 | ¹H NMR (400 MHz, DMSO-$d_6$): 12.28 (br, 1H), 7.53-7.42 (m, 3H), 7.29-7.20 (m, 3H), 7.17-7.10 (m, 2H), 4.64-4.58 (m, 1H), 3.79-3.77 (m, 1H), 3.22-3.17 (m, 2H), 3.11-3.08 (m, 1H), 2.97-2.87 (m, 1H), 2.21-2.16 (m, 3H), 1.93-1.85 (m, 3H), 1.75-1.72 (m, 2H), 1.55-1.30 (m, 5H), 1.19 (d, J = 6.9 Hz, 6H), 1.08-0.95 (m, 1H) |
| 68b | Isomer 1,4-[2-(N-(3,3-difluorocyclohexyl)anilino)-2-oxo-ethyl]-1-(2-fluoro-4-isopropyl-benzoyl)piperidine-4-carboxylic acid | 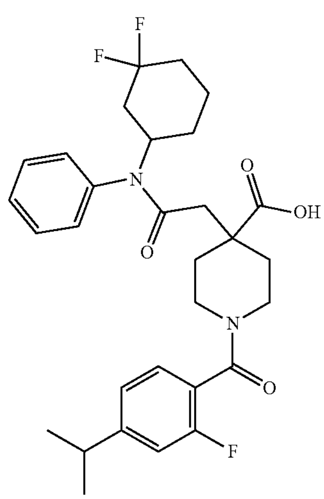 [SMILES: CC(C)c1ccc(C(=O)N2CCC(CC(=O)N(c3ccccc3)C3CCCC(F)(F)C3)(C(=O)O)CC2)c(F)c1] | 545.5 | ¹H NMR (400 MHz, DMSO-$d_6$): 7.53-7.42 (m, 3H), 7.29-7.20 (m, 3H), 7.17-7.10 (m, 2H), 4.64-4.58 (m, 1H), 3.79-3.77 (m, 1H), 3.22-3.17 (m, 2H), 3.11-3.08 (m, 1H), 2.97-2.87 (m, 1H), 2.21-2.16 (m, 3H), 1.93-1.85 (m, 3H), 1.75-1.72 (m, 2H), 1.55-1.30 (m, 5H), 1.19 (d, J = 6.9 Hz, 6H), 1.08-0.95 (m, 1H) |

Step 6 and 7: 4-[2-(N-cyclohexylanilino)-2-oxo-ethyl]-1-(2-pyridyl)piperidine-4-carboxylic acid (Example No. 49)

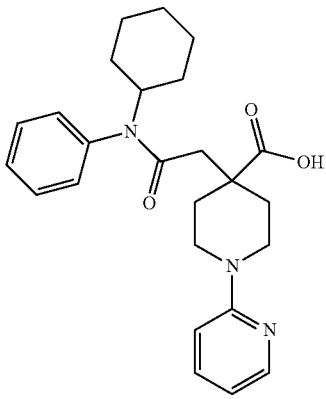 [SMILES: O=C(CC1(C(=O)O)CCN(c2ccccn2)CC1)N(c1ccccc1)C1CCCCC1]

2-chloropyridine (0.032 mL, 0.033 mmol) was added to a solution of methyl 4-[2-(N-cyclohexylanilino)-2-oxo-ethyl] piperidine-4-carboxylate (0.10 g, 0.28 mmol), sodium tert butoxide (0.110 mg, 1.14 mmol), chloro-(2-dicyclohexylphosphino-2',6'-diisopropoxy-1,1'-biphenyl)[2-(2-aminoethyl)phenyl]palladium(II)-methyl-t-butyl ether adduct, RuPhos palladacycle (0.035 mg, 0.041 mmol), in dioxane (1.40 mL) sealed, and stirred at 100° C. After 24 hours, the reaction mixture was cooled and loaded on SCX-2, eluted with acetonitrile and 2.0 M ammonia in methanol. Filtrate was concentrated under reduced pressure to give the residue which was purified by reverse phase prep-HPLC, using XBridge C18 150*19 mm*5 m column, mobile phase A: 20 mM NH4CO3 pH9, B: CH₃CN, eluting 30% B to 60% B. The appropriate fractions were collected and lyophilized to give the title compound (63 mg, 5400 yield). MS m/z 422.2 (M+H). ¹H NMR (DMSO-d₆) δ 12.04 (s, 1H), 8.05 (dd, J=1.3, 4.8 Hz, 1H), 7.49-7.43 (m, 4H), 7.18-7.16 (m, 2H), 6.73 (d, J=8.8 Hz, 1H), 6.56 (dd, J=4.9, 6.6 Hz, 1H), 4.41-4.34 (m, 1H), 3.50-3.22 (m, 4H), 2.15 (s, 2H), 1.89 (ddd, J=13.1, 6.1, 3.2 Hz, 2H), 1.75-1.66 (m, 4H), 1.53-1.37 (m, 5H), 0.97-0.85 (m, 3H)

The compounds in the table below were prepared according to the procedures above.

| Example No. | Chemical Name | Structure | ES/MS (m/z) (M + H) | ¹H NMR (400 MHz, DMSO-d₆) |
|---|---|---|---|---|
| 48 | 4-[2-(N-cyclohexyl-anilino)-2-oxo-ethyl]-1-phenyl-piperidine-4-carboxylic acid | 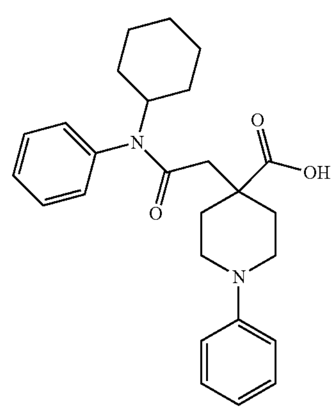 | 412.2 | 12.09 (s, 1H), 7.47-7.40 (m, 3H), 7.18-7.13 (m, 4H), 6.84 (d, J = 8.1 Hz, 2H), 6.71 (t, J = 7.3 Hz, 1H), 4.40-4.34 (m, 1H), 3.06-2.99 (m, 4H), 2.15 (s, 2H), 1.97-1.92 (m, 2H), 1.75-1.65 (m, 4H), 1.52-1.45 (m, 3H), 1.32-1.22 (m, 2H), 0.97-0.87 (m, 3H). |
| 89 | 4-[2-(N-cyclohexyl-anilino)-2-oxo-ethyl]-1-(4-methyl-2-pyridyl)piperidine-4-carboxylic acid | 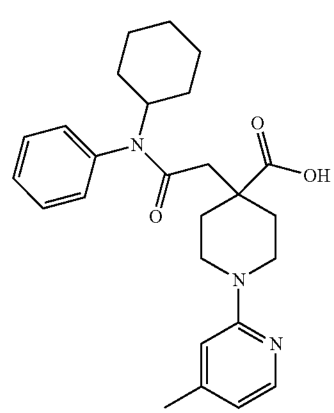 | 436.2 | 12.14 (s, 1H), 7.91 (d, J = 4.9 Hz, 1H), 7.48-7.41 (m, 3H), 7.18-7.16 (m, 2H), 6.57 (s, 1H), 6.42 (d, J = 5.1 Hz, 1H), 4.41-4.34 (m, 1H), 3.51-3.22 (m, 4H), 2.17 (d, J = 11.7 Hz, 5H), 1.91-1.85 (m, 2H), 1.76-1.66 (m, 4H), 1.53-1.36 (m, 5H), 0.97-0.86 (m, 3H) |

-continued

| Example No. | Chemical Name | Structure | ES/MS (m/z) (M + H) | $^1$H NMR (400 MHz, DMSO-d$_6$) |
|---|---|---|---|---|
| 90 | 4-[2-(N-cyclohexyl-anilino)-2-oxo-ethyl]-1-(5-methyl-2-pyridyl)piperidine-4-carboxylic acid | 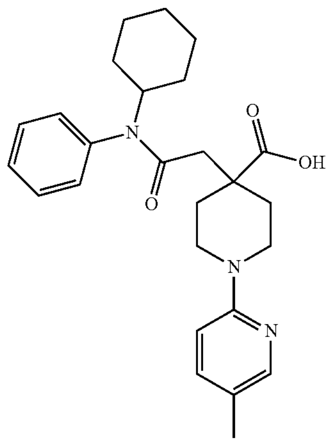 [SMILES: Cc1ccc(N2CCC(CC(=O)N(c3ccccc3)C3CCCCC3)(C(=O)O)CC2)nc1] | 436.2 | 12.14 (s, 1H), 7.90 (d, J = 2.2 Hz, 1H), 7.48-7.42 (m, 3H), 7.32 (dd, J = 2.1, 8.7 Hz, 1H), 7.18-7.16 (m, 2H), 6.68 (d, J = 8.8 Hz, 1H), 4.42-4.34 (m, 1H) 3.44-3.22 (m, 4H), 2.13 (d, J = 13.7 Hz, 5H), 1.91-1.83 (m, 2H), 1.76-1.66 (m, 4H), 1.53-1.36 (m, 5H), 0.97-0.86 (m, 3H). |
| 91 | 4-[2-(N-cyclohexyl-anilino)-2-oxo-ethyl]-1-(6-methyl-2-pyridyl)piperidine-4-carboxylic acid | 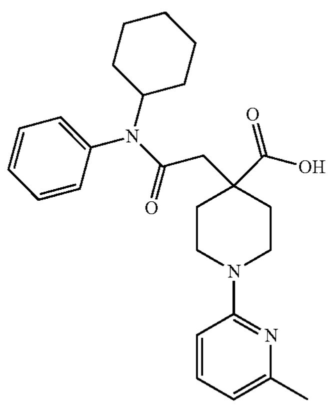 | 436.2 | 12.14 (s, 1H), 7.49-7.32 (m, 4H), 7.20-7.15 (m, 2H), 6.52 (d, J = 9.0 Hz, 1H), 6.43 (d, J = 7.5 Hz, 1H), 4.46-4.34 (m, 1H), 3.59-3.22 (m, 4H), 2.25 (s, 3H), 2.15 (s, 2H), 1.94-1.82 (m, 2H), 1.79-1.62 (m, 4H), 1.57-1.19 (m, 5H), 1.02-0.78 (m, 3H). |
| 92 | 4-[2-(N-cyclohexyl-anilino)-2-oxo-ethyl]-1-(3-methyl-2-pyridyl)piperidine-4-carboxylic acid | 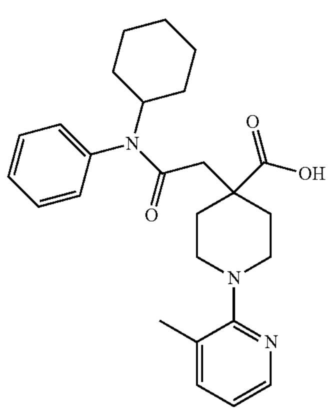 | 436.2 | 11.98 (s, 1H), 8.06-8.02 (m, 1H), 7.52-7.39 (m, 4H), 7.23-7.15 (m, 2H), 6.89-6.83 (m, 1H), 4.46-4.34 (m, 1H), 3.05-2.80 (m, 4H), 2.24-2.18 (m, 5H), 2.05-1.92 (m, 2H), 1.79-1.62 (m, 4H), 1.58-1.44 (m, 3H), 1.37-1.20 (m, 2H) 1.02-0.78 (m, 3H). |

| Example No. | Chemical Name | Structure | ES/MS (m/z) (M + H) | $^1$H NMR (400 MHz, DMSO-d$_6$) |
|---|---|---|---|---|
| 93 | 4-[2-(N-cyclohexyl-anilino)-2-oxo-ethyl]-1-(4-fluorophenyl)piperidine-4-carboxylic acid | 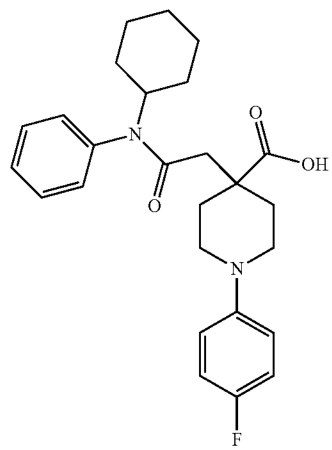 [SMILES: O=C(CC1(C(=O)O)CCN(c2ccc(F)cc2)CC1)N(c1ccccc1)C1CCCCC1] | 439.2 | 12.09 (s, 1H), 7.49-7.37 (m, 3H), 7.18-7.13 (m, 2H), 7.03-6.95 (m, 2H), 6.84 -6.81 (m, 2H), 4.40-4.34 (m, 1H), 3.06-2.99 (m, 4H), 2.15 (s, 2H), 2.00-1.90 (m, 2H), 1.75-1.62 (m, 4H), 1.56-1.44 (m, 3H), 1.35-1.20 (m, 2H), 0.97-0.87 (m, 3H). |
Example No. 21, 22, 23, 24, 25, 27, 28, 29, 30, 31 and 32 were Prepared According to Scheme 6
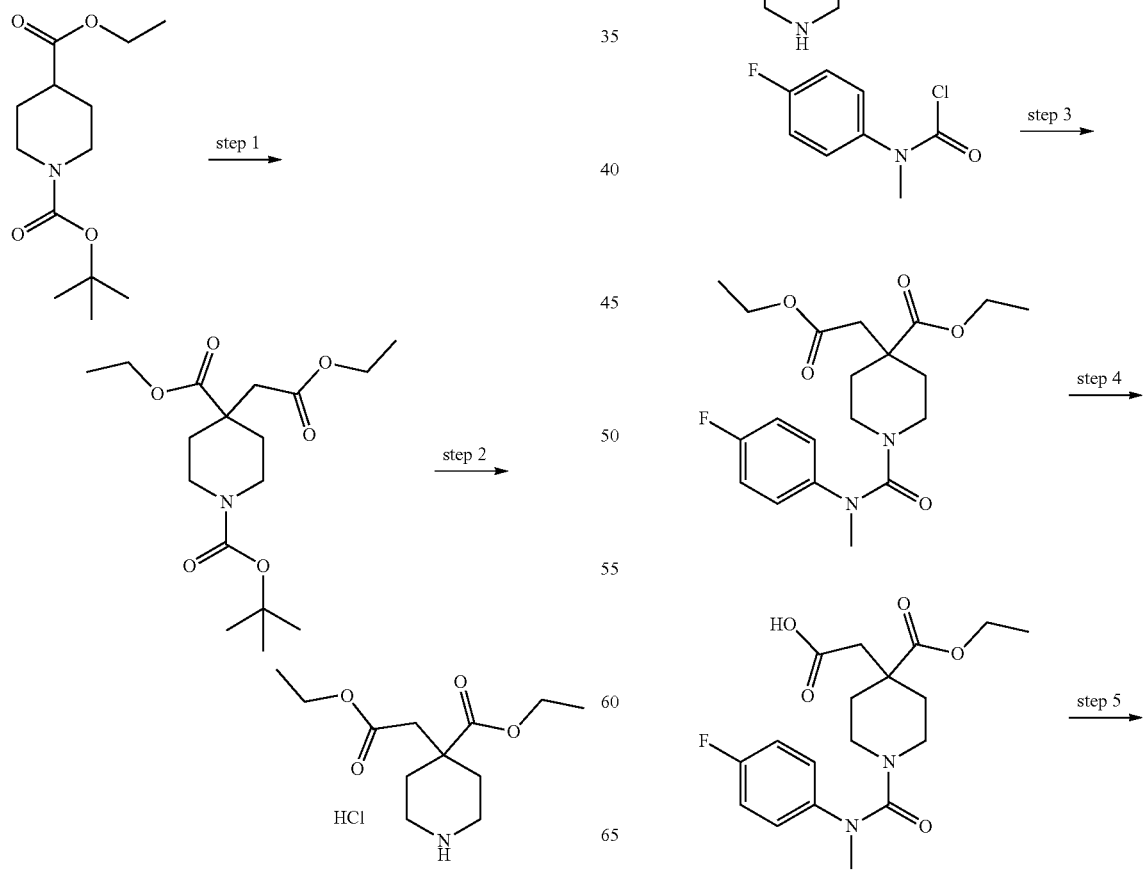

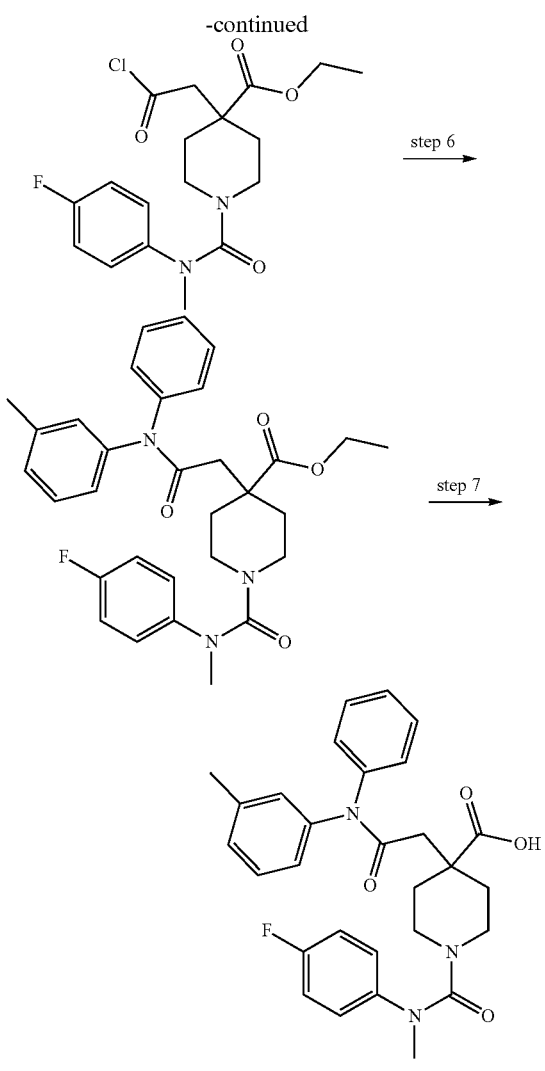

Step 1, and Step 2, were Synthesized According to Scheme 4

Step 3: ethyl 4-(2-ethoxy-2-oxo-ethyl)-1-[(4-fluorophenyl)-methyl-carbamoyl]piperidine-4-carboxylate

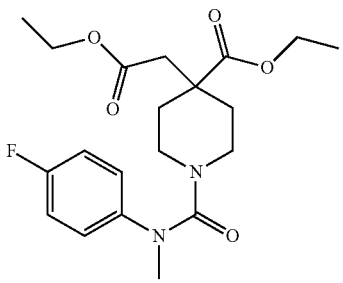 [SMILES: CCOC(=O)CC1(C(=O)OCC)CCN(C(=O)N(C)c2ccc(F)cc2)CC1]

N-(4-fluorophenyl)-N-methyl-carbamoyl chloride (9.65 g, 51.4 mmol) in acetonitrile (100 mL) was added at 0° C. to ethyl 4-(2-ethoxy-2-oxo-ethyl)piperidine-4-carboxylate; hydrochloride (6.00 g, 21.4 mmol) in DCM (20 mL) at 0° C. Potassium carbonate (8.9 g, 64.3 mmol) was added and stirred at 76° C. After 18 hours, the solvent was concentrated under reduced pressure and the mixture was extracted with DCM. The organic layers were combined, extracted with brine, dried over MgSO$_4$, filtered, and concentrated under reduced pressure to give a residue. The residue was purified by silica gel flash chromatography, eluting with 1-80% of EtOAc/hexane to give the title compound (4.03 g, 47% yield). MS m/z 395.0

Step 4: 2-[4-ethoxycarbonyl-1-[(4-fluorophenyl)-methyl-carbamoyl]-4-piperidyl]acetic acid

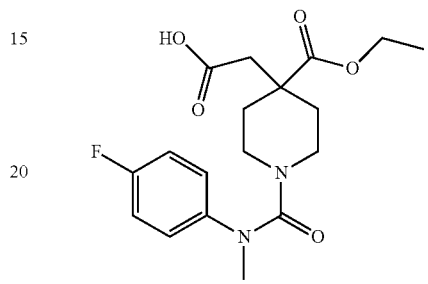

Potassium carbonate (2.40 g, 17.4 mmol) was added to ethyl 4-(2-ethoxy-2-oxo-ethyl)-1-[(4-fluorophenyl)-methyl-carbamoyl]piperidine-4-carboxylate (4.03 g, 10.20 mmol) in methanol (50 mL), water (2 mL) and stirred at 50° C. After 18 hours, the reaction was cooled, 5 N aqueous hydrochloric acid was added until pH 3.0 and the mixture was extracted with DCM. The organic layers were combined; dried over MgSO$_4$; filtered and concentrated under reduced pressure to give a residue. The residue was purified by silica gel flash chromatography, eluting with DCM to 40% of (MeOH:DCM (20:80)) to give the title compound (3.00 g, 80% yield). MS m/z 367.0 (M+H).

Step 5 and 6: ethyl 1-[(4-fluorophenyl)-methyl-carbamoyl]-4-[2-[N-(m-tolyl)anilino]-2-oxo-ethyl]piperidine-4-carboxylate Thionyl chloride (0.12 mL, 1.6 mmol) in chloroform (0.60 mL) was added to a solution of (2-[4-ethoxycarbonyl-1-[(4-fluorophenyl)-methyl-carbamoyl]-4-piperidyl]acetic acid (0.10 g, 0.27 mmol) in tetrahydrofuran (0.19 mL) and stirred at 60° C. After 2 hours, concentrated under reduced pressure to give ethyl 4-(2-chloro-2-oxo-ethyl)-1-[(4-fluorophenyl)-methyl-carbamoyl]piperidine-4-carboxylate (0.13 g, 99% yield)

3-methyl-N-phenyl-aniline (0.06 g, 0.30 mmol) in pyridine (0.16 mL, 1.98 mmol) was added to a solution of ethyl 4-(2-chloro-2-oxo-ethyl)-1-(indoline-1-carbonyl)piperidine-4-carboxylate (0.13 g, 0.35 mmol) in DCM (0.97 mL) and stirred at 40° C. After 16 hours, the reaction mixture was quenched with MeOH (0.5 mL) and concentrated under nitrogen stream. The residue was extracted with DCM (2.5 mL) and saturated sodium bicarbonate (1.0 mL). The organic layers were separated and dried over diatomaceous earth and concentrated under nitrogen stream. The crude product was purified by reverse phase prep-HPLC, using XBridge C18 150*19 mm*5 μm column, mobile phase A: 20 mM NH4CO3 pH9, B: CH₃CN, eluting 60% B to 90% B. The appropriate fractions were collected and lyophilized to give the title compound (55 mg, 98 mass %, 29% yield). MS m/z 332.2 (M+H).

Step 7: 1-[(4-fluorophenyl)-methyl-carbamoyl]-4-[2-[N-(m-tolyl)anilino]-2-oxo-ethyl]piperidine-4-carboxylic acid (Example No. 23)

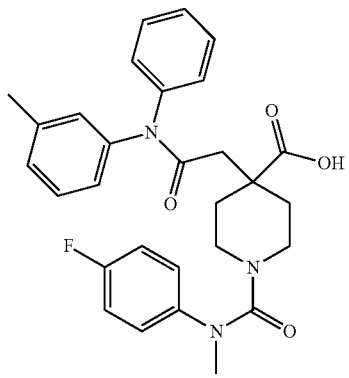 [SMILES: Cc1cccc(N(C(=O)CC2(C(=O)O)CCN(C(=O)N(C)c3ccc(F)cc3)CC2)c2ccccc2)c1]

5 N aqueous sodium hydroxide (0.20 mL, 1.0 mmol) was added to a solution of 1-[(4-fluorophenyl)-methyl-carbamoyl]-4-[2-[N-(m-tolyl)anilino]-2-oxo-ethyl]piperidine-4-carboxylate (0.05 g, 0.17 mmol) in ethanol (1.50 mL) and stirred at 80° C. After 18 hours, the reaction mixture was concentrated under nitrogen stream. Water (0.50 mL) was added, and the mixture was extracted with ethyl acetate. The organic layers were separated and discarded. The aqueous layer was acidified with HCl (4.0M, 0.0.45 mL) until pH-2 and extracted with ethyl acetate (1.0 mL×2), combined organic layers dried over diatomaceous earth and concentrated under nitrogen stream to give a residue. The crude product was purified by reverse phase prep-HPLC, using XBridge C18 150*19 mm*5 μm column, mobile phase A: 20 mM NH4CO3 pH9, B: CH₃CN, eluting 600 B to 90 B. The appropriate fractions were collected and lyophilized to give the title compound (15 mg, 100 mass %, 23% yield). MS m/z 504.2 (M+H). ¹H NMR (DMSO-d₆) δ 12.49 (s, 1H), 7.360-7.17 (m, 13H), 3.20-3.11 (m, 2H), 3.00 (s, 3H), 3.00-2.92 (m, 2H), 2.41 (s, 2H), 2.29 (s, 3H), 1.77-1.73 (m, 2H), 1.32-1.24 (m, 2H).

Example Nos. 21, 22, 24, 25, 27, 28, 29, 30, 31, and 32 were Prepared According to Above Procedure

| Example No. | Chemical Name | Structure | ES/MS (m/z) (M + H) | ¹H NMR (400 MHz, DMSO-d₆) |
|---|---|---|---|---|
| 21 | 4-[2-(N-cyclohexyl-4-fluoro-anilino)-2-oxo-ethyl]-1-[(4-fluorophenyl)-methyl-carbamoyl]piperidine-4-carboxylic acid | 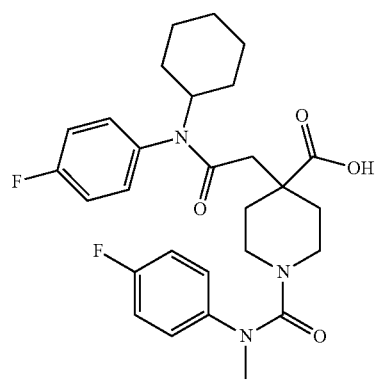 [SMILES: CN(C(=O)N1CCC(CC(=O)N(c2ccc(F)cc2)C2CCCCC2)(C(=O)O)CC1)c1ccc(F)cc1] | 514.2 | 12.49 (s, 1H), 7.36-7.24 (m, 2H), 7.23-7.05 (m, 6H), 4.62-4.30 (m, 1H), 3.18 (s, 3H), 3.13-2.88 (m, 7H), 2.0 (s, 2H), 1.73-1.59 (m, 7H), 1.35-1.11 (m, 2H), 0.97-0.77 (m, 2H) |

| Example No. | Chemical Name | Structure | ES/MS (m/z) (M + H) | ¹H NMR (400 MHz, DMSO-d₆) |
|---|---|---|---|---|
| 22 | 1-[(4-fluorophenyl)-methyl-carbamoyl]-4-[2-(N-(3-methyl-cyclohexyl)anilino)-2-oxo-ethyl]piperidine-4-carboxylic acid | 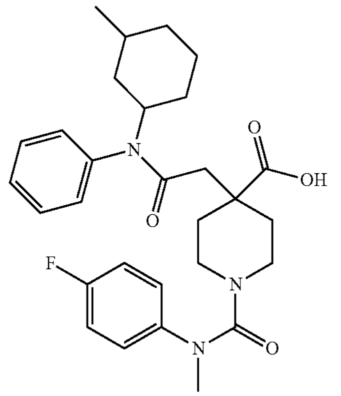 [SMILES: CC1CCCC(N(C(=O)CC2(C(=O)O)CCN(C(=O)N(C)c3ccc(F)cc3)CC2)c2ccccc2)C1] | 510.2 | 12.04 (s, 1H), 7.56-7.35 (m, 3H), 7.23-6.99 (m, 6H), 4.62-4.30 (m, 1H), 3.16 (s, 3H), 3.13-2.88 (m, 5H), 2.0 (s, 2H), 1.73-1.20 (m, 7H), 1.20-1.05 (m, 2H), 0.99 (d, J = 7.3 Hz, 3H), 0.83-0.79 (m, 2H) |
| 24 | 4-[2-(N-(3-fluorophenyl)anilino)-2-oxo-ethyl]-1-[(4-fluorophenyl)-methyl-carbamoyl]piperidine-4-carboxylic acid | 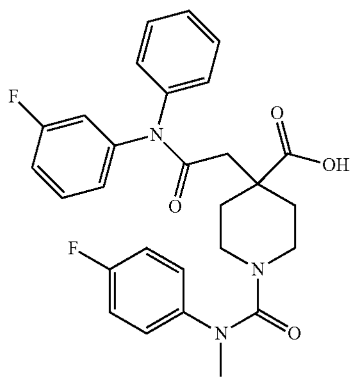 [SMILES: CN(C(=O)N1CCC(CC(=O)N(c2ccccc2)c2cccc(F)c2)(C(=O)O)CC1)c1ccc(F)cc1] | 508.2 | 12.33 (s, 1H), 7.57-6.97 (m, 13H), 3.24-3.10 (m, 2H), 3.05 (s, 3H), 3.07-2.93 (m, 2H), 2.41 (s, 2H), 1.81-1.67 (m, 2H), 1.39-1.22 (m, 2H). |
| 25 | 1-[(4-fluorophenyl)-methyl-carbamoyl]-4-[2-(N-(3-methoxyphenyl)anilino)-2-oxo-ethyl]piperidine-4-carboxylic acid | 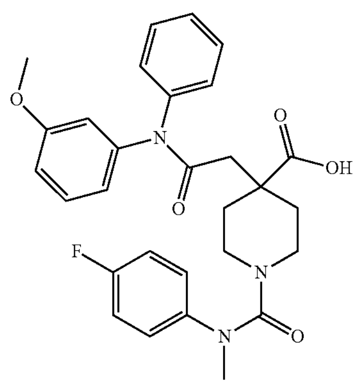 [SMILES: COc1cccc(N(C(=O)CC2(C(=O)O)CCN(C(=O)N(C)c3ccc(F)cc3)CC2)c2ccccc2)c1] | 520.2 | 12.25 (s, 1H), 7.57-6.63 (m, 13H), 3.70 (s, 3H), 3.22-3.10 (m, 2H), 3.05-2.90 (m, 4H), 2.41 (s, 3H), 1.79-1.69 (m, 2H), 1.35-1.22 (m, 2H). |
| 27 | 4-[2-(N-cyclohexyl-3-fluoro-anilino)-2-oxo-ethyl]-1-[(4-fluorophenyl)-methyl-carbamoyl]piperidine-4-carboxylic acid | 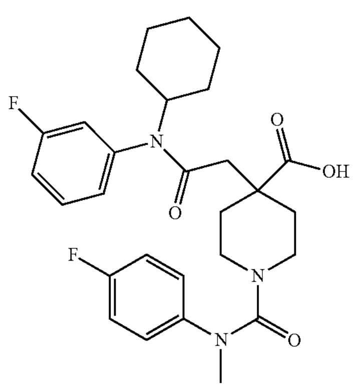 [SMILES: CN(C(=O)N1CCC(CC(=O)N(c2cccc(F)c2)C2CCCCC2)(C(=O)O)CC1)c1ccc(F)cc1] | 514.2 | 12.13 (s, 1H), 7.50 (q, J = 7.6 Hz, 1H), 7.29 (td, J = 8.4, 2.1 Hz, 1H), 7.16-7.07 (m, 5H), 6.99 (d, J = 8.1 Hz, 1H), 4.34-4.27 (m, 1H) 3.16-2.86 (m, 6H), 2.0 (s, 2H), 1.76-1.58 (m, 5H), 1.55-1.43 (m, 2H), 1.32-1.12 (m, 5H), 0.96-0.79 (m, 3H) |

-continued

| Example No. | Chemical Name | Structure | ES/MS (m/z) (M + H) | $^1$H NMR (400 MHz, DMSO-$d_6$) |
|---|---|---|---|---|
| 28 | 1-[(4-fluorophenyl)-methyl-carbamoyl]-4-[2-(N-(4-isopropylphenyl)anilino)-2-oxo-ethyl]piperidine-4-carboxylic acid | 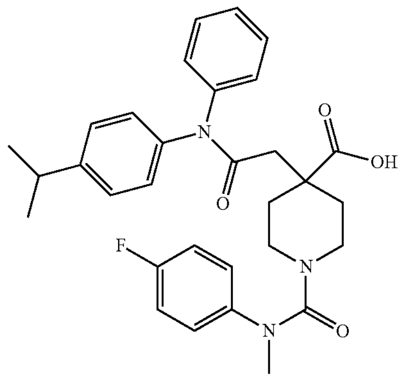 [SMILES: CC(C)c1ccc(N(C(=O)CC2(C(=O)O)CCN(C(=O)N(C)c3ccc(F)cc3)CC2)c2ccccc2)cc1] | 532.2 | 12.27 (s, 1H), 7.56-6.93 (m, 13H), 3.20-3.09 (m, 2H), 3.05-2.81 (m, 5H), 2.40 (s, 2H), 1.80-1.68 (m, 2H), 1.34-1.09 (m, 9H) |
| 29 | 1-[(4-fluorophenyl)-methyl-carbamoyl]-4-[2-oxo-2-[N-(p-tolyl)anilino]ethyl]piperidine-4-carboxylic | 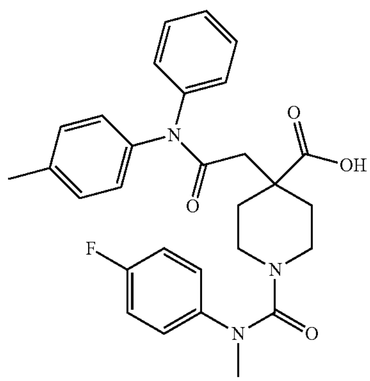 [SMILES: Cc1ccc(N(C(=O)CC2(C(=O)O)CCN(C(=O)N(C)c3ccc(F)cc3)CC2)c2ccccc2)cc1] | 504.2 | 12.27 (s, 1H), 7.51-6.97 (m, 13H), 3.20-3.10 (m, 2H), 3.05-2.91 (m, 5H), 2.42-2.22 (m, 3H), 1.79-1.68 (m, 2H), 1.33-1.20 (m, 4H) |
| 30 | 4-[2-(N-(4-fluorophenyl)anilino)-2-oxo-ethyl]-1-[(4-fluorophenyl)-methyl-carbamoyl]piperidine-4-carboxylic acid | 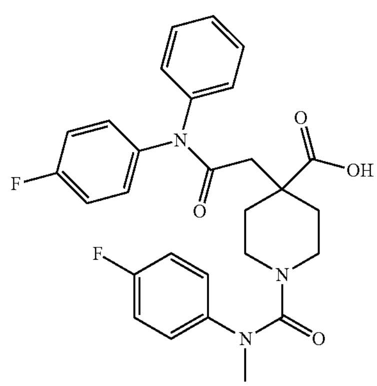 [SMILES: CN(C(=O)N1CCC(CC(=O)N(c2ccccc2)c2ccc(F)cc2)(C(=O)O)CC1)c1ccc(F)cc1] | 508.2 | 12.29 (s, 1H), 7.51-6.97 (m, 13H), 3.19-3.08 (m, 2H), 3.05-2.91 (m, 5H), 2.40 (s, 2H), 1.79-1.69 (m, 2H), 1.34-1.17 (m, 2H) |
| 31 | -[2-(N-(4-chlorophenyl)anilino)-2-oxo-ethyl]-1-[(4-fluorophenyl)-methyl-carbamoyl]piperidine-4-carboxylic acid | 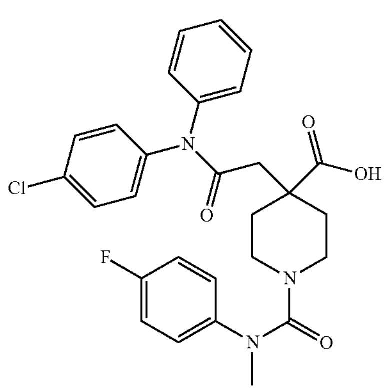 [SMILES: CN(C(=O)N1CCC(CC(=O)N(c2ccccc2)c2ccc(Cl)cc2)(C(=O)O)CC1)c1ccc(F)cc1] | 524.2 | 12.32 (s, 1H), 7.72-7.03 (m, 13H), 3.19-3.08 (m, 2H), 3.05-2.91 (m, 5H), 2.41 (s, 2H), 1.79-1.69 (m, 2H), 1.36-1.19 (m, 2H) |

-continued
| Example No. | Chemical Name | Structure | ES/MS (m/z) (M + H) | ¹H NMR (400 MHz, DMSO-d₆) |
|---|---|---|---|---|
| 32 | 4-[2-(N-(2-fluorophenyl)anilino)-2-oxo-ethyl]-1-[(4-fluorophenyl)-methyl-carbamoyl]piperidine-4-carboxylic acid | 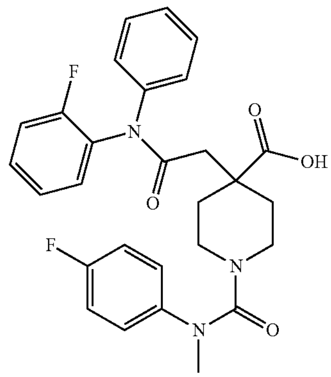 [SMILES: CN(C(=O)N1CCC(CC(=O)N(c2ccccc2)c2ccccc2F)(C(=O)O)CC1)c1ccc(F)cc1] | 508.2 | 12.29 (s, 1H), 7.60-7.02 (m, 13H), 3.19-3.08 (m, 2H), 3.05-2.91 (m, 5H), 2.06 (s, 2H), 1.79-1.69 (m, 2H), 1.36-1.19 (m, 2H) |
Example No. 20 was Prepared According to Scheme 7
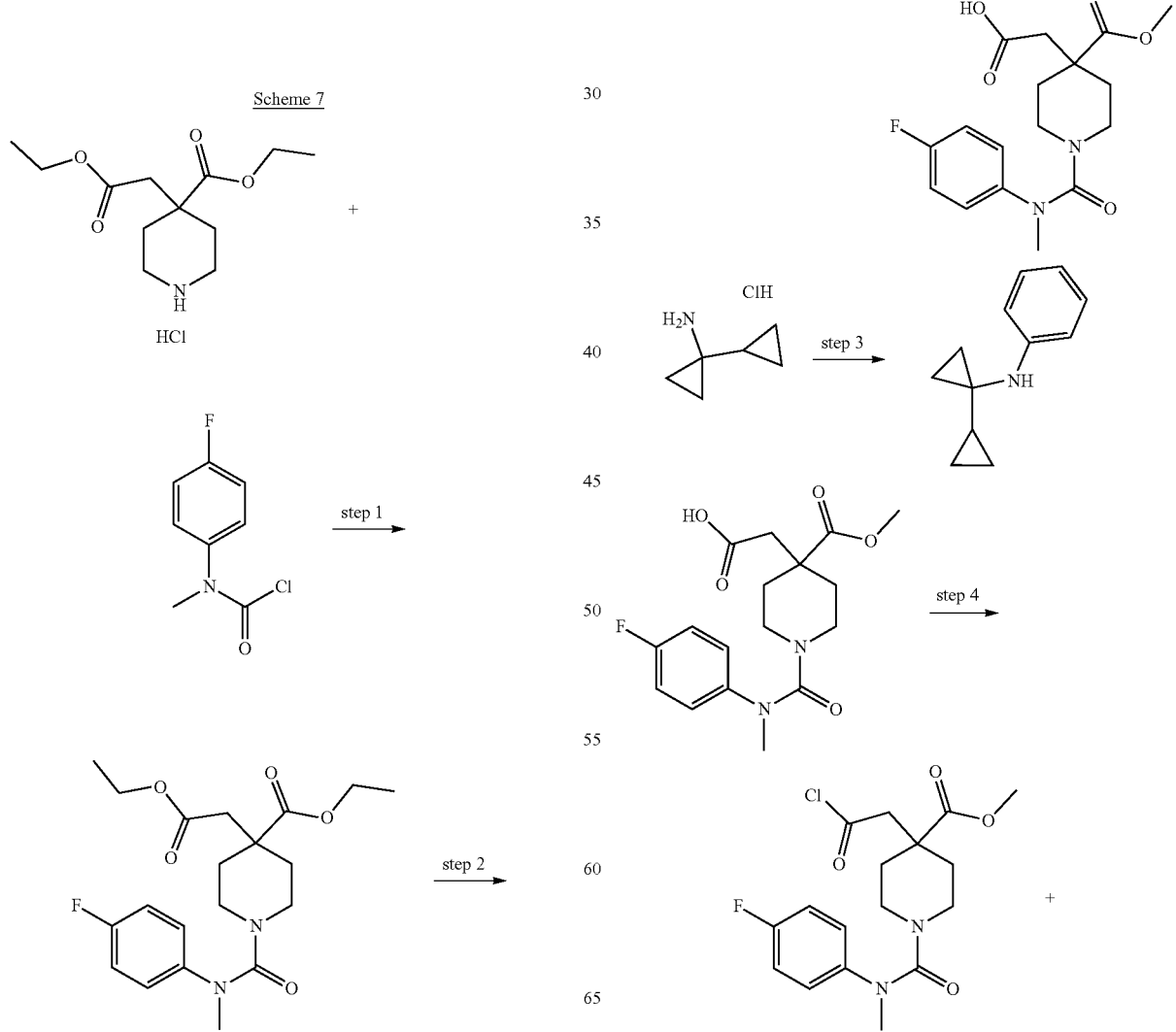

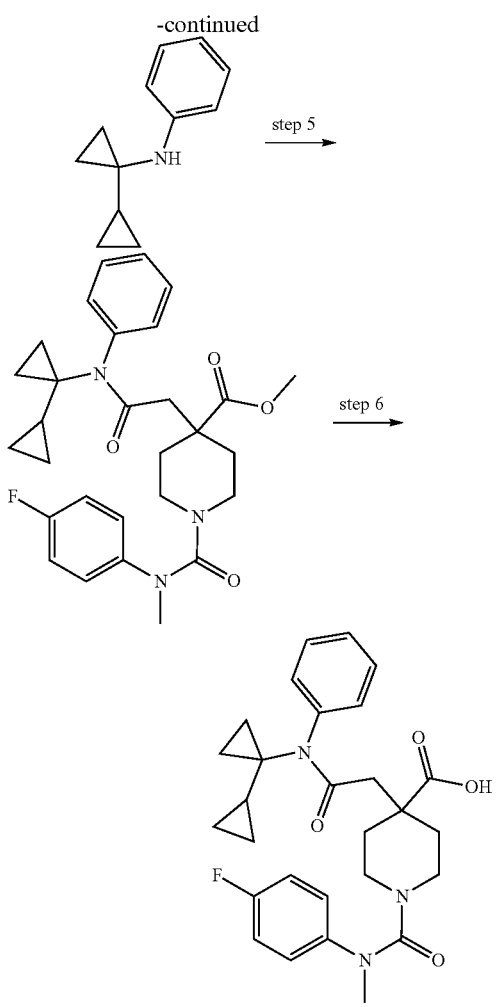

Step 1 was Prepared According to Scheme 5 Step 3

Step 2: 2-[1-[(4-fluorophenyl)-methyl-carbamoyl]-4-methoxycarbonyl-4-piperidyl]acetic acid

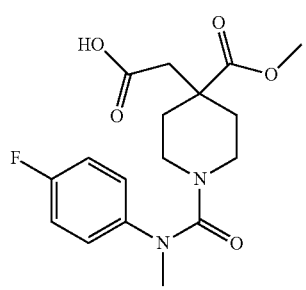 [SMILES: COC(=O)C1(CC(=O)O)CCN(C(=O)N(C)c2ccc(F)cc2)CC1]

Potassium carbonate (3.00 g, 21.7 mmol) was added to ethyl 4-(2-ethoxy-2-oxo-ethyl)-1-[(4-fluorophenyl)-methyl-carbamoyl]piperidine-4-carboxylate (5.03 g, 12.68 mmol) in methanol (20 mL), water (2 mL) and stirred at 60° C. After 18 hours, the reaction was cooled, 5 N aqueous hydrochloric acid was added until pH 3.0 and the mixture was extracted with DCM. The organic layers were combined; dried over MgSO₄; filtered and concentrated under reduced pressure to give a residue. The residue was purified by silica gel flash chromatography, eluting with DCM to 40% of (MeOH:DCM (20:80)) to give the title compound (0.80 g, 20% yield). MS m/z 353.2 (M+H).

Step 3: N-(1-cyclopropylcyclopropyl)aniline

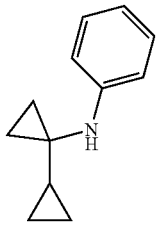 [SMILES: c1ccc(NC2(C3CC3)CC2)cc1]

In the glove box, 1-cyclopropylcyclopropanamine;hydrochloride (0.30 g, 2.25 mmol), sodium tert butoxide (0.48 g, 4.9 mmol) and [BrettPhos Pd(crotyl)]OTf (0.83 g, 0.098 mmol) were added as solids to a 25 mL Biotage tube containing a stir bar. 1,4-dioxane (4.5 mL) and chlorobenzene (0.27 g, 2.41 mmol) were then added. The tube was capped and removed from the glove box. It was heated at 85° C. in a Biotage Initiator microwave. After 10 minutes of heating, the temperature was stable at 85° C. and the pressure 0 bar. After 12 hours, the reaction mixture was cooled and filtered through a small plug of celite. The celite was rinsed with DCM. The filtrate was diluted to 45 mL with DCM. The solution was washed with 20 mL of saturated ammonium chloride. The organics were dried over Na₂SO₄ and evaporated. The residue was dissolved in dichloromethane and loaded onto silica gel and purified on a 40 g silica column using 5%-20% EtOAc in hexanes. Fractions were combined and evaporated. The residue was then dried under vacuum to give the title compound (0.240 g, 61% yield). MS m/z 174.2 (M+H). $^1$H NMR (CD₂Cl₂) d: 7.19-7.14 (m, 2H), 6.84-6.81 (m, 2H), 6.71-6.67 (m, 1H), 4.39-4.28 (m, 1H), 1.41-1.34 (m, 1H), 0.73-0.69 (m, 2H), 0.66-0.63 (m, 2H), 0.45-0.40 (m, 2H), 0.19-0.15 (m, 2H).

Step 4 and Step 5: methyl 4-[2-(N-(1-cyclopropylcyclopropyl)anilino)-2-oxo-ethyl]-1-[(4-fluorophenyl)-methyl-carbamoyl]piperidine-4-carboxylate

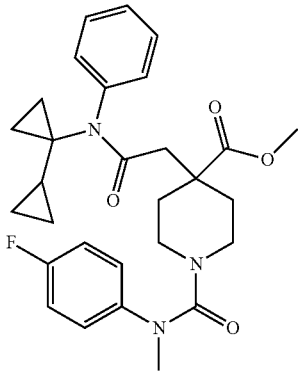 [SMILES: COC(=O)C1(CC(=O)N(c2ccccc2)C2(C3CC3)CC2)CCN(C(=O)N(C)c2ccc(F)cc2)CC1]

Thionyl chloride (1.0 mL, 13.7 mmol) was added was added to a solution of (2-[4-methoxycarbonyl-1-[(4-fluorophenyl)-methyl-carbamoyl]-4-piperidyl]acetic acid (0.47 g, 1.33 mmol) in chloroform (20 mL) and tetrahydrofuran (10 mL) and stirred at 60° C. After 1 hours, concentrated under reduced pressure to give methyl 4-(2-chloro-2-oxo-ethyl)-1-[(4-fluorophenyl)-methyl-carbamoyl]piperidine-4-carboxylate (0.49 g, 99% yield).

N-(1-cyclopropylcyclopropyl)aniline (0.23 g, 0.30 mmol) in DCM (10.0 mL) and pyridine (0.600 mL, 7.42 mmol) was added to a solution of methyl 4-(2-chloro-2-oxo-ethyl)-1-[(4-fluorophenyl)-methyl-carbamoyl]piperidine-4-carboxylate (0.49 g, 1.33 mmol) in DCM (10 mL) and stirred at 60° C. After 2 hours, the reaction mixture was quenched with brine and extracted with ethyl acetate. The organic layers were combined, dried over MgSO₄, filtered, and concentrated under reduced pressure to give a residue. The residue was purified by silica gel flash chromatography, eluting with EtOAc: hexane (90:10) to give the title compound (0.10 g, 14% yield). MS m/z 508.4 (M+H).

Step 6: 4-[2-(N-(1-cyclopropylcyclopropyl)anilino)-2-oxo-ethyl]-1-[(4-fluorophenyl)-methyl-carbamoyl]piperidine-4-carboxylic acid (Example No. 20)

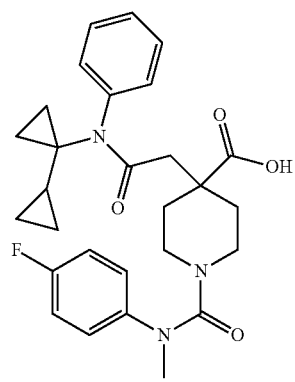 [SMILES: CN(C(=O)N1CCC(CC(=O)N(c2ccccc2)C2(C3CC3)CC2)(C(=O)O)CC1)c1ccc(F)cc1]

N aqueous sodium hydroxide (4.81 mL, 24.0 mmol) was added to a solution of methyl 4-[2-(N-(1-cyclopropylcyclopropyl)anilino)-2-oxo-ethyl]-1-[(4-fluorophenyl)-methyl-carbamoyl]piperidine-4-carboxylate (0.10 g, 1.00 mmol) in methanol (5 mL) and stirred at 80° C. After 18 hours, the reaction mixture was concentrated under reduced pressure. The aqueous layer was acidified with HCl until pH-2 and extracted with dichloromethane. The organic layers were combined, dried over MgSO₄, filtered, and concentrated under reduced pressure to give a residue. The residue was purified by reverse phase prep-HPLC water BEH HILIC 100×30 mm 5u, 110A with 15×30 mm BEH HILIC guard column and column Phenomenex Kinetex EVO C18, 100×30 mm, 5u, 100A with 15×30 mm EVO guard column using inline heater at 50° C. using high pH is aqueous 10 mM ammonium bicarbonate pH 10/5% MeOH (A solvent) and ACN (B solvent), eluting 14%-48% B in 10 minutes. The appropriate fractions were collected and lyophilized to give title compound (0.021 g, 21.6% yield). MS m/z 494.2 (M+H). ¹H NMR (DMSO-d₆) δ 7.58-7.01 (m, 9H), 3.63-2.83 (m, 7H), 2.12-1.63 (m, 7H), 1.29-1.13 (m, 2H), 0.65-0.31 (m, 6H).

Example No. 42 was Prepared According to Scheme 8

Scheme 8

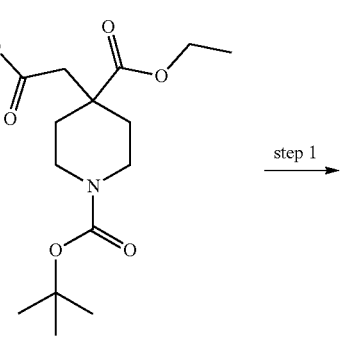

step 1

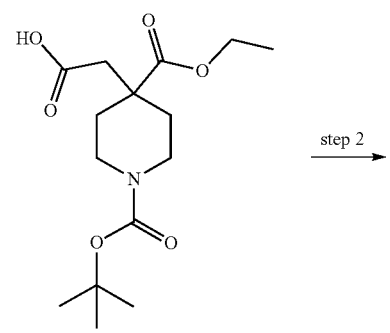

step 2

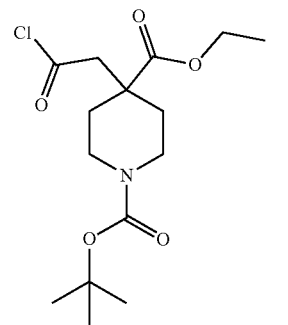

+

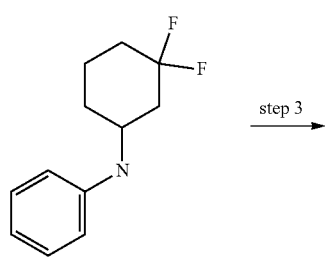

step 3

-continued

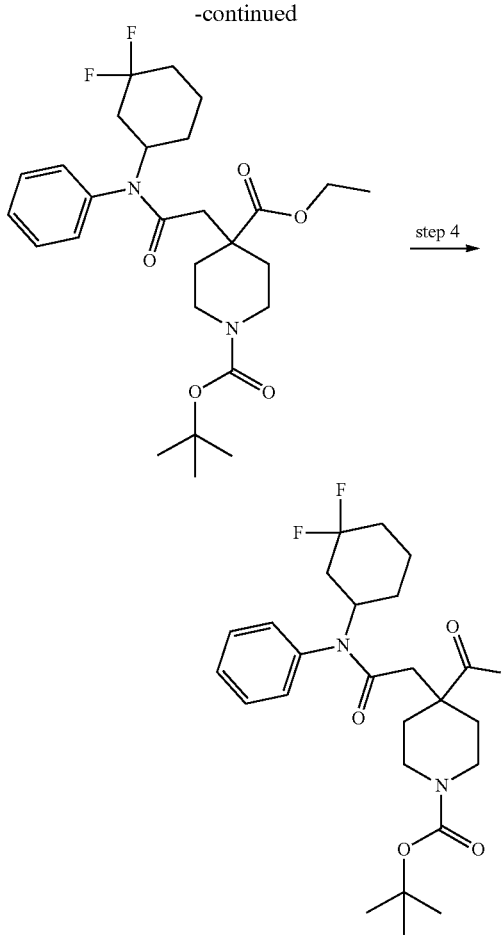

step 4

Step 1

2-(1-tert-butoxycarbonyl-4-ethoxycarbonyl-4-piperidyl)acetic acid

To a 1 L round bottom flask, potassium carbonate (8.6 g, 62 mmol) was added in the solution of 1-tert-butyl 4-ethyl 4-(2-ethoxy-2-oxo-ethyl)piperidine-1,4-dicarboxylate (10.4 g, 30.3 mmol) in methanol (100 mL) and water (5 mL). Reaction was stirred at 60° C. After 14 h, the reaction was concentrated under reduced pressure, then diluted in EtOAc and concentrated again. The reaction was diluted in EtOAc and water, then adjusted pH to ~pH3 using 5 N HCl. The reaction was extracted with EtOAc, the combined organic solution was washed with brine, dried over Na$_2$SO$_4$, filtered, and concentrated to give title product, the material was used directly in the next step. MS (m/z): 216.0 (M+H-Boc).

Steps 2 and 3

Racemic 1-tert-butyl 4-ethyl 4-[2-(N-(3,3-difluorocyclohexyl)anilino)-2-oxo-ethyl]piperidine-1,4-dicarboxylate

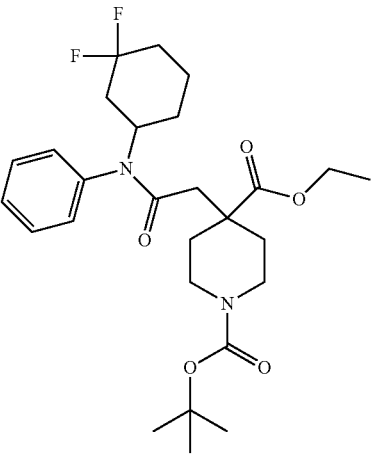 [SMILES: CCOC(=O)C1(CC(=O)N(c2ccccc2)C2CCCC(F)(F)C2)CCN(C(=O)OC(C)(C)C)CC1]

Step 2: Thionyl chloride (10 mL, 137.3 mmol, 100 mass %) was added to the solution of 2-(1-tert-butoxycarbonyl-4-ethoxycarbonyl-4-piperidyl)acetic acid (8.9 g, 28 mmol) in chloroform (100 mL) and reaction was heated at 60° C. for 30 minutes. The reaction solvent was evaporated, the treated with toluene and concentrated (repeated twice) to remove excess of thionyl chloride, the crude product was dried in the vacuum oven at 50° C. for an hour and used directly in the next step.

Step 3: 1-tert-butyl 4-ethyl 4-(2-chloro-2-oxo-ethyl)piperidine-1,4-dicarboxylate (13.76 g, 29.27 mmol, 71 mass %) in CAN (150 mL, 2850 mmol, 99.8 mass %) was combined with N-(3,3-difluorocyclohexyl)aniline (Scheme 2/step 9, 6.2 g, 29 mmol, 100 mass %) followed by pyridine (12 mL, 151.7 mmol, 100 mass %) and heated to 60° C. under nitrogen. Held the reaction at this temperature for an hour, then concentrated to give a residue, which was loaded on 25 g silica column and subjected to flash chromatography, 300 g of silica gel column, eluted with 0 to 100% EtOAc/hexanes, the fraction containing product was pulled together and concentrated to give a mixture. This mixture was dissolved in minimum volume of DMSO and purified on reverse phase chromatography using C18 column. The product containing fractions were combined, removed CH3CN and then extracted with EtOAc X2 (2×100 mL), washed with brine, dried over Na$_2$SO$_4$, filtered, and concentrated to the title product. MS m/z 509.0 (M+H-Boc). ES/MS (m/z) (M+H) 509.0.

Chiral separation of racemic 1-tert-butyl 4-ethyl 4-[2-(N-(3,3-difluorocyclohexyl)anilino)-2-oxo-ethyl]piperidine-1,4-dicarboxylate The racemic racemic 1-tert-butyl 4-ethyl 4-[2-(N-(3,3-difluorocyclohexyl)anilino)-2-oxo-ethyl]piperidine-1,4-dicarboxylate 1.6 g was purified by SFC-80, Chiralpak IG (30×250 mm); mobile phase: A: CO2; B: EtOH, eluting with 10% B, flow rate: 70 mL/min The eluent of first peak was collected and lyophilized to give the isomer 1 of title compound (583.7 mg, 48.6% yield, ee: >99%). MS (m/z) 509.2 (M+H). The eluent of second peak was collected and lyophilized to give the isomer 2 of title compound (567.2 mg, 47.2% yield, ee: 98.4%). MS (m/z) 509.2 (M+H).

Step 4

Isomer 2 1-tert-butyl 4-ethyl 4-[2-oxo-2-(N-3,3-difluorocyclohexyl]anilino)ethyl]piperidine-1,4-dicarboxylate, (Example No. 42)

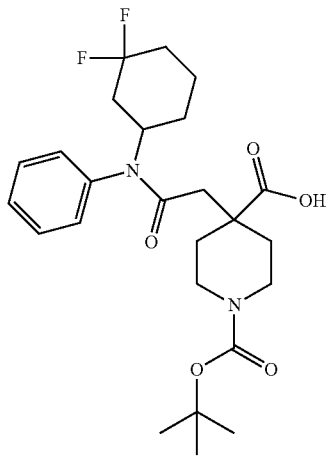 [SMILES: CC(C)(C)OC(=O)N1CCC(CC(=O)N(c2ccccc2)C2CCCC(F)(F)C2)(C(=O)O)CC1]

To a solution of isomer 2, 1-tert-butyl 4-ethyl 4-[2-oxo-2-(N-3,3-difluorocyclohexyl]anilino)ethyl]piperidine-1,4-dicarboxylate, (50 mg, 0.098 mmol, 100 mass %) in tetrahydrofuran (2 mL), a sodium hydroxide aqueous solution (10 mol/L, 1 ml) with methanol (1 mL) was added. The reaction was heated to 80° C. After overnight heating, the reaction was cooled to room temperature and then evaporated all volatiles under a stream of nitrogen with heat. Diluted mixture with EtOAc (~15 mL) and ~5 mL water, then added hydrochloric acid (1 mol/L) in diethyl ether (1 mL, 5 mmol, 5 mol/L) to neutralize pH. Extracted organics with EtOAc twice, the combined organic solvent was washed with brine, dried over $Na_2SO_4$, filtered, concentrated and dried in vacuum oven the weekend at 50° C. to give title product. MS (m/z): 479.4 (M−H). 1H NMR (400.13 MHz, $CDCl_3$): 7.53-7.49 (m, 3H), 7.11 (br s, 2H), 4.86-4.80 (m, 1H), 3.62-3.53 (m, 2H), 3.31-3.23 (m, 2H), 2.33-2.24 (m, 3H), 2.11-2.01 (m, 3H), 1.96-1.89 (m, 1H), 1.85-1.73 (m, 1H), 1.71-1.57 (m, 2H), 1.45 (s, 9H), 1.35-1.28 (m, 3H), 1.25-1.18 (m, 1H).

Example 2. Assay for In Vitro Binding Affinity

Compound Solubilization

Test and reference compounds were received as dry powder reagents, weighed, and solubilized in 100% DMSO to generate a working stock concentration of 10 mM.
Membrane Preparation Protocol ($hAT_2R$ HEK293 and $rAT_2R$ HEK293)

$hAT_2R$ membranes were prepared from human embryonic kidney (HEK293) cells which were stably transfected with recombinant human angiotensin-II receptor subtype 2 ($hAT_2R$). Cells from the stable cell lines were expanded in tissue culture flasks to generate a large population of cells; cell pellet (>1 gm), and these cell pellets were stored frozen prior to initiating this membrane isolation procedure for each receptor isoform. Frozen cell pellets were thawed in ice-cold homogenization/resuspension buffer (50 mM Tris-HCl, pH 7.5) containing one Complete© protease inhibitor tablet with EDTA (Roche Diagnostics) per 50 mL buffer, and cell pellet was resuspended at a ratio of 10 mL homogenization buffer to gram of starting cell pellet. Cell suspension was homogenized with an overhead motor-driven Teflon-glass homogenizer using 15 to 20 strokes, followed by centrifugation at 1100×g for 10 minutes at 4° C. The supernatant was saved on ice, pellets were homogenized as before, and centrifuged at 1100×g for 10 minutes at 4° C. Both supernatants were combined and subsequently centrifuged at 35,000×g for 60 minutes at 4° C. The final centrifugation pellet (pellet 2) containing the isolated membranes was resuspended in buffer (4 to 5 mL/g of starting cell paste) containing protease inhibitors and quick frozen in liquid nitrogen prior to storage at −80° C. Protein concentration was determined using a BCA kit (ThermoScientific, Inc.) with bovine serum albumin (BSA) as standard.

Membranes hATIR/CHO were Purchased from PerkinElmer, Inc.

Cellular membranes prepared from Chinese hamster ovary (CHO) cells which expressed recombinant human angiotensin-II receptor subtype I ($hAT_1R$), were purchased from PerkinElmer (Catalog Number ES-072-M400UA).

Receptor Binding Protocol

Receptor binding affinities ($K_i$) were determined from a competitive radioligand binding assay with human recombinant ($[^{125}I]$-Tyr4)-Angiotensin-II (2200 Ci/mmol) from Perkin Elmer (Cat. #NEX1050). The assays were performed with a scintillation proximity assay (SPA) method using polyvinyltoluene (PVT) wheat germ agglutinin-coupled SPA beads (Perkin Elmer Cat. #RPNQ0001). Assay buffer containing BSA (50 mM Tris-HCl, pH 7.5, 150 mM NaCl, 0.1% w/v fatty-acid free BSA) was used for preparing radioligand, membrane and SPA bead reagent dilution to working stock concentrations. Reference control and test compounds were diluted to obtain ten-point concentration response curves using a four-fold serial dilution protocol onto assay plates, dispensed acoustically from DMSO stock using automated ECHO instrument technology (Labcyte, Inc.). Concentration response curves were routinely generated with the highest final assay concentration for the reference angiotensin-II control at 50 nM, and the highest final assay concentration for the test compounds at 50 μM. To quantitate the concentration of [125I]-tyr4 angiotensin-II used in each assay, after this radioligand was diluted on the day of testing (2.5-fold working stock), direct counts of this stock were measured by removing four aliquots of 20 μL and counted on a Wizard2 Gamma Counter (PerkinElmer). The $hAT_2R$ membrane was combined with PVT-WGA SPA beads to obtain a final assay concentration of 0.25 μg/well $hAT_2R$ membrane+0.1 mg/well PVT-WGA SPA bead. And the $hAT_1R$ membrane PVT-WGA SPA bead final concentrations was 0.5 μg/well $hAT_1R$ membrane+0.1 mg/well PVT-WGA SPA bead. All binding assays were initiated by dispensing the 2.5-fold radioligand stock directly into the 384 well assay plate (Greiner bio-one, Catalog #781095, white clear bottom), adding 20 μL of this radioligand stock to a calculated final assay concentration of 66 μM. For all assays, radioligand addition was followed by the addition of membrane-SPA bead mixture, i.e., the $hAT_2R$ membrane-SPA bead mixture (30 μL), the $rAT_2R$ membrane-SPA bead mixture, or the $AT_1R$ membrane-SPA bead mixture (30 μL) into the assay plate. All dispensing steps were added using a Multiflo FX (Biotek, Inc.) bulk dispensing instrument. After reagent addition steps, assay plates were sealed, and plate contents mixed for one minute on a benchtop microplate shaker. Following a 10-hour incubation at room temperature to allow for bead settling and radioligand binding, bound radioactivity was quantitated using a Microbeta Trilux scintillation counter (Perkin Elmer) and expressed as counts per minute (CPM). The unlabeled angiotensin-II control was included on each plate as an experimental assay reference. Results for experimental test compounds were confirmed in duplicate experiments; run in separate experiments to obtain an n=2, or greater.

Data Analysis Procedures

Compounds were tested in a 10-point concentration response curve (CRC) format, with each plate containing the positive control angiotensin-II positive reference compound, and experimental compounds. Maximum binding response (Max) was determined in 32 control wells per plate using assay buffer treatment only, and the minimum binding controls or nonspecific binding response (Min) was also determined in 32 wells per plate by the treatment with 50 nM angiotensin-II. All test sample concentration responses were normalized to the control response and calculated as a percent of the maximal response after correcting for nonspecific binding as shown below:

% Specific inhibition=100%−[(CPM−Min)/(Max−Min)×100%]

Percent specific binding (y-axis) was plotted versus the log concentration of compound (x-axis). The concentration causing 50% inhibition of binding ($IC_{50}$) was determined from 4-parameter logistic non-linear regression analysis (Analyzer, version 17, GeneData Screener). The affinity constant ($K_i$) was calculated from the $IC_{50}$ value from the equation:

$$K_i = IC_{50}/(1+L/K_d)$$

where L was the radioligand concentration used in the experiment (determined for each experiment by counting aliquots of the radioligand mix) and $K_d$ was the equilibrium binding affinity constant of the radioligand determined from saturation binding analysis: $hAT_2R$ $K_d$=0.066 nM, and $hAT_1R$ $K_d$=0.178 nM.

Binding affinities for compounds of the present disclosure were determined according to the assay described herein.

| Example No. | $AT_2R$ Ki (μM) | $AT_1R$ Ki (μM) |
|---|---|---|
| 1 | 0.0832 | 80.3 |
| 2 | 0.000352 | 37.33 |
| 3 | 0.00536 | |
| 4 | 0.00513 | |
| 5 | 0.00915 | |
| 6 | 0.00908 | |
| 7 | 0.000382 | |
| 8 | 0.00302 | |
| 9 | 0.00262 | |
| 10 | 0.00156 | |
| 11 | 0.000336 | |
| 12 | 0.000521 | |
| 13 | 0.00144 | |
| 14 | 0.00258 | |
| 15 | 0.00169 | |
| 16 | 0.00176 | |
| 17 | 0.00582 | |
| 18 | 0.00959 | |
| 19 | 0.000428 | 37.3 |
| 20 | 0.00211 | |
| 21 | 0.00401 | |
| 22 | 0.000573 | |
| 23 | 0.000823 | |
| 24 | 0.000774 | |
| 25 | 0.0027 | |
| 26 | 0.00539 | |
| 27 | 0.0004 | |
| 28 | 0.00339 | |
| 29 | 0.00311 | |
| 30 | 0.000716 | 37.3 |
| 31 | 0.00189 | |
| 32 | 0.000345 | |
| 33 | 0.00194 | |
| 34 | 0.00432 | |
| 35 | 0.00279 | 37.3 |
| 35A (isomer 1) | 0.0108 | |
| 35B (isomer 2) | 0.00103 | 37.3 |
| 36 | 0.00443 | |
| 37 | 0.000987 | |
| 38 | 0.00646 | |
| 39 | 0.00282 | |
| 40 | 0.00137 | |
| 41 | 0.0166 | |
| 41A (isomer 1) | 0.00889 | |
| 41B (isomer 2) | 0.0147 | |
| 42 | 0.00394 | |
| 43 | 0.00293 | |
| 43A (isomer 1) | 0.00219 | |
| 43B (isomer 2) | 0.0201 | |
| 44 | 0.000311 | |
| 44A (isomer 1) | 0.000899 | |
| 44B (isomer 2) | 0.000114 | 37.3 |
| 45 | 0.00312 | |
| 45A (isomer 1) | 0.00155 | |
| 45B (isomer 2) | 0.00268 | |
| 46 | 0.000409 | |
| 47 | 0.00134 | 37.3 |
| 48 | 0.00359 | |
| 49 | 0.00521 | |
| 50 | 0.00138 | 37.3 |
| 51 | 0.000471 | 37.3 |
| 52 | 0.000580 | |
| 53 | 0.000342 | 37.3 |
| 54 | 0.002 | |
| 55 | 0.00311 | |
| 56 | 0.00299 | |
| 57 | 0.00782 | |
| 58 | 0.00986 | |
| 59 | 0.00423 | |
| 60 | 0.00318 | |
| 61 | 0.00373 | |
| 62 | 0.00104 | |
| 63 | 0.00119 | |
| 64 | 0.00104 | |
| 65 | 0.00255 | |
| 66 | 0.000619 | 37.3 |
| 67 | 0.00231 | 37.3 |
| 68 | 0.00293 | |
| 69 | 0.00924 | |
| 70 | 0.00939 | |
| 71 | 0.00314 | |
| 72 | 0.00109 | |
| 72A (isomer 1) | 0.00814 | |
| 72B (isomer 2) | 0.000383 | |
| 73 | 0.00303 | |
| 74B (isomer 2) | 0.00128 | >49.9 |

Example 3. Comparative Data for $AT_2R$ and $AT_1R$ Ex Vivo Human Binding Affinity Binding affinities for compounds of the present disclosure were determined according to the assay described above.

| Example No. | AT$_2$R Ki (μM) | AT$_1$R Ki (μM) |
| --- | --- | --- |
| 1 | 0.0832 | 80.3 |
| 2 | 0.000352 | 37.33 |
| 19 | 0.000428 | 37.3 |
| 30 | 0.000716 | 37.3 |
| 35 | 0.00279 | 37.3 |
| 35B (isomer 2) | 0.00103 | 37.3 |
| 44B (isomer 2) | 0.000114 | 37.3 |
| 47 | 0.00134 | 37.3 |
| 50 | 0.00138 | 37.3 |
| 51 | 0.000471 | 37.3 |
| 53 | 0.000342 | 37.3 |
| 66 | 0.000619 | 37.3 |
| 67 | 0.00231 | 37.3 |
| 74B (isomer 2) | 0.00128 | >49.9 |

Select compounds of the present disclosure are up to 10,000-fold more selective for AT$_2$R compared to AT$_1$R. Compounds selective for AT$_2$R compared to AT$_1$R may provide more potent analgesic effects.

Example 4. AT$_2$R Ex Vivo Autoradiography and Rat Binding Affinity

The ability for a compound to engage its target may be measured by determining compound's receptor occupancy. An ex vivo autoradiography assay was conducted as described herein.

Twenty male Sprague Dawley rats (140-150 gms, Envigo) were maintained under controlled laboratory conditions on a 12 hr light cycle with ad lib access to food and water. On the morning of the experiment, rats were orally dosed with vehicle (1% (w/v) hydroxyethylcellulose, 0.25% (w/v) polysorbate 80, 0.05% (v/v) antifoam 1510-US in purified water) or appropriate doses of test compound (5 mL/kg, n=4 rats/group) using the same vehicle. Following a pre-determined survival time, plasma and adrenals were collected and frozen at −80° C. until analyzed. Frozen 20 μm sections of an adrenal from each animal were collected onto gelatin-coated slides and stored at −80° C. Autoradiography to detect AT$_2$R occupancy (RO) was conducted under cold conditions using methods modified from F. M. J. Heemskerk, et al, Brain Research 677 (1995) 29-38. Total binding was defined by 0.3 nM $^{125}$I-CGP42112 (selective AT$_2$R agonist, Perkin Elmer, Inc) with the addition of 10 μM unlabeled AngII used to define non-specific binding. Following exposure to a phosphoimager plate (BAS TR2025, GE Healthcare), the bound radioactivity is calculated with use of MCID software (Imaging Research, Inc) and calibrated $^{125}$I standards (American Radiolabeled Chemicals, Inc). The specific ligand binding for each animal is calculated by subtracting the non-specific binding from the total bound.

Following the above procedure, the RO of select compounds was determined as shown below. Compounds of the present disclosure showed high levels of RO.

| Example No. | rat K$_i$ (nM) | dose (mg/kg) | % RO |
| --- | --- | --- | --- |
| EMA401 | 4.47 | 10 | 17.32 |
| | | 30 | 84.74 |
| | | 100 | 93.74 |
| 1 | 28.2 | 3 | 23.41 |
| | | 10 | 44.60 |
| | | 30 | 41.65 |
| | | 100 | 54.63 |
| 2 | 0.476 | 0.03 | 32.484 |
| | | 0.01 | 38.138 |
| | | 0.3 | 69.001 |
| | | 1 | 88.562 |
| | | 3 | 91.343 |
| | | 10 | 93.211 |
| | | 30 | 87.251 |
| 3 | 2.19 | 0.3 | 37.84 |
| | | 1 | 61.87 |
| | | 3 | 83.52 |
| | | 10 | 90.53 |
| 7 | 1.09 | 3 | 89.99 |
| | | 10 | 96.82 |
| | | 30 | 101.83 |
| | | 100 | 96.71 |
| 18 | 0.614 | 0.01 | 16.323 |
| | | 0.03 | 64.997 |
| | | 0.1 | 76.306 |
| | | 0.3 | 79.307 |
| | | 1 | 93.157 |
| | | 3 | 90.865 |
| | | 10 | 92.964 |
| 30 | 0.6 | 0.03 | 3.458 |
| | | 0.01 | 30.365 |
| | | 0.3 | 45.608 |
| | | 3 | 88.705 |
| 74B | 0.67 | | |

Further, the amount of test compound present in each plasma sample was determined and plotted vs % receptor occupancy values to calculate the IC50/IC80 values as shown below (GraphPad Prism).

| Example No. | dose (mg/kg) | [plasma, free, nM] | ex vivo IC50 (nM) | ex vivo IC80 (nM) | ex vivo IC50 (TER) | ex vivo IC80 (TER) |
| --- | --- | --- | --- | --- | --- | --- |
| EMA401 | 10 | 2.14 | 0.483 | 3.03 | 0.108 | 0.678 |
| | 30 | 6.28 | | | | |
| | 100 | 15.7 | | | | |
| | 1 | 6.39 | | | | |
| | 3 | 18.9 | | | | |
| | 10 | 58.2 | | | | |
| 1 | 3 | 0.729 | 5.643 | 22.57 | 0.200 | 0.800 |
| | 10 | 2.25 | | | | |
| | 30 | 6.42 | | | | |
| | 100 | 10.4 | | | | |
| 2 | 0.03 | 0.0403 | 0.08 | 0.236 | 0.168 | 0.496 |
| | 0.01 | 0.0697 | | | | |
| | 0.3 | 0.153 | | | | |
| | 3 | 0.772 | | | | |
| 3 | 0.3 | 0.482 | 0.8211 | 3.339 | 0.375 | 1.525 |
| | 1 | 1.74 | | | | |
| | 3 | 5.99 | | | | |
| | 10 | 15.8 | | | | |
| 18 | 0.01 | 0.0298 | 0.114 | 0.449 | 0.186 | 0.731 |
| | 0.03 | 0.224 | | | | |
| | 0.1 | 0.476 | | | | |
| | 1 | 2.57 | | | | |
| 74B | | | 1.58 | 3.82 | 2.358 | 5.701 |

Example 5. Inhibition of C21-Induced Increase in Dermal Blood Flow

Male Sprague Dawley rats (n=6-8/group, 250-350 grams, Envigo) were maintained under controlled laboratory conditions on a 12-hour light cycle with ad lib access to food and water. On the day of testing, rats were dosed (p.o. or s.c.) with the test compound or the corresponding vehicle. At a pre-determined time post-dosing of the test compound, anesthesia was induced with 5% isoflurane. Once anesthetized the abdomen was shaved and the animal was placed in a custom-made dark box instrumented with a heater (WPI Air Therm) that maintained the temperature in the box between 29 and 30° C. A rectal temperature probe, heating pad and temperature controller (Harvard Apparatus) was also used to maintain body temperature of the rat during the procedure. Anesthesia was maintained during the entire experiment utilizing lower doses of isoflurane (1-3%). Once the body temperature was stabilized at approximately 36.5° C., two baseline dermal blood flow scans were performed 2.5 minutes apart using Moor Laser Doppler Imager (Model LDI2-IR). The $AT_2R$ agonist C21, or vehicle, was injected intradermally (30 uL) and dermal blood flow was monitored for 25 minutes. Data were analyzed using Moor version 6.0 software in the region of interest and the inhibition of increased dermal blood flow was calculated. Inhibition of the C21-induced dermal blood flow indicates the compounds are acting as $AT_2R$ antagonists. It is understood that the compounds of the present disclosure may act as $AT_2R$ antagonists, as exemplified by Example No. 3 acting as a antagonist.

| Example No. | rat $K_i$ (nM) | dose (mg/kg) | % Inhibition | |
|---|---|---|---|---|
| EMA401 | 4.47 | 1 | 7.8 | |
| | | 3 | 47.2 | |
| | | 10 | 67.6 | |
| | | 30 | 86.9 | 97.3 |
| 3 | 2.19 | 0.3 | 49.6 | |
| | | 3 | 62.9 | |
| | | 10 | 74.3 | 95.6 |

Example 6. X-Ray Crystallographic Analysis on Example No. 44B

X-ray crystal analysis was performed to determine the absolute configuration of Example No. 44B as described below.

Description of Equipment and Data Collection

Instrument: Rigaku Oxford Diffraction XtaLAB Synergy four-circle diffractometer equipped with a HyPix-6000HE area detector.

Cryogenic system: Oxford Cryostream 800

Cu: λ=1.54184 Å, 50W, Micro focus source with multi-layer mirror (μ-CMF).

Distance from the crystal to the CCD detector: d=35 mm

Tube Voltage: 50 kV

Tube Current: 1 mA

A total of 46940 reflections were collected in the 2θ range from 7.622 to 133.178. The limiting indices were: $-9 \leq h \leq 10$, $-15 \leq k \leq 15$, $-27 \leq l \leq 27$; which yielded 9241 unique reflections (Rint=0.0489). The structure was solved using SHELXT (Sheldrick, G. M. 2015. Acta Cryst. A71, 3-8) and refined using SHELXL (against $F^2$) (Sheldrick, G. M. 2015. Acta Cryst. C71, 3-8). The total number of refined parameters was 835, compared with 9241 data. All reflections were included in the refinement. The goodness of fit on $F^2$ was 1.073 with a final R value for [I>2σ (I)] R1=0.0412 and wR2=0.1114. The largest differential peak and hole were 0.57 and −0.38 Å-3, respectively.

Description of Crystal Preparation 48 mg of the amorphous compound was dissolved in 480 μL methanol and kept in a half sealed 4 mL vial. The solution was allowed to evaporate slowly at room temperature. Crystals were observed in the second day.

Results Summary

The crystal was a colourless block with the following dimensions: 0.20×0.20×0.10 mm³. The symmetry of the crystal structure was assigned the monoclinic space group P21 with the following parameters: a=8.92190(10) Å, b=12.6874(2) Å, c=23.2348(3) Å, α=90°, β=93.1960(10°), γ=90°, V=2625.99(6) Å3, Z=4, Dc=1.345 g/cm3, F(000)=1120.0, μ(CuKα)=0.878 mm-1, and T=150.00(10) K. The absolute configuration structure is as follows:

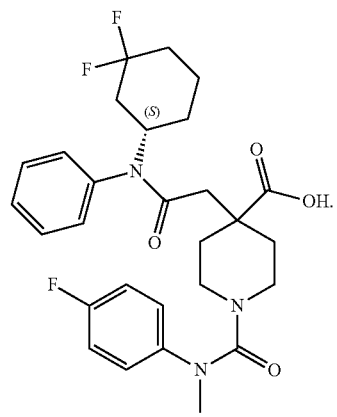

Absolute configuration structure

We claim:
1. A compound of formula (I):

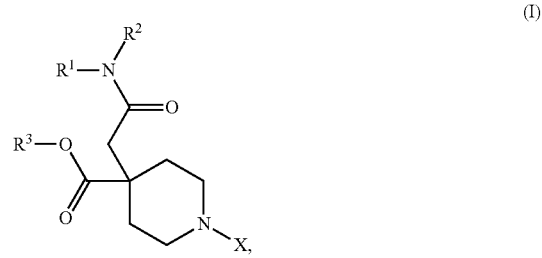

wherein:
$R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;
each $R^{1a}$ independently is halogen, $C_1$-$C_6$ alkyl, $C_1$-$C_6$ alkoxyl, or $C_3$-$C_6$ cycloalkyl;
$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;
each $R^{2a}$ independently is halogen, $C_1$-$C_6$ alkyl, $C_1$-$C_6$ alkoxyl, or $C_3$-$C_6$ cycloalkyl;
$R^3$ is H or $C_1$-$C_6$ alkyl;
X is $C_5$-$C_{10}$ heteroaryl, $C_6$-$C_{10}$ aryl,

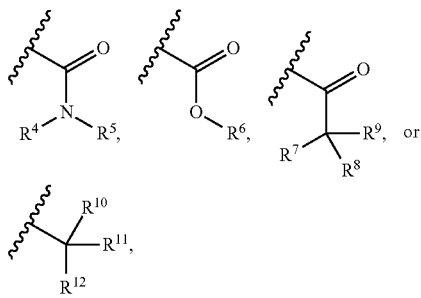

wherein the $C_5$-$C_{10}$ heteroaryl or $C_6$-$C_{10}$ aryl is optionally substituted with one or more $X^a$;
  each $X^a$ independently is halogen, $C_1$-$C_6$ alkyl, $C_1$-$C_6$ alkoxyl, or $C_3$-$C_6$ cycloalkyl;
  $R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;
  each $R^{4a}$ independently is halogen, cyano, $C_1$-$C_6$ alkyl, $C_1$-$C_6$ alkoxyl, or $C_3$-$C_6$ cycloalkyl;
  $R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;
  each $R^{5a}$ independently is halogen, cyano, $C_1$-$C_6$ alkyl, $C_1$-$C_6$ alkoxyl, or $C_3$-$C_6$ cycloalkyl;
  $R^6$ is H or $C_1$-$C_6$ alkyl;
  $R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;
  each $R^{7a}$ independently is halogen, cyano, or $C_3$-$C_6$ cycloalkyl;
  $R^8$ is H, halogen, or $C_1$-$C_6$ alkyl;
  $R^9$ is H, halogen, or $C_1$-$C_6$ alkyl, wherein $R^8$ and $R^9$ may alternatively come together to form a $C_3$-$C_6$ cycloalkyl;
  $R^{10}$ and $R^{11}$ are each H or $R^{10}$ and $R^{11}$ together form an oxo;
  $R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and
  each $R^{12a}$ independently is halogen, cyano, $C_1$-$C_6$ alkyl, $C_1$-$C_6$ alkoxyl, or $C_3$-$C_6$ cycloalkyl,
or a pharmaceutically acceptable salt thereof.

2. The compound of claim 1, wherein the compound is of formula,

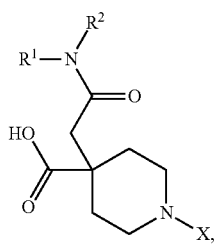

wherein:
  $R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;
  each $R^{1a}$ independently is halogen, $C_1$-$C_6$ alkyl, $C_1$-$C_6$ alkoxyl, or $C_3$-$C_6$ cycloalkyl;
  $R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;
  each $R^{2a}$ independently is halogen, $C_1$-$C_6$ alkyl, $C_1$-$C_6$ alkoxyl, or $C_3$-$C_6$ cycloalkyl;
  X is $C_5$-$C_{10}$ heteroaryl, $C_6$-$C_{10}$ aryl,

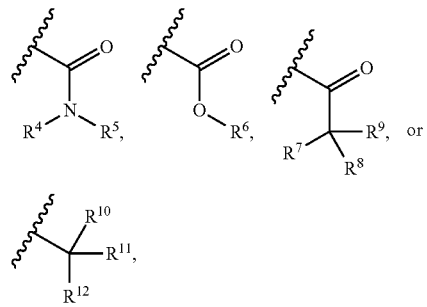

wherein the $C_5$-$C_{10}$ heteroaryl or $C_6$-$C_{10}$ aryl is optionally substituted with one or more $X^a$;
  each $X^a$ independently is halogen, $C_1$-$C_6$ alkyl, $C_1$-$C_6$ alkoxyl, or $C_3$-$C_6$ cycloalkyl;
  $R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;
  each $R^{4a}$ independently is halogen, cyano, $C_1$-$C_6$ alkyl, $C_1$-$C_6$ alkoxyl, or $C_3$-$C_6$ cycloalkyl;
  $R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;
  each $R^{5a}$ independently is halogen, cyano, $C_1$-$C_6$ alkyl, $C_1$-$C_6$ alkoxyl, or $C_3$-$C_6$ cycloalkyl;
  $R^6$ is H or $C_1$-$C_6$ alkyl;
  $R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;
  each $R^{7a}$ independently is halogen, cyano, or $C_3$-$C_6$ cycloalkyl;
  $R^8$ is H, halogen, or $C_1$-$C_6$ alkyl;
  $R^9$ is H, halogen, or $C_1$-$C_6$ alkyl; or
  $R^8$ and $R^9$ together form a $C_3$-$C_6$ cycloalkyl;
  $R^{10}$ and $R^{11}$ are each H or $R^{10}$ and $R^{11}$ together form an oxo;
  $R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and
  each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

3. The compound of claim 1, wherein the compound is of formula,

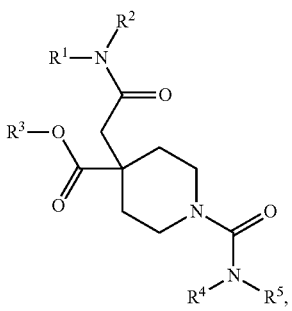

wherein:
R$^1$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{1a}$;
each R$^{1a}$ independently is halogen, C$_1$-C$_6$ alkyl, C$_1$-C$_6$ alkoxyl, or C$_3$-C$_6$ cycloalkyl;
R$^2$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{2a}$;
each R$^{2a}$ independently is halogen, C$_1$-C$_6$ alkyl, C$_1$-C$_6$ alkoxyl, or C$_3$-C$_6$ cycloalkyl;
R$^3$ is H or C$_1$-C$_6$ alkyl;
R$^4$ is H, C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{4a}$;
each R$^{4a}$ independently is halogen, cyano, C$_1$-C$_6$ alkyl, C$_1$-C$_6$ alkoxyl, or C$_3$-C$_6$ cycloalkyl;
R$^5$ is H, C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{5a}$; and
each R$^{5a}$ independently is halogen, cyano, C$_1$-C$_6$ alkyl, C$_1$-C$_6$ alkoxyl, or C$_3$-C$_6$ cycloalkyl; or a pharmaceutically acceptable salt thereof.

4. The compound of claim 1, wherein the compound is of formula,

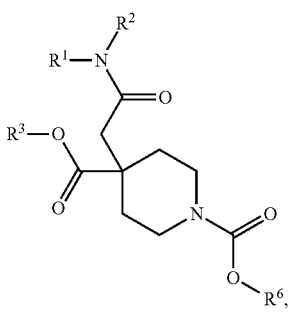

wherein:
R$^1$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{1a}$;
each R$^{1a}$ independently is halogen, C$_1$-C$_6$ alkyl, C$_1$-C$_6$ alkoxyl, or C$_3$-C$_6$ cycloalkyl;
R$^2$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{2a}$;
each R$^{2a}$ independently is halogen, C$_1$-C$_6$ alkyl, C$_1$-C$_6$ alkoxyl, or C$_3$-C$_6$ cycloalkyl;
R$^3$ is H or C$_1$-C$_6$ alkyl; and
R$^6$ is H or C$_1$-C$_6$ alkyl; or a pharmaceutically acceptable salt thereof.

5. The compound of claim 1, wherein the compound is of formula,

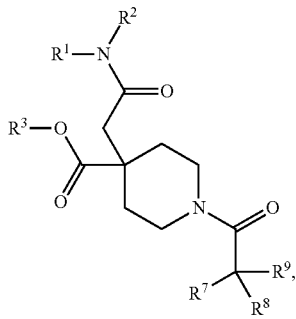

wherein:
R$^1$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{1a}$;
each R$^{1a}$ independently is halogen, C$_1$-C$_6$ alkyl, C$_1$-C$_6$ alkoxyl, or C$_3$-C$_6$ cycloalkyl;
R$^2$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{2a}$;
each R$^{2a}$ independently is halogen, C$_1$-C$_6$ alkyl, C$_1$-C$_6$ alkoxyl, or C$_3$-C$_6$ cycloalkyl;
R$^3$ is H or C$_1$-C$_6$ alkyl;
R$^7$ is C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{7a}$;
each R$^{7a}$ independently is halogen, cyano, or C$_3$-C$_6$ cycloalkyl;
R$^8$ is H, halogen, or C$_1$-C$_6$ alkyl; and
R$^9$ is H, halogen, or C$_1$-C$_6$ alkyl; or
R$^8$ and R$^9$ together form a C$_3$-C$_6$ cycloalkyl; or a pharmaceutically acceptable salt thereof.

6. The compound of claim 1, wherein the compound is of formula,

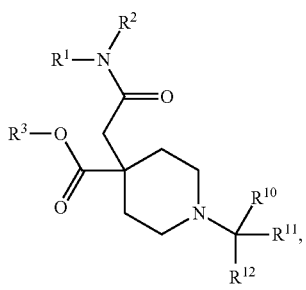

wherein:
R$^1$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{1a}$;

each $R^{1a}$ independently is halogen, $C_1$-$C_6$ alkyl, $C_1$-$C_6$ alkoxyl, or $C_3$-$C_6$ cycloalkyl;

$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;

each $R^{2a}$ independently is halogen, $C_1$-$C_6$ alkyl, $C_1$-$C_6$ alkoxyl, or $C_3$-$C_6$ cycloalkyl;

$R^3$ is H or $C_1$-$C_6$ alkyl;

$R^{10}$ and $R^{11}$ are each H or $R^{10}$ and $R^{11}$ together form an oxo;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

7. The compound of claim 1, wherein the compound is of formula,

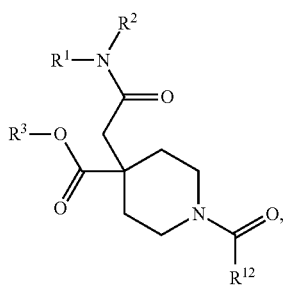

wherein:

$R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;

each $R^{1a}$ independently is halogen, $C_1$-$C_6$ alkyl, $C_1$-$C_6$ alkoxyl, or $C_3$-$C_6$ cycloalkyl;

$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;

each $R^{2a}$ independently is halogen, $C_1$-$C_6$ alkyl, $C_1$-$C_6$ alkoxyl, or $C_3$-$C_6$ cycloalkyl;

$R^3$ is H or $C_1$-$C_6$ alkyl;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

8. The compound of claim 1, wherein the compound is of formula,

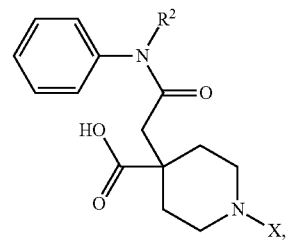

wherein:

$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;

each $R^{2a}$ independently is halogen, $C_1$-$C_6$ alkyl, $C_1$-$C_6$ alkoxyl, or $C_3$-$C_6$ cycloalkyl;

X is $C_5$-$C_{10}$ heteroaryl, $C_6$-$C_{10}$ aryl,

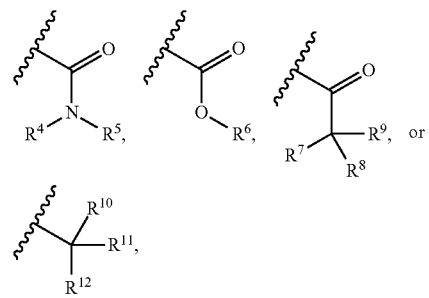

wherein the $C_5$-$C_{10}$ heteroaryl or $C_6$-$C_{10}$ aryl is optionally substituted with one or more $X^a$;

each $X^a$ independently is halogen, $C_1$-$C_6$ alkyl, $C_1$-$C_6$ alkoxyl, or $C_3$-$C_6$ cycloalkyl;

$R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;

each $R^{4a}$ independently is halogen, cyano, $C_1$-$C_6$ alkyl, $C_1$-$C_6$ alkoxyl, or $C_3$-$C_6$ cycloalkyl;

$R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;

each $R^{5a}$ independently is halogen, cyano, $C_1$-$C_6$ alkyl, $C_1$-$C_6$ alkoxyl, or $C_3$-$C_6$ cycloalkyl;

$R^6$ is H or $C_1$-$C_6$ alkyl;

$R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;

each $R^{7a}$ independently is halogen, cyano, or $C_3$-$C_6$ cycloalkyl;

$R^8$ is H, halogen, or $C_1$-$C_6$ alkyl;

$R^9$ is H, halogen, or $C_1$-$C_6$ alkyl; or $R^8$ and $R^9$ together form a $C_3$-$C_6$ cycloalkyl;

$R^{10}$ and $R^{11}$ are each H or $R^{10}$ and $R^{11}$ together form an oxo;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

9. The compound of claim 1, wherein the compound is of formula,

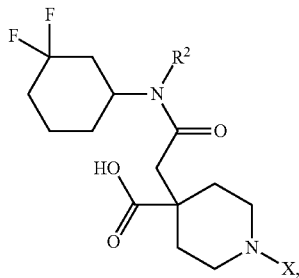

wherein:
R$^2$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{2a}$;
each R$^{2a}$ independently is halogen, C$_1$-C$_6$ alkyl, C$_1$-C$_6$ alkoxyl, or C$_3$-C$_6$ cycloalkyl;
X is C$_5$-C$_{10}$ heteroaryl, C$_6$-C$_{10}$ aryl,

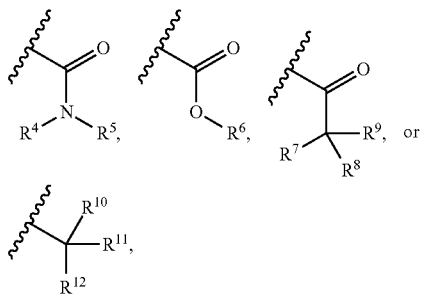

wherein the C$_5$-C$_{10}$ heteroaryl or C$_6$-C$_{10}$ aryl is optionally substituted with one or more X$^a$;
each X$^a$ independently is halogen, C$_1$-C$_6$ alkyl, C$_1$-C$_6$ alkoxyl, or C$_3$-C$_6$ cycloalkyl;
R$^4$ is H, C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{4a}$;
each R$^{4a}$ independently is halogen, cyano, C$_1$-C$_6$ alkyl, C$_1$-C$_6$ alkoxyl, or C$_3$-C$_6$ cycloalkyl;
R$^5$ is H, C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{5a}$;
each R$^{5a}$ independently is halogen, cyano, C$_1$-C$_6$ alkyl, C$_1$-C$_6$ alkoxyl, or C$_3$-C$_6$ cycloalkyl;
R$^6$ is H or C$_1$-C$_6$ alkyl;
R$^7$ is C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{7a}$;
each R$^{7a}$ independently is halogen, cyano, or C$_3$-C$_6$ cycloalkyl;
R$^8$ is H, halogen, or C$_1$-C$_6$ alkyl;
R$^9$ is H, halogen, or C$_1$-C$_6$ alkyl; or
R$^8$ and R$^9$ together form a C$_3$-C$_6$ cycloalkyl;
R$^{10}$ and R$^{11}$ are each H or R$^{10}$ and R$^{11}$ together form an oxo;
R$^{12}$ is C$_1$-C$_6$ alkyl, C$_3$-C$_6$ cycloalkyl, C$_6$-C$_{10}$ aryl, C$_1$-C$_3$-(phenyl), or C$_3$-C$_{10}$ heterocycloalkyl wherein the C$_1$-C$_6$ alkyl, C$_3$-C$_6$ cycloalkyl, C$_6$-C$_{10}$ aryl, C$_1$-C$_3$-(phenyl), or C$_3$-C$_{10}$ heterocycloalkyl is optionally substituted with one or more R$^{12a}$; and
each R$^{12a}$ independently is halogen, cyano, C$_1$-C$_6$ alkyl, C$_1$-C$_6$ alkoxyl, or C$_3$-C$_6$ cycloalkyl; or a pharmaceutically acceptable salt thereof.

10. The compound of claim 1, wherein the compound is of formula,

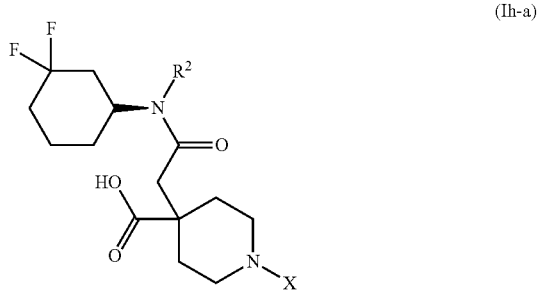

(Ih-a)

wherein:
R$^2$ is C$_1$-C$_6$ alkyl, C$_3$-C$_6$ cycloalkyl, C$_3$-C$_9$ heterocycloalkyl, or C$_6$-C$_{10}$ aryl, wherein the C$_1$-C$_6$ alkyl, C$_3$-C$_6$ cycloalkyl, C$_3$-C$_9$ heterocycloalkyl, or C$_6$-C$_{10}$ aryl is optionally substituted with one or more R$^{2a}$;
each R$^{2a}$ independently is halogen, C$_1$-C$_6$ alkyl, C$_1$-C$_6$ alkoxyl, or C$_3$-C$_6$ cycloalkyl;
X is C$_5$-C$_{10}$ heteroaryl, C$_6$-C$_{10}$ aryl,

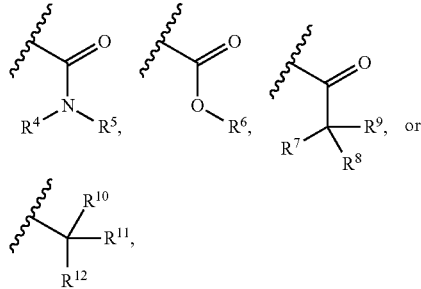

wherein the C$_5$-C$_{10}$ heteroaryl or C$_6$-C$_{10}$ aryl is optionally substituted with one or more X$^a$;
each X$^a$ independently is halogen, C$_1$-C$_6$ alkyl, C$_1$-C$_6$ alkoxyl, or C$_3$-C$_6$ cycloalkyl;
R$^4$ is H, C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{4a}$;
each R$^{4a}$ independently is halogen, cyano, C$_1$-C$_6$ alkyl, C$_1$-C$_6$ alkoxyl, or C$_3$-C$_6$ cycloalkyl;
R$^5$ is H, C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{5a}$;
each R$^{5a}$ independently is halogen, cyano, C$_1$-C$_6$ alkyl, C$_1$-C$_6$ alkoxyl, or C$_3$-C$_6$ cycloalkyl;
R$^6$ is H or C$_1$-C$_6$ alkyl;
R$^7$ is C$_1$-C$_6$ alkyl, C$_3$-C$_6$ cycloalkyl, or C$_6$-C$_{10}$ aryl, wherein the C$_1$-C$_6$ alkyl, C$_3$-C$_6$ cycloalkyl, or C$_6$-C$_{10}$ aryl is optionally substituted with one or more R$^{7a}$;
each R$^{7a}$ independently is halogen, cyano, or C$_3$-C$_6$ cycloalkyl;
R$^8$ is H, halogen, or C$_1$-C$_6$ alkyl;
R$^9$ is H, halogen, or C$_1$-C$_6$ alkyl; or
R$^8$ and R$^9$ together form a C$_3$-C$_6$ cycloalkyl;

$R^{10}$ and $R^{11}$ are each H or $R^{10}$ and $R^{11}$ together form an oxo;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

11. The compound of claim 1, wherein the compound is of formula,

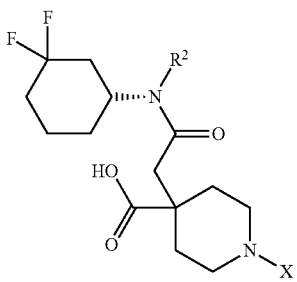

wherein:
$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$;

each $R^{2a}$ independently is halogen, $C_1$-$C_6$ alkyl, $C_1$-$C_6$ alkoxyl, or $C_3$-$C_6$ cycloalkyl;

X is $C_5$-$C_{10}$ heteroaryl, $C_6$-$C_{10}$ aryl,

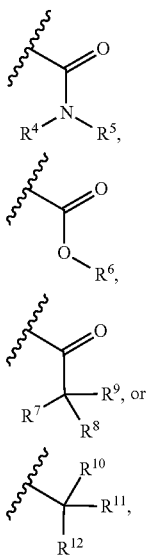

wherein the $C_5$-$C_{10}$ heteroaryl or $C_6$-$C_{10}$ aryl is optionally substituted with one or more $X^a$;

each $X^a$ independently is halogen, $C_1$-$C_6$ alkyl, $C_1$-$C_6$ alkoxyl, or $C_3$-$C_6$ cycloalkyl;

$R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;

each $R^{4a}$ independently is halogen, cyano, $C_1$-$C_6$ alkyl, $C_1$-$C_6$ alkoxyl, or $C_3$-$C_6$ cycloalkyl;

$R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;

each $R^{5a}$ independently is halogen, cyano, $C_1$-$C_6$ alkyl, $C_1$-$C_6$ alkoxyl, or $C_3$-$C_6$ cycloalkyl;

$R^6$ is H or $C_1$-$C_6$ alkyl;

$R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;

each $R^{7a}$ independently is halogen, cyano, or $C_3$-$C_6$ cycloalkyl;

$R^8$ is H, halogen, or $C_1$-$C_6$ alkyl;

$R^9$ is H, halogen, or $C_1$-$C_6$ alkyl; or $R^8$ and $R^9$ together form a $C_3$-$C_6$ cycloalkyl;

$R^{10}$ and $R^{11}$ are each H or $R^{10}$ and $R^{11}$ together form an oxo;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

12. The compound of claim 1, wherein the compound is of formula,

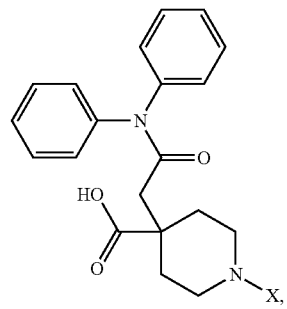

wherein:
X is $C_5$-$C_{10}$ heteroaryl, $C_6$-$C_{10}$ aryl,

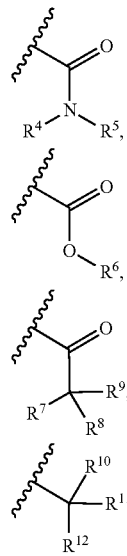

wherein the $C_5$-$C_{10}$ heteroaryl or $C_6$-$C_{10}$ aryl is optionally substituted with one or more $X^a$;

each $X^a$ independently is halogen, $C_1$-$C_6$ alkyl, $C_1$-$C_6$ alkoxyl, or $C_3$-$C_6$ cycloalkyl;

$R^4$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{4a}$;

each $R^{4a}$ independently is halogen, cyano, $C_1$-$C_6$ alkyl, $C_1$-$C_6$ alkoxyl, or $C_3$-$C_6$ cycloalkyl;

$R^5$ is H, $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{5a}$;

each $R^{5a}$ independently is halogen, cyano, $C_1$-$C_6$ alkyl, $C_1$-$C_6$ alkoxyl, or $C_3$-$C_6$ cycloalkyl;

$R^6$ is H or $C_1$-$C_6$ alkyl;

$R^7$ is $C_1$-$C_6$ alkyl, $C_3$-$C_6$ cycloalkyl, or $C_6$-$C_{10}$ aryl, wherein the $C_1$-$C_6$ alkyl, $C_3$-$C_6$ cycloalkyl, or $C_6$-$C_{10}$ aryl is optionally substituted with one or more $R^{7a}$;

each $R^{7a}$ independently is halogen, cyano, or $C_3$-$C_6$ cycloalkyl;

$R^8$ is H, halogen, or $C_1$-$C_6$ alkyl;

$R^9$ is H, halogen, or $C_1$-$C_6$ alkyl; or $R^8$ and $R^9$ together form a $C_3$-$C_6$ cycloalkyl;

$R^{10}$ and $R^{11}$ are each H or $R^{10}$ and $R^{11}$ together form an oxo;

$R^{12}$ is $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl wherein the $C_1$-$C_6$ alkyl, $C_3$-$C_6$ cycloalkyl, $C_6$-$C_{10}$ aryl, $C_1$-$C_3$-(phenyl), or $C_3$-$C_{10}$ heterocycloalkyl is optionally substituted with one or more $R^{12a}$; and each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

13. The compound of claim 1, wherein the compound is of formula,

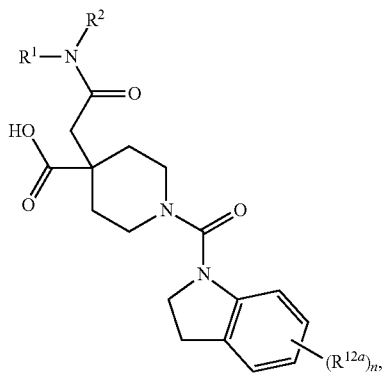

wherein:
n is 0, 1, or 2;
$R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;

each $R^{1a}$ independently is halogen, $C_1$-$C_6$ alkyl, $C_1$-$C_6$ alkoxyl, or $C_3$-$C_6$ cycloalkyl;

$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$; and each $R^{2a}$ independently is halogen, $C_1$-$C_6$ alkyl, $C_1$-$C_6$ alkoxyl, or $C_3$-$C_6$ cycloalkyl;

each $R^{12a}$ independently is halogen, cyano, $C_1$-$C_6$ alkyl, $C_1$-$C_6$ alkoxyl, or $C_3$-$C_6$ cycloalkyl; or a pharmaceutically acceptable salt thereof.

14. The compound of claim 1, wherein the compound is of formula,

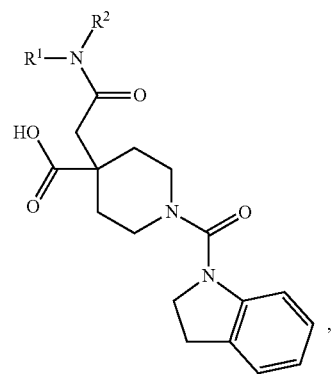

wherein:
$R^1$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{1a}$;

each $R^{1a}$ independently is halogen, $C_1$-$C_6$ alkyl, $C_1$-$C_6$ alkoxyl, or $C_3$-$C_6$ cycloalkyl;

$R^2$ is $C_1$-$C_6$ alkyl, $C_3$-$C_6$ cycloalkyl, $C_3$-$C_9$ heterocycloalkyl, or $C_6$-$C_{10}$ aryl, wherein the $C_1$-$C_6$ alkyl, $C_3$-$C_6$ cycloalkyl, $C_3$-$C_9$ heterocycloalkyl, or $C_6$-$C_{10}$ aryl is optionally substituted with one or more $R^{2a}$; and each $R^{2a}$ independently is halogen, $C_1$-$C_6$ alkyl, $C_1$-$C_6$ alkoxyl, or $C_3$-$C_6$ cycloalkyl; or a pharmaceutically acceptable salt thereof.

15. The compound of claim 1, wherein:
$R^1$ is methyl, ethyl, propyl, butan-2-yl, pentyl, 3-methylbutan-2-yl, cyclopropyl, cyclopentyl, cyclohexyl, tetrahydropyranyl, or phenyl, wherein the methyl, ethyl, propyl, butan-2-yl, pentyl, 3-methylbutan-2-yl, cyclopropyl, cyclopentyl, cyclohexyl, tetrahydropyranyl, or phenyl is optionally substituted with one or more $R^{1a}$;

each $R^{1a}$ independently is fluorine, chlorine, methyl, isopropyl, methoxyl, or cyclopropyl;

$R^2$ is methyl, ethyl, propyl, butan-2-yl, pentyl, 3-methylbutan-2-yl, cyclopropyl, cyclopentyl, cyclohexyl, tetrahydropyranyl, or phenyl, wherein the methyl, ethyl, propyl, butan-2-yl, pentyl, 3-methylbutan-2-yl, cyclopropyl, cyclopentyl, cyclohexyl, tetrahydropyranyl, or phenyl is optionally substituted with one or more $R^{2a}$;

each $R^{2a}$ independently is fluorine, chlorine, methyl, isopropyl, methoxyl, or cyclopropyl;

X is triazolyl, pyrimidinyl, pyridinyl, phenyl,

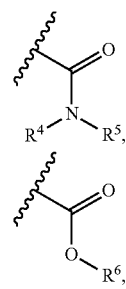

-continued

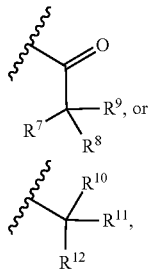

wherein the triazolyl, pyrimidinyl, pyridinyl, phenyl is optionally substituted with one or more $X^a$;
  each $X^a$ independently is bromine, pentyl, or cyclopropyl;
  $R^4$ is methyl, ethyl, isopropyl, pentyl, cyclopentyl, or phenyl, wherein the methyl, ethyl, isopropyl, pentyl, cyclopentyl, or phenyl is optionally substituted with one or more $R^{4a}$;
  each $R^{4a}$ independently is fluorine, methyl, methoxyl, or cyclopropyl;
  $R^5$ is methyl, ethyl, isopropyl, pentyl, cyclopentyl, or phenyl, wherein the methyl, ethyl, isopropyl, pentyl, cyclopentyl, or phenyl is optionally substituted with one or more $R^{5a}$;
  each $R^{5a}$ independently is fluorine, methyl, methoxyl, or cyclopropyl $R^6$ is tert-butyl;
  $R^7$ is phenyl optionally substituted with one or more $R^{7a}$;
  each $R^{7a}$ independently is fluorine;
  $R^8$ is H, F, or methyl;
  $R^9$ is H, F, or methyl; or
  $R^8$ and $R^9$ together form cyclopropyl;
  $R^{10}$ and $R^{11}$ are each H or $R^{10}$ and $R^{11}$ together form an oxo;
  $R^{12}$ is pyridyl, indolinyl, tetrahydroquinolinyl, phenyl, or isopropyl-phenyl, wherein the pyridyl, indolinyl, tetrahydroquinolinyl, phenyl, or isopropyl-phenyl is optionally substituted with one or more $R^{12a}$; and
  each $R^{2a}$ independently is fluorine, cyano, isopropyl, methoxyl, or cyclopropyl;
or a pharmaceutically acceptable salt thereof.

16. The compound of claim 1, wherein $R^1$ is phenyl and $R^2$ is phenyl, or a pharmaceutically acceptable salt thereof.

17. The compound of claim 1, wherein X is

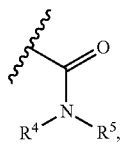

$R^4$ is phenyl, and $R^5$ is methyl, or a pharmaceutically acceptable salt thereof.

18. The compound of claim 1, wherein X is

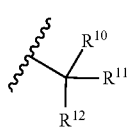

and $R^{10}$ and $R^{11}$ together form an oxo, or a pharmaceutically acceptable salt thereof.

19. The compound of claim 1, wherein at least one of $R^1$ and $R^2$ are

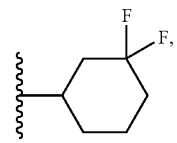

or a pharmaceutically acceptable salt thereof.

20. The compound of claim 1, wherein the compound is

| Structure |
| --- |
| 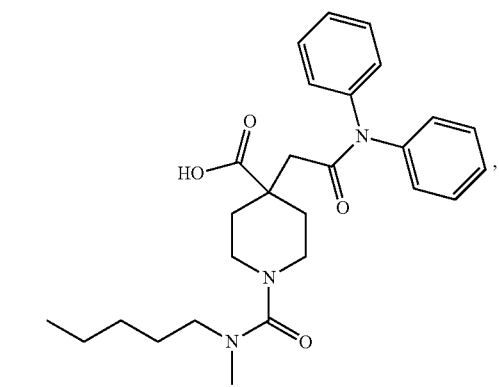 [SMILES: CCCCCN(C)C(=O)N1CCC(CC(=O)N(c2ccccc2)c2ccccc2)(C(=O)O)CC1] |
| 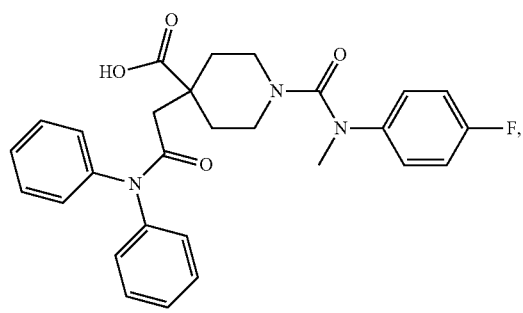 [SMILES: CN(C(=O)N1CCC(CC(=O)N(c2ccccc2)c2ccccc2)(C(=O)O)CC1)c1ccc(F)cc1] |
| 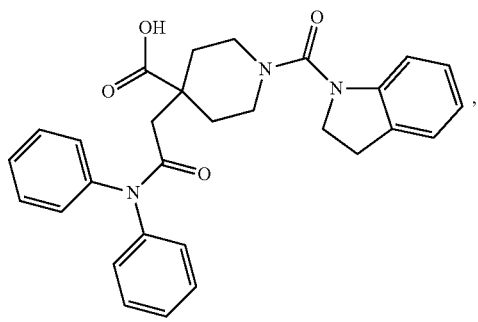 [SMILES: O=C(N1CCC(CC(=O)N(c2ccccc2)c2ccccc2)(C(=O)O)CC1)N1CCc2ccccc21] |

313
-continued
| Structure |
|---|
| 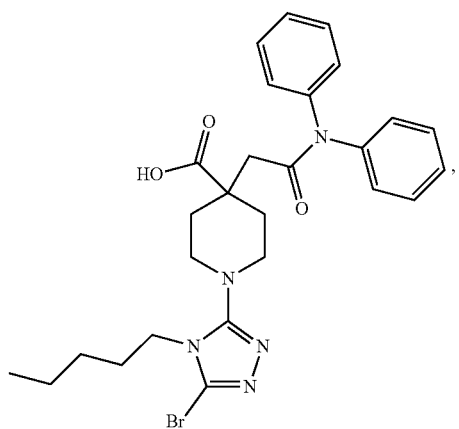 [SMILES: CCCCCn1c(Br)nnc1N1CCC(CC(=O)N(c2ccccc2)c2ccccc2)(C(=O)O)CC1] |
| 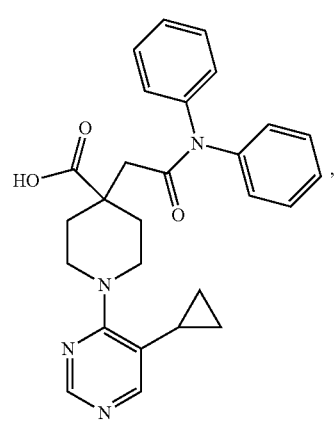 [SMILES: O=C(CC1(C(=O)O)CCN(c2ncncc2C2CC2)CC1)N(c1ccccc1)c1ccccc1] |
| 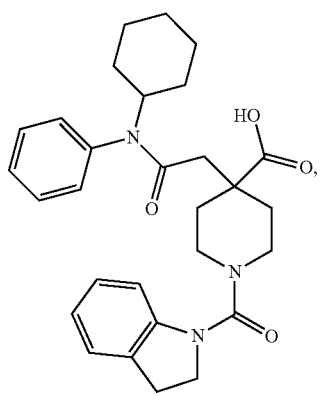 [SMILES: O=C(N1CCC(CC(=O)N(c2ccccc2)C2CCCCC2)(C(=O)O)CC1)N1CCc2ccccc21] |
| 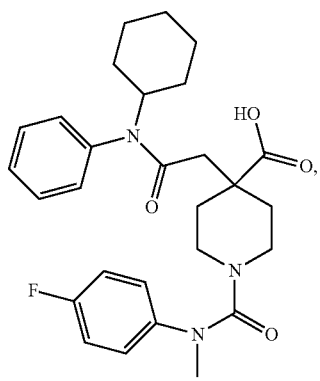 [SMILES: CN(C(=O)N1CCC(CC(=O)N(c2ccccc2)C2CCCCC2)(C(=O)O)CC1)c1ccc(F)cc1] |
314
-continued
| Structure |
|---|
| 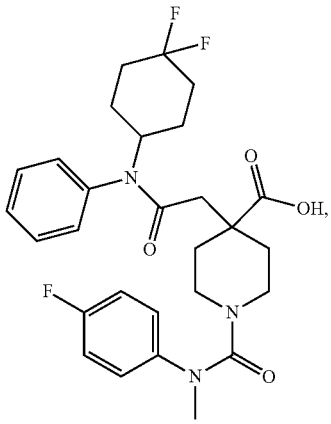 [SMILES: CN(C(=O)N1CCC(CC(=O)N(c2ccccc2)C2CCC(F)(F)CC2)(C(=O)O)CC1)c1ccc(F)cc1] |
| 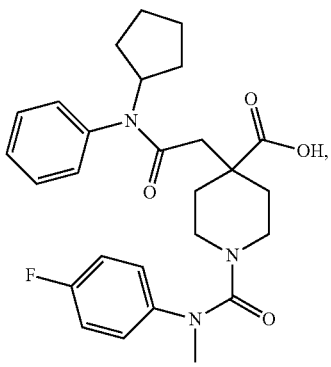 [SMILES: CN(C(=O)N1CCC(CC(=O)N(c2ccccc2)C2CCCC2)(C(=O)O)CC1)c1ccc(F)cc1] |
| 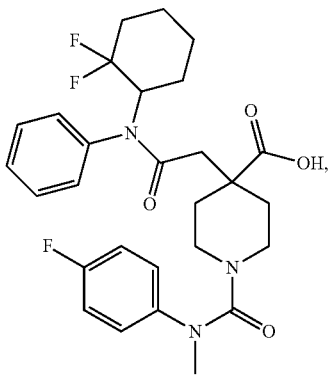 [SMILES: CN(C(=O)N1CCC(CC(=O)N(c2ccccc2)C2CCCCC2(F)F)(C(=O)O)CC1)c1ccc(F)cc1] |
| 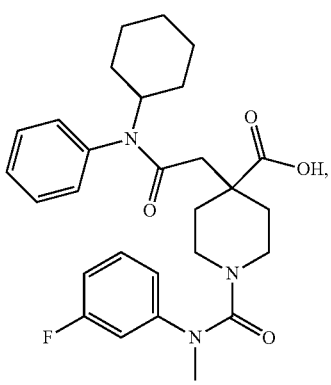 [SMILES: CN(C(=O)N1CCC(CC(=O)N(c2ccccc2)C2CCCCC2)(C(=O)O)CC1)c1cccc(F)c1] |

US 12,122,750 B2
| 315 -continued | 316 -continued |
|---|---|
| Structure | Structure |
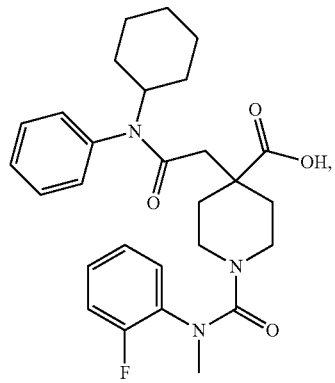 [SMILES: CN(C(=O)N1CCC(CC(=O)N(c2ccccc2)C2CCCCC2)(C(=O)O)CC1)c1ccccc1F]
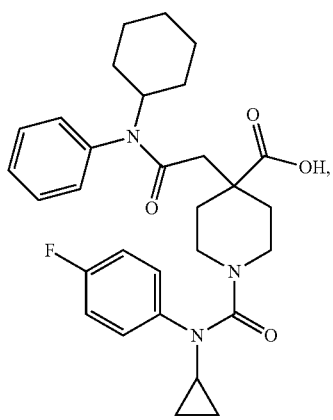 [SMILES: O=C(CC1(C(=O)O)CCN(C(=O)N(c2ccc(F)cc2)C2CC2)CC1)N(c1ccccc1)C1CCCCC1]

| 317 -continued | 318 -continued |
|---|---|
| Structure | Structure |
| 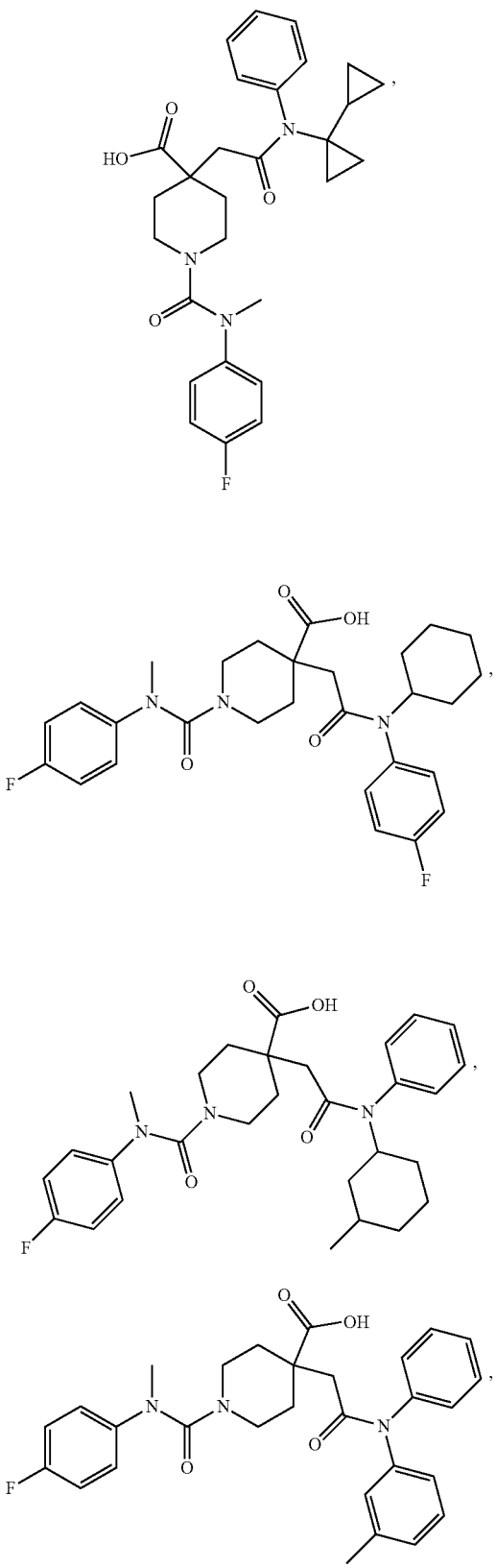 | 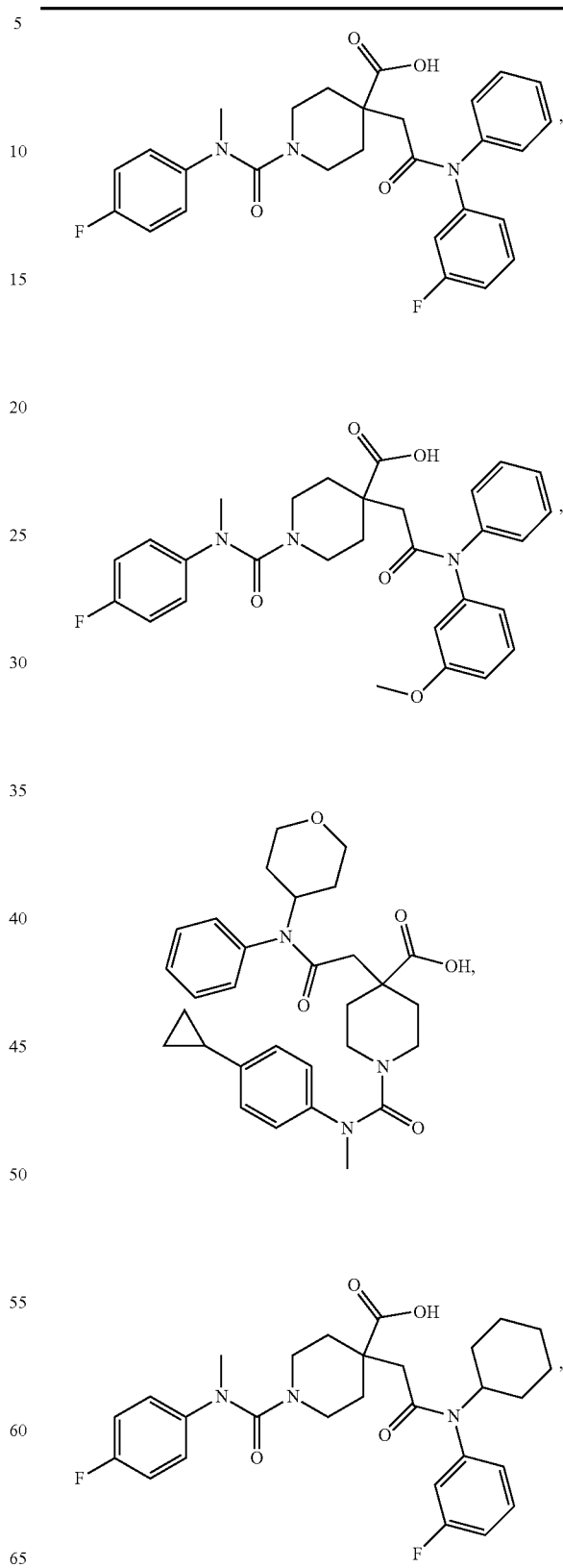 |

| 319 -continued | 320 -continued |
|---|---|
| Structure | Structure |
| 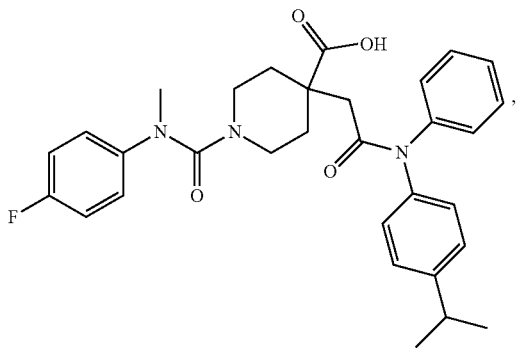 [SMILES: CC(C)c1ccc(N(C(=O)CC2(C(=O)O)CCN(C(=O)N(C)c3ccc(F)cc3)CC2)c2ccccc2)cc1] | 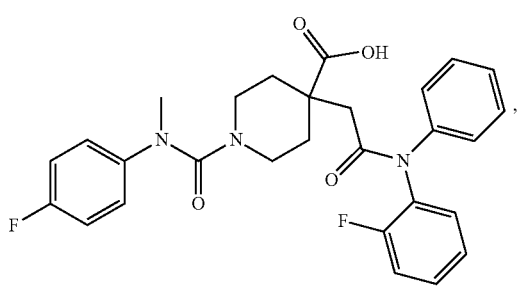 |
| 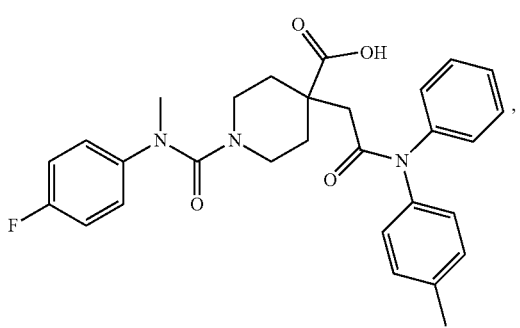 [SMILES: Cc1ccc(N(C(=O)CC2(C(=O)O)CCN(C(=O)N(C)c3ccc(F)cc3)CC2)c2ccccc2)cc1] | 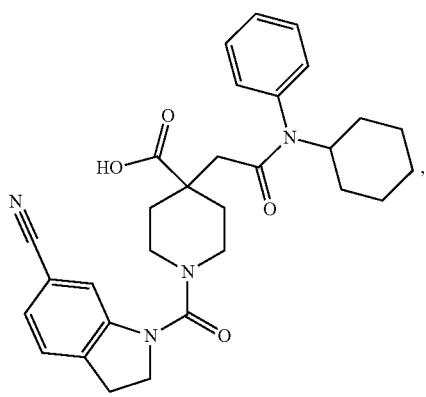 |
| 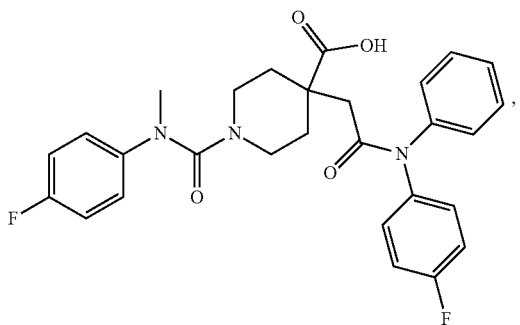 [SMILES: CN(C(=O)N1CCC(CC(=O)N(c2ccccc2)c2ccc(F)cc2)(C(=O)O)CC1)c1ccc(F)cc1] | 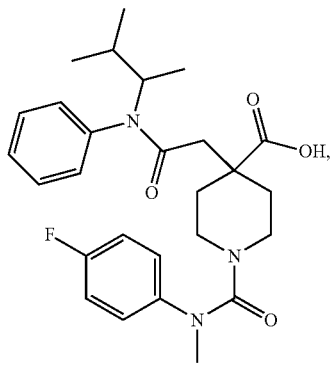 |
| 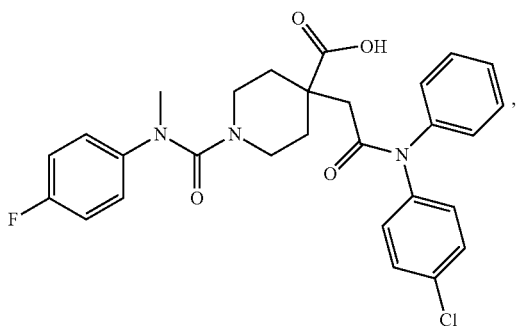 [SMILES: CN(C(=O)N1CCC(CC(=O)N(c2ccccc2)c2ccc(Cl)cc2)(C(=O)O)CC1)c1ccc(F)cc1] | 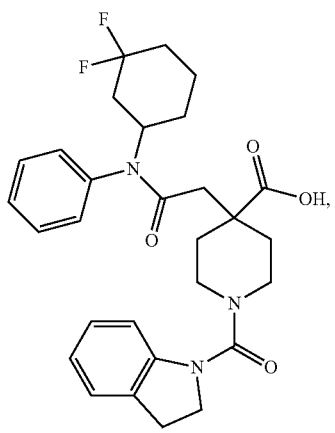 [SMILES: O=C(N1CCC(CC(=O)N(c2ccccc2)C2CCCC(F)(F)C2)(C(=O)O)CC1)N1CCc2ccccc21] |

| 321 -continued | 322 -continued |
|---|---|
| Structure | Structure |
| 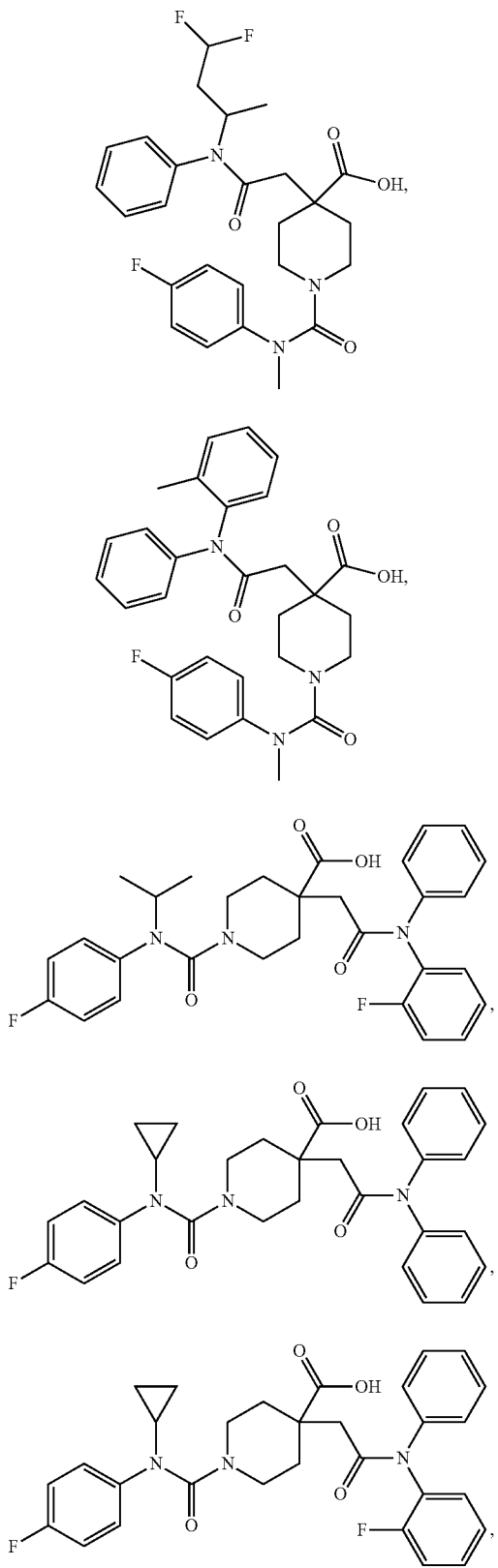 | 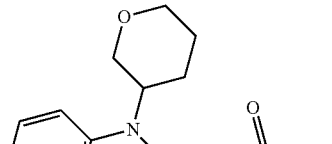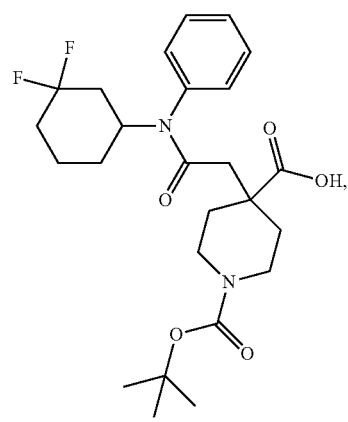 [SMILES: CC(C)(C)OC(=O)N1CCC(CC(=O)N(c2ccccc2)C2CCCC(F)(F)C2)(C(=O)O)CC1]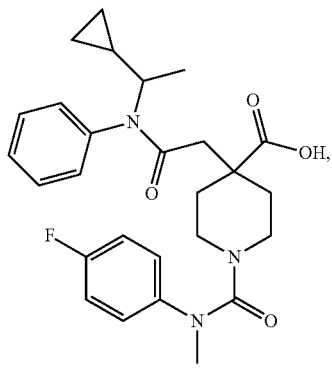 [SMILES: CC(C1CC1)N(C(=O)CC1(C(=O)O)CCN(C(=O)N(C)c2ccc(F)cc2)CC1)c1ccccc1]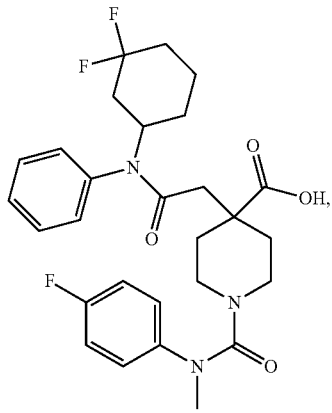 |

| 323 -continued | 324 -continued |
|---|---|
| Structure | Structure |
| 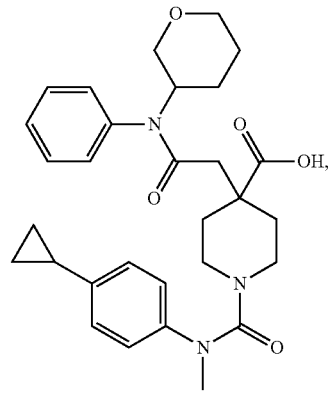 [SMILES: CN(C(=O)N1CCC(CC(=O)N(c2ccccc2)C2CCCOC2)(C(=O)O)CC1)c1ccc(C2CC2)cc1] 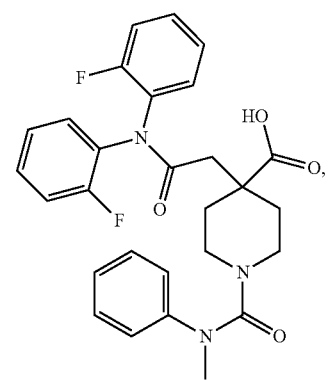 [SMILES: CN(C(=O)N1CCC(CC(=O)N(c2ccccc2F)c2ccccc2F)(C(=O)O)CC1)c1ccccc1] 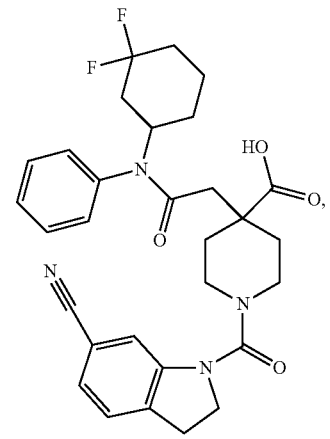 [SMILES: N#Cc1ccc2c(c1)N(C(=O)N1CCC(CC(=O)N(c3ccccc3)C3CCCC(F)(F)C3)(C(=O)O)CC1)CC2] 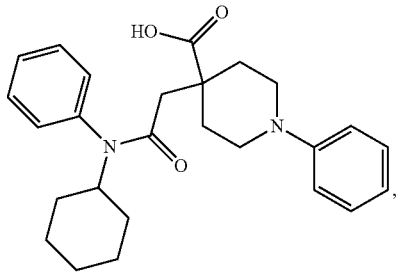 [SMILES: O=C(CC1(C(=O)O)CCN(c2ccccc2)CC1)N(c1ccccc1)C1CCCCC1] | 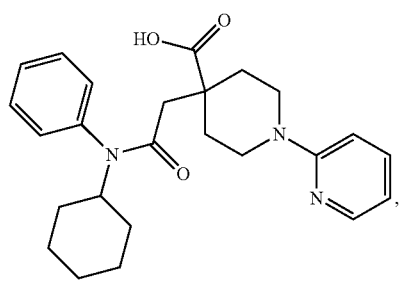 [SMILES: O=C(CC1(C(=O)O)CCN(c2ccccn2)CC1)N(c1ccccc1)C1CCCCC1] 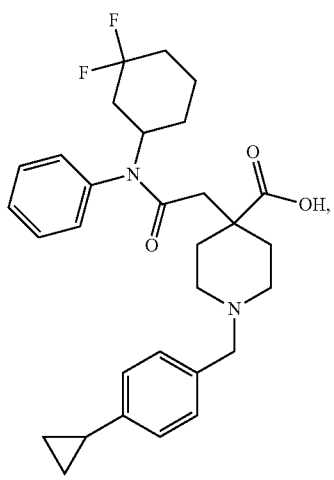 [SMILES: O=C(CC1(C(=O)O)CCN(Cc2ccc(C3CC3)cc2)CC1)N(c1ccccc1)C1CCCC(F)(F)C1] 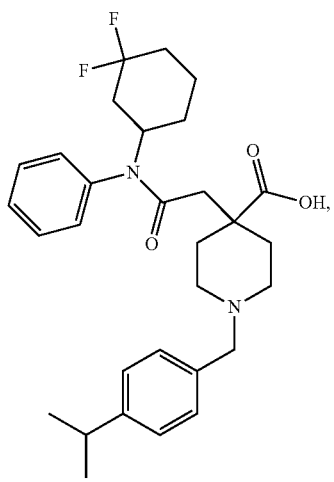 [SMILES: CC(C)c1ccc(CN2CCC(CC(=O)N(c3ccccc3)C3CCCC(F)(F)C3)(C(=O)O)CC2)cc1] |

| 325 -continued | 326 -continued |
|---|---|
| Structure | Structure |

| 327 -continued | 328 -continued |
|---|---|
| Structure | Structure |
| 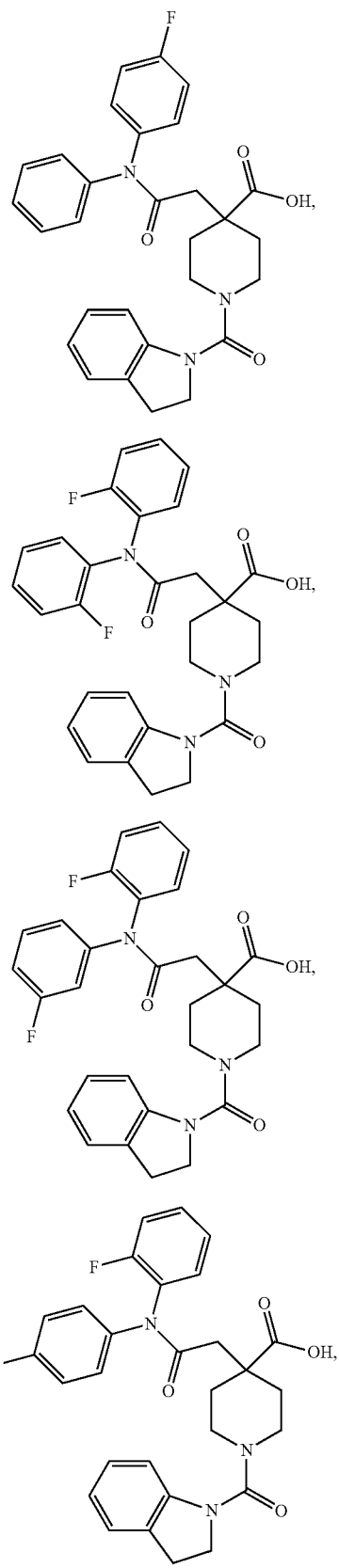 | 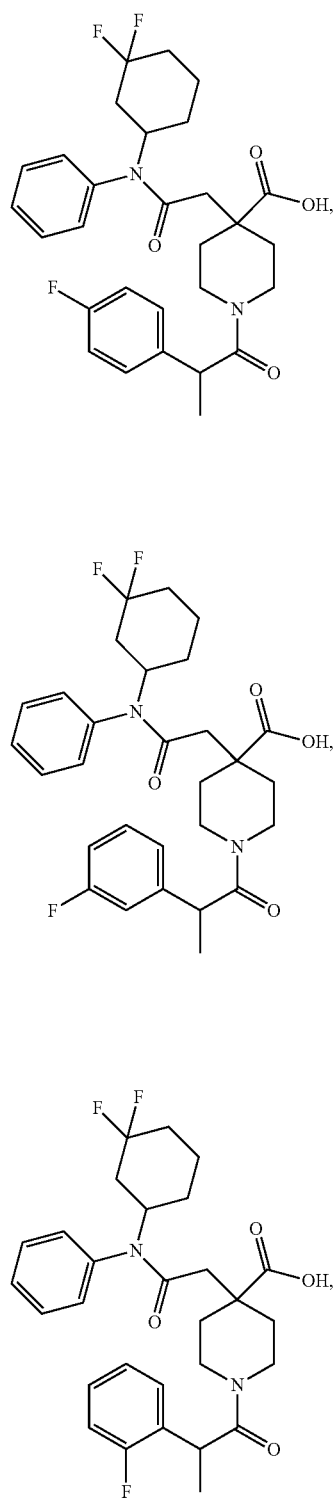 |

| 329 -continued | 330 -continued |
|---|---|
| Structure | Structure |
| 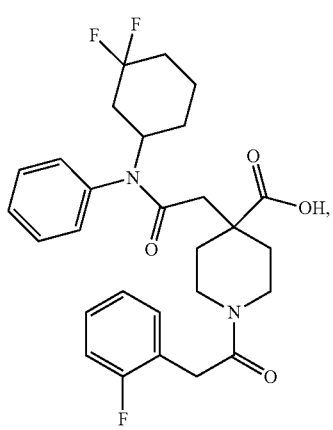 [SMILES: O=C(Cc1ccccc1F)N1CCC(CC(=O)N(c2ccccc2)C2CCCC(F)(F)C2)(C(=O)O)CC1] | 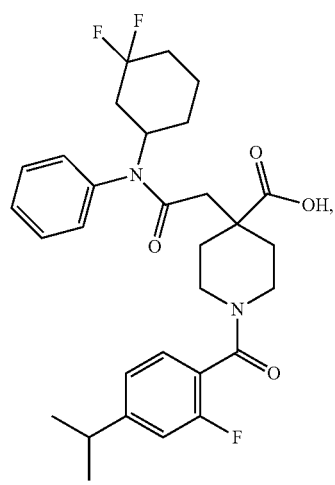 |
| 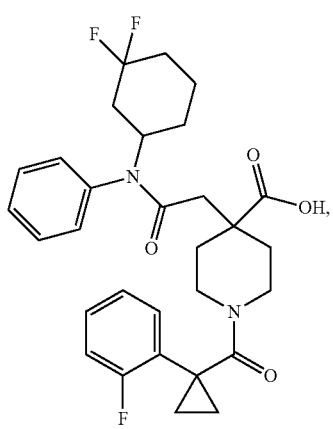 [SMILES: O=C(CC1(C(=O)O)CCN(C(=O)C2(c3ccccc3F)CC2)CC1)N(c1ccccc1)C1CCCC(F)(F)C1] | 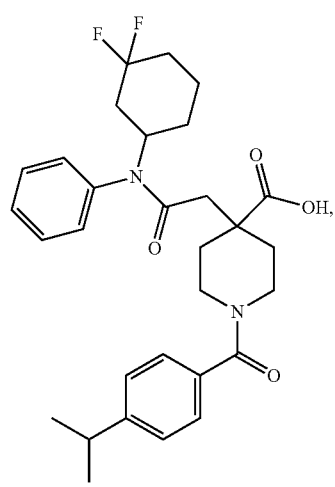 |
| 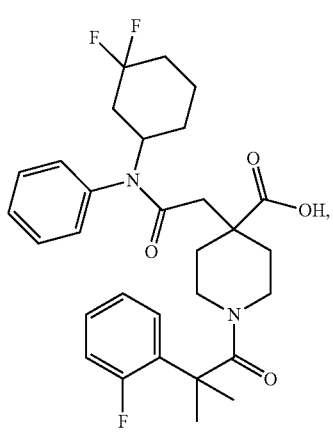 [SMILES: CC(C)(C(=O)N1CCC(CC(=O)N(c2ccccc2)C2CCCC(F)(F)C2)(C(=O)O)CC1)c1ccccc1F] | 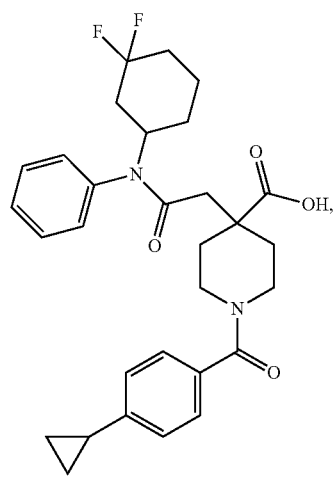 [SMILES: O=C(c1ccc(C2CC2)cc1)N1CCC(CC(=O)N(c2ccccc2)C2CCCC(F)(F)C2)(C(=O)O)CC1] |

| 331 -continued | 332 -continued |
|---|---|
| Structure | Structure |
| 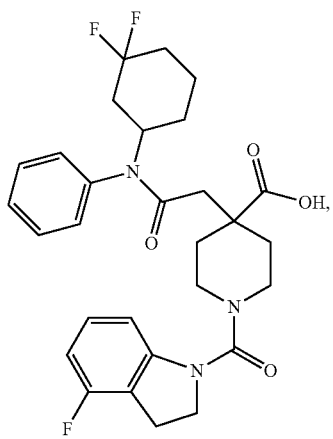 [SMILES: O=C(N1CCC(CC(=O)N(c2ccccc2)C2CCCC(F)(F)C2)(C(=O)O)CC1)N1CCc2c(F)cccc21] | 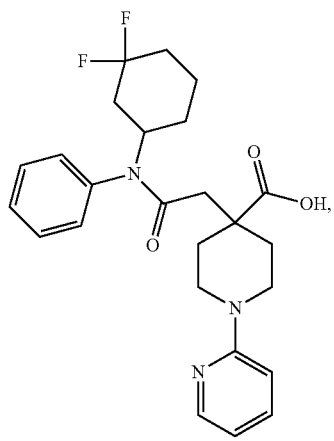 |
| 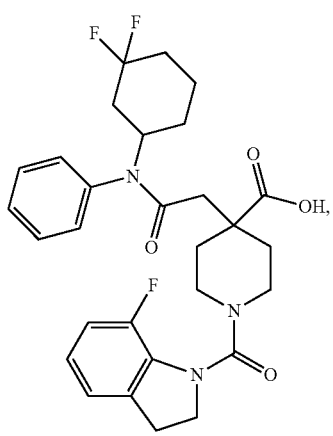 [SMILES: O=C(N1CCC(CC(=O)N(c2ccccc2)C2CCCC(F)(F)C2)(C(=O)O)CC1)N1CCc2cccc(F)c21] | 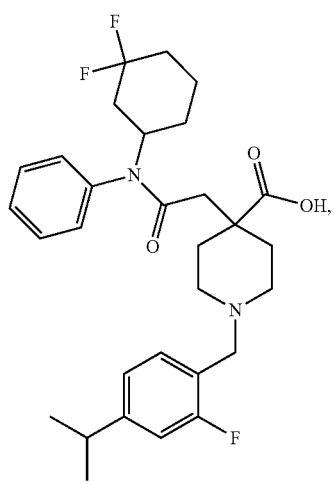 [SMILES: CC(C)c1ccc(CN2CCC(CC(=O)N(c3ccccc3)C3CCCC(F)(F)C3)(C(=O)O)CC2)c(F)c1] |
| | 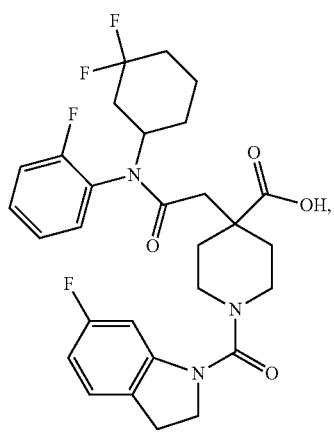 [SMILES: O=C(N1CCC(CC(=O)N(c2ccccc2F)C2CCCC(F)(F)C2)(C(=O)O)CC1)N1CCc2ccc(F)cc21] |

| 333 -continued | 334 -continued |
|---|---|
| Structure | Structure |
| 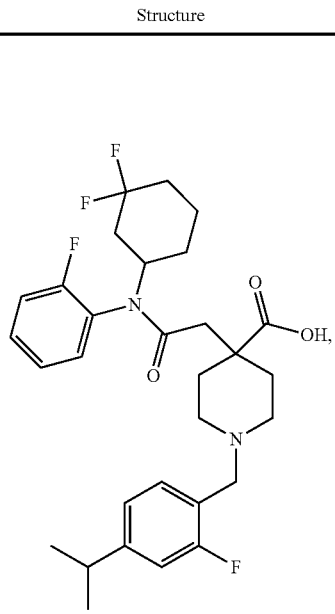 | 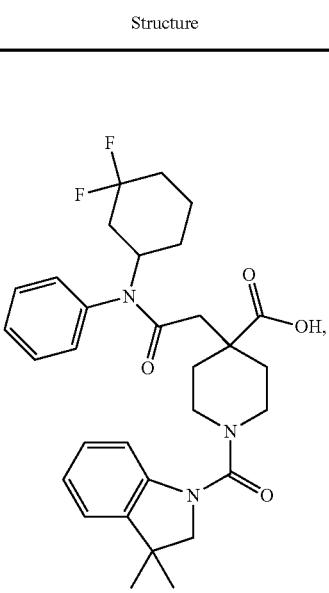 |
| 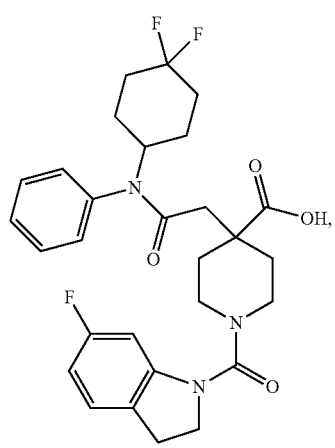 [SMILES: O=C(N1CCC(CC(=O)N(c2ccccc2)C2CCC(F)(F)CC2)(C(=O)O)CC1)N1CCc2ccc(F)cc21] | 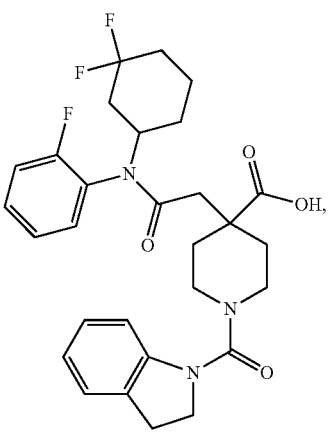 |
| 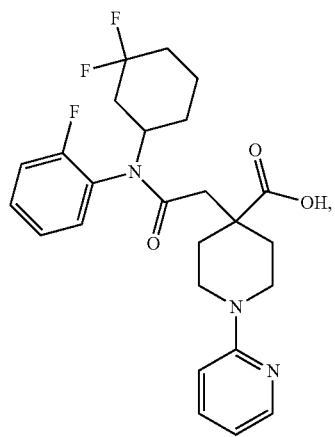 [SMILES: O=C(CC1(C(=O)O)CCN(c2ccccn2)CC1)N(c1ccccc1F)C1CCCC(F)(F)C1] | 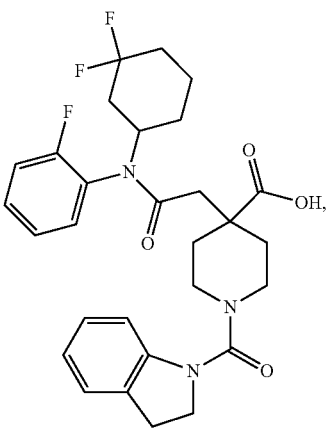 [SMILES: O=C(N1CCC(CC(=O)N(c2ccccc2F)C2CCCC(F)(F)C2)(C(=O)O)CC1)N1CCc2ccccc21] |

| 335 -continued | 336 -continued |
|---|---|
| Structure | Structure |
| 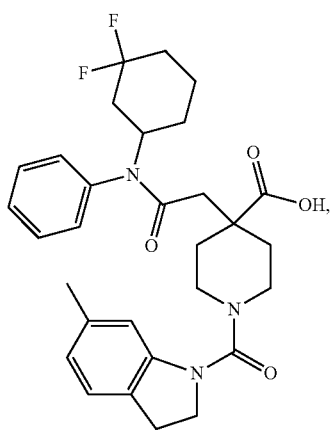 [SMILES: Cc1ccc2c(c1)N(C(=O)N1CCC(CC(=O)N(c3ccccc3)C3CCCC(F)(F)C3)(C(=O)O)CC1)CC2] | 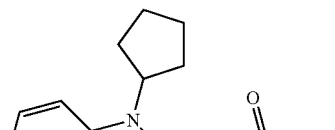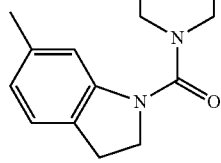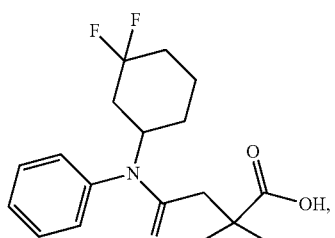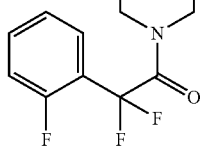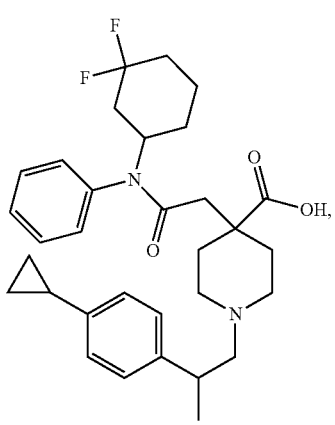 [SMILES: CC(CN1CCC(CC(=O)N(c2ccccc2)C2CCCC(F)(F)C2)(C(=O)O)CC1)c1ccc(C2CC2)cc1]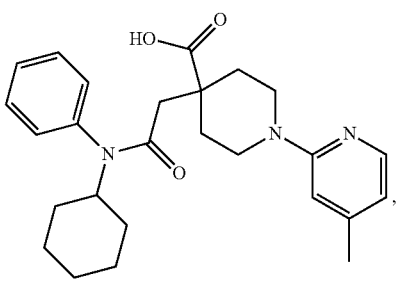 [SMILES: Cc1ccnc(N2CCC(CC(=O)N(c3ccccc3)C3CCCCC3)(C(=O)O)CC2)c1] |

| 337 -continued | | 338 -continued |
|---|---|---|
| Structure | | Structure |
| 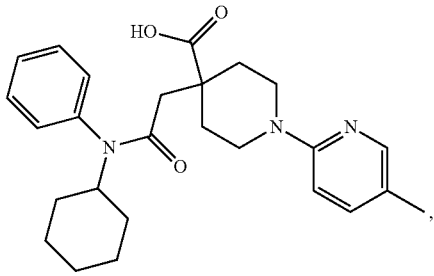 [SMILES: Cc1ccc(N2CCC(CC(=O)N(c3ccccc3)C3CCCCC3)(C(=O)O)CC2)nc1] | | 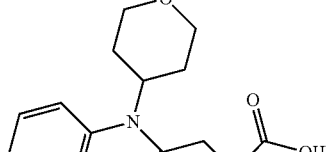 |
| 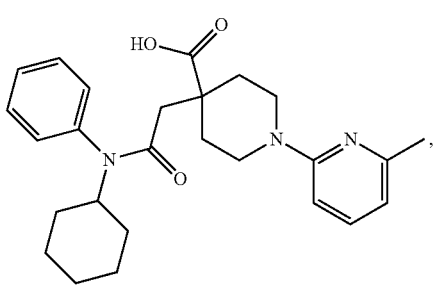 [SMILES: Cc1cccc(N2CCC(CC(=O)N(c3ccccc3)C3CCCCC3)(C(=O)O)CC2)n1] | | 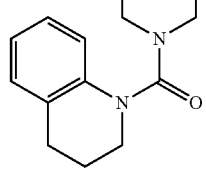 |
| 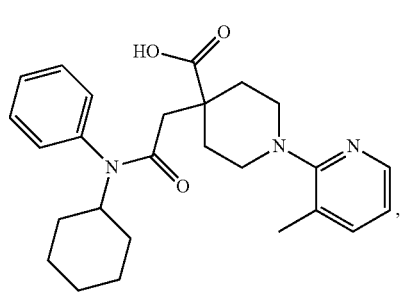 [SMILES: Cc1cccnc1N1CCC(CC(=O)N(c2ccccc2)C2CCCCC2)(C(=O)O)CC1] | | 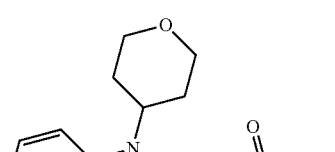 |
| 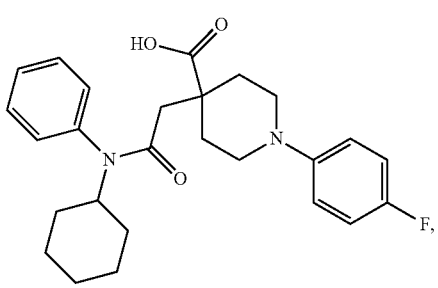 [SMILES: O=C(CC1(C(=O)O)CCN(c2ccc(F)cc2)CC1)N(c1ccccc1)C1CCCCC1] | | 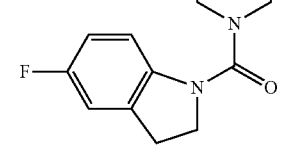 |
| 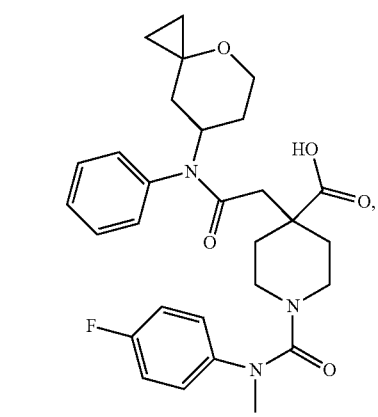 [SMILES: CN(C(=O)N1CCC(CC(=O)N(c2ccccc2)C2CCOC3(CC3)C2)(C(=O)O)CC1)c1ccc(F)cc1] | | 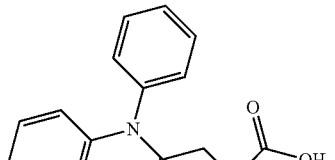 |
| | | 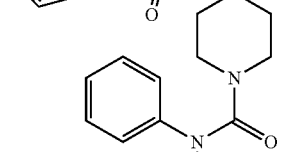 |
| | | 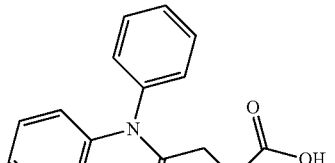 |
| | | 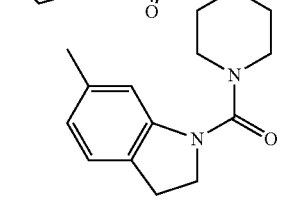 |

| 339 -continued | 340 -continued |
|---|---|
| Structure | Structure |
| 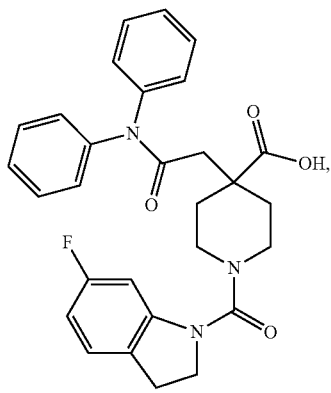 [SMILES: O=C(N1CCC(CC(=O)N(c2ccccc2)c2ccccc2)(C(=O)O)CC1)N1CCc2ccc(F)cc21] | 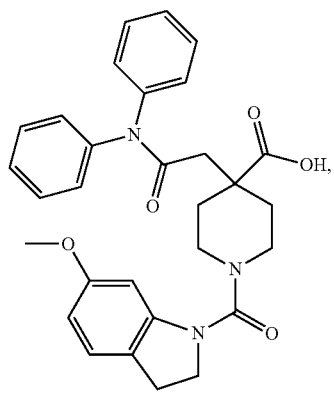 |
| 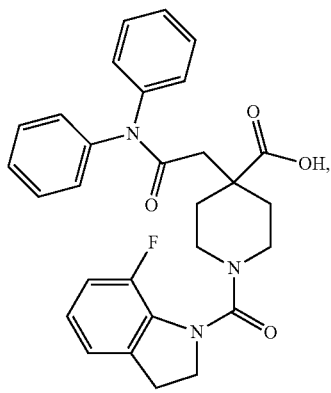 [SMILES: O=C(N1CCC(CC(=O)N(c2ccccc2)c2ccccc2)(C(=O)O)CC1)N1CCc2cccc(F)c21] | 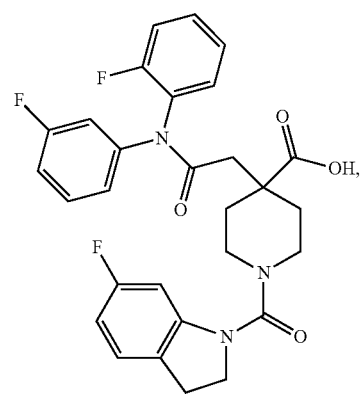 |
| 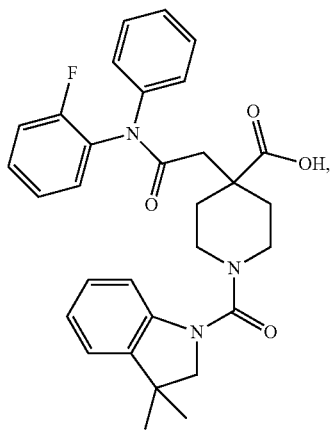 [SMILES: CC1(C)CN(C(=O)N2CCC(CC(=O)N(c3ccccc3)c3ccccc3F)(C(=O)O)CC2)c2ccccc21] | 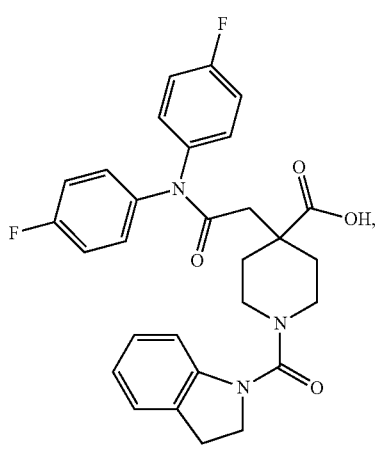 [SMILES: O=C(N1CCC(CC(=O)N(c2ccc(F)cc2)c2ccc(F)cc2)(C(=O)O)CC1)N1CCc2ccccc21] |

| 341 -continued | 342 -continued |
|---|---|
| Structure | Structure |
| 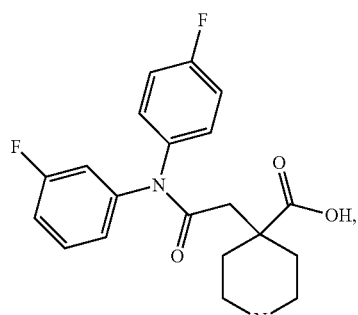 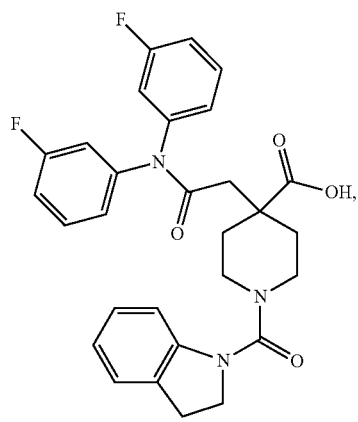 [SMILES: O=C(N1CCC(CC(=O)N(c2cccc(F)c2)c2cccc(F)c2)(C(=O)O)CC1)N1CCc2ccccc21] 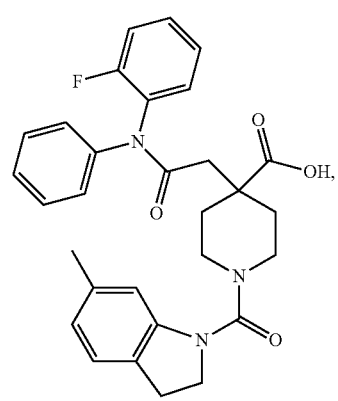 [SMILES: Cc1ccc2c(c1)N(C(=O)N1CCC(CC(=O)N(c3ccccc3)c3ccccc3F)(C(=O)O)CC1)CC2] | 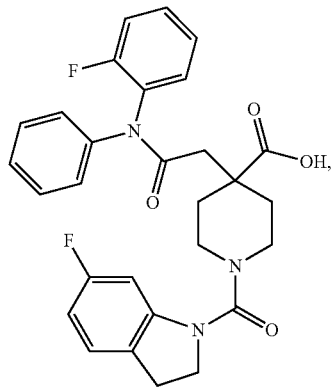 [SMILES: O=C(N1CCC(CC(=O)N(c2ccccc2)c2ccccc2F)(C(=O)O)CC1)N1CCc2ccc(F)cc21] 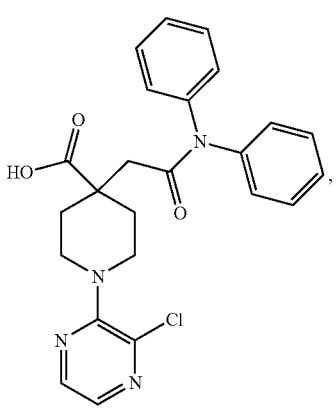 [SMILES: O=C(CC1(C(=O)O)CCN(c2nccnc2Cl)CC1)N(c1ccccc1)c1ccccc1] 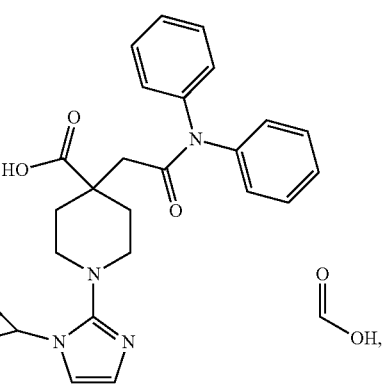 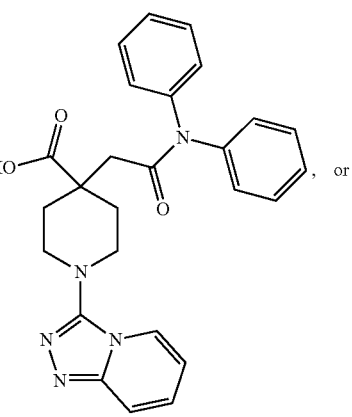 |

| Structure |
|---|
| 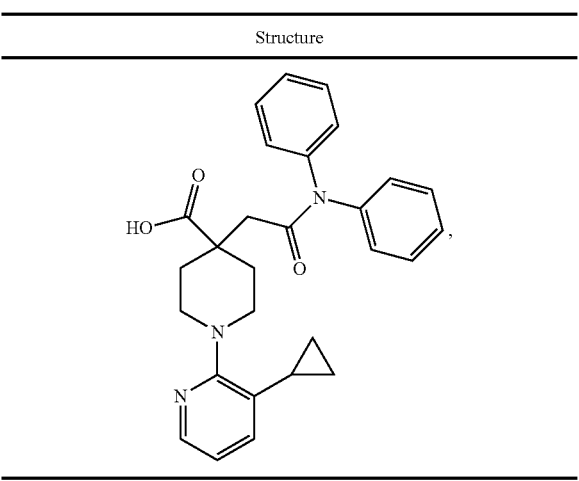 |
or a pharmaceutically acceptable salt thereof.
21. The compound of claim 1, wherein the compound is
| Structure |
|---|
| 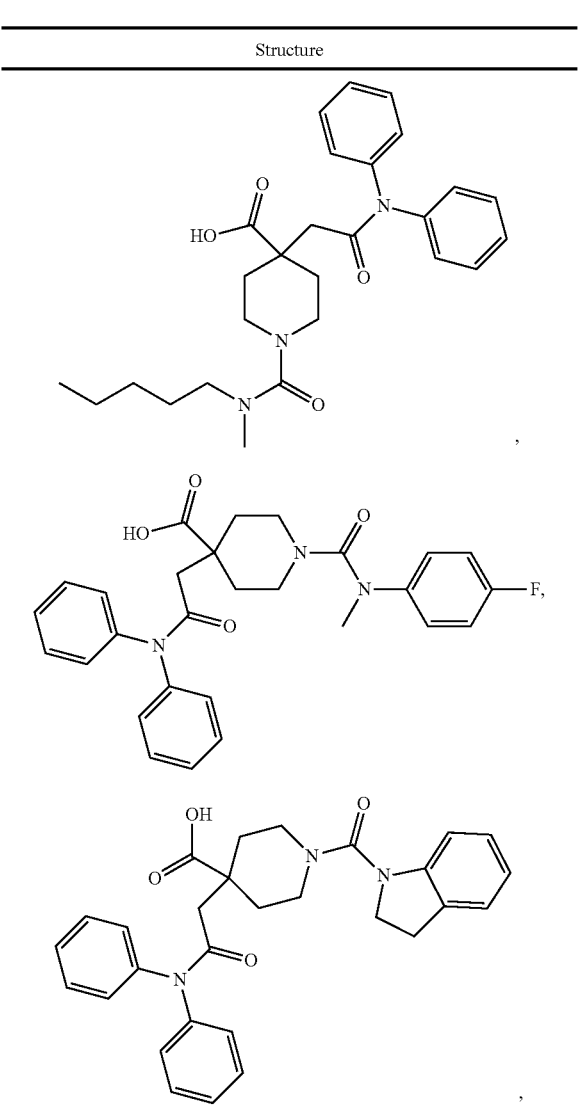 |
| Structure |
|---|
| 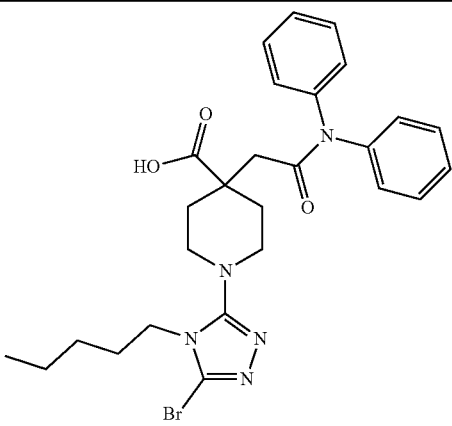 |
| 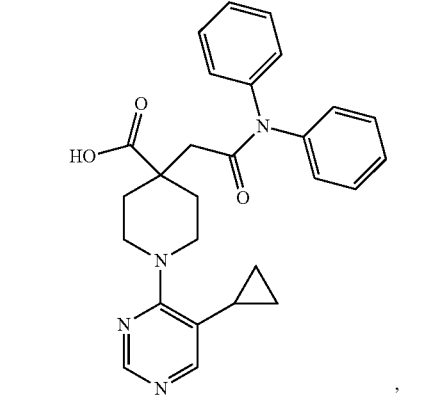 [SMILES: O=C(CC1(C(=O)O)CCN(c2ncncc2C2CC2)CC1)N(c1ccccc1)c1ccccc1] |
| 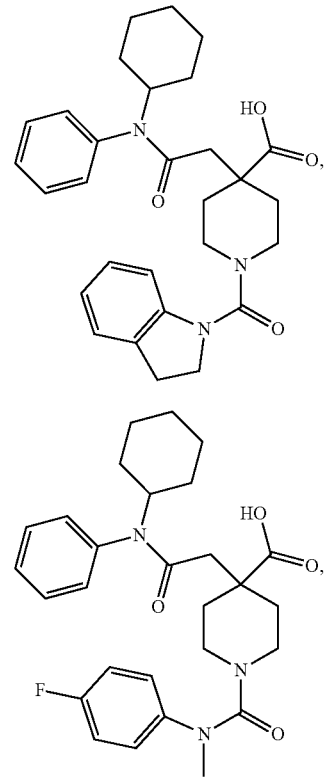 |

| 345 -continued | 346 -continued |
|---|---|
| Structure | Structure |
| 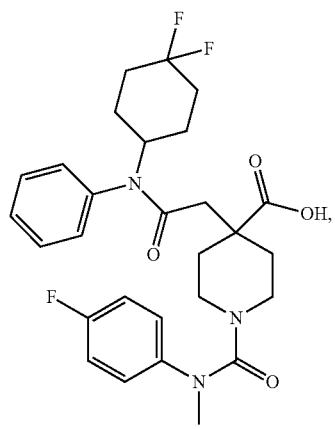 [SMILES: CN(C(=O)N1CCC(CC(=O)N(c2ccccc2)C2CCC(F)(F)CC2)(C(=O)O)CC1)c1ccc(F)cc1] | 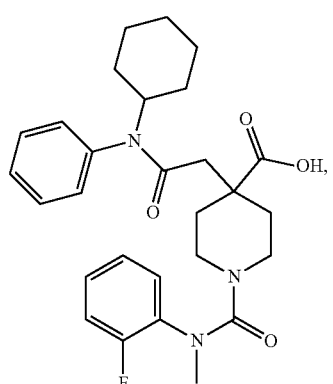 |
| 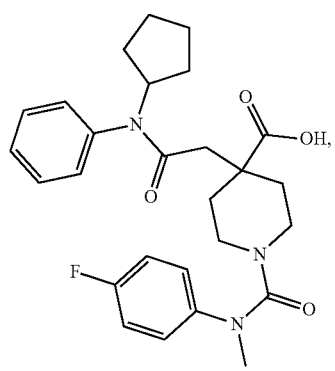 [SMILES: CN(C(=O)N1CCC(CC(=O)N(c2ccccc2)C2CCCC2)(C(=O)O)CC1)c1ccc(F)cc1] | 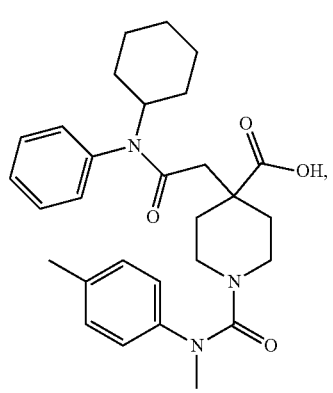 |
| 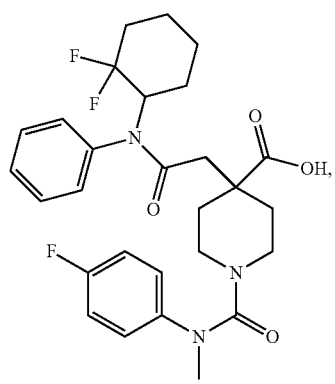 [SMILES: CN(C(=O)N1CCC(CC(=O)N(c2ccccc2)C2CCCCC2(F)F)(C(=O)O)CC1)c1ccc(F)cc1] | 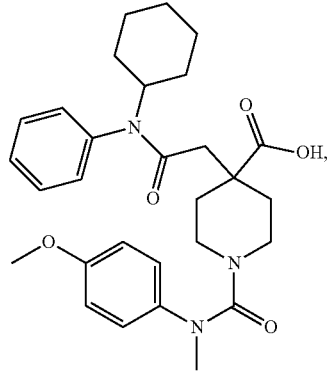 |
| 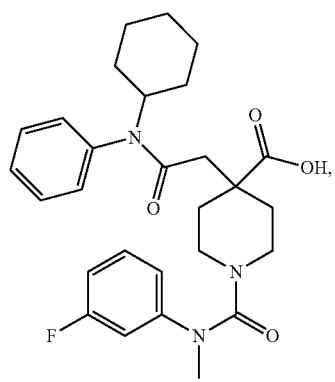 [SMILES: CN(C(=O)N1CCC(CC(=O)N(c2ccccc2)C2CCCCC2)(C(=O)O)CC1)c1cccc(F)c1] | 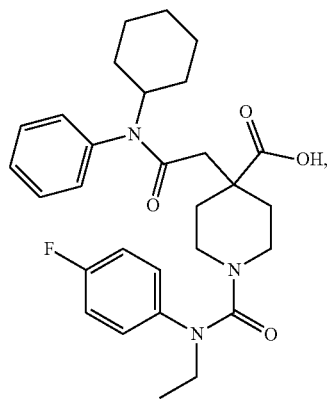 [SMILES: CCN(C(=O)N1CCC(CC(=O)N(c2ccccc2)C2CCCCC2)(C(=O)O)CC1)c1ccc(F)cc1] |

| 347 -continued | 348 -continued |
|---|---|
| Structure | Structure |
| 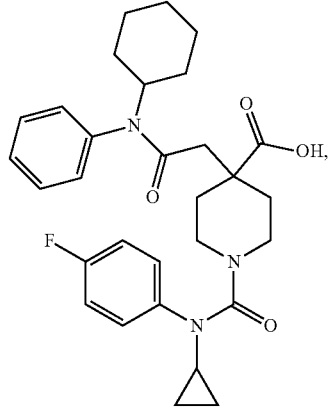 [SMILES: O=C(CC1(C(=O)O)CCN(C(=O)N(c2ccc(F)cc2)C2CC2)CC1)N(c1ccccc1)C1CCCCC1] 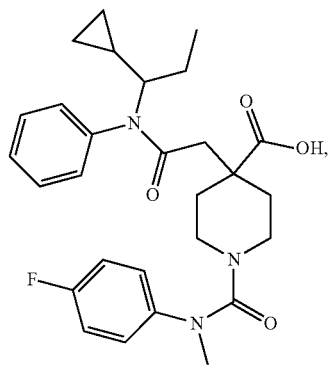 [SMILES: CCC(C1CC1)N(C(=O)CC1(C(=O)O)CCN(C(=O)N(C)c2ccc(F)cc2)CC1)c1ccccc1] 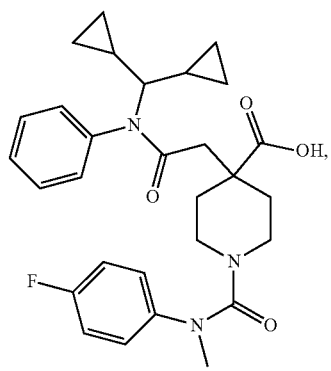 [SMILES: CN(C(=O)N1CCC(CC(=O)N(c2ccccc2)C(C2CC2)C2CC2)(C(=O)O)CC1)c1ccc(F)cc1] 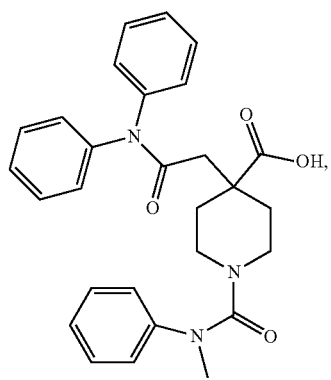 [SMILES: CN(C(=O)N1CCC(CC(=O)N(c2ccccc2)c2ccccc2)(C(=O)O)CC1)c1ccccc1] | 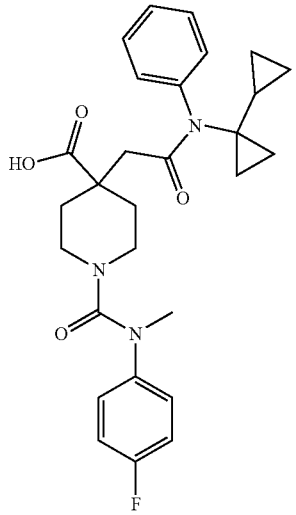 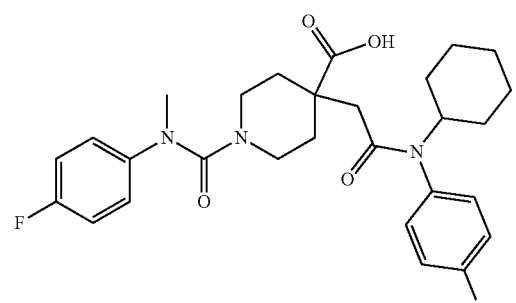 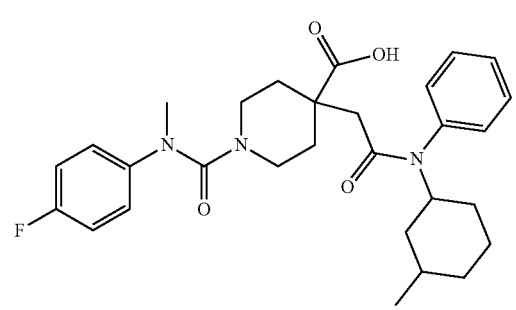 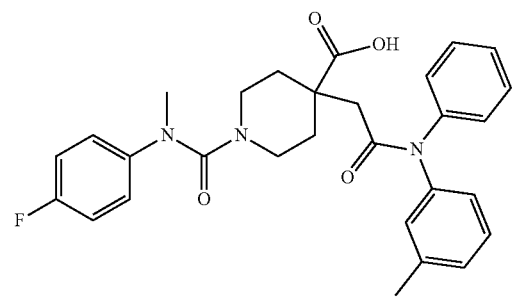 |

| 349 -continued | 350 -continued |
|---|---|
| Structure | Structure |
| 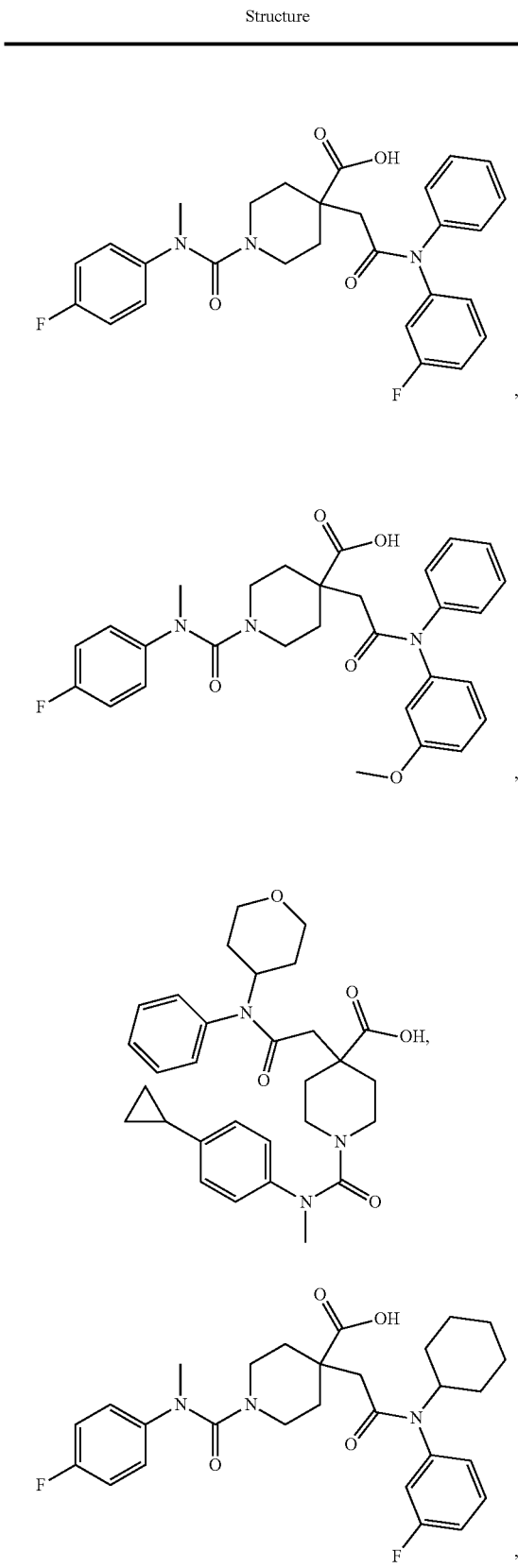 | 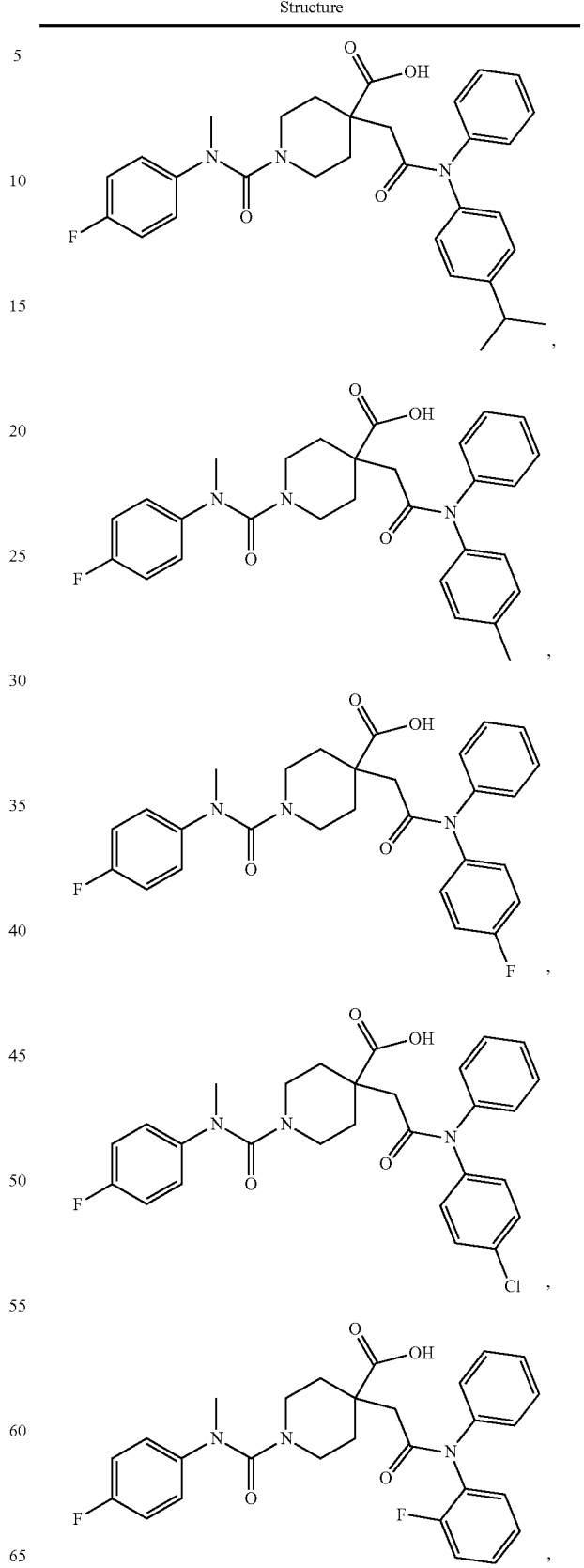 |

| 351 -continued | 352 -continued |
|---|---|
| Structure | Structure |
| 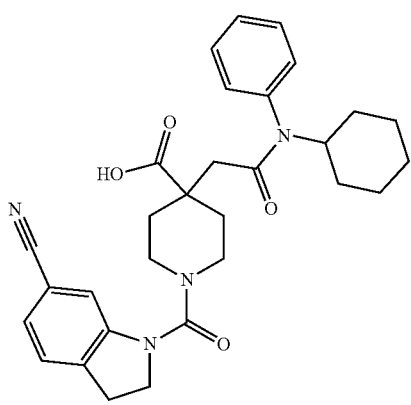 | 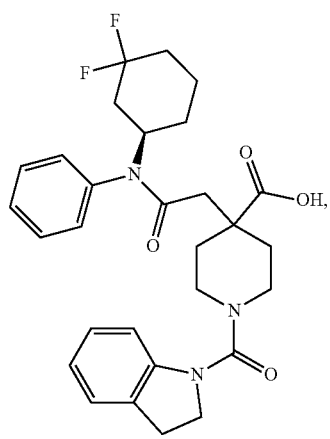 |
| 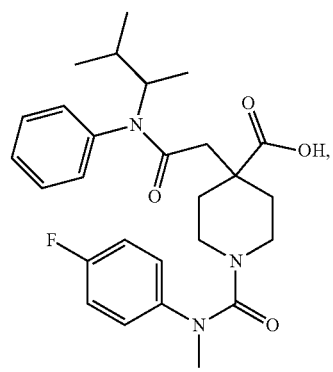 [SMILES: CC(C)C(C)N(C(=O)CC1(C(=O)O)CCN(C(=O)N(C)c2ccc(F)cc2)CC1)c1ccccc1] | 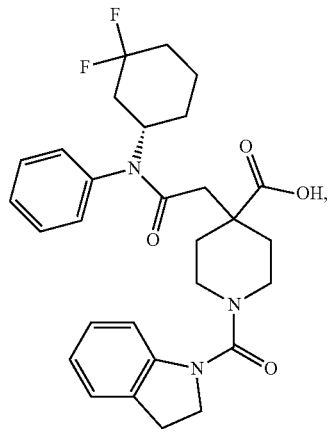 [SMILES: O=C(N1CCC(CC(=O)N(c2ccccc2)[C@H]2CCCC(F)(F)C2)(C(=O)O)CC1)N1CCc2ccccc21] |
| 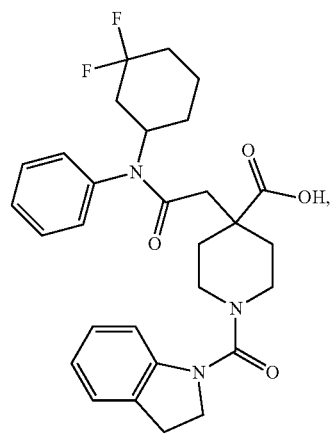 | 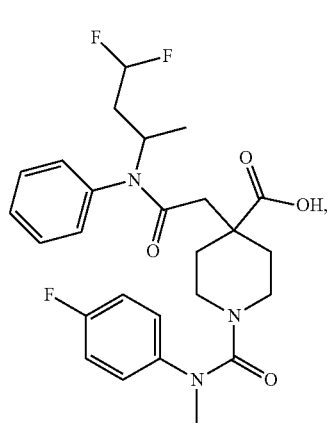 [SMILES: CC(CC(F)F)N(C(=O)CC1(C(=O)O)CCN(C(=O)N(C)c2ccc(F)cc2)CC1)c1ccccc1] |

| 353 -continued | 354 -continued |
|---|---|
| Structure | Structure |
| 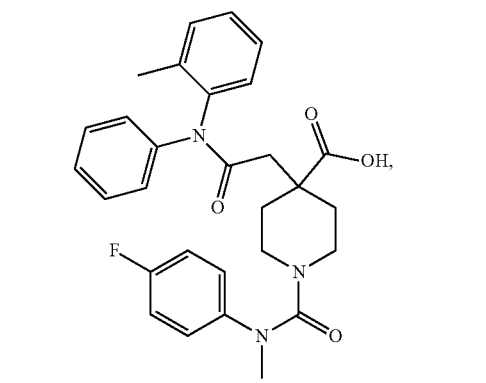 [SMILES: Cc1ccccc1N(C(=O)CC1(C(=O)O)CCN(C(=O)N(C)c2ccc(F)cc2)CC1)c1ccccc1] | 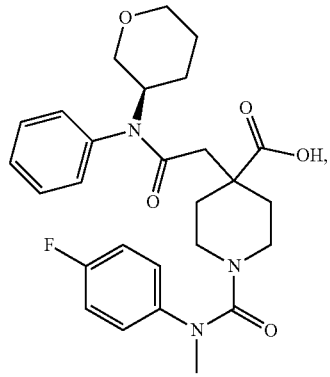 |
| 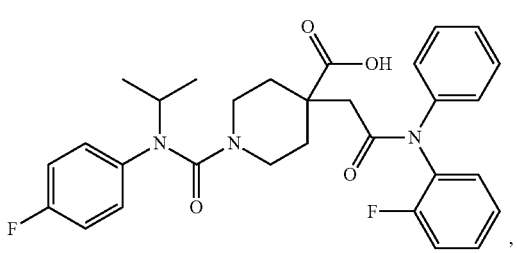 [SMILES: CC(C)N(C(=O)N1CCC(CC(=O)N(c2ccccc2)c2ccccc2F)(C(=O)O)CC1)c1ccc(F)cc1] | 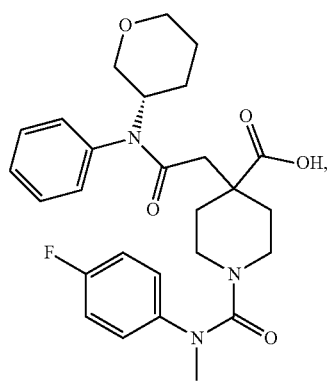 |
| 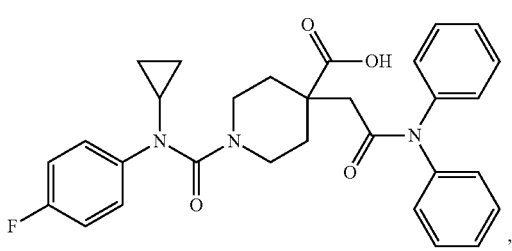 [SMILES: O=C(CC1(C(=O)O)CCN(C(=O)N(c2ccc(F)cc2)C2CC2)CC1)N(c1ccccc1)c1ccccc1] | 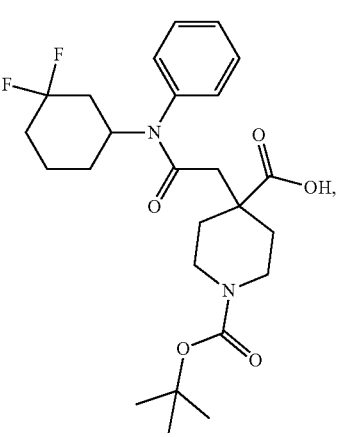 [SMILES: CC(C)(C)OC(=O)N1CCC(CC(=O)N(c2ccccc2)C2CCCC(F)(F)C2)(C(=O)O)CC1] |
| 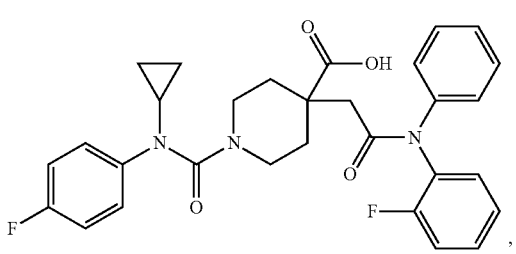 | 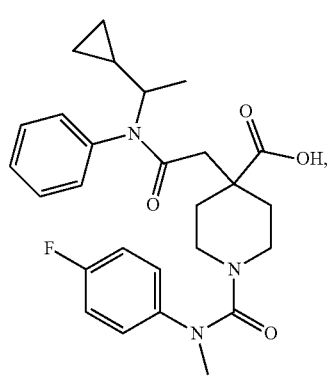 [SMILES: CC(C1CC1)N(C(=O)CC1(C(=O)O)CCN(C(=O)N(C)c2ccc(F)cc2)CC1)c1ccccc1] |
| 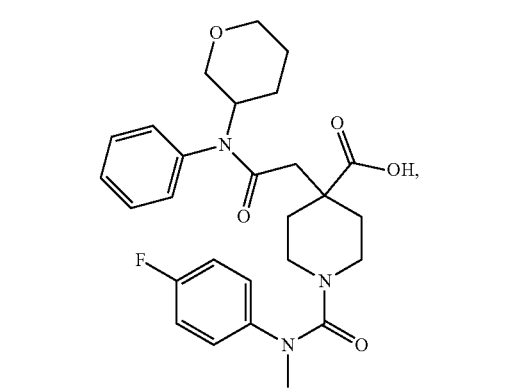 | |

| 355 -continued | 356 -continued |
|---|---|
| Structure | Structure |
| 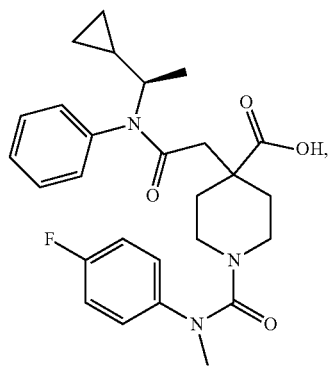 [SMILES: C[C@H](C1CC1)N(C(=O)CC1(C(=O)O)CCN(C(=O)N(C)c2ccc(F)cc2)CC1)c1ccccc1] | 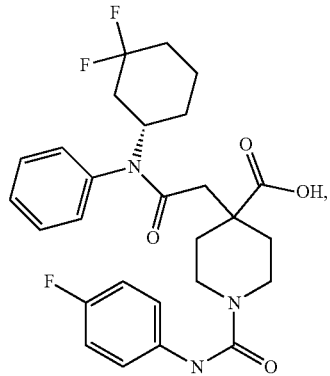 |
| 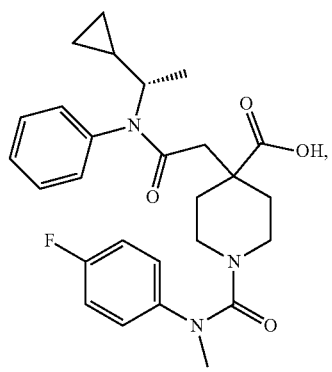 [SMILES: C[C@@H](C1CC1)N(C(=O)CC1(C(=O)O)CCN(C(=O)N(C)c2ccc(F)cc2)CC1)c1ccccc1] | 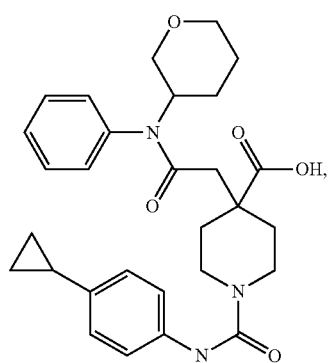 |
| 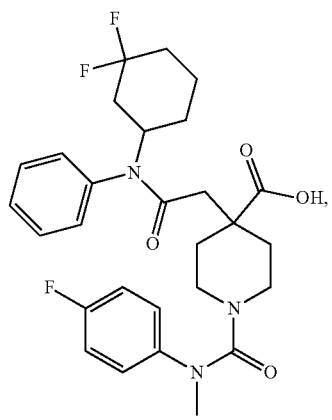 [SMILES: CN(C(=O)N1CCC(CC(=O)N(c2ccccc2)C2CCCC(F)(F)C2)(C(=O)O)CC1)c1ccc(F)cc1] | 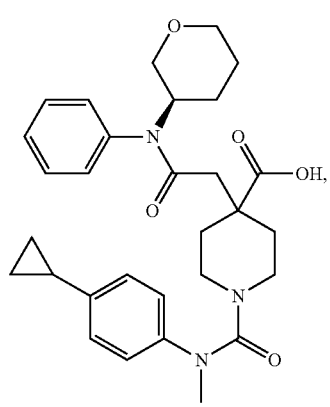 |
| 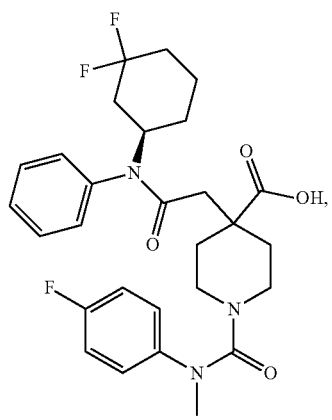 [SMILES: CN(C(=O)N1CCC(CC(=O)N(c2ccccc2)[C@@H]2CCCC(F)(F)C2)(C(=O)O)CC1)c1ccc(F)cc1] | 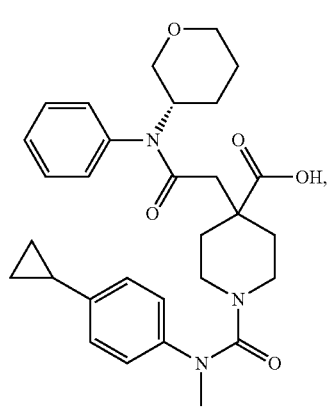 [SMILES: CN(C(=O)N1CCC(CC(=O)N(c2ccccc2)[C@H]2CCCOC2)(C(=O)O)CC1)c1ccc(C2CC2)cc1] |

| 357 -continued | 358 -continued |
|---|---|
| Structure | Structure |
| 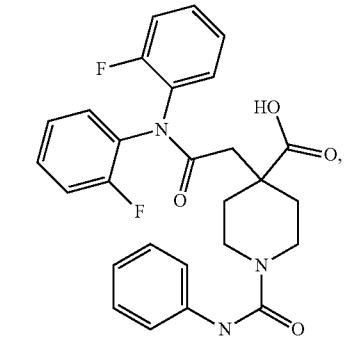 | 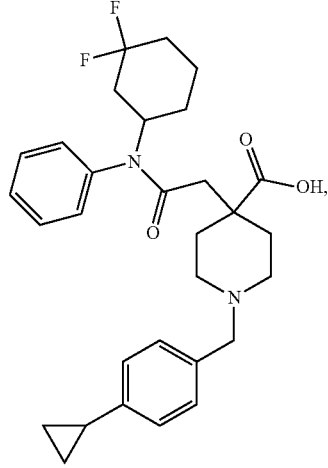 |
| 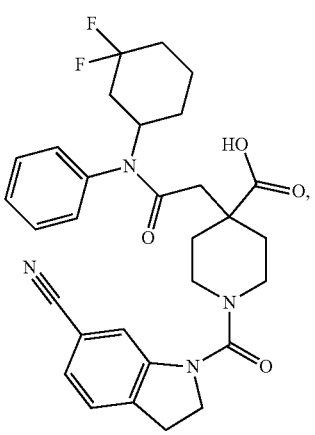 [SMILES: N#Cc1ccc2c(c1)N(C(=O)N1CCC(CC(=O)N(c3ccccc3)C3CCCC(F)(F)C3)(C(=O)O)CC1)CC2] | 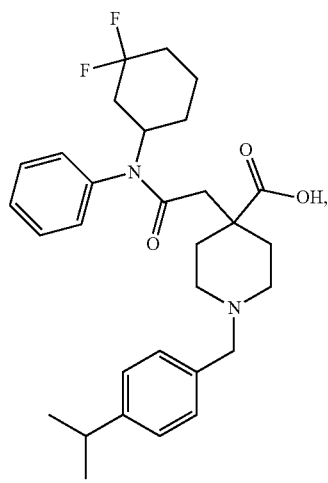 |
| 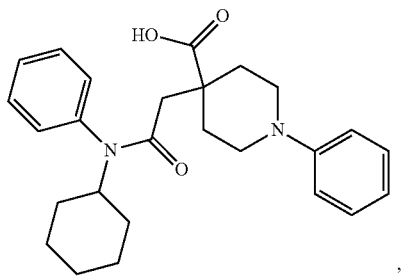 [SMILES: O=C(CC1(C(=O)O)CCN(c2ccccn2)CC1)N(c1ccccc1)C1CCCCC1] | 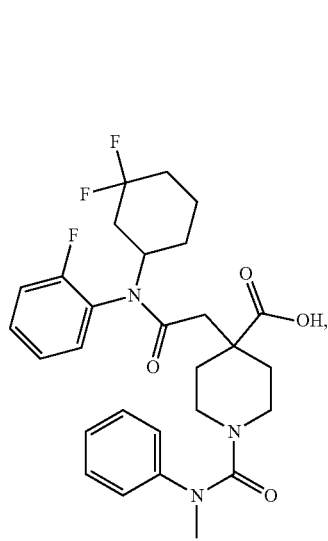 [SMILES: CN(C(=O)N1CCC(CC(=O)N(c2ccccc2F)C2CCCC(F)(F)C2)(C(=O)O)CC1)c1ccccc1] |
| 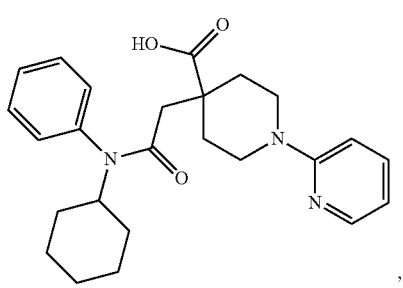 | |

| 359 -continued | 360 -continued |
|---|---|
| Structure | Structure |
| 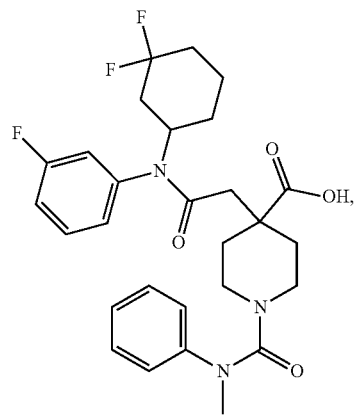 [SMILES: CN(C(=O)N1CCC(CC(=O)N(c2cccc(F)c2)C2CCCC(F)(F)C2)(C(=O)O)CC1)c1ccccc1] 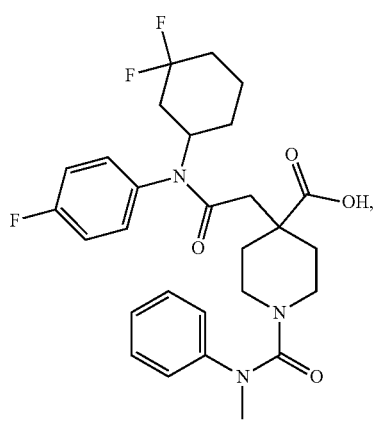 [SMILES: CN(C(=O)N1CCC(CC(=O)N(c2ccc(F)cc2)C2CCCC(F)(F)C2)(C(=O)O)CC1)c1ccccc1] 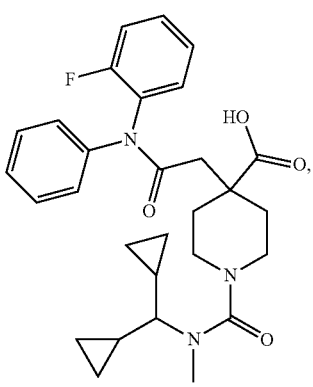 [SMILES: CN(C(=O)N1CCC(CC(=O)N(c2ccccc2)c2ccccc2F)(C(=O)O)CC1)C(C1CC1)C1CC1] 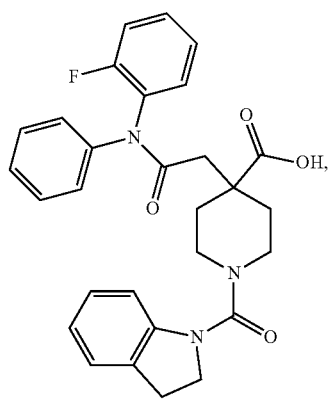 [SMILES: O=C(N1CCC(CC(=O)N(c2ccccc2)c2ccccc2F)(C(=O)O)CC1)N1CCc2ccccc21] | 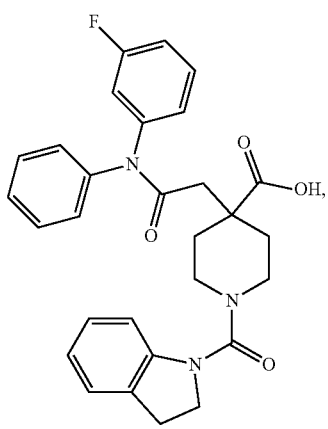 [SMILES: O=C(N1CCC(CC(=O)N(c2ccccc2)c2cccc(F)c2)(C(=O)O)CC1)N1CCc2ccccc21] 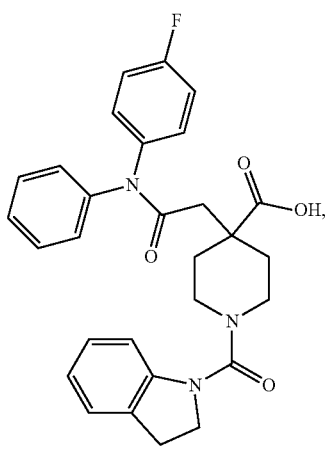 [SMILES: O=C(N1CCC(CC(=O)N(c2ccccc2)c2ccc(F)cc2)(C(=O)O)CC1)N1CCc2ccccc21] 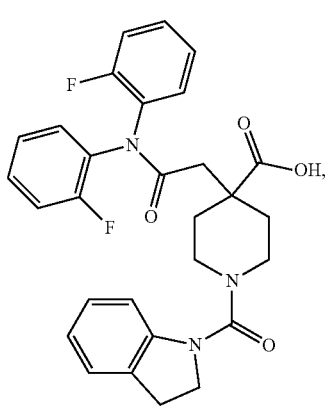 [SMILES: O=C(N1CCC(CC(=O)N(c2ccccc2F)c2ccccc2F)(C(=O)O)CC1)N1CCc2ccccc21] |

| 361 -continued | 362 -continued |
|---|---|
| Structure | Structure |
| 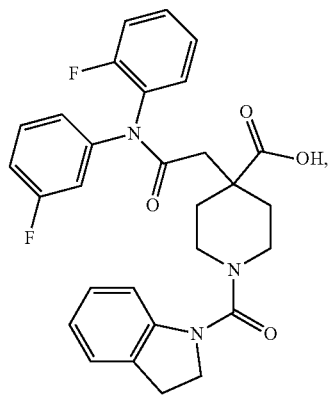 [SMILES: O=C(N1CCC(CC(=O)N(c2cccc(F)c2)c2ccccc2F)(C(=O)O)CC1)N1CCc2ccccc21] | 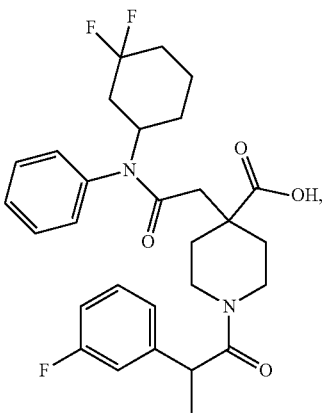 |
| 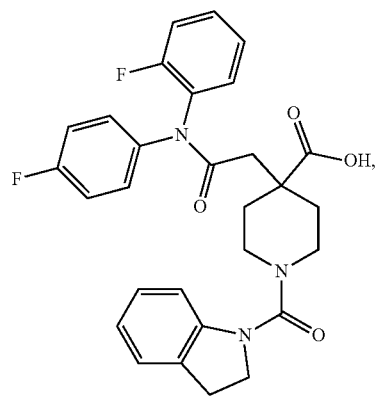 [SMILES: O=C(N1CCC(CC(=O)N(c2ccc(F)cc2)c2ccccc2F)(C(=O)O)CC1)N1CCc2ccccc21] | 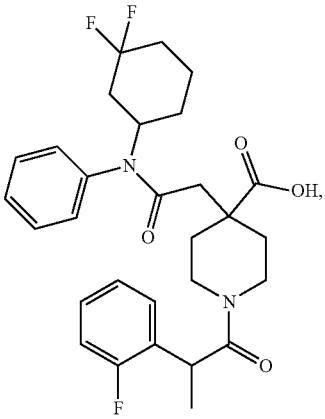 |
| 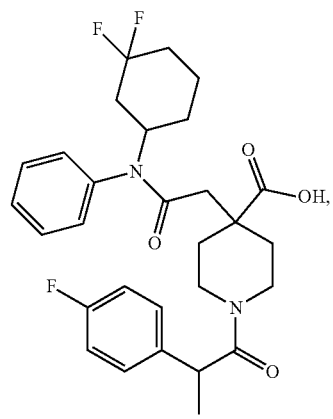 [SMILES: CC(C(=O)N1CCC(CC(=O)N(c2ccccc2)C2CCCC(F)(F)C2)(C(=O)O)CC1)c1ccc(F)cc1] | 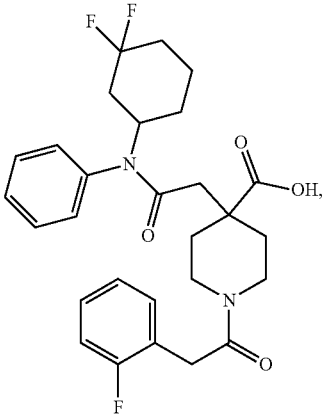 [SMILES: O=C(Cc1ccccc1F)N1CCC(CC(=O)N(c2ccccc2)C2CCCC(F)(F)C2)(C(=O)O)CC1] |

| 363 -continued | 364 -continued |
|---|---|
| 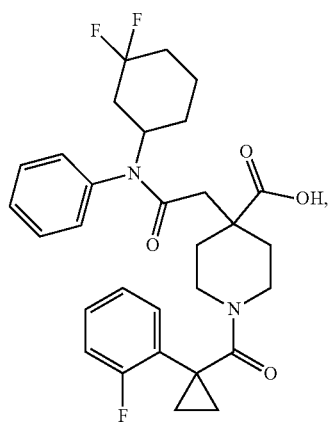 [SMILES: O=C(CC1(C(=O)O)CCN(C(=O)C2(c3ccccc3F)CC2)CC1)N(c1ccccc1)C1CCCC(F)(F)C1] | 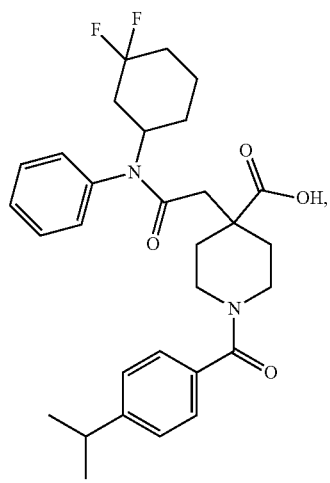 |
| 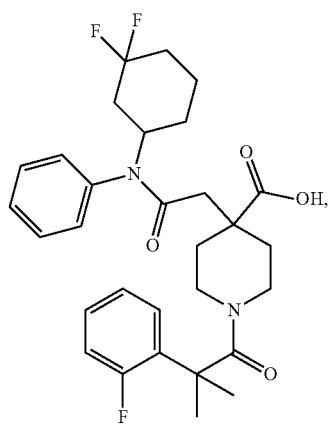 [SMILES: CC(C)(C(=O)N1CCC(CC(=O)N(c2ccccc2)C2CCCC(F)(F)C2)(C(=O)O)CC1)c1ccccc1F] | 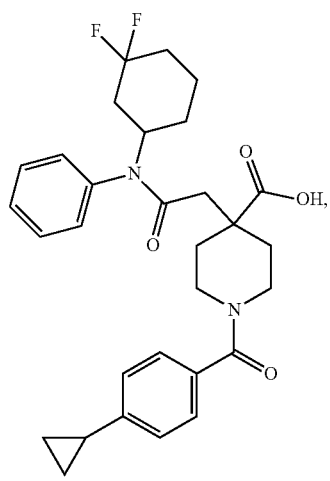 |
| 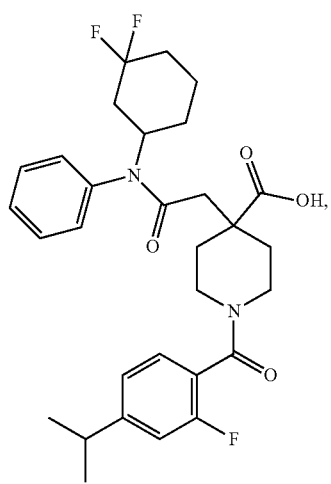 [SMILES: CC(C)c1ccc(C(=O)N2CCC(CC(=O)N(c3ccccc3)C3CCCC(F)(F)C3)(C(=O)O)CC2)c(F)c1] | 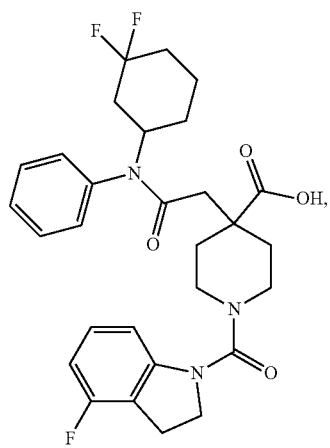 [SMILES: O=C(N1CCC(CC(=O)N(c2ccccc2)C2CCCC(F)(F)C2)(C(=O)O)CC1)N1CCc2c(F)cccc21] |

| 365 -continued | 366 -continued |
|---|---|
| Structure | Structure |
| 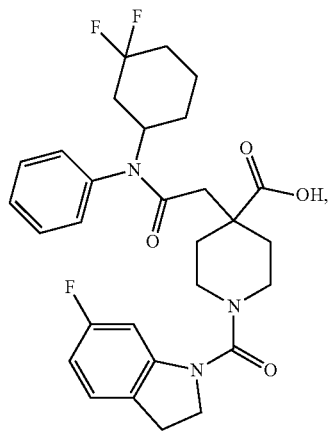 [SMILES: O=C(N1CCC(CC(=O)N(c2ccccc2)C2CCCC(F)(F)C2)(C(=O)O)CC1)N1CCc2ccc(F)cc21] | 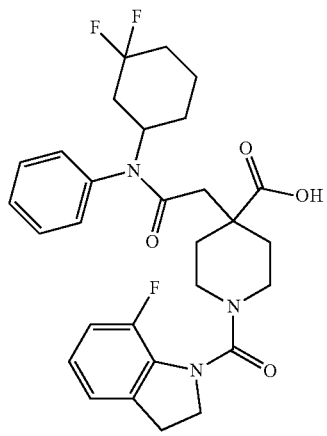, or |
| 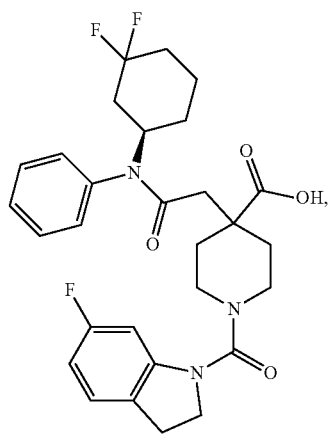 [SMILES: O=C(N1CCC(CC(=O)N(c2ccccc2)[C@@H]2CCCC(F)(F)C2)(C(=O)O)CC1)N1CCc2ccc(F)cc21] | 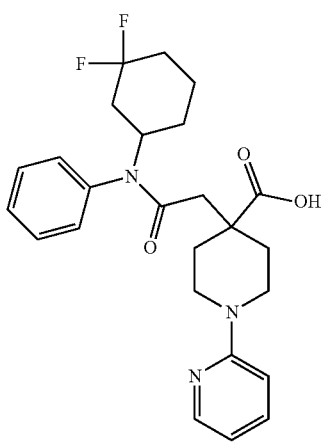 |
| 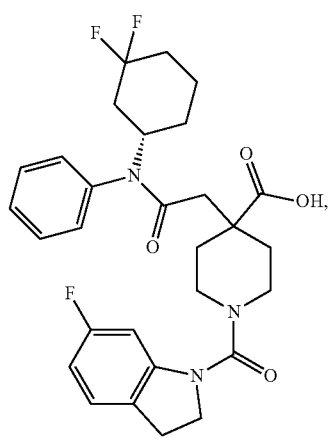 | |
or a pharmaceutically acceptable salt thereof.
22. The compound of claim 1, wherein the compound is
| Structure |
|---|
| 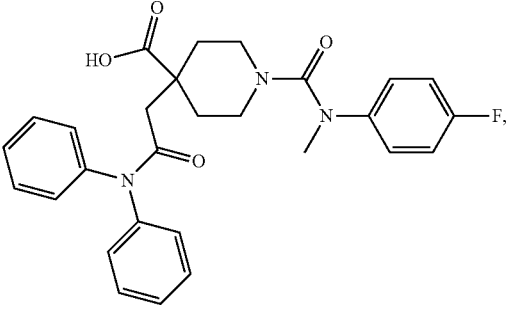 [SMILES: CN(C(=O)N1CCC(CC(=O)N(c2ccccc2)c2ccccc2)(C(=O)O)CC1)c1ccc(F)cc1] |

| 367 -continued | 368 -continued |
|---|---|
| Structure | Structure |
| 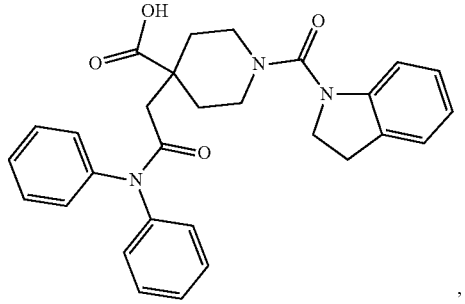 [SMILES: O=C(N1CCC(CC(=O)N(c2ccccc2)c2ccccc2)(C(=O)O)CC1)N1CCc2ccccc21]<br><br>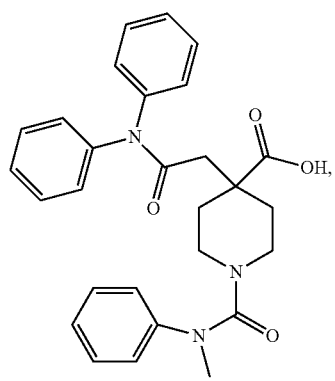 [SMILES: CN(C(=O)N1CCC(CC(=O)N(c2ccccc2)c2ccccc2)(C(=O)O)CC1)c1ccccc1]<br><br>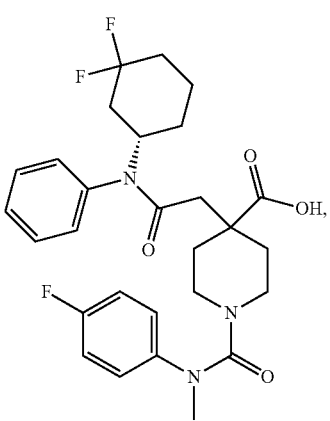 [SMILES: CN(C(=O)N1CCC(CC(=O)N(c2ccccc2)[C@H]2CCCC(F)(F)C2)(C(=O)O)CC1)c1ccc(F)cc1]<br><br>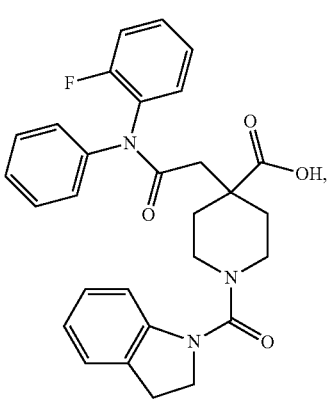 [SMILES: O=C(N1CCC(CC(=O)N(c2ccccc2)c2ccccc2F)(C(=O)O)CC1)N1CCc2ccccc21] | 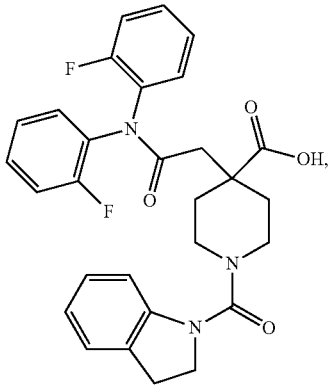 [SMILES: O=C(N1CCC(CC(=O)N(c2ccccc2F)c2ccccc2F)(C(=O)O)CC1)N1CCc2ccccc21]<br><br>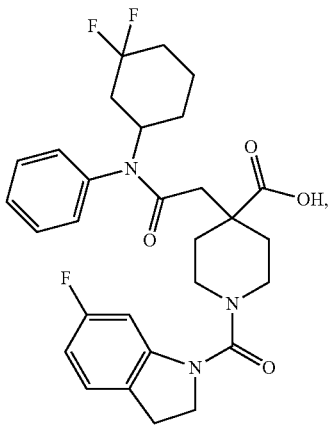 [SMILES: O=C(N1CCC(CC(=O)N(c2ccccc2)C2CCCC(F)(F)C2)(C(=O)O)CC1)N1CCc2ccc(F)cc21]<br><br>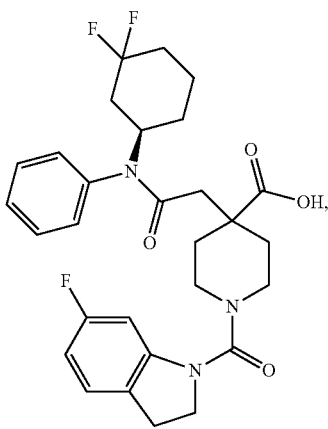 [SMILES: O=C(N1CCC(CC(=O)N(c2ccccc2)[C@@H]2CCCC(F)(F)C2)(C(=O)O)CC1)N1CCc2ccc(F)cc21] |

| 369 -continued | 370 -continued |
|---|---|
| Structure | Structure |

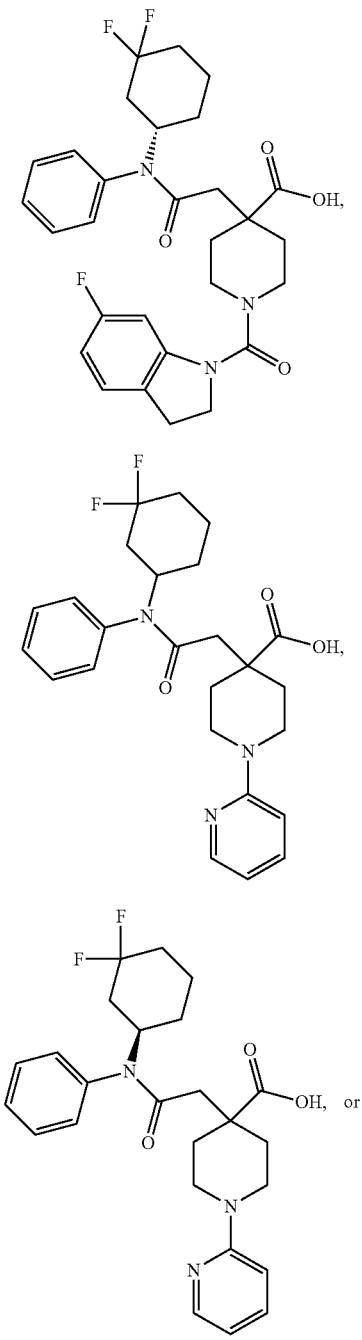

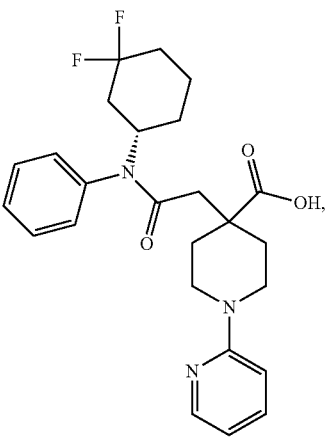 [SMILES: O=C(CC1(C(=O)O)CCN(c2ccccn2)CC1)N(c1ccccc1)[C@H]1CCCC(F)(F)C1]

or a pharmaceutically acceptable salt thereof.

23. A pharmaceutical composition comprising the compound of claim 1, or a pharmaceutically acceptable salt thereof, and one or more pharmaceutically acceptable carrier, diluent, or excipient.

24. A method of treating pain comprising administering to a subject in need thereof a therapeutically effective amount of the compound of claim 1, or a pharmaceutically acceptable salt thereof.

25. The method of claim 24, wherein the pain is neuropathic pain, inflammatory pain, nociceptive pain, mixed nociceptive and neuropathic pain, visceral pain, post-operative pain, post-herpetic pain, traumatic pain, phantom-limb pain, fibromyalgia syndrome, back pain, cancer pain, chemotherapy induced neuropathic pain (CINP), or osteoarthritic (OA) pain.

26. The method of claim 24, wherein the pain is neuropathic pain.

27. The method of claim 26, wherein the neuropathic pain is diabetic peripheral neuropathic pain.

28. The method of claim 24, wherein the pain is chronic lower back pain.

* * * * *

UNITED STATES PATENT AND TRADEMARK OFFICE
CERTIFICATE OF CORRECTION

PATENT NO. : 12,122,750 B2
APPLICATION NO. : 18/315533
DATED : October 22, 2024
INVENTOR(S) : Thomas James Beauchamp et al.

Page 1 of 1

It is certified that error appears in the above-identified patent and that said Letters Patent is hereby corrected as shown below:

In the Claims

In Column 311, Line 40, Claim 15, delete "R2a" and insert -- R12a --.

Signed and Sealed this
Sixteenth Day of September, 2025

Coke Morgan Stewart
*Acting Director of the United States Patent and Trademark Office*